United States Patent [19]
Gillespie et al.

[11] Patent Number: 6,093,680
[45] Date of Patent: Jul. 25, 2000

[54] COMPOSITION AND METHOD FOR TREATING PLANTS WITH EXOGENOUS CHEMICALS

[75] Inventors: Jane L. Gillespie, St. Louis; Ronald J. Brinker, Ellisville; Anthony J. I. Ward, Clayton; Xiaodong C. Xu, St. Louis, all of Mo.

[73] Assignee: Monsanto Company, Saint Louis, Mo.

[21] Appl. No.: 08/957,764

[22] Filed: Oct. 24, 1997

Related U.S. Application Data

[60] Provisional application No. 60/029,317, Oct. 25, 1996, provisional application No. 60/034,887, Jan. 31, 1997, and provisional application No. 60/039,789, Mar. 4, 1997.

[51] Int. Cl.$^7$ .................................................. A01N 25/30
[52] U.S. Cl. .................. 504/116; 504/206; 504/235; 504/250; 514/561; 514/563; 514/772
[58] Field of Search ............................. 504/116, 206, 504/235, 250; 514/561, 563, 772

[56] References Cited

U.S. PATENT DOCUMENTS

| | | | |
|---|---|---|---|
| 4,115,313 | 9/1978 | Lyon | 252/309 |
| 4,235,871 | 11/1980 | Papahadjopoulos | 424/19 |
| 4,311,712 | 1/1982 | Evans | 424/365 |
| 4,394,149 | 7/1983 | Szoka | 71/28 |
| 4,481,026 | 11/1984 | Prisbylla | 71/86 |
| 4,506,831 | 3/1985 | Ghyczy | 239/10 |
| 4,567,161 | 1/1986 | Posanski | 514/23 |
| 4,576,626 | 3/1986 | Bauer | 71/28 |
| 4,681,617 | 7/1987 | Ghyczy | 71/86 |
| 4,822,407 | 4/1989 | Esposito | 71/94 |
| 4,834,908 | 5/1989 | Hazen | 252/356 |
| 4,840,659 | 6/1989 | Franz | 71/86 |
| 4,874,553 | 10/1989 | Hager | 260/403 |
| 4,902,333 | 2/1990 | Quimby | 71/79 |
| 5,037,847 | 8/1991 | Sutter | 514/427 |
| 5,084,087 | 1/1992 | Hazen et al. | 71/123 |
| 5,123,950 | 6/1992 | Homma | 71/11 |
| 5,131,946 | 7/1992 | Franke | 71/90 |
| 5,264,213 | 11/1993 | Shibahara | 424/409 |
| 5,308,827 | 5/1994 | Sakamoto et al. | 504/206 |
| 5,332,573 | 7/1994 | Yamaguchi | 504/117 |
| 5,466,458 | 11/1995 | Martin | 424/405 |
| 5,466,659 | 11/1995 | Keeney | 504/130 |
| 5,482,529 | 1/1996 | Ahlnas | 71/33 |
| 5,512,079 | 4/1996 | Jahnke | 71/64.08 |
| 5,558,806 | 9/1996 | Policello | 252/355 |
| 5,580,567 | 12/1996 | Roberts | 424/405 |

FOREIGN PATENT DOCUMENTS

| | | |
|---|---|---|
| 91373/82 | 6/1983 | Australia . |
| 60702/94 | 7/1995 | Australia . |
| 2081254 | 4/1993 | Canada . |
| 2099631 | of 1994 | Canada . |
| 0 019 384 | 11/1980 | European Pat. Off. . |
| 0 068 293 | 1/1983 | European Pat. Off. . |
| 0 068 294 | 1/1983 | European Pat. Off. . |
| 0 068 295 | 1/1983 | European Pat. Off. . |
| 0 099 029 | 1/1984 | European Pat. Off. ....... A01N 57/12 |
| 0 124 351 | 11/1984 | European Pat. Off. . |
| 0 146 238 | 6/1985 | European Pat. Off. . |
| 0 095 071 | 7/1985 | European Pat. Off. . |
| 0 342 685 | 11/1989 | European Pat. Off. . |
| 0 485 207 | 5/1992 | European Pat. Off. ....... A01N 25/04 |
| 0 503 989 | 9/1992 | European Pat. Off. . |
| 0 579 052 | 1/1994 | European Pat. Off. ....... A01N 25/02 |
| 0 579 951 | 1/1994 | European Pat. Off. . |
| 0 582 561 | 2/1994 | European Pat. Off. . |

(List continued on next page.)

OTHER PUBLICATIONS

Anderson & Panetta (1995). Fireweed response to boom-spray applications of different herbicides and adjuvants. Plant Protection Quarterly 10(4), 152–153.

Anon. (no date). LI–700. Brochure of Agridyne, Pont–du–Casse, France.

Anon. (1993). 40 CFR § 180.1001, 435–458.

Anon. (1995). McCutcheon's Volume 1: Emulsifiers & Detergents. North American Edition, pp. 4, 8, 9, 42, 48, 149, 163, 164, 316.

Anon. (1996). The right tool for the right job? Adverisement by Loveland Industries, Inc. Farm Chemicals, Oct. 1996, p. 51.

Anon. (1997). Crop protection round–up: adjuvants. Farm Chemicals, Mar. 1997, 56–57.

Balneaves (1992). A comparison of surfactants to aid control of gorse and scotch broom with herbicides. Plant Protection Quarterly 7(4), 174–177.

Boothroyd et al. (1993) *Alopecurus myosuroides* control using fenoxaprop ethyl dose adjustments, adjuvants and mixes. Proceedings, Brighton Crop Protection Conference, vol. 2, 601–606.

Bravais et al. (1993). Influence of triolein and methyl, ethyl and propyl oleate on the deposit shape and the foliar penetration of phenmedipham and quizalofop–ethyl. Mededelingen Faculteit Landbouwwetenschappen Rijksuniversiteit Gent 58(3a), 803–807.

Bridges (1989). Adjuvant and pH effects on sethoxydim and clethodim activity on rhizome johnsongrass (*Sorghum halepense*). Weed Technology 3, 615–620.

(List continued on next page.)

*Primary Examiner*—S. Mark Clardy
*Attorney, Agent, or Firm*—James C. Forbes

[57] ABSTRACT

Methods and compositions are disclosed wherein exogenous chemicals are applied to plants to generate a desired biological response. One embodiment of the present invention is a plant treatment composition that comprises (a) an exogenous chemical; (b) a first excipient substance which is a compound or mixture of compounds having the formula $$R^{14}\text{—CO—A—}R^{15}$$

wherein $R^{14}$ is a hydrocarbyl group having about 5 to about 21 carbon atoms, $R^{15}$ is a hydrocarbyl group having 1 to about 14 carbon atoms, the total number of carbon atoms in $R^{14}$ and $R^{15}$ is about 11 to about 27, and A is O or NH; and (c) a second excipient substance which is an amphiphilic substance having a critical packing parameter greater than $\frac{1}{3}$.

50 Claims, No Drawings

FOREIGN PATENT DOCUMENTS

| | | |
|---|---|---|
| 0 597 488 | 5/1994 | European Pat. Off. . |
| 0 648 413 | 4/1995 | European Pat. Off. . |
| 0 664 954 | 8/1995 | European Pat. Off. . |
| 0 729 700 | 9/1996 | European Pat. Off. . |
| 3226498 A1 | of 1984 | Germany . |
| 32 26 498 | 1/1984 | Germany ................ A01N 25/32 |
| 32 47 050 | 6/1984 | Germany ................ A01N 25/30 |
| 4 318 673 | 1/1995 | Germany . |
| 67 542 | 4/1995 | Hungary . |
| 61-229804 | 10/1986 | Japan . |
| 2-169545 | 6/1990 | Japan . |
| 2-169546 | 6/1990 | Japan . |
| 2-172950 | 7/1990 | Japan . |
| 2-172951 | 7/1990 | Japan . |
| 4-134001 | 5/1992 | Japan . |
| 5-065201 | 3/1993 | Japan . |
| 5-078204 | 3/1993 | Japan . |
| 5-085901 | 4/1993 | Japan . |
| 5-112414 | 5/1993 | Japan . |
| 5-148105 | 6/1993 | Japan . |
| 6-234603 | 8/1994 | Japan . |
| 6-263576 | 9/1994 | Japan . |
| 7-187915 | 7/1995 | Japan . |
| 8-151308 | 6/1996 | Japan . |
| 8-225402 | 9/1996 | Japan . |
| 83/4882 | of 1983 | South Africa . |
| 89/3661 | 1/1990 | South Africa . |
| 2 188 900 | 10/1987 | United Kingdom . |
| 2 247 622 | 3/1992 | United Kingdom . |
| 2 257 044 | 1/1993 | United Kingdom . |
| WO 83/03608 | 10/1983 | WIPO . |
| WO 87/04595 | 8/1987 | WIPO . |
| WO 88/06881 | 9/1988 | WIPO . |
| WO 90/07272 | 7/1990 | WIPO . |
| WO 91/08666 | of 1991 | WIPO . |
| WO 92/06596 | 10/1992 | WIPO . |
| WO 92/18103 | 10/1992 | WIPO . |
| WO 93/05652 | 4/1993 | WIPO . |
| WO 93/21763 | 11/1993 | WIPO . |
| WO 93/21768 | 11/1993 | WIPO . |
| WO 94/10979 | 5/1994 | WIPO . |
| WO 94/13140 | 6/1994 | WIPO . |
| WO 94/19941 | 9/1994 | WIPO . |
| WO 94/20072 | 9/1994 | WIPO . |
| WO 95/12977 | of 1995 | WIPO . |
| WO 95/16351 | of 1995 | WIPO . |
| WO 95/07614 | 3/1995 | WIPO . |
| WO 95/13795 | 5/1995 | WIPO . |
| WO 95/13796 | 5/1995 | WIPO . |
| WO 95/20944 | 8/1995 | WIPO . |
| 95/31970 | 11/1995 | WIPO ................ A61K 9/127 |
| WO 95/31898 | 11/1995 | WIPO . |
| WO 95/34200 | 12/1995 | WIPO . |
| WO 96/00010 | 1/1996 | WIPO . |
| WO 96/01047 | 1/1996 | WIPO . |
| 96/03871 | 2/1996 | WIPO ................ A01N 25/04 |
| WO 96/22020 | 7/1996 | WIPO . |
| WO 96/28973 | 9/1996 | WIPO . |
| WO 97/12515 | 4/1997 | WIPO . |
| WO 97/27743 | 8/1997 | WIPO . |
| WO 97/36494 | 10/1997 | WIPO . |
| WO 97/41730 | 11/1997 | WIPO . |

OTHER PUBLICATIONS

Bridges et al. (1991). Effect of adjuvant on foliar absorption and activity of clethodim and polar degradation products of clethodim. Weed Science 39, 543–547.

Bridges et al. (1992). Stability and activity of clethodim as influenced by pH, UV light and adjuvant. In Foy, ed.: Adjuvant for Agrochemicals, 215–223. Boca Raton: CRC Press.

Bruce et al. (1993). Absorption and activity of nicosulfuron and primisulfuron in quackgrass (Elytrigia repens) as affected by adjuvants. Weed Science 41, 218–224.

De Villiers et al. (1996). Optimizing tralkoxydim efficacy with carrier water high in sodium bicarbonate. FRI Bulletin 193 (Proceedings, Fourth International Symposium on Adjuvants for Agrochemicals, 1995), 207–210.

Eberlein et al. (1992). Hairy nightshade (Solanum sarrachoides) control in potatoes (Solanum tuberosum) with bentazon plus additives. Weed Technology 6, 85–90.

Florence & Whitehill (1980). Some features of breakdown in water–in–oil–in–water multiple emulsions. Journal of Colloid and Interface Science 79, 243–256.

Foy (1996). Adjuvants—current trends and technology. Pesticide Formulation Adjuvant Technology (Formulations Forum 1994), 323–352. Boca Raton: CRC Press.

Foy & Witt (1993). Effects of methylated crop oils and other selected adjuvants on the herbicidal efficacy and selectivity of imazethapyr in soybeans. Pesticide Science 38, 260–262.

Froment & Cooper (1994). Evaluation of fenoxaprop ethyl alone and in mixtures against blackgrass (Alopecurus myosuroides) in winter wheat. Tests of Agrochemicals and Cultivars 15, 60–61.

Garr & Hanks (1996). Effects of adjuvant on velvetleaf control with chlorimuron and imazethapyr in soybeans. FRI Bulletin 193 (Proceedings, Fourth International Symposium on Adjuvants for Agrochemicals, 1995), 432–436.

Gauvrit et al. (1995). Influence of ester derivatives of oleic–sunflower seed oil on the foliar penetration of herbicides. Mededelingen Faculteit Landbouwwetenschappen Rijksuniversiteit Gent 60(2a), 183–189.

Gimesi (1986). Increasing the phytotoxicity of glyphosate by using subsidiary materials. Novenytermeles 35, 319–324. Abstract in English.

Glass (1988). Entrapment of herbidcides $^{14}$C–picloram and $^{14}$C–dicamba in phospholipid vesicles. Pesticide Biochemistry and Physiology 32, 93–96. Abstract only.

Hamilton (1993). Structure and general properties of mineral and vegetable oils used as spray adjuvants. Pesticide Science 37, 141–146.

Harker (1992). Effects of various adjuvants on sethoxydim activity. Weed Technology 6, 865–870.

Hart et al. (1992). Influence of adjuvants on the efficacy, absorption and spray retention of primisulfuron. Weed Technology 6, 592–598.

Harvey (1989). A guide to agricultural spray adjuvants used in the United States, 1990–91 ed., p. 94. Fresno: Thomson Publications.

Hickey (1987). Methyl esters of fatty acids as pesticide formulation and application aids. ASTM Special Technical Publication 968, 67–74.

Killick et al. (1996). Ethylated esterified seed oils—a second generation of herbicide adjuvants. FRI Bulletin 193 (Proceedings, Fourth International Symposium on Adjuvants for Agrochemicals, 1995), 78–83.

Knoche & Bukovac (1993). Interaction of surfactant and leaf surface in glyphosate absorption. Weed Science 41, 87–93.

Krawczyk (1996). Lecithin: consider the possibilities. Inform 7(11), 1158–1167.

Kwon & Penner (1996). The effect of piperonly butoxide and adjuvants on sulfonylurea herbicide activity. Weed Technology 10, 127–133.

Lasic (1997). Liposomes in Gene Delivery. Chap. 6, pp. 67–112. Boca Raton: CRC Press.

Leskovar & Boales (1996). Azadirachtin: potential use for controlling lepidopterous insects and increasing marketability of cabbage. Horticultural Science 31, 405–409.

Mack et al. (1996). Effects of several adjuvant classes on two herbicides for weed control FRI Bulletin 193 (Proceedings, Fourth International Symposium on Adjuvants for Agrochemicals, 1995), 448–453.

Manthey et al. (1989a). Herbicide–oil–water emulsions. Weed Technology 3, 13–19.

Manthey et al. (1989b). Esterified seed oils with herbicides. In Chow et al., ed.: Adjuvants and Agrochemicals, vol. 2, 139–148. Boca Raton: CRC Press.

Manthey et al. (1990). Small grain and grass weed response to BAS–514 with adjuvants. Weed Technology 4, 366–370.

Manthey et al. (1992). Foliar absorption and phytotoxicity of quizalofop with lipid compounds. Weed Science 40, 558–562.

McMullan (1992). Effect of adjuvant and acidifying agent on imazamethabenz efficacy. Canadian Journal of Plant Science 72, 1389–1392.

Miller et al. (1996). The influence of adjuvants on droplet production. FRI Bulletin 193 (Proceedings, Fourth International Symposium on Adjuvants for Agrochemicals, 1995), 95–102.

Nalewaja (1986). Seed oils with herbicides. Mededelingen Faculteit Landbouwwetenschappen Rijksuniversiteit Gent 51(2a), 301–310.

Nalewaja & Matysiak (1993). Optimizing adjuvants to overcome glyphosate antagonistic salts. Weed Technology 7, 337–342.

Nalewaja et al. (1990). Imazethapyr efficacy with adjuvants and environments. Weed Technology 4, 765–770.

Nandula et al. (1995). Effectiveness of adjuvants with nicosulfuron and primisulfuron for wirestem muhly (*Muhlenbergia frondosa*) control in no–till corn (*Zea mays*). Weed Technology 9, 525–530.

Omotosho et al. (1989). Methotrexate transport from the internal phase of multiple w/o/w emulsions. Journal of Microencapsulation 6, 183–192.

Parnham (1996). The importance of phospholipid terminolgy. Inform 7(11), 1168–1175.

Percival & Baker (1990). Chlorophyll fluorescence—a possible application in plant growth regulator research. Monograph, British Society of Plant Growth Regulation 19, 1–14.

Quinn (1985). The chemico–physical properties of membrane lipids and their relevance to plant growth and protection. In St John, ed.: Frontiers of Membrane Research in Agriculture (Beltsville Symposium 9), 55–75.

Quinn et al. (1986). An evaluation of soya lecithin in crop spray performance. Atomisation and Spray Technology 2, 235–246.

Rahman et al. (1994). Control of phenoxy herbicide resistant nodding thistle (*Carduus nutans*) in pasture. Proceedings, New Zealand Plant Protection Conference 47, 68–74.

Rimmer et al. (1992). Nutrient application to potatoes and wheat with various spray adjuvants. Abstracts, Third International Symposium on Adjuvants for Agrochemicals. No page number.

Roberts (1992). Laboratory procedures applicable to the evaluation of spray adjuvants utilizing methylated seed oils. Abstracts, Third International Symposium on Adjuvants for Agrochemicals. No page number.

Salakhutdinov et al. (1992). Polymorphous transformations in model membranes caused by amphiphilic fungicides. Doklady Akademii Nauk Respubliki Uzbekistan 1, 45–46.

Santier & Chamel (1996). Penetration of triolein and methyl oleate through isolated plant cuticles and their effect on penetration of [$^{14}$C] quizalofop–ethyl and [$^{14}$C] fenoxaprop––ethyl. Weed Research 36, 167–174.

Schönherr (1993). Effects of monodisperse alcohol ethoxylates on mobility of 2,4–D in isolated plant cuticles. Pesticide Science 38, 155–164.

Schönherr & Baur (1994). Modelling penetration of plant cuticles by crop protection agents and effects of adjuvants on their rates of penetration. Pesticide Science 42, 185–208.

Skelton (1993). Pesticide microemulsion concentrate formulations utilizing fatty acid methyl esters as solvent alternatives. ASTM Special Technical Publication 1183, 114–120.

Skrzypezak & Nalewaja (1987). Influence of various fatty acid formulations on the uptake and translocation of sethoxydim and fluazifop–butyl. Roczniki Nauk Rolniczych, Ser. E 16(2), 143–150. Abstract only.

Stock et al. (1992). Surfactant–enhanced foliar uptake of some organic compounds interactions with two model polyoxyethylene aliphatic alcohols. Pesticide Science 34, 233–242.

Swietlik (1989). Adjuvants affect the efficacy of glyphosate on selected perennial weeds. Horticultural Science 24, 470–472.

Tadros (1989). Colloidal aspects of pesticidal and pharmaceutical formulations—an overivew. Pesticide Science 26, 51–77.

Tann et al. (1996), Effect of various carbon chain length methyl esters as agricultural tank mix adjuvants. FRI Bulletin 193 (Proceedings, Fourth International Symposium on Adjuvants for Agrochemicals, 1995), 72–77.

Thompson et al. (1996). Adjuvant effects on Imazethapyr, 2,4–D and picloram absorption by leafy spurge (*Euphorbia esula*). Weed Science 44, 469–475.

Townson (1990). Influence of formulation and application variables in relation to the performance of glyphosate and imazapyr for control of *Imperata cylindrica* (L.) Raeuschel. Ph.D. Thesis, University of Bristol. 312 pp.

Urvoy & Gauvrit (1991). Seed oils as adjuvants; penetration of glycerol trioleate, methanol oleate and diclofop–methyl in maize leaves. Proceedings, Brighton Crop Protection Conference, vol. 1, 337–342.

Urvoy et al. (1992). Seed oils as additives: penetration of triolein, methyl oleate and diclofop–methyl in maize leaves. Weed Research 32, 375–383.

Van Toor et al. (1994). Relationships between the herbicidal activity and foliar uptake of surfactant–containing solutions of glyphosate applied to foliage of oats and field beans. Crop Protection 13, 260–270.

Wallach & Philippot (1993). New type of lipid vesicle: Novasome™. In Gregoriadis, ed.: Liposome Technology, 2nd ed., vol. 1, pp. 141–156, Boca Raton: CRC Press.

Wells (1989). Adjuvants, glyphosate efficacy and post–spraying rainfall. Plant Protection Quarterly 4(4), 158–164.

Whitson & Adam (1990). Leafy spurge (*Euphorbia esula*L.) control with various adjuvants combined with picloram and fluroxypyr. Proceedings, Western Society of Weed Science 43, 37.

Wills et al. (1993). Evaluation of the effect of a paraffinic petroleum oil–based adjuvant and an organosilicone–modified methylated vegetable oil–based adjuvant on the efficacy of imazethapyr herbicide as applied in conventional and ultra–low volumes. Pesticide Science 38, 280–282.

Woznika & Messersmith (1994). Evaluation of adjuvants for glyphosate. Materialy Sesji Naukowej Instytutu Ochrony Roslin 34(2), 98–101. Abstract in English.

Woznica & Messersmith (1994). Glyphosate retention and absorption by cattail (*Typha X glauca* Godr.) as influenced by nonionic surfactants. Roczniki Nauk Rolniczych, Ser. E 24, 87–91.

Yaduraju & Ahuja (1995). Response of herbicide resistant *Phalaris minor* to pre– and post–emergence herbicides, herbicide mixtures and adjuvants. Proceedings, Brighton Crop Protection Conference, vol. 1, 225–230.

Young (1983). Glyphosate plus adjuvants. Proceedings, Northeastern Weed Science Society 37, 250–254.

Chemical Abstracts, vol. 120, mo. 21, May 23, 1994, Columbus, Ohio, US; Abstract No. 263749, Serre, I., et al.: seed oil derivatives as adjubants: influence of methyl to octadecyl oleates on the penetration of herbicides through various plant cuticles XP002059236.

Wyrill, J.B., et al., "Glyphosate Toxicity to Common Milkweed and Hemp Dogbane as Infrluenced by Surfactants," *Weed Science;* vol. 25, No. 3, pp. 275–287 May 1997 XP002034447.

Gaskin, R. E. & Holloway, P. J. (1992). Some physiochemical factors influencing foliar uptake enhancement of glyphosate–mono(isopropylammonium) by polyoxyethylene surfactants. Pesticide Science 34, 195–206.

Serre, I. et al. (1993). Seed oil derivatives as adjuvants: influence of methyl to octadecyl oleates on the penetration of herbicides through various plant cuticles. Mededelingen, Faculteit Landbouwwetenschappen Rijksuniversiteit Gent 58(3a), 795–802. CA Abstract 120:263749.

COMPOSITION AND METHOD FOR TREATING PLANTS WITH EXOGENOUS CHEMICALS

This application claims the benefit of provisional application serial No. 60/029,317, filed Oct. 25, 1996; provisional application serial No. 60/034,887, filed Jan. 31, 1997; and provisional application serial No. 60/039,789, filed Mar. 4, 1997. Each of those applications is incorporated here by reference.

BACKGROUND OF THE INVENTION

This invention relates to formulations and methods for enhancing the efficacy of exogenous chemicals used in treating plants. An exogenous chemical, as defined herein, is any chemical substance, whether naturally or synthetically derived, which (a) has biological activity or is capable of releasing in a plant an ion, moiety or derivative which has biological activity, and (b) is applied to a plant with the intent or result that the chemical substance or its biologically active ion, moiety or derivative enter living cells or tissues of the plant and elicit a stimulatory, inhibitory, regulatory, therapeutic, toxic or lethal response in the plant itself or in a pathogen, parasite or feeding organism present in or on the plant. Examples of exogenous chemical substances include, but are not limited to, chemical pesticides (such as herbicides, algicides, fungicides, bactericides, viricides, insecticides, aphicides, miticides, nematicides, molluscicides, and the like), plant growth regulators, fertilizers and nutrients, gametocides, defoliants, desiccants, mixtures thereof, and the like.

Exogenous chemicals, including foliar-applied herbicides, have at times been formulated with surfactants, so that when water is added, the resulting sprayable composition is more easily and effectively retained on the foliage (e.g., the leaves or other photosynthesizing organs) of plants. Surfactants can also bring other benefits, including improved contact of spray droplets with a waxy leaf surface and, in some cases, improved penetration of the accompanying exogenous chemical into the interior of leaves. Through these and perhaps other effects, surfactants have long been known to increase the biological effectiveness of herbicide compositions, or other compositions of exogenous chemicals, when added to or included in such compositions. Thus, for example, the herbicide glyphosate (N-phosphonomethylglycine) has been formulated with surfactants such as polyoxyalkylene-type surfactants including, among other surfactants, polyoxyalkylene alkylamines. Commercial formulations of glyphosate herbicide marketed under the trademark ROUNDUP® have been formulated with a surfactant composition based on such a polyoxyalkylene alkylamine, in particular a polyethoxylated tallowamine, this surfactant composition being identified as MON 0818. Surfactants have generally been combined with glyphosate or other exogenous chemicals either in a commercial concentrate (herein referred to as a "coformulation"), or in a diluted mixture that is prepared from separate compositions, one comprising an exogenous chemical (e.g. glyphosate) and another comprising surfactant, prior to use in the field (i.e., a tank mix).

Various combinations of exogenous chemicals and surfactants or other adjuvants have been tested in the past. In some instances, the addition of a particular surfactant has not produced uniformly positive or negative changes in the effect of the exogenous chemical on the plant (e.g., a surfactant that may enhance the activity of a particular herbicide on certain weeds may interfere with, or antagonize, the herbicidal efficacy on another weed species).

Some surfactants tend to degrade fairly rapidly in aqueous solutions. As a result, surfactants that exhibit this property can only be used effectively in tank mixes (i.e., mixed with the other ingredients in solution or dispersion in the tank soon before spraying is to occur), rather than being coformulated in an aqueous composition with the other ingredients in the first instance. This lack of stability, or inadequate shelf-life, has hindered the use of certain surfactants in some exogenous chemical formulations.

Other surfactants, though chemically stable, are physically incompatible with certain exogenous chemicals, particularly in concentrate coformulations. For example, most classes of nonionic surfactant, including polyoxyethylene alkylether surfactants, do not tolerate solutions of high ionic strength, as for example in a concentrated aqueous solution of a salt of glyphosate. Physical incompatibility can also lead to inadequate shelf-life. Other problems that can arise from such incompatibility include the formation of aggregates large enough to interfere with commercial handling and application, for example by blocking spray nozzles.

Another problem that has been observed in the past is the effect of environmental conditions on uptake of an exogenous chemical composition into foliage of a plant. For example, conditions such as temperature, relative humidity, presence or absence of sunlight, and health of the plant to be treated, can affect the uptake of a herbicide into the plant. As a result, spraying exactly the same herbicidal composition in two different situations can result in different herbicidal control of the sprayed plants.

One consequence of the above-described variability is that often a higher rate of herbicide per unit area is applied than might actually be required in that situation, in order to be certain that adequate control of undesired plants will be achieved. For similar reasons, other foliar-applied exogenous chemicals are also typically applied at significantly higher rates than needed to give the desired biological effect in the particular situation where they are used, to allow for the natural variability that exists in efficiency of foliar uptake. A need therefore exists for compositions of exogenous chemicals that, through more efficient uptake into plant foliage, allow reduced use rates.

Many exogenous chemicals are commercially packaged as a liquid concentrate that contains a significant amount of water. The packaged concentrate is shipped to distributors or retailers. Ultimately the packaged concentrate ends up in the hands of an end user, who further dilutes the concentrate by adding water in accordance with label instructions on the package. The dilute composition thus prepared is then sprayed on plants.

A significant portion of the cost of such packaged concentrates is the cost of transporting the concentrate from the manufacturing site to the location where the end user purchases it. Any liquid concentrate formulation that contained relatively less water and thus more exogenous chemical would reduce the cost per unit amount of exogenous chemical. However, one important limit on the ability of the manufacturer to increase the loading of the exogenous chemical in the concentrate is the stability of that formulation. With some combinations of ingredients, a limit will be reached at which any further reduction of water content in the concentrate will cause it to become unstable (e.g., to separate into discrete layers), which may make it commercially unacceptable.

Accordingly, a need exists for improved formulations of exogenous chemicals, particularly herbicides, that are stable, effective, less sensitive to environmental conditions, and permit the use of reduced amounts of exogenous chemical to achieve the desired biological effect in or on plants. A need also exists for stable liquid concentrate formulations of exogenous chemicals that contain less water and more exogenous chemical than prior art concentrates.

SUMMARY OF THE INVENTION

The present invention relates to novel methods and compositions wherein exogenous chemicals are applied to plants to generate a desired biological response.

One embodiment of the present invention is a plant treatment composition that comprises (a) an exogenous chemical; (b) a first excipient substance which is a compound or mixture of compounds having the formula

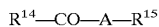

$$R^{14}\text{—CO—A—}R^{15} \quad\quad\quad \text{VII}$$

wherein $R^{14}$ is a hydrocarbyl group having about 5 to about 21 carbon atoms, $R^{15}$ is a hydrocarbyl group having 1 to about 14 carbon atoms, the total number of carbon atoms in $R^{14}$ and $R^{15}$ is about 11 to about 27, and A is O or NH; and (c) a second excipient substance which is an amphiphilic substance having a critical packing parameter greater than ⅓. "Amphiphilic" means having at least one polar, water-soluble head group which is hydrophilic and at least one water-insoluble organic tail which is hydrophobic, contained within the same molecule. An "excipient substance" as that term is used in this patent is any substance other than an exogenous chemical and water that is added to the composition. "Excipient substances" include inert ingredients, although an excipient substance useful in the present invention does not have to be devoid of biological activity.

In one preferred embodiment, the weight/weight ratio of second excipient substance to the exogenous chemical is from about 1:3 to about 1:100. It is particularly preferred that the weight/weight ratio of first excipient substance to the exogenous chemical is also from about 1:3 to about 1:100. In another embodiment, $R^{14}$ is saturated in from about 40 to 100 percent by weight of all compounds having the stated formula present in the composition. $R^{14}$ preferably has about 11 to about 21 carbon atoms, $R^{15}$ preferably has 1 to about 6 carbon atoms and A is preferably O.

In certain preferred embodiments of the present invention, the first excipient substance is a $C_{1-4}$ alkyl ester of a $C_{12-18}$ fatty acid, more preferably a $C_{1-4}$ alkyl ester of a $C_{12-18}$ saturated fatty acid. Propyl, isopropyl or butyl esters of $C_{12-18}$ fatty acids, such as butyl stearate, are especially preferred.

A wide variety of exogenous chemicals can be used in the compositions and methods of the present invention. A preferred class is foliar-applied exogenous chemicals, i.e. exogenous chemicals that are normally applied post-emergence to foliage of plants. A preferred subclass of foliar-applied exogenous chemicals is those that are water-soluble. By "water-soluble" in this context is meant having a solubility in distilled water at 25° C. greater than about 1% by weight. Especially preferred water-soluble exogenous chemicals are salts that have an anion portion and a cation portion. In one embodiment of the invention, at least one of the anion and cation portions is biologically active and has a molecular weight of less than about 300. Particular examples of such exogenous chemicals where the cation portion is biologically active are paraquat, diquat and chlormequat. More commonly it is the anion portion that is biologically active.

Another preferred subclass of exogenous chemicals is those that exhibit systemic biological activity in the plant.

Within this subclass, an especially preferred group of exogenous chemicals is N-phosphonomethylglycine and its herbicidal derivatives. N-phosphonomethylglycine, often referred to by its common name glyphosate, can be used in its acid form, but is more preferably used in the form of a salt. Any water-soluble salt of glyphosate can be used in the practice of this invention. Some preferred salts include the sodium, potassium, ammonium, mono-, di-, tri- and tetra-$C_{1-4}$-alkylammonium, mono-, di- and tri-$C_{1-4}$-alkanolammonium, mono-, di- and tri-$C_{1-4}$-alkylsulfonium and sulfoxonium salts. The ammonium, monoisopropylammonium and trimethylsulfonium salts of glyphosate are especially preferred. Mixtures of salts can also be useful in certain situations.

Compositions of the present invention can be used in methods of treating plants. Foliage of a plant is contacted with a biologically effective amount of the composition. "Contacting" in this context means placing the composition on the foliage.

A composition of the present invention comprising an exogenous chemical and a first excipient substance as described above can have a number of different physical forms. For example, the composition can further comprise water in an amount effective to make the composition a dilute aqueous composition ready for application to foliage of a plant. Such a composition typically contains about 0.02 to about 2 percent by weight of the exogenous chemical, but for some purposes can contain up to about 10 percent by weight or even more of the exogenous chemical.

Alternatively, the composition can be a shelf-stable concentrate composition comprising the exogenous chemical substance in an amount of about 10 to about 90 percent by weight. Such shelf-stable concentrates can be, for example, (1) a solid composition comprising the exogenous chemical substance in an amount of about 30 to about 90 percent by weight, such as a water-soluble or water-dispersible granular formulation, or (2) a composition that further comprises a liquid diluent, wherein the composition comprises the exogenous chemical substance in an amount of about 10 to about 60 percent by weight. In this latter embodiment, it is especially preferred for the exogenous chemical substance to be water-soluble and present in an aqueous phase of the composition in an amount of about 15 to about 45 percent by weight of the composition. In this embodiment the first excipient substance is present predominantly in an oil phase of the composition, such composition typically being in the form of an emulsion, which can more specifically be, for example, an oil-in-water emulsion, a water-in-oil emulsion, or a water-in-oil-in-water multiple emulsion. In one particular embodiment of the invention, the solid or aqueous composition further comprises a solid inorganic particulate colloidal material.

As described above, one embodiment of the invention is a sprayable composition that comprises an exogenous chemical, an aqueous diluent, and a first excipient substance. The term "spray composition" is sometimes used herein to mean a sprayable composition.

In a related embodiment of the invention, a concentrate composition is provided which, upon dilution, dispersion or dissolution in water forms the sprayable composition just described. The concentrate composition contains a reduced amount of the aqueous diluent, or, in a particular embodiment, is a dry composition having less than about 5% water by weight. Typically a concentrate composition of the invention contains at least about 10% by weight of the exogenous chemical, preferably at least about 15%.

An alternative embodiment is a composition that does not itself comprise an exogenous chemical, but is intended for application to a plant in conjunction with or as a carrier for the application of an exogenous chemical. This composition comprises a first excipient substance and a second excipient substance as described above. Such a composition may be sprayable, in which case it also comprises an aqueous diluent, or it may be a concentrate, requiring dilution, dispersion or dissolution in water to provide a sprayable composition. Thus, this embodiment of the invention can be provided as a stand-alone product and applied to a plant, diluted as appropriate with water, simultaneously with the application of an exogenous chemical (for example in tank mix with the exogenous chemical), or before or after the application of the exogenous chemical, preferably within about 96 hours before or after application of the exogenous chemical.

In all embodiments, it is believed that the second excipient substance forms supramolecular aggregates in aqueous solution or dispersion. In particular it is believed that aqueous compositions of the present invention form aggregates in aqueous solution or dispersion the majority of which are not simple micelles. "Majority" means that more than 50% by weight of the second excipient substance present is in the form of complex aggregates other than simple micelles, e.g. as bilayers or multilamellar structures. Preferably, more than 75% by weight is in the form of complex aggregates other than simple micelles.

Whether or not an amphiphilic substance forms such aggregates depends on its molecular architecture. The effects of molecular architecture of supramolecular self-assembly of amphiphilic molecules, as set forth for example by J. N. Israelachvili, D. J. Mitchell and B. W. Ninham in *Faraday Transactions II,* Volume 72, pp. 1525–1568 (1976) and in numerous later articles and monographs, are well known and understood. An important aspect is "critical packing parameter" (P) which is defined in the literature by the following equation:

$$P = V/lA$$

where V is the volume of the hydrophobic tail of the molecule, l is the effective length of the hydrophobic tail, and A is the area occupied by the hydrophilic headgroup. These dimensions can be calculated from physical measurements as described in the literature and have been published for numerous amphiphilic compounds.

Amphiphilic substances useful as the second excipient substance herein have a critical packing parameter greater than $\frac{1}{3}$. The second excipient substance forms aggregates in aqueous solution or dispersion which preferably have at least one dimension that is greater than two times the molecular length of the second excipient substance.

In one embodiment of the invention, the second excipient substance is a liposome-forming material. One class of liposome-forming material is an amphiphilic compound or mixture of such compounds, preferably having two hydrophobic moieties, each of which is a saturated alkyl or acyl chain having from about 8 to about 22 carbon atoms. The amphiphilic compound or mixture of such compounds having said two hydrophobic moieties with about 8 to about 22 carbon atoms preferably constitutes from about 40 to 100 percent by weight of all amphiphilic compounds having two hydrophobic moieties present in the liposome-forming material. Preferably the liposome-forming material has a hydrophilic head group comprising a cationic group. More preferably, the cationic group is an amine or ammonium group.

In a preferred embodiment of the invention, the second excipient substance comprises a liposome-forming compound having a hydrophobic moiety comprising two independently saturated or unsaturated hydrocarbyl groups $R^1$ and $R^2$ each independently having about 7 to about 21 carbon atoms. A number of subclasses of such liposome-forming compounds are known.

One subclass has the formula $$N^+(CH_2R^1)(CH_2R^2)(R^3)(R^4)Z^- \qquad \text{I}$$

wherein $R^3$ and $R^4$ are independently hydrogen, $C_{1-4}$ alkyl or $C_{1-4}$ hydroxyalkyl and Z is a suitable agriculturally acceptable anion.

A second subclass has the formula $$N^+(R^5)(R^6)(R^7)CH_2CH(OCH_2R^1)CH_2(OCH_2R^2)Z^- \qquad \text{II}$$

wherein $R^5$, $R^6$ and $R^7$ are independently hydrogen, $C_{1-4}$ alkyl or $C_{1-4}$ hydroxyalkyl and Z is a suitable anion.

A third subclass has the formula $$N^+(R^5)(R^6)(R^7)CH_2CH(OCOR^1)CH_2(OCOR^2)Z^- \qquad \text{III}$$

wherein $R^5$, $R^6$, $R^7$ and Z are as defined above.

A fourth subclass has the formula $$N^+(R^5)(R^6)(R^7)CH_2CH_2OPO(O^-)OCH_2CH(OCOR^1)CH_2(OCOR^2) \qquad \text{IV}$$

wherein $R^5$, $R^6$, and $R^7$ are as defined above.

Compounds of formulas I–IV will have the indicated formulas in an acid medium, for example at a pH of 4 and may have the same formulas at other pH's as well. It should be understood, however, that compositions of the present invention are not limited to use at a pH of 4.

It is preferred that about 40–100 percent of the $R^1$ and $R^2$ groups in the second excipient substance are saturated straight chain alkyl groups having about 7 to about 21 carbon atoms. Examples of suitable agriculturally acceptable anions Z include hydroxide, chloride, bromide, iodide, sulfate, phosphate and acetate.

In all of the above subclasses of liposome-forming substances, the hydrophilic moiety comprises a cationic group, specifically an amine or ammonium group. The compound as a whole is in some cases cationic (as in I, II and III) and in some cases neutral (as in IV). Where the amine group is quaternary, it behaves as a cationic group independently of pH. Where the amine group is secondary or tertiary, it behaves as a cationic group when protonated, i.e. in an acid medium, for example at a pH of 4.

Other subclasses of liposome-forming substances having two hydrophobic chains each comprising a $C_{7-21}$ hydrocarbyl group can also be used as the second excipient substance in compositions of the invention. While substances having a cationic group in the hydrophilic moiety are preferred, nonionic or anionic substances can be used if desired.

In another embodiment, the second excipient substance is a phospholipid selected from the group consisting of di-$C_{8-22}$-alkanoylphosphatidylcholines and di-$C_{8-22}$-alkanoylphosphatidylethanolamines. In a particular preferred embodiment, the first excipient substance is a dipalmitoyl or distearoyl ester of phosphatidylcholine or a mixture thereof.

In a further embodiment of the invention, the second excipient substance is an alkylether surfactant or mixture of such surfactants having the formula $$R^{12}-O-(CH_2CH_2O)_n(CH(CH_3)CH_2O)_m-R^{13} \quad VI$$

wherein $R^{12}$ is an alkyl or alkenyl group having about 16 to about 22 carbon atoms, n is an average number of about 10 to about 100, m is an average number of 0 to about 5 and $R^{13}$ is hydrogen or $C_{1-4}$ alkyl. The term "alkylether" as used herein should be understood to include alkenylether surfactants. Preferably $R^{12}$ is a saturated straight-chain alkyl group, $R^{13}$ is hydrogen, m is 0 and n is from about 10 to about 40, more preferably from about 20 to about 40. Most preferably the alkylether surfactant is a polyoxyethylene cetyl or stearyl ether or mixture thereof having 20–40 moles of ethylene oxide (EO).

Aqueous compositions of the present invention can comprise supramolecular aggregates formed from the first and/or second excipient substances. In one preferred embodiment, the second excipient substance is a vesicle-forming amphiphilic substance, such as a vesicle-forming lipid, and when the substance is dispersed in water the majority (greater than 50% by weight, preferably greater than 75% by weight) of the second excipient substance is present as vesicles or liposomes. In another preferred embodiment the second excipient substance is present as bilayers or multilamellar structures which are not organized as vesicles or liposomes. Compositions of the present invention can also include, without limitation, colloidal systems such as emulsions (water/oil, oil/water, or multiple, e.g., water/oil/water), foams, microemulsions, and suspensions or dispersions of microparticulates, nanoparticulates, or microcapsules. Compositions of the invention can include more than one type of aggregate or colloidal system; examples include liposomes or vesicles dispersed in a microemulsion, and compositions having characteristics of both emulsions and suspensions, e.g. suspo-emulsions. The present invention also encompasses any formulation, which may or may not contain a significant amount of water, that on dilution in an aqueous medium forms such colloidal systems, and/or systems comprising vesicles, liposomes, bilayers or multilamellar structures, so long as the other requirements stipulated herein are met.

The weight ratio of each of the first and second excipient substances to the exogenous chemical preferably is between about 1:3 and about 1:100. We have been surprised by the high level of biological effectiveness, specifically herbicidal effectiveness of a glyphosate composition, exhibited at such low ratios of such excipient substances to exogenous chemical. Higher ratios can also be effective but are likely to be uneconomic in most situations and increase the risk of producing an antagonistic effect on effectiveness of the exogenous chemical.

It is surprising that the enhancement of biological activity that has been observed when using the present invention can be achieved with the addition of relatively small amounts of such excipient substances.

In any of the above particular embodiments, the exogenous chemical and/or first excipient substance can be encapsulated within or associated with aggregates (e.g., liposomes) formed by the second excipient substance, but do not necessarily have to be encapsulated or associated. "Associated" in this context means bound to or at least partly intercalated in some fashion in a vesicle wall, as opposed to being encapsulated. In yet another embodiment of the invention where the second excipient substance forms liposomes, the exogenous chemical and/or first excipient substance is not encapsulated in or associated with the liposomes at all. Although the present invention does not exclude the possibility of so encapsulating or associating the exogenous chemical, a presently preferred dilute sprayable liposomal composition encapsulates less than 5% by weight of the exogenous chemical that is present in the overall composition. Another dilute sprayable liposomal embodiment of the present invention has no substantial amount (i.e., less than 1% by weight) of the exogenous chemical encapsulated in the liposomes. As a droplet of such a liposomal composition dries on foliage of a plant, the proportion of the exogenous chemical that is encapsulated in the liposomes may change.

The compositions and methods of the present invention have a number of advantages. They provide enhanced biological activity of exogenous chemicals in or on plants in comparison with prior formulations, either in terms of greater ultimate biological effect, or obtaining an equivalent biological effect while using a reduced application rate of exogenous chemical. Certain herbicide formulations of the present invention can avoid antagonism that has been observed in some prior art herbicide formulations, and can minimize quick production of necrotic lesions on leaves that in some situations hinder overall translocation of herbicide in the plant. Certain herbicide compositions of the invention modify the spectrum of activity of the herbicide across a range of plant species. For example, certain formulations of the present invention containing glyphosate can provide good herbicidal activity against broadleaf weeds while not losing any herbicidal effectiveness on narrowleaf weeds. Others can enhance herbicidal effectiveness on narrowleaf weeds to a greater extent than on broadleaf weeds. Still others can have enhanced effectiveness which is specific to a narrow range of species or even a single species.

Another advantage of the present invention is that it employs relatively small amounts of the first and second excipient substances in relation to the amount of exogenous chemical employed. This makes the compositions and methods of the present invention relatively inexpensive, and also tends to reduce instability problems in specific compositions where one or both excipient substances are physically incompatible with the exogenous chemical (e.g., alkylether surfactants in solutions of high ionic strength, such as concentrated glyphosate salt solutions).

Even at the low concentrations of the excipient substances used in the present invention, there may be limits on the maximum concentration of exogenous chemical that can be used without causing compatibility problems (e.g., separation of the composition into discrete layers). In some preferred embodiments of the invention, composition stability at high loadings of exogenous chemical is maintained by adding other ingredients such as, for example, colloidal particulates. Some compositions of the present invention exhibit enhanced biological activity and have a higher loading of exogenous chemical than possible in prior art compositions.

Further, compositions of the present invention are less sensitive in some instances to environmental conditions such as relative humidity at the time of application to the plant. Also, the present invention allows the use of smaller amounts of herbicides or other pesticides, while still obtaining the required degree of control of weeds or other undesired organisms.

DESCRIPTION OF ILLUSTRATIVE EMBODIMENTS

Examples of exogenous chemical substances that can be included in compositions of the present invention include, but are not limited to, chemical pesticides (such as herbicides, algicides, fungicides, bactericides, viricides, insecticides, aphicides, miticides, nematicides, molluscicides and the like), plant growth regulators, fertilizers and nutrients, gametocides, defoliants, desiccants, mixtures thereof and the like. In one embodiment of the invention, the exogenous chemical is polar.

A preferred group of exogenous chemicals are those that are normally applied post-emergence to the foliage of plants, i.e. foliar-applied exogenous chemicals.

Some exogenous chemicals useful in the present invention are water-soluble, for example salts that comprise biologically active ions, and also comprise counterions, which may be biologically inert or relatively inactive. A particularly preferred group of these water-soluble exogenous chemicals or their biologically active ions or moieties are systemic in plants, that is, they are to some extent translocated from the point of entry in the foliage to other parts of the plant where they can exert their desired biological effect. Especially preferred among these are herbicides, plant growth regulators and nematicides, particularly those that have a molecular weight, excluding counterions, of less than about 300. More especially preferred among these are exogenous chemical compounds having one or more functional groups selected from amine, carboxylate, phosphonate and phosphinate groups.

Among such compounds, an even more preferred group are herbicidal or plant growth regulating exogenous chemical compounds having at least one of each of amine, carboxylate, and either phosphonate or phosphinate functional groups. Salts of N-phosphonomethylglycine are examples of this group of exogenous chemicals. Further examples include salts of glufosinate, for instance the ammonium salt (ammonium DL-homoalanin-4-yl (methyl) phosphinate).

Another preferred group of exogenous chemicals which can be applied by the method of the invention are nematicides such as those disclosed in U.S. Pat. No. 5,389,680, the disclosure of which is incorporated herein by reference. Preferred nematicides of this group are salts of 3,4,4-trifluoro-3-butenoic acid or of N-(3,4,4-trifluoro-1-oxo-3-butenyl)glycine.

Exogenous chemicals which can usefully be applied by the method of the present invention are normally, but not exclusively, those which are expected to have a beneficial effect on the overall growth or yield of desired plants such as crops, or a deleterious or lethal effect on the growth of undesirable plants such as weeds. The method of the present invention is particularly useful for herbicides, especially those that are normally applied post-emergence to the foliage of unwanted vegetation.

Herbicides which can be applied by the method of the present invention include but are not limited to any listed in standard reference works such as the "Herbicide Handbook," *Weed Science Society of America*, 1994, 7th Edition, or the "Farm Chemicals Handbook," Meister Publishing Company, 1997 Edition. Illustratively these herbicides include acetanilides such as acetochlor, alachlor and metolachlor, aminotriazole, asulam, bentazon, bialaphos, bipyridyls such as paraquat, bromacil, cyclohexenones such as clethodim and sethoxydim, dicamba, diflufenican, dinitroanilines such as pendimethalin, diphenylethers such as acifluorfen, fomesafen and oxyfluorfen, fatty acids such as $C_{9-10}$ fatty acids, fosamine, flupoxam, glufosinate, glyphosate, hydroxybenzonitriles such as bromoxynil, imidazolinones such as imazaquin and imazethapyr, isoxaben, norflurazon, phenoxies such as 2,4-D, phenoxypropionates such as diclofop, fluazifop and quizalofop, picloram, propanil, substituted ureas such as fluometuron and isoproturon, sulfonylureas such as chlorimuron, chlorsulfuron, halosulfaron, metsulfuron, primisulfuron, sulfometuron and sulfosulfuron, thiocarbamates such as triallate, triazines such as atrazine and metribuzin, and triclopyr. Herbicidally active derivatives of any known herbicide are also within the scope of the present invention. A herbicidally active derivative is any compound which is a minor structural modification, most commonly but not restrictively a salt or ester, of a known herbicide. These compounds retain the essential activity of the parent herbicide, but may not necessarily have a potency equal to that of the parent herbicide. These compounds may convert to the parent herbicide before or after they enter the treated plant. Mixtures or coformulations of a herbicide with other ingredients, or of more than one herbicide, may likewise be employed.

An especially preferred herbicide is N-phosphonomethylglycine (glyphosate), a salt, adduct or ester thereof, or a compound which is converted to glyphosate in plant tissues or which otherwise provides glyphosate ion. Glyphosate salts that can be used according to this invention include but are not restricted to alkali metal, for example sodium and potassium, salts; ammonium salt; alkylamine, for example dimethylamine and isopropylamine, salts; alkanolamine, for example ethanolamine, salts; alkylsulfonium, for example trimethylsulfonium, salts; sulfoxonium salts; and mixtures thereof. The herbicidal compositions sold by Monsanto Company as ROUNDUP® and ACCORD® contain the monoisopropylamine (IPA) salt of N-phosphonomethylglycine. The herbicidal compositions sold by Monsanto Company as ROUNDUP® Dry and RIVAL® contain the monoammonium salt of N-phosphonomethylglycine. The herbicidal composition sold by Monsanto Company as ROUNDUP® Geoforce contains the monosodium salt of N-phosphonomethylglycine. The herbicidal composition sold by Zeneca as TOUCHDOWN® contains the trimethylsulfonium salt of N-phosphonomethylglycine. The herbicidal properties of N-phosphonomethylglycine and its derivatives were first discovered by Franz, then disclosed and patented in U.S. Pat. No. 3,799,758, issued Mar. 26, 1974. A number of herbicidal salts of N-phosphonomethylglycine were patented by Franz in U.S. Pat. No. 4,405,531, issued Sep. 20, 1983. The disclosures of both of these patents are hereby incorporated by reference.

Because the commercially most important herbicidal derivatives of N-phosphonomethylglycine are certain salts thereof, the glyphosate compositions useful in the present invention will be described in more detail with respect to such salts. These salts are well known and include ammonium, IPA, alkali metal (such as the mono-, di-, and trisodium salts, and the mono-, di-, and tripotassium salts), and trimethylsulfonium salts. Salts of N-phosphonomethylglycine are commercially significant in part because they are water soluble. The salts listed immediately above are highly water soluble, thereby allowing for highly concentrated solutions that can be diluted at the site of use. In accordance with the method of this invention as it pertains to glyphosate herbicide, an aqueous solution containing a herbicidally effective amount of glyphosate and other components in accordance with the invention is applied to foliage of plants. Such an aqueous solution can be obtained by dilution of a concentrated glyphosate salt solution with water, or dissolution or dispersion in water of a dry (e.g. granular, powder, tablet or briquette) glyphosate formulation.

Exogenous chemicals should be applied to plants at a rate sufficient to give the desired biological effect. These application rates are usually expressed as amount of exogenous chemical per unit area treated, e.g. grams per hectare (g/ha). What constitutes a "desired effect" varies according to the standards and practice of those who investigate, develop, market and use a specific class of exogenous chemicals. For example, in the case of a herbicide, the amount applied per unit area to give 85% control of a plant species as measured by growth reduction or mortality is often used to define a commercially effective rate.

Herbicidal effectiveness is one of the biological effects that can be enhanced through this invention. "Herbicidal effectiveness," as used herein, refers to any observable measure of control of plant growth, which can include one or more of the actions of (1) killing, (2) inhibiting growth, reproduction or proliferation, and (3) removing, destroying, or otherwise diminishing the occurrence and activity of plants.

The herbicidal effectiveness data set forth herein report "inhibition" as a percentage following a standard procedure in the art which reflects a visual assessment of plant mortality and growth reduction by comparison with untreated plants, made by technicians specially trained to make and record such observations. In all cases, a single technician makes all assessments of percent inhibition within any one experiment or trial. Such measurements are relied upon and regularly reported by Monsanto Company in the course of its herbicide business.

The selection of application rates that are biologically effective for a specific exogenous chemical is within the skill of the ordinary agricultural scientist. Those of skill in the art will likewise recognize that individual plant conditions, weather and growing conditions, as well as the specific exogenous chemical and formulation thereof selected, will affect the efficacy achieved in practicing this invention. Useful application rates for exogenous chemicals employed can depend upon all of the above conditions. With respect to the use of the method of this invention for glyphosate herbicide, much information is known about appropriate application rates. Over two decades of glyphosate use and published studies relating to such use have provided abundant information from which a weed control practitioner can select glyphosate application rates that are herbicidally effective on particular species at particular growth stages in particular environmental conditions.

Herbicidal compositions of glyphosate or derivatives thereof are used to control a very wide variety of plants worldwide. Such compositions can be applied to a plant in a herbicidally effective amount, and can effectively control one or more plant species of one or more of the following genera without restriction: Abutilon, Amaranthus, Artemisia, Asclepias, Avena, Axonopus, Borreria, Brachiaria, Brassica, Bromus, Chenopodiun, Cirsium, Commelina, Convolvulus, Cynodon, Cyperus, Digitaria, Echinochloa, Eleusine, Elymus, Equisetum, Erodium, Helianthus, Imperata, Ipomoea, Kochia, Lolium, Malva, Oryza, Ottochloa, Panicum, Paspalum, Phalaris, Phragmites, Polygonum, Portulaca, Pteridium, Pueraria, Rubus, Salsola, Setaria, Sida, Sinapis, Sorghum, Triticum, Typha, Ulex, Xanthium, and Zea.

Particularly important species for which glyphosate compositions are used are exemplified without limitation by the following:
  Annual broadleaves:
  velvetleaf (*Abutilon theophrasti*)
  pigweed (Amaranthus spp.)
  buttonweed (Borreria spp.)
  oilseed rape, canola, indian mustard, etc. (Brassica spp.)
  commelina (Commelina spp.)
  filaree (Erodium spp.)
  sunflower (Helianthus spp.)
  morningglory (Ipomoea spp.)
  kochia (*Kochia scoparia*)
  mallow (Malva spp.)
  wild buckwheat, smartweed, etc. (Polygonum spp.)
  purslane (Portulaca spp.)
  russian thistle (Salsola spp.)
  sida (Sida spp.)
  wild mustard (*Sinapis arvensis*)
  cocklebur (Xanthium spp.)
  Annual narrowleaves:
  wild oat (*Avena fatua*)
  carpetgrass (Axonopus spp.)
  downy brome (*Bromus tectorum*)
  crabgrass (Digitaria spp.)
  barnyardgrass (*Echinochloa crus-galli*)
  goosegrass (*Eleusine indica*)
  annual ryegrass (*Lolium multiflorum*)
  rice (*Oryza sativa*)
  ottochloa (*Ottochloa nodosa*)
  bahiagrass (*Paspalum notatum*)
  canarygrass (Phalaris spp.)
  foxtail (Setaria spp.)
  wheat (*Triticum aestivum*)
  corn (*Zea mays*)
  Perennial broadleaves:
  mugwort (Artemisia spp.)
  milkweed (Asclepias spp.)
  canada thistle (*Cirsium arvense*)
  field bindweed (*Convolvulus arvensis*)
  kudzu (Pueraria spp.)
  Perennial narrowleaves:
  brachiaria (Brachiaria spp.)
  bermudagrass (*Cynodon dactylon*)
  yellow nutsedge (*Cyperus esculentus*)
  purple nutsedge (*C. rotundus*)
  quackgrass (*Elymus repens*)
  lalang (*Imperata cylindrica*)
  perennial ryegrass (*Lolium perenne*)
  guineagrass (*Panicum maximum*)
  dallisgrass (*Paspalum dilatatum*)
  reed (Phragmites spp.)
  johnsongrass (*Sorghum halepense*)
  cattail (Typha spp.)
  Other perennials:
  horsetail (Equisetun spp.)
  bracken (*Pteridium aquilinum*)
  blackberry (Rubus spp.)
  gorse (*Ulex europaeus*)

Thus, the method of the present invention, as it pertains to glyphosate herbicide, can be useful on any of the above species.

Effectiveness in greenhouse tests, usually at exogenous chemical rates lower than those normally effective in the field, is a proven indicator of consistency of field performance at normal use rates. However, even the most promising composition sometimes fails to exhibit enhanced performance in individual greenhouse tests. As illustrated in the Examples herein, a pattern of enhancement emerges over a series of greenhouse tests; when such a pattern is identified this is strong evidence of biological enhancement that will be useful in the field.

Compounds useful as the first excipient substance are amides or esters of formula VII above.

$R^{14}$ in formula VII is preferably aliphatic and has about 7 to about 21 carbon atoms, more preferably about 13 to about 21 carbon atoms. It is especially preferred that $R^{14}$ be a saturated straight-chain alkyl group. $R^{15}$ is preferably an aliphatic group having 1–6 carbon atoms, more preferably alkyl or alkenyl having 2–4 carbon atoms. An especially preferred compound of formula VII for use as the first excipient substance is butyl stearate.

As compounds of formula VII, including butyl stearate, are generally oily liquids, aqueous compositions containing them are typically emulsions having at least one aqueous phase and at least one oil phase, with the compound of formula VII being present predominantly in the oil phase. Such emulsions may be water-in-oil, oil-in-water or water-in-oil-in-water (W/O/W) multiple emulsions.

Compositions of the present invention comprise a second excipient substance which is one or more amphiphilic materials, of which two classes are preferred.

The first class of such second excipient substances can be defined as amphiphilic liposome-forming substances. These include various lipids of synthetic, animal, or plant origin, including phospholipids, ceramides, sphingolipids, dialkyl surfactants, and polymeric surfactants. A variety of these materials are known to those skilled in the art, and are commercially available. Lecithins are particularly rich in phospholipids and can be derived from a number of plant and animal sources. Soybean lecithin is one particular example of a relatively inexpensive commercially available material that includes such substances.

Many other substances have been described which can be used to form liposomes; the present invention includes compositions comprising any such liposome-forming substances, so long as other requirements set out above are met, and use of such compositions for enhancing biological effectiveness of exogenous chemicals applied to foliage of plants. For example, U.S. Pat. No. 5,580,859, incorporated here by reference, discloses liposome-forming substances having a cationic group, including N-(2,3-di-(9-(Z)-octadecenyloxy))-prop-1-yl-N,N,N-trimethylammonium chloride (DOTMA) and 1,2-bis(oleoyloxy)-3-(trimethylammonio)propane (DOTAP). Liposome-forming substances which are not themselves cationic, but do contain a cationic group as part of the hydrophilic moiety, include for example dioleoylphosphatidylcholine (DOPC) and dioleoylphosphatidylethanolamine (DOPE). Liposome-forming substances that do not contain a cationic group include dioleoylphosphatidylglycerol (DOPG). Any of these liposome-forming substances can be used with or without the addition of cholesterol.

These substances contain portions that are hydrophilic and hydrophobic within the same molecule. They have the ability to self-assemble in aqueous solution or dispersion into structures that are more complex than simple micelles. The nature of the aggregate that will be formed can be related to the critical packing parameter P by the following equation:

$$P=V/lA$$

where V is the volume of the hydrophobic tail of the molecule, l is the effective length of the hydrophobic tail, and A is the area occupied by the hydrophilic headgroup in the surface of the aggregate. The most probable self-assembled structures are spherical micelles when P is less than ⅓, rodlike micelles when P is between ⅓ and ½, lamellar when P is between 1 and ½, and inverse structures when P is greater than 1. The preferred materials in the present invention have P greater than ⅓.

Cationic liposome-forming substances having a hydrophobic moiety comprising two hydrocarbyl chains are accompanied by a counterion (anion), identified as Z in formulas I, II and III above. Any suitable anion can be used, including agriculturally acceptable anions such as hydroxide, chloride, bromide, iodide, sulfate, phosphate and acetate. In a specific embodiment where the exogenous chemical has a biologically active anion, that anion can serve as the counterion for the liposome-forming substance. For example, glyphosate can be used in its acid form together with the hydroxide of a cationic liposome-forming substance such as a compound of formula I.

Compounds of formula I known in the art to be liposome-forming include distearyldimethylammonium chloride and bromide (also known in the art as DODAC and DODAB respectively). Compounds of formula II known in the art to be liposome-forming include DOTMA referenced above and dimyristooxypropyldimethylhydroxyethylammonium bromide (DMRIE). Compounds of formula III known in the art to be liposome-forming include dioleoyloxy-3-(dimethylammonio)propane (DODAP) and DOTAP referenced above. Compounds of formula IV known in the art to be liposome-forming include DOPC and DOPE, both referenced above.

In many liposome-forming substances known in the art, the hydrophobic hydrocarbyl chains are unsaturated, having one or more double bonds. Particularly commonly used in the pharmaceutical art are dioleyl or dioleoyl compounds. A potential problem with these is that in an oxidizing environment they become oxidized at the site of the double bond. This can be inhibited by including in the formulation an antioxidant such as ascorbic acid. Alternatively the problem can be avoided by use of liposome-forming substances wherein a high proportion of the hydrophobic hydrocarbyl chains are fully saturated. Thus in a preferred embodiment of the invention, $R^1$ and $R^2$ in formulas I–IV are independently saturated straight-chain alkyl groups. Particularly preferred compositions use liposome-forming substances in which $R^1$ and $R^2$ are both palmityl (cetyl) or palmitoyl or, alternatively, are both stearyl or stearoyl groups.

Phospholipids, because of their low cost and favorable environmental properties, are particularly favored among liposome-forming substances in the method and compositions of the invention. Vegetable lecithins, such as soybean lecithin, have successfully been used in accordance with the invention. The phospholipid content of the lecithin product can range from about 10% to close to 100%. While acceptable results have been obtained with crude lecithin (10–20% phospholipid), it is generally preferred to use lecithin that is at least partially de-oiled, so that the phospholipid content is in the region of about 45% or more. Higher grades, such as 95%, provide excellent results but the much higher cost is unlikely to be justified for most applications.

The phospholipid component of lecithin, or any phospholipid composition used in the present invention, may comprise one or more phosphatides of natural or synthetic origin. Each of these phosphatides is generally a phosphoric ester that on hydrolysis yields phosphoric acid, fatty acid(s), polyhydric alcohol and, typically, a nitrogenous base. A phosphatide component may be present in a partially hydrolyzed form, e.g. as phosphatidic acid. Suitable phosphatides include, without limitation, phosphatidylcholine, hydrogenated phosphatidylcholine, phosphatidylinositol, phosphatidylserine, phosphatidic acid, phosphatidylglycerol, phosphatidylethanolamine, N-acyl phosphatidylethanolamine, and mixtures of any of these.

In vegetable lecithins a high proportion of the hydrophobic hydrocarbyl chains of the phospholipid compounds are typically unsaturated. One preferred embodiment of compositions in accordance with the present invention comprises both saturated phospholipid and unsaturated phospholipid, with the weight ratio of saturated phospholipid to unsaturated phospholipid being greater than about 1:2. In various particularly preferred embodiments, (1) at least 50% by weight of the phospholipids are di-$C_{12-22}$-saturated alkanoyl phospholipid, (2) at least 50% by weight of the phospholipids are di-$C_{16-18}$-saturated alkanoyl phospholipid, (3) at least 50% by weight of the phospholipids are distearoyl phospholipid, (4) at least 50% by weight of the phospholipids are dipalmitoyl phospholipid, or (5) at least 50% by weight of the phospholipids are distearoyl phosphatidylcholine, dipalmitoyl phosphatidylcholine, or a mixture thereof. Higher proportions of saturated alkanoyl phospholipids are generally found in lecithins of animal origin, such as for example egg yolk lecithin, than in vegetable lecithins.

Phospholipids are known to be chemically unstable, at least in acid media, where they tend to degrade to their lyso-counterparts. Thus where phospholipids rather than more stable liposome-forming substances are used, it is usually preferable to adjust the pH of the composition upward. In the case of glyphosate compositions, the pH of a composition based on a mono-salt such as the monoisopropylammonium (IPA) salt is typically around 5 or lower. When phospholipids are used as the first excipient substance in a glyphosate composition of the invention, it will therefore be preferable to raise the pH of the composition, for example to around 7. Any convenient base can be used for this purpose; it will often be most convenient to use the same base as used in the glyphosate salt, for example isopropylamine in the case of glyphosate IPA salt.

A second class of amphiphilic substance useful as the second excipient substance according to the present invention is a long-chain alkylether surfactant having the formula VI above. $R^{12}$ can be branched or unbranched, saturated or unsaturated. $R^{12}$ is preferably straight-chain saturated $C_{16}$ alkyl (cetyl) or straight-chain saturated $C_{16}$ alkyl (stearyl). In preferred alkylethers m is 0, n is an average number from about 20 to about 40 and $R^{12}$ is preferably hydrogen. Among especially preferred alkylether surfactants are those identified in the International Cosmetic Ingredient Dictionary as ceteth-20, ceteareth-20, ceteareth-27, steareth-20 and steareth-30.

Aqueous concentrate compositions in some circumstances are limited in the degree to which an exogenous chemical such as glyphosate can be loaded. At some point, as the loading of exogenous chemical is increased, the composition will not remain suitably stable. This is particularly true, for example, where the exogenous chemical is glyphosate and the second excipient substance is an alkylether surfactant of formula VI. Addition of a small amount of colloidal particulate to such compositions has surprisingly been found to greatly increase loading ability while retaining desired stability. Oxides of silicon, aluminum and titanium are preferred colloidal particulate materials. Particle size is preferably such that specific surface area is in the range from about 50 to about 400 $m^2/g$. Where the exogenous chemical is glyphosate, the use of colloidal particulate enables loadings of at least 30% by weight for compositions containing sufficient alkylether and fatty acid ester to show enhanced herbicidal effectiveness, or at least 40% for compositions containing alkylether but no fatty acid ester, and showing herbicidal effectiveness at least equal to current commercial products loaded at about 30%. We have found especially useful improvement in storage stability can be obtained using colloidal particulates having specific surface area between about 180 and about 400 $m^2/g$.

Other means of improving stability of highly loaded compositions may also be possible and are within the scope of the present invention.

Compositions in accordance with the present invention are typically prepared by combining water, the exogenous chemical (unless it is a formulation which will not contain an exogenous chemical) and the first and second excipient substances. Where the second excipient substance is a liposome-forming material that requires high shear to disperse in water, it is presently preferred to sonicate or microfluidize the second excipient substance in water. This can be done before or after the first excipient substance and/or the exogenous chemical is added. The sonication or microfluidization will generally produce liposomes or other aggregate structures other than simple micelles. The precise nature, including average size, of liposomes or other aggregates depends among other things on the energy input during sonication or microfluidization. Higher energy input generally results in smaller liposomes. Although it is possible to entrap or otherwise bind loosely or tightly the exogenous chemical in or on liposomes or with other supramolecular aggregates, the exogenous chemical does not need to be so entrapped or bound, and in fact the present invention is effective when the exogenous chemical is not entrapped or bound in the aggregates at all.

In a particular embodiment of the invention, the liposomes or other aggregates have an average diameter of at least 20 nm, more preferably at least 30 nm. We have determined by light scattering that certain liposomal compositions of the invention have average liposome diameters ranging from 54 to 468 nm as calculated using linear fit and from 38 to 390 nm as calculated using quadratic fit.

We have found for compositions of the present invention containing a fatty acid ester such as butyl stearate as the first excipient substance and lecithin as the second excipient substance, it is preferable to first hydrate the lecithin and then microfluidize the lecithin in water together with the fatty acid ester.

The concentrations of the various components will vary, in part depending on whether a concentrate is being prepared that will be further diluted before spraying onto a plant, or whether a solution or dispersion is being prepared that can be sprayed without further dilution.

In an aqueous glyphosate formulation that includes a $C_{16-18}$ alkylether surfactant and butyl stearate, suitable concentrations can be: glyphosate 0.1–400 g a.e./l, alkylether surfactant 0.001–10% by weight, and butyl stearate 0.001–10% by weight. To achieve the higher concentrations in these ranges, it is often beneficial to add other ingredients to provide acceptable storage stability, for example colloidal particulate silica or aluminum oxide at 0.5–2.5% by weight. In an aqueous glyphosate formulation that includes a $C_{16-18}$ alkylether surfactant but no butyl stearate, glyphosate concentration can suitably be increased to 500 g a.e./l or more, in the presence of a colloidal particulate at 0.5–2.5% by weight.

In solid glyphosate formulations, higher concentrations of ingredients are possible because of the elimination of most of the water.

Weight/weight ratios of ingredients may be more important than absolute concentrations. For example, in a glyphosate formulation containing lecithin and a fatty acid ester, the ratio of lecithin to glyphosate a.e. preferably is in the range from about 1:3 to about 1:100. It is generally preferred to use a ratio of lecithin to glyphosate a.e. close to as high as can be incorporated in the formulation while maintaining stability, in the presence of an amount of the fatty acid ester sufficient to give the desired enhancement of herbicidal effectiveness. For example, a lecithin/glyphosate a.e. ratio in the range from about 1:3 to about 1:10 will generally be found useful, although lower ratios, from about 1:10 to about 1:100, can have benefits on particular weed species in particular situations. The ratio of fatty acid ester to glyphosate a.e. is preferably in the range from about 1:3 to about 1:100, more preferably in the lower part of this range, for example from about 1:10 to about 1:100.

Where the second excipient substance is an alkylether surfactant of formula VI, a suitable weight/weight ratio of alkylether surfactant to glyphosate a.e. is again in the range from about 1:3 to about 1:100, preferably from about 1:3 to about 1:10.

The ratio of fatty acid ester to second excipient substance is preferably in the range from about 1:20 to about 5:1, more preferably in the range from about 1:15 to about 1:1, for example around 1:10. The ranges disclosed herein can be used by one of skill in the art to prepare compositions of the invention having suitable concentrations and ratios of ingredients. Preferred or optimum concentrations and ratios of ingredients for any particular use or situation can be determined by routine experimentation.

Although the combination of the components might be done in a tank mix, it is preferred in the present invention that the combination be made further in advance of the application to the plant, in order to simplify the tasks required of the person who applies the material to plants. We have found, however, that in some cases the biological effectiveness of a liposome-containing composition prepared from scratch as a dilute spray composition is superior to that of a composition having the same ingredients at the same concentrations but diluted from a previously prepared concentrate formulation.

Although various compositions of the present invention are described herein as comprising certain listed materials, in some preferred embodiments of the invention the compositions consist essentially of the indicated materials.

Optionally, other agriculturally acceptable materials can be included in the compositions. For example, more than one exogenous chemical can be included. Also, various agriculturally acceptable adjuvants can be included, whether or not their purpose is to directly contribute to the effect of the exogenous chemical on a plant. For example, when the exogenous chemical is a herbicide, liquid nitrogen fertilizer or ammonium sulfate might be included in the composition. As another example, stabilizers can be added to the composition. In some instances it might be desirable to include microencapsulated acid in the composition, to lower the pH of a spray solution on contact with a leaf. One or more surfactants can also be included. Surfactants mentioned here by trade name, and other surfactants that can be useful in the method of the invention, are indexed in standard reference works such as McCutcheon's Emulsifiers and Detergents, 1997 edition, Handbook of Industrial Surfactants, 2nd Edition, 1997, published by Gower, and International Cosmetic Ingredient Dictionary, 6th Edition, 1995.

The compositions of the present invention can be applied to plants by spraying, using any conventional means for spraying liquids, such as spray nozzles, atomizers, or the like. Compositions of the present invention can be used in precision farming techniques, in which apparatus is employed to vary the amount of exogenous chemical applied to different parts of a field, depending on variables such as the particular plant species present, soil composition, and the like. In one embodiment of such techniques, a global positioning system operated with the spraying apparatus can be used to apply the desired amount of the composition to different parts of a field.

The composition at the time of application to plants is preferably dilute enough to be readily sprayed using standard agricultural spray equipment. Preferred application rates for the present invention vary depending upon a number of factors, including the type and concentration of active ingredient and the plant species involved. Useful rates for applying an aqueous composition to a field of foliage can range from about 25 to about 1,000 liters per hectare (l/ha) by spray application. The preferred application rates for aqueous solutions are in the range from about 50 to about 300 l/ha.

Many exogenous chemicals (including glyphosate herbicide) must be taken up by living tissues of the plant and translocated within the plant in order to produce the desired biological (e.g., herbicidal) effect. Thus, it is important that a herbicidal composition not be applied in such a manner as to excessively injure and interrupt the normal functioning of the local tissue of the plant so quickly that translocation is reduced. However, some limited degree of local injury can be insignificant, or even beneficial, in its impact on the biological effectiveness of certain exogenous chemicals.

A large number of compositions of the invention are illustrated in the Examples that follow. Many concentrate compositions of glyphosate have provided sufficient herbicidal effectiveness in greenhouse tests to warrant field testing on a wide variety of weed species under a variety of application conditions. Water-in-oil-in-water multiple emulsion compositions tested in the field have included:

| | | % w/w | | | | | | | |
|---|---|---|---|---|---|---|---|---|---|
| Field composition | Glyphosate g a.e./l | Fatty acid ester | Emulsifier #1 | Emulsifier #2 | % in inner aq. phase Water | Glyphosate | Emulsifier #1 | Emulsifier #2 | Type of fatty acid ester |
| F-1 | 100 | 18.0 | 3.0 | 5.0 | 13.8 | 20 | Span 80 | Tween 20 | Bu stearate |
| F-2 | 100 | 7.5 | 3.0 | 5.0 | 5.6 | 20 | Span 80 | Tween 20 | Bu stearate |
| F-3 | 100 | 7.5 | 3.0 | 5.0 | 5.6 | 0 | Span 80 | Tween 20 | Bu stearate |
| F-4 | 160 | 7.5 | 3.0 | 5.0 | 5.6 | 0 | Span 80 | Tween 20 | Bu stearate |

The above compositions were prepared by process (vi) as described in the Examples.

Aqueous compositions tested in the field having a fatty acid ester as the first excipient substance and containing a nonionic surfactant have included:

| Field composition | Glyphosate g a.e./l | % w/w Fatty acid ester | % w/w Surfactant | Type of surfactant | Type of fatty acid ester |
|---|---|---|---|---|---|
| F-5 | 163 | 1.0 | 10.0 | oleth-20 | Bu stearate |
| F-6 | 163 | 1.0 | 10.0 | Tween 80 | Bu stearate |
| F-7 | 163 | 1.0 | 10.0 | Neodol 25-20 | Bu stearate |
| F-8 | 163 | 1.0 | 10.0 | steareth-20 | Bu stearate |
| F-9 | 163 | 1.0 | 10.0 | Neodol 25-12 | Bu stearate |
| F-10 | 105 | 7.5 | 10.0 | Tween 80 | Bu stearate |
| F-11 | 163 | 0.5 | 5.0 | oleth-20 | Bu stearate |
| F-12 | 163 | 0.3 | 5.0 | oleth-20 | Bu stearate |
| F-13 | 163 | 0.3 | 2.5 | oleth-20 | Bu stearate |
| F-14 | 163 | 1.0 | 10.0 | Neodol 25-12 | Bu stearate |
| F-15 | 163 | 0.3 | 5.0 | Genapol UD-110 | Bu stearate |
| F-16 | 163 | 0.5 | 5.0 | steareth-20 | Bu stearate |
| F-17 | 163 | 0.5 | 5.0 | ceteth-20 | Bu stearate |
| F-18 | 163 | 0.5 | 5.0 | laureth-23 | Bu stearate |
| F-19 | 163 | 0.5 | 5.0 | ceteareth-27 | Bu stearate |
| F-20 | 163 | 0.5 | 5.0 | Neodol 25-12 | Bu stearate |
| F-21 | 163 | 0.5 | 5.0 | Neodol 25-20 | Bu stearate |
| F-25 | 163 | 0.3 | 5.0 | ceteareth-27 | Bu stearate |
| F-26 | 163 | 0.3 | 2.5 | ceteareth-27 | Bu stearate |
| F-28 | 163 | 0.5 | 5.0 | ceteareth-27 | Me stearate |
| F-29 | 163 | 0.5 | 5.0 | steareth-20 | Me stearate |
| F-31 | 163 | 0.5 | 5.0 | Neodol 45-13 | Bu stearate |
| F-33 | 163 | 0.5 | 5.0 | ceteareth-15 | Bu stearate |
| F-35 | 163 | 0.5 | 5.0 | steareth-30 | Bu stearate |

The above compositions were prepared by process (vii) as described in the Examples.

Aqueous compositions tested in the field containing colloidal particulates have included:

| Field composition | Glyphosate g a.e./l | % w/w Fatty acid ester | % w/w Surfactant | % w/w Colloidal particulate | Type of surfactant | Type of colloidal particulate | Type of fatty acid ester |
|---|---|---|---|---|---|---|---|
| F-36 | 360 | 1.0 | 10.0 | 1.3 | steareth-20 | Aerosil 380 | Bu stearate |
| F-37 | 360 | 1.0 | 10.0 | 1.3 | oleth-20 | Aerosil 380 | Bu stearate |
| F-38 | 360 | 1.0 | 10.0 | 1.3 | steareth-30 | Aerosil 380 | Bu stearate |
| F-50 | 360 | 1.0 | 10.0 | 1.3 | ceteareth-15 | Aerosil 380 | Bu stearate |
| F-51 | 360 | 1.0 | 10.0 | 1.3 | ceteth-20 | Aerosil 380 | Bu stearate |
| F-52 | 360 | 1.0 | 10.0 | 1.3 | steareth-20 | Aerosil 380 | Bu stearate |
| F-53 | 360 | 1.0 | 10.0 | 1.3 | oleth-20 | Aerosil 380 | Bu stearate |
| F-54 | 360 | 1.0 | 10.0 | 1.3 | ceteareth-27 | Aerosil 380 | Bu stearate |
| F-55 | 360 | 1.0 | 10.0 | 1.3 | steareth-30 | Aerosil 380 | Bu stearate |
| F-60 | 360 | 1.0 | 10.0 | 1.3 | ceteareth-27 | Aerosil 380 | Me stearate |
| F-61 | 360 | 1.0 | 10.0 | 1.3 | ceteareth-27 | Aerosil 380 | Me palmitate |

The above compositions were prepared by process (ix) as described in the Examples.

Aqueous compositions tested in the field having fatty acid ester as the first excipient substance and soybean lecithin (45% phospholipid, Avanti) as the second excipient substance have included:

| Field composition | Glyphosate g a.e./l | % w/w Lecithin | % w/w MON 0818 | % w/w Fatty acid ester | % w/w Surfactant | Type of surfactant | Type of fatty acid ester |
|---|---|---|---|---|---|---|---|
| F-135 | 360 | 0.5 | 6.0 | 7.5 | 6.0 | Ethomeen T/25 | Bu stearate |
| F-136 | 360 | 6.0 | 4.5 | 1.5 | 3.0 + 4.5 | ceteareth-27 + Ethomeen T/25 | Bu stearate |
| F-137 | 228 | 6.0 | 3.0 | 1.5 | 3.0 | Ethomeen T/25 | Bu stearate |
| F-138 | 228 | 0.8 |  | 3.8 | 3.0 + 3.0 | ceteareth-27 + Ethomeen T/25 | Bu stearate |
| F-139 | 228 | 1.5 |  | 1.5 | 3.0 + 3.0 | ceteareth-27 + Ethomeen T/25 | Bu stearate |
| F-140 | 228 | 6.7 | 0.8 | 0.7 | 0.8 | Ethomeen T/25 | Bu stearate |
| F-141 | 228 | 6.7 | 1.7 | 0.7 | 1.7 | Ethomeen T/25 | Bu stearate |
| F-142 | 228 | 6.7 | 3.3 | 0.7 | 3.3 | Ethomeen T/25 | Bu stearate |
| F-143 | 228 | 3.3 | 0.8 | 0.7 | 0.8 | Ethomeen T/25 | Bu stearate |
| F-144 | 228 | 3.3 | 1.7 | 0.7 | 1.7 | Ethomeen T/25 | Bu stearate |

-continued

| Field composition | Glyphosate g a.e./l | Lecithin | MON 0818 | Fatty acid ester | Surfactant | Type of surfactant | Type of fatty acid ester |
|---|---|---|---|---|---|---|---|
| | | | % w/w | | | | |
| F-145 | 228 | 3.3 | 2.5 | 0.7 | 2.5 | Ethomeen T/25 | Bu stearate |
| F-146 | 228 | 3.3 | 3.3 | 0.7 | 3.3 | Ethomeen T/25 | Bu stearate |
| F-147 | 228 | 6.7 | 2.5 | 0.7 | 2.5 | Ethomeen T/25 | Bu stearate |
| F-148 | 228 | | 3.0 | 0.5 | 3.0 | Ethomeen T/25 | Bu stearate |
| F-149 | 228 | 2.0 | 2.5 | 0.5 | 2.5 | Ethomeen T/25 | Bu stearate |
| F-150 | 228 | 4.0 | 6.0 | 0.5 | | | Bu stearate |
| F-151 | 228 | 4.0 | 6.0 | 2.0 | | | Bu stearate |
| F-152 | 228 | 4.0 | 6.0 | 1.0 | | | Bu stearate |
| F-153 | 228 | 2.0 | 2.0 | 0.5 | | | Bu stearate |
| F-154 | 228 | 2.0 | 4.0 | 0.5 | | | Bu stearate |
| F-155 | 228 | | 6.0 | 0.5 | | | Bu stearate |

The above compositions were prepared by process (x) as described in the Examples.

Dry compositions tested in the field have included:

| Field composition | Glyphosate a.e. | Lecithin | Butyl stearate | Surfactant | Colloidal particulate | Type of surfactant | Type of colloidal particulate |
|---|---|---|---|---|---|---|---|
| | | | % w/w | | | | |
| F-164 | 64 | 12.0 | 3.0 | 12.0 | | MON 0818 | |
| F-165 | 64 | 6.7 | 6.7 | 13.2 | | MON 0818 | |
| F-167 | 66 | | 2.0 | 20.0 | 2.0 | steareth-20 | Aerosil blend 1 |
| F-169 | 66 | | 2.0 | 20.0 | 2.0 | oleth-20 | Aerosil blend 1 |
| F-170 | 66 | | 2.0 | 20.0 | 2.0 | ceteareth-27 | Aerosil blend 1 |

Aerosil blend 1: Aerosil MOX-80 + Aerosil MOX-170 (1:1)

The above compositions were prepared by the process described for dry granular compositions in Example 64.

EXAMPLES

In the following Examples illustrative of the invention, greenhouse tests were conducted to evaluate relative herbicidal effectiveness of glyphosate compositions. Compositions included for comparative purposes included the following:

Formulation B: which consists of 41% by weight of glyphosate IPA salt in aqueous solution. This formulation is sold in the USA by Monsanto Company under the ACCORD® trademark.

Formulation C: which consists of 41% by weight of glyphosate IPA salt in aqueous solution with a coformulant (15% by weight) of a surfactant (MON 0818 of Monsanto Company) based on polyoxyethylene (15) tallowamine. This formulation is sold in Canada by Monsanto Company under the ROUNDUP® trademark.

Formulation J: which consists of 41% by weight of glyphosate IPA salt in aqueous solution, together with surfactant. This formulation is sold in the USA by Monsanto Company under the ROUNDUP® ULTRA trademark.

Formulation K: which consists of 75% by weight of glyphosate ammonium salt together with surfactant, as a water-soluble dry granular formulation. This formulation is sold in Australia by Monsanto Company under the ROUNDUP® DRY trademark.

Formulations B, C and J contain 356 grams of glyphosate acid equivalent per liter (g a.e./l). Formulation K contains 680 grams of glyphosate acid equivalent per kilogram (g a.e./kg).

Various proprietary excipients were used in compositions of the Examples. They may be identified as follows:

| Trade name | Manufacturer | Chemical description |
|---|---|---|
| Aerosil 90 | Degussa | amorphous silica, 90 m$^2$/g |
| Aerosil 380 | Degussa | amorphous silica, 380 m$^2$/g |
| Aerosil MOX-80 | Degussa | amorphous silica/aluminum oxide, 80 m$^2$/g |
| Aerosil MOX-170 | Degussa | amorphous silica/aluminum oxide, 170 m$^2$/g |
| Aerosil OX-50 | Degussa | amorphous silica, 50 m$^2$/g |
| Aerosil R-202 | Degussa | amorphous hydrophobic silica (dimethylsiloxane surface group) |
| Aerosil R-805 | Degussa | amorphous hydrophobic silica (octyl surface group) |
| Aerosil R-812 | Degussa | amorphous hydrophobic silica (trimethylsilyl surface group) |
| Aerosil OT | Cytec | dioctyl sulfosuccinate, Na salt |
| Agrimer AL-25 | ISP | 1-ethenyl hexadecyl-2-pyrrolidinone |
| Agrimer AL-30 | ISP | 1-ethenyl-2-pyrrolidinone polymer |
| Aluminum oxide C | Degussa | aluminum oxide, 100 m$^2$/g |
| Arcosolve DPM | Arco | dipropyleneglycol monomethyl ether |
| Dowanol PNB | Dow | propylene glycol n-butyl ether |
| Dowanol TPNB | Dow | tripropylene glycol n-butyl ether |
| Emerest 2421 | Henkel | glyceryl oleate |
| Emerest 2661 | Henkel | PEG-12 laurate |
| Emid 6545 | Henkel | oleic diethanolamide |
| Ethomeen C/12 | Akzo | cocoamine 2EO |
| Ethomeen T/12 | Akzo | tallowamine 2EO |
| Ethomeen T/25 | Akzo | tallowamine 15EO |
| Exxate 700 | Exxon | C$_7$ alkyl acetate |
| Exxate 1000 | Exxon | C$_7$ alkyl acetate |
| Exxol D-130 | Exxon | dearomatized aliphatic solvent |

-continued

| Trade name | Manufacturer | Chemical description |
| --- | --- | --- |
| Fluorad FC-135 | 3M | fluorinated alkyl quaternary ammonium iodide |
| Fluorad FC-754 | 3M | fluorinated alkyl quaternary ammonium chloride |
| Genapol UD-110 | Hoechst | $C_{11}$ oxo alcohol 11EO |
| Isopar V | Exxon | isoparaffinic oil |
| MON 0818 | Monsanto | tallowamine 15EO-based surfactant |
| Myrj 52 | ICI | PEG-40 stearate |
| Myrj 59 | ICI | PEG-100 stearate |
| Neodol 1-7 | Shell | $C_{11}$ linear alcohol 7EO |
| Neodol 1-9 | Shell | $C_{11}$ linear alcohol 9EO |
| Neodol 25-12 | Shell | $C_{11-15}$ linear alcohol 12EO |
| Neodol 25-20 | Shell | $C_{11-15}$ linear alcohol 20EO |
| Neodol 25-3 | Shell | $C_{11-15}$ linear alcohol 3EO |
| Neodol 25-9 | Shell | $C_{11-15}$ linear alcohol 9EO |
| Neodol 45-13 | Shell | $C_{13-15}$ linear alcohol 13EO |
| Neodol 91-2.5 | Shell | $C_{9-11}$ linear alcohol 2.5EO |
| Orchex 796 | Exxon | paraffinic oil |
| Pluronic F-108 | BASF | 128EO-54PO-128EO block copolymer |
| Pluronic F-127 | BASF | 98EO-67PO-98EO block copolymer |
| Pluronic F-68 | BASF | 75EO-30PO-75EO block copolymer |
| Pluronic L-43 | BASF | 7EO-21PO-7EO block copolymer |
| Pluronic L-81 | BASF | 6EO-39PO-6EO block copolymer |
| Pluronic P-84 | BASF | 27EO-39PO-27EO block copolymer |
| Silwet 800 | Witco | heptamethyltrisiloxane EO |
| Silwet L-77 | Witco | heptamethyltrisiloxane 7EO methyl ether |
| Span 60 | ICI | sorbitan monostearate |
| Span 65 | ICI | sorbitan tristearate |
| Span 80 | ICI | sorbitan monooleate |
| Span 85 | ICI | sorbitan trioleate |
| Surfynol 104 | Air Products | tetramethyldecyne diol |
| Tergitol 15-S-15 | Union Carbide | $C_{15}$ branched secondary alcohol 15EO |
| Tergitol 15-S-20 | Union Carbide | $C_{15}$ branched secondary alcohol 20EO |
| Tergitol 15-S-30 | Union Carbide | $C_{15}$ branched secondary alcohol 30EO |
| Tergitol 15-S-40 | Union Carbide | $C_{15}$ branched secondary alcohol 40EO |
| Toximul 8240 | Stepan | PEG-36 castor oil |
| Tween 20 | ICI | sorbitan monolaurate 20EO |
| Tween 40 | ICI | sorbitan monopalmitate 20EO |
| Tween 80 | ICI | sorbitan monooleate 20EO |
| Tween 85 | ICI | sorbitan trioleate 20EO |

Fluorad FC-135, though defined only generically as above in 3M product literature and in standard directories, has been specifically identified as

$C_8F_{17}SO_2NH(CH_2)_3N^+(CH_3)_3I^-$ in a paper by J. Linert & J. N. Chasman of 3M, titled "The effects of fluorochemical surfactants on recoatability" in the Dec. 20, 1993 issue of American Paint & Coatings Journal, and reprinted as a trade brochure by 3M. Fluorad FC-754 is believed to have the structure $C_8F_{17}SO_2NH(CH_2)_3N^+(CH_3)_3Cl^-$ that is, identical to Fluorad FC-135 but with a chloride anion replacing iodide.

Fatty alcohol ethoxylate surfactants are referred to in the Examples by their generic names as given in the International Cosmetic Ingredient Dictionary, 6th Edition, 1995 (Cosmetic, Toiletry and Fragrance Association, Washington, DC). They were interchangeably sourced from various manufacturers, for example:

Laureth-23: Brij 35 (ICI), Trycol 5964 (Henkel).
Ceteth-10: Brij 56 (ICI).
Ceteth-20: Brij 58 (ICI).
Steareth-10: Brij 76 (ICI).
Steareth-20: Brij 78 (ICI), Emthox 5888-A (Henkel), STA-20 (Heterene).
Steareth-30: STA-30 (Heterene).
Steareth-100: Brij 700 (ICI).
Ceteareth-15: CS-15 (Heterene).
Ceteareth-20: CS-20 (Heterene).
Ceteareth-27: Plurafac A-38 (BASF).
Ceteareth-55: Plurafac A-39 (BASF).
Oleth-2: Brij 92 (ICI).
Oleth-10: Brij 97 (ICI).
Oleth-20: Brij 98 (ICI), Trycol 5971 (Henkel).

Where a proprietary excipient is a surfactant supplied as a solution in water or other solvent, the amount to be used was calculated on a true surfactant basis, not an "as is" basis. For example, Fluorad FC-135 is supplied as 50% true surfactant, together with 33% isopropanol and 17% water; thus to provide a composition containing 0.1% w/w Fluorad FC-135 as reported herein, 0.2 g of the product as supplied was included in 100 g of the composition. The amount of lecithin, however, is always reported herein on an "as is" basis, regardless of the content of phospholipid in the lecithin sample used.

Spray compositions of the Examples contained an exogenous chemical, such as glyphosate IPA salt, in addition to the excipient ingredients listed. The amount of exogenous chemical was selected to provide the desired rate in grams per hectare (g/ha) when applied in a spray volume of 93 l/ha. Several exogenous chemical rates were applied for each composition. Thus, except where otherwise indicated, when spray compositions were tested, the concentration of exogenous chemical varied in direct proportion to exogenous chemical rate, but the concentration of excipient ingredients was held constant across different exogenous chemical rates.

Concentrate compositions were tested by dilution, dissolution or dispersion in water to form spray compositions. In these spray compositions prepared from concentrates, the concentration of excipient ingredients varied with that of exogenous chemical.

For spray compositions of the Examples, unless otherwise indicated, the preparation procedure was one of the following processes (i) to (iii).

(i) For compositions not containing lecithin or phospholipids, aqueous compositions were prepared by simple mixing of ingredients under mild agitation.

(ii) A weighed quantity of lecithin in powder form was dissolved in 0.4 ml chloroform in a 100 ml bottle. The resulting solution was air-dried to leave a thin film of lecithin, to which was added 30 ml deionized water. The bottle and its contents were then sonicated in a Fisher Sonic Dismembrator, Model 550, fitted with a 2.4 cm probe tip, set at output level 8, and operated continuously for 3 minutes. The resulting aqueous dispersion of lecithin was then allowed to cool to room temperature, and formed a lecithin stock which was later mixed in the required amounts with other ingredients under mild agitation. In some cases, as indicated in the Examples, certain ingredients were added to the lecithin in water before sonication, so that the lecithin and these ingredients were sonicated together. Without being bound by theory, it is believed that by sonicating a formulation ingredient together with lecithin, at least some of that ingredient becomes encapsulated within, or otherwise bound to or trapped by, vesicles or other aggregates formed by phospholipids present in the lecithin.

(iii) The procedure of process (ii) was followed except that, before sonication, the step of forming a lecithin solution in chloroform was omitted. Instead, lecithin in powder form was placed in a beaker, water was added and the beaker and its contents were then sonicated.

For concentrate compositions of the Examples containing lecithin, the preparation procedure was one of the following processes (iv) or (v), or in some cases process (x) below.

(iv) A weighed amount of lecithin powder of the type indicated was placed in a beaker and deionized water was added in no more than the amount required for the desired final composition. The beaker and its contents were then placed in a Fisher Sonic Dismembrator, Model 550, fitted with a 2.4 cm probe tip, set at output level 8, and operated for 5 minutes. The resulting lecithin dispersion formed the basis to which other ingredients were added with mild agitation to make the aqueous concentrate formulation. The order of addition of these ingredients was varied and was sometimes found to affect the physical stability of the concentrate formulation. Where a fluoro-organic surfactant such as Fluorad FC-135 or FC-754 was to be included, it was generally added first, followed by other surfactants if required and then by the exogenous chemical. Where the exogenous chemical used was glyphosate IPA salt, this was added in the form of a 62% (45% a.e.) solution by weight, at a pH of 4.4 to 4.6. A final adjustment with water took place if necessary as the last step. In some cases certain ingredients of the concentrate formulation were added before rather than after sonication, so that they were sonicated with the lecithin.

(v) A weighed amount of lecithin powder of the type indicated was placed in a beaker and deionized water was added in sufficient quantity to provide, after sonication as detailed below, a lecithin stock at a convenient concentration, normally in the range from 10% to 20% w/w and typically 15% w/w. The beaker and its contents were then placed in a Fisher Sonic Dismembrator, Model 550, fitted with a 2.4 cm probe tip with the pulse period set at 15 seconds with 1 minute intervals between pulses to allow cooling. Power output was set at level 8. After a total of 3 minutes of sonication (12 pulse periods) the resulting lecithin stock was finally adjusted to the desired concentration if necessary with deionized water. To prepare an aqueous concentrate formulation, the following ingredients were mixed in the appropriate proportions with mild agitation, normally in the order given although this was sometimes varied and was found in some cases to affect the physical stability of the concentrate formulation: (a) exogenous chemical, for example glyphosate IPA salt as a 62% w/w solution at pH 4.4–4.6; (b) lecithin stock; (c) other ingredients if required; and (d) water.

Many of the Examples feature aqueous concentrate compositions of the invention. Except where otherwise indicated, these aqueous concentrate compositions were prepared by the following general processes (vi) to (ix).

(vi) Water-in-oil-in-water (W/O/W) multiple emulsions were prepared as follows. First a water-in-oil emulsion was prepared. To do this, the required amounts of the selected oil and a first emulsifier (referred to in the Examples as "emulsifier #1") were mixed thoroughly. If it was desired to prepare the formulation with glyphosate in the inner aqueous phase, a measured amount of concentrated (62% w/w) aqueous solution of glyphosate IPA salt was added to the mixture of oil and first emulsifier with agitation to ensure homogeneity. The amount of water required in the inner aqueous phase was then added to complete the water-in-oil emulsion, which was finally subjected to high-shear mixing, typically using a Silverson L4RT-A mixer fitted with a fine emulsor screen operated for 3 minutes at 10,000 rpm. The required amount of a second emulsifier (referred to in the Examples as "emulsifier #2") was next added to the water-in-oil emulsion with agitation to ensure homogeneity. If it was desired to prepare the formulation with glyphosate in the outer aqueous phase, a measured amount of concentrated (62% w/w) aqueous solution of glyphosate IPA salt was added to the blend of the water-in-oil emulsion and the second emulsifier with further agitation. To complete the water-in-oil-in-water multiple emulsion composition, the amount of water required in the outer aqueous phase was added. The composition was finally subjected to high-shear mixing, typically using a Silverson L4RT-A mixer fitted with a medium emulsor screen, operated for 3 minutes at 7,000 rpm.

(vii) Oil-in-water (O/W) emulsions were prepared as follows. The required amount of the selected oil and surfactant (sometimes referred to in the Examples as "emulsifier #2" as it corresponds to the second emulsifier in process (vi)) were mixed thoroughly. If the surfactant selected was not free-flowing at ambient temperature, heat was applied to bring the surfactant into a flowable condition before mixing with the oil. A measured amount of concentrated (62% w/w) aqueous solution of glyphosate IPA salt was added to the surfactant-oil mixture with agitation. The required amount of water was added to bring the concentration of glyphosate and other ingredients to the desired level. The composition was finally subjected to high-shear mixing, typically using a Silverson L4RT-A mixer fitted with a medium emulsor screen, operated for 3 minutes at 7,000 rpm.

(viii) Surfactant-containing aqueous solution concentrates having no oil component were prepared as follows. A concentrated (62% w/w) aqueous solution of glyphosate IPA salt was added in the desired amount to a weighed quantity of the selected surfactant(s). If the surfactant selected is not free-flowing at ambient temperature, heat was applied to bring the surfactant into a flowable condition before adding the glyphosate solution. The required amount of water was added to bring the concentration of glyphosate and other ingredients to the desired level. The composition was finally subjected to high-shear mixing, typically using a Silverson L4RT-A mixer fitted with a medium emulsor screen, operated for 3 minutes at 7,000 rpm.

(ix) For compositions containing a colloidal particulate, the required amount by weight of the selected colloidal particulate was suspended in a concentrated (62% w/w) aqueous solution of glyphosate IPA salt and agitated with cooling to ensure homogeneity. To the resulting suspension was added the required amount by weight of the selected surfactant(s). For a surfactant which is not free-flowing at ambient temperature, heat was applied to bring the surfactant into a flowable condition before adding it to the suspension. In those instances where an oil, such as butyl stearate, was also to be included in the composition, the oil was first thoroughly mixed with the surfactant and the surfactant-oil mixture added to the suspension. To complete the aqueous concentrate, the required amount of water was added to bring the concentration of glyphosate and other ingredients to the desired level. The concentrate was finally subjected to high-shear mixing, typically using a Silverson L4RT-A mixer fitted with a medium emulsor screen, operated for 3 minutes at 7,000 rpm.

(x) The procedure for preparing aqueous concentrate formulations containing lecithin and butyl stearate was different from that followed for other lecithin-containing concentrates. Exogenous chemical, for example glyphosate IPA salt, was first added, with mild agitation, to deionized water in a formulation jar. The selected surfactant (other than lecithin) was then added, while continuing the agitation, to form a preliminary exogenous chemical/ surfactant mixture. Where the surfactant is not free-flowing at ambient temperature, the order of addition was not as above. Instead, the non-free-flowing surfactant was first added to water together with any other surfactant (other than lecithin) required in the composition, and was then heated to 55° C. in a shaker bath for 2 hours. The resulting mixture was allowed to cool, then exogenous chemical was added with mild agitation to form the preliminary exogenous chemical/ surfactant mixture. A weighed amount of the selected lecithin was added to the preliminary exogenous chemical/ surfactant mixture, with stirring to break up lumps. The mixture was left for about 1 hour to allow the lecithin to hydrate, then butyl stearate was added, with further stirring until no phase separation occurred. The mixture was then transferred to a microfluidizer (Microfluidics International Corporation, Model M-110F) and microfluidized for 3 to 5 cycles at 10,000 psi (69 MPa). In each cycle, the formulation jar was rinsed with microfluidized mixture. In the last cycle, the finished composition was collected in a clean dry beaker.

The following procedure was used for testing compositions of the Examples to determine herbicidal effectiveness, except where otherwise indicated.

Seeds of the plant species indicated were planted in 85 mm square pots in a soil mix which was previously steam sterilized and prefertilized with a 13-13-14 NPK slow release fertilizer at a rate of 3.6 kg/m$^3$. The pots were placed in a greenhouse with sub-irrigation. About one week after emergence, seedlings were thinned as needed, including removal of any unhealthy or abnormal plants, to create a uniform series of test pots.

The plants were maintained for the duration of the test in the greenhouse where they received a minimum of 14 hours of light per day. If natural light was insufficient to achieve the daily requirement, artificial light with an intensity of approximately 475 microeinsteins was used to make up the difference. Exposure temperatures were not precisely controlled but averaged about 27° C. during the day and about 18° C. during the night. Plants were sub-irrigated throughout the test to ensure adequate soil moisture levels.

Pots were assigned to different treatments in a fully randomized experimental design with 3 replications. A set of pots was left untreated as a reference against which effects of the treatments could later be evaluated.

Application of glyphosate compositions was made by spraying with a track sprayer fitted with a 9501E nozzle calibrated to deliver a spray volume of 93 liters per hectare (l/ha) at a pressure of 166 kilopascals (kPa). After treatment, pots were returned to the greenhouse until ready for evaluation.

Treatments were made using dilute aqueous compositions. These could be prepared as spray compositions directly from their ingredients, or by dilution with water of preformulated concentrate compositions.

For evaluation of herbicidal effectiveness, all plants in the test were examined by a single practiced technician, who recorded percent inhibition, a visual measurement of the effectiveness of each treatment by comparison with untreated plants. Inhibition of 0% indicates no effect, and inhibition of 100% indicates that all of the plants are completely dead. Inhibition of 85% or more is in most cases considered acceptable for normal herbicidal use; however in greenhouse tests such as those of the Examples it is normal to apply compositions at rates which give less than 85% inhibition, as this makes it easier to discriminate among compositions having different levels of effectiveness.

Example 1

Invert (water-in-oil) emulsion formulations containing glyphosate IPA salt were prepared as follows. In 235 g of a selected oil, 15 g soybean lecithin (20% phospholipid, Avanti) was dissolved to provide an oil feedstock. To a weighed amount of the oil feedstock in a Waring blender, a small quantity of concentrated (62% w/w) aqueous solution of glyphosate IPA salt was added quickly under high shear to make a ready-to-spray water-in-oil emulsion. The precise quantity of oil feedstock and glyphosate salt solution varied depending on the desired application rate. For a glyphosate rate of 100 g a.e./ha in a spray volume of 93 l/ha, 0.12 g glyphosate salt solution was added to 49.9 g oil feedstock. For higher rates, the amount of glyphosate salt solution was increased pro rata and the total weight of emulsion prepared kept constant at 50 g. Table 1a shows the composition of the oil feedstocks used.

TABLE 1a

| Oil feedstock no. | % w/w Oil | % w/w Lecithin | Type of oil |
|---|---|---|---|
| 1-01 | 94.0 | 6.0 | mineral oil |
| 1-02 | 94.0 | 6.0 | methyl oleate |
| 1-03 | 94.0 | 6.0 | silicone oil |

Velvetleaf (*Abutilon theophrasti,* ABUTH) and Japanese millet (*Echinochloa crus-galli,* ECHCF) plants were grown and treated by the standard procedures given above. Applications of spray compositions were made 14 days after planting ABUTH and 17 days after planting ECHCF. Evaluation of herbicidal inhibition was done 19 days after application.

Formulation C was applied in 93 l/ha of aqueous spray solution as a comparative treatment. Results, averaged for all replicates of each treatment, are shown in Table 1b.

Table 1b

| Spray composition | Glyphosate rate g a.e./ha | % Inhibition ABUTH | % Inhibition ECHCF |
|---|---|---|---|
| Formulation C | 100 | 40 | 65 |
| | 300 | 80 | 83 |
| | 400 | 93 | 89 |
| | 500 | 99 | 95 |
| 1-01 + glyphosate IPA salt | 0 | 20 | 0 |
| | 100 | 0 | 0 |
| | 300 | 10 | 11 |
| | 400 | 8 | 0 |
| | 500 | 5 | 10 |
| 1-02 + glyphosate IPA salt | 0 | 8 | 0 |
| | 100 | 30 | 3 |
| | 300 | 25 | 3 |
| | 400 | 38 | 3 |
| | 500 | 20 | 13 |
| 1-03 + glyphosate IPA salt | 0 | 0 | 0 |
| | 100 | 3 | 6 |
| | 300 | 48 | 0 |
| | 400 | 5 | 0 |
| | 500 | 25 | 0 |

Water-in-oil emulsion compositions of this Example did not show a high degree of herbicidal effectiveness.

Example 2

Aqueous spray compositions were prepared containing glyphosate IPA salt and excipient ingredients as shown in Table 2a. Process (iii) was followed for all compositions, using soybean lecithin (20% phospholipid, Avanti).

TABLE 2a

| Spray composition | Lecithin g/l | Fluorad FC-135 | Silwet L-77 | Methyl caprate | Sodium cholate | Components sonicated with lecithin |
|---|---|---|---|---|---|---|
| 2-01 | 5.0 | | | | | none |
| 2-02 | 5.0 | | 0.50 | | | none |
| 2-03 | 5.0 | | 0.50 | | | L-77 |
| 2-04 | 2.5 | | | | | none |
| 2-05 | 0.5 | | | | | none |
| 2-06 | 2.5 | | 0.50 | | | none |
| 2-07 | 2.5 | | 0.50 | | | L-77 |
| 2-08 | 0.5 | | 0.50 | | | none |
| 2-09 | 0.5 | | 0.50 | | | L-77 |
| 2-10 | 2.5 | 0.25 | | | | none |
| 2-11 | 2.5 | 0.10 | | | | none |
| 2-12 | 2.5 | 0.05 | | | | none |
| 2-13 | 0.5 | 0.25 | | | | none |
| 2-14 | 0.5 | 0.10 | | | | none |
| 2-15 | 0.5 | 0.05 | | | | none |
| 2-16 | 2.5 | | | 0.10 | | Me caprate |
| 2-17 | 2.5 | | | | 0.10 | Na cholate |

Velvetleaf (*Abutilon theophrasti*, ABUTH) and Japanese millet (*Echinochloa crus-galli*, ECHCF) plants were grown and treated by the standard procedures given above. Applications of spray compositions were made 18 days after planting ABUTH and 21 days after planting ECHCF, and evaluation of herbicidal inhibition was done 18 days after application.

In addition to compositions 2-01 to 2-17, spray compositions were prepared by tank mixing Formulations B and C with Fluorad FC-135 at various concentrations. Formulations B and C, alone and tank mixed with 0.5% Silwet L-77, were applied as comparative treatments. Results, averaged for all replicates of each treatment, are shown in Table 2b.

TABLE 2b

| Spray composition | Glyphosate rate g a.e./ha | % Inhibition ABUTH | % Inhibition ECHCF |
|---|---|---|---|
| Formulation B | 200 | 53 | 69 |
| | 300 | 76 | 85 |
| | 400 | 77 | 81 |
| Formulation B + Silwet L-77 0.5% v/v | 200 | 100 | 28 |
| | 300 | 100 | 35 |
| | 400 | 100 | 47 |
| Formulation C | 200 | 57 | 81 |
| | 300 | 73 | 90 |
| | 400 | 98 | 94 |
| Formulation C + Silwet L-77 0.5% v/v | 200 | 99 | 28 |
| | 300 | 98 | 53 |
| | 400 | 99 | 56 |
| Formulation B + Fluorad FC-135 0.25% w/v | 200 | 76 | 85 |
| | 300 | 95 | 81 |
| | 400 | 100 | 100 |
| Formulation B + Fluorad FC-135 0.1% w/v | 200 | 77 | 70 |
| | 300 | 94 | 81 |
| | 400 | 98 | 87 |
| Formulation B + Fluorad FC-135 0.05% w/v | 200 | 65 | 73 |
| | 300 | 84 | 94 |
| | 400 | 88 | 96 |
| Formulation C + Fluorad FC-135 0.25% w/v | 200 | 83 | 78 |
| | 300 | 98 | 94 |
| | 400 | 97 | 95 |
| Formulation C + Fluorad FC-135 0.1% w/v | 200 | 65 | 66 |
| | 300 | 89 | 86 |
| | 400 | 97 | 89 |
| Formulation C + Fluorad FC-135 0.05% w/v | 200 | 70 | 78 |
| | 300 | 79 | 84 |
| | 400 | 96 | 98 |
| 2-01 | 200 | 93 | 71 |
| | 300 | 91 | 89 |
| | 400 | 97 | 97 |
| 2-02 | 200 | 95 | 59 |
| | 300 | 97 | 68 |
| | 400 | 99 | 79 |
| 2-03 | 200 | 97 | 55 |
| | 300 | 98 | 62 |
| | 400 | 100 | 76 |
| 2-04 | 200 | 83 | 72 |
| | 300 | 87 | 84 |
| | 400 | 95 | 100 |
| 2-05 | 200 | 69 | 78 |
| | 300 | 92 | 93 |
| | 400 | 98 | 97 |
| 2-06 | 200 | 94 | 61 |
| | 300 | 99 | 67 |
| | 400 | 100 | 76 |
| 2-07 | 200 | 99 | 52 |
| | 300 | 99 | 63 |
| | 400 | 100 | 80 |
| 2-08 | 200 | 96 | 47 |
| | 300 | 99 | 57 |
| | 400 | 99 | 55 |
| 2-09 | 200 | 99 | 23 |
| | 300 | 98 | 58 |
| | 400 | 100 | 53 |
| 2-10 | 200 | 89 | 91 |
| | 300 | 91 | 99 |
| | 400 | 98 | 100 |
| 2-11 | 200 | 81 | 91 |
| | 300 | 91 | 99 |
| | 400 | 92 | 100 |
| 2-12 | 200 | 66 | 96 |
| | 300 | 86 | 100 |
| | 400 | 94 | 99 |
| 2-13 | 200 | 80 | 97 |
| | 300 | 98 | 98 |
| | 400 | 99 | 100 |
| 2-14 | 200 | 68 | 92 |
| | 300 | 89 | 100 |
| | 400 | 99 | 98 |
| 2-15 | 200 | 84 | 95 |
| | 300 | 94 | 100 |
| | 400 | 97 | 100 |
| 2-16 | 200 | 73 | 94 |
| | 300 | 89 | 100 |
| | 400 | 99 | 100 |
| 2-17 | 200 | 58 | 94 |
| | 300 | 77 | 96 |
| | 400 | 90 | 90 |

In this test addition of 0.1% methyl caprate to 0.25% lecithin, the methyl caprate being sonicated together with the lecithin, enhanced performance on ECHCF but not on ABUTH (compare compositions 2-16 and 2-04).

Example 3

Compositions 2-01 to 2-17 of Example 2, and tank mixtures of Formulations B and C with Fluorad FC-135, were tested in this Example. Prickly sida (*Sida spinosa*, SIDSP) plants were grown and treated by the standard procedures given above. Applications of spray compositions were made 22 days after planting SIDSP, and evaluation of herbicidal inhibition was done 19 days after application.

Formulations B and C, alone and tank mixed with 0.5% Silwet L-77, were applied as comparative treatments. Results, averaged for all replicates of each treatment, are shown in Table 3.

Note: The Fluorad FC-135 0.05% w/v entry at top of Table 2b-continued shows:
| Fluorad FC-135 0.05% w/v | 300 | 79 | 84 |
| | 400 | 96 | 98 |

TABLE 3

| Spray composition | Glyphosate rate g a.e./ha | % Inhibition SIDSP |
|---|---|---|
| Formulation B | 200 | 46 |
|  | 300 | 75 |
|  | 400 | 80 |
| Formulation B + Silwet L-77 0.5% v/v | 200 | 96 |
|  | 300 | 89 |
|  | 400 | 87 |
| Formulation C | 200 | 80 |
|  | 300 | 98 |
|  | 400 | 98 |
| Formulation C + Silwet L-77 0.5% v/v | 200 | 75 |
|  | 300 | 91 |
|  | 400 | 94 |
| Formulation B + Fluorad FC-135 0.25% w/v | 200 | 82 |
|  | 300 | 94 |
|  | 400 | 98 |
| Formulation B + Fluorad FC-135 0.1% w/v | 200 | 70 |
|  | 300 | 93 |
|  | 400 | 88 |
| Formulation B + Fluorad FC-135 0.05% w/v | 200 | 79 |
|  | 300 | 92 |
|  | 400 | 99 |
| Formulation C + Fluorad FC-135 0.25% w/v | 200 | 79 |
|  | 300 | 97 |
|  | 400 | 97 |
| Formulation C + Fluorad FC-135 0.1% w/v | 200 | 90 |
|  | 300 | 96 |
|  | 400 | 97 |
| Formulation C + Fluorad FC-135 0.05% w/v | 200 | 80 |
|  | 300 | 96 |
|  | 400 | 99 |
| 2-01 | 200 | 93 |
|  | 300 | 97 |
|  | 400 | 98 |
| 2-02 | 200 | 71 |
|  | 300 | 89 |
|  | 400 | 89 |
| 2-03 | 200 | 71 |
|  | 300 | 87 |
|  | 400 | 98 |
| 2-04 | 200 | 76 |
|  | 300 | 100 |
|  | 400 | 100 |
| 2-05 | 200 | 91 |
|  | 300 | 99 |
|  | 400 | 97 |
| 2-06 | 200 | 57 |
|  | 300 | 95 |
|  | 400 | 88 |
| 2-07 | 200 | 64 |
|  | 300 | 68 |
|  | 400 | 94 |
| 2-08 | 200 | 89 |
|  | 300 | 96 |
|  | 400 | 99 |
| 2-09 | 200 | 80 |
|  | 300 | 77 |
|  | 400 | 94 |
| 2-10 | 200 | 90 |
|  | 300 | 94 |
|  | 400 | 98 |
| 2-11 | 200 | 81 |
|  | 300 | 100 |
|  | 400 | 96 |
| 2-12 | 200 | 86 |
|  | 300 | 92 |
|  | 400 | 95 |
| 2-13 | 200 | 86 |
|  | 300 | 99 |
|  | 400 | 100 |
| 2-14 | 200 | 97 |
|  | 300 | 100 |
|  | 400 | 100 |
| 2-15 | 200 | 99 |
|  | 300 | 100 |
|  | 400 | 100 |
| 2-16 | 200 | 92 |
|  | 300 | 100 |
|  | 400 | 100 |
| 2-17 | 200 | 92 |
|  | 300 | 99 |
|  | 400 | 100 |

Herbicidal effectiveness of Formulation C was very high on SIDSP in this test and accordingly enhancements are difficult to discern. However, 0.1% methyl caprate (composition 2-16) enhanced the effectiveness of a composition containing 0.25% lecithin (2-04)

Example 4

Aqueous spray compositions were prepared containing glyphosate IPA salt and excipient ingredients as shown in Table 4a. Process (iii) was followed for all compositions, using soybean lecithin (20% phospholipid, Avanti).

TABLE 4a

| Spray comp. | Lecithin g/l | % w/w FC-135 | % w/w Other | (*) Other ingredient | Components sonicated with lecithin |
|---|---|---|---|---|---|
| 4-01 | 2.5 |  |  |  | none |
| 4-02 | 2.5 |  |  |  | glyphosate |
| 4-03 | 2.5 | 0.25 |  |  | none |
| 4-04 | 2.5 | 0.25 |  |  | glyphosate |
| 4-05 | 2.5 |  | 0.25 | Silwet 800 | none |
| 4-06 | 2.5 |  | 0.25 | Silwet 800 | Silwet 800 |
| 4-07 | 2.5 |  | 0.25 | Silwet 800 | Silwet, glyphosate |
| 4-08 | 0.5 |  |  |  | none |
| 4-09 | 0.5 |  |  |  | glyphosate |
| 4-10 | 0.5 | 0.05 |  |  | none |
| 4-11 | 0.5 | 0.05 |  |  | glyphosate |
| 4-12 | 0.5 | 0.03 | 0.02 | Silwet L-77 | Silwet L-77 |
| 4-13 | 0.5 |  | 0.05 | methyl caprate | Me caprate |
| 4-14 | 0.5 | 0.05 | 0.05 | methyl caprate | Me caprate |
| 4-15 | 0.5 | 0.05 | 0.05 | methyl caprate | Me caprate, glyphosate |
| 4-16 | 0.5 |  | 0.01 | PVA | none |
| 4-17 | 0.5 |  | 0.01 | PVA | glyphosate |
| 4-18 | 0.5 | 0.05 | 0.01 | PVA | glyphosate |
| 4-19 | 0.5 |  | 0.05 + 0.01 | L-77 + PVA | Silwet L-77 |

Velvetleaf (*Abutilon theophrasti*, ABUTH) and Japanese millet (*Echinochloa crus-galli*, ECHCF) plants were grown and treated by the standard procedures given above. Applications of spray compositions were made 19 days after planting ABUTH and 21 days after planting ECHCF, and evaluation of herbicidal inhibition was done 17 days after application.

In addition to compositions 4-01 to 4-19, spray compositions were prepared by tank mixing Formulations B and C with Fluorad FC-135 at two concentrations. Formulations B and C, alone and tank mixed with 0.5% Silwet 800, were applied as comparative treatments. Results, averaged for all replicates of each treatment, are shown in Table 4b.

TABLE 4b

| Spray composition | Glyphosate rate g a.e./ha | % Inhibition ABUTH | % Inhibition ECHCF |
|---|---|---|---|
| Formulation B | 150 | 13 | 28 |
|  | 250 | 37 | 51 |
|  | 350 | 56 | 38 |
| Formulation B + Silwet 800 0.25% v/v | 150 | 81 | 15 |
|  | 250 | 89 | 17 |
|  | 350 | 91 | 20 |
| Formulation C | 150 | 32 | 65 |
|  | 250 | 59 | 91 |
|  | 350 | 85 | 89 |
| Formulation C + Silwet 800 0.25% v/v | 150 | 91 | 17 |
|  | 250 | 91 | 23 |
|  | 350 | 95 | 48 |
| Formulation B + Fluorad FC-135 0.25% w/v | 150 | 31 | 58 |
|  | 250 | 53 | 68 |
|  | 350 | 71 | 84 |
| Formulation B + Fluorad FC-135 0.05% w/v | 150 | 31 | 29 |
|  | 250 | 44 | 69 |
|  | 350 | 95 | 79 |
| Formulation C + Fluorad FC-135 0.25% w/v | 150 | 46 | 45 |
|  | 250 | 69 | 79 |
|  | 350 | 86 | 77 |
| Formulation C + Fluorad FC-135 0.05% w/v | 150 | 44 | 57 |
|  | 250 | 60 | 87 |
|  | 350 | 86 | 88 |
| 4-01 | 150 | 55 | 50 |
|  | 250 | 87 | 81 |
|  | 350 | 89 | 88 |
| 4-02 | 150 | 56 | 54 |
|  | 250 | 89 | 69 |
|  | 350 | 87 | 98 |
| 4-03 | 150 | 89 | 68 |
|  | 250 | 89 | 84 |
|  | 350 | 91 | 90 |
| 4-04 | 150 | 63 | 68 |
|  | 250 | 89 | 86 |
|  | 350 | 99 | 89 |
| 4-05 | 150 | 81 | 51 |
|  | 250 | 87 | 84 |
|  | 350 | 94 | 26 |
| 4-06 | 150 | 67 | 0 |
|  | 250 | 93 | 62 |
|  | 350 | 94 | 81 |
| 4-07 | 150 | 81 | 35 |
|  | 250 | 84 | 51 |
|  | 350 | 95 | 62 |
| 4-08 | 150 | 59 | 51 |
|  | 250 | 84 | 69 |
|  | 350 | 98 | 90 |
| 4-09 | 150 | 64 | 59 |
|  | 250 | 85 | 61 |
|  | 350 | 94 | 96 |
| 4-10 | 150 | 73 | 74 |
|  | 250 | 87 | 83 |
|  | 350 | 98 | 96 |
| 4-11 | 150 | 76 | 64 |
|  | 250 | 88 | 79 |
|  | 350 | 94 | 81 |
| 4-12 | 150 | 59 | 46 |
|  | 250 | 82 | 88 |
|  | 350 | 92 | 82 |
| 4-13 | 150 | 61 | 45 |
|  | 250 | 90 | 69 |
|  | 350 | 93 | 90 |
| 4-14 | 150 | 76 | 50 |
|  | 250 | 95 | 73 |
|  | 350 | 99 | 91 |
| 4-15 | 150 | 78 | 67 |
|  | 250 | 95 | 80 |
|  | 350 | 99 | 85 |
| 4-16 | 150 | 48 | 42 |
|  | 250 | 77 | 87 |
|  | 350 | 87 | 75 |
| 4-17 | 150 | 47 | 63 |
|  | 250 | 85 | 67 |
|  | 350 | 90 | 78 |
| 4-18 | 150 | 55 | 46 |
|  | 250 | 82 | 77 |
|  | 350 | 90 | 87 |
| 4-19 | 150 | 32 | 23 |
|  | 250 | 43 | 31 |
|  | 350 | 76 | 65 |

In this test, addition of methyl caprate to compositions containing lecithin with or without Fluorad FC-135 (4-13 to 4-15) improved herbicidal effectiveness on ABUTH but had little effect on ECHCF.

Example 5

Aqueous spray compositions were prepared containing glyphosate IPA salt and excipient ingredients as shown in Table 5a. Process (iii) was followed for all compositions, using soybean lecithin (20% phospholipid, Avanti).

TABLE 5a

| Spray composition | Lecithin g/l | % w/w FC-135 | % w/w Aerosol OT | % w/w Methyl caprate | Components sonicated with lecithin |
|---|---|---|---|---|---|
| 5-01 | 2.5 |  |  |  | none |
| 5-02 | 2.5 |  |  |  | glyphosate |
| 5-03 | 1.0 |  |  |  | none |
| 5-04 | 1.0 |  |  |  | glyphosate |
| 5-05 | 0.5 |  |  |  | none |
| 5-06 | 0.5 |  |  |  | glyphosate |
| 5-07 | 0.2 |  |  |  | none |
| 5-08 | 0.2 |  |  |  | glyphosate |
| 5-09 | 0.5 |  | 0.05 |  | none |
| 5-10 | 0.5 |  | 0.05 |  | AOT, glyphosate |
| 5-11 | 0.5 |  | 0.05 |  | AOT |
| 5-12 | 2.5 | 0.25 |  |  | none |
| 5-13 | 0.5 | 0.05 |  |  | none |
| 5-14 | 0.5 | 0.05 |  |  | glyphosate |
| 5-15 | 0.5 |  |  | 0.05 | Me caprate |
| 5-16 | 0.5 | 0.05 |  | 0.05 | Me caprate |
| 5-17 | 0.2 | 0.02 |  |  | none |
| 5-18 | 0.2 | 0.02 |  |  | glyphosate |
| 5-19 | 0.2 |  |  | 0.02 | Me caprate |

Velvetleaf (*Abutilon theophrasti*, ABUTH), Japanese millet (*Echinochloa crus-galli*, ECHCF), and prickly sida (*Sida spinosa*, SIDSP) plants were grown and treated by the standard procedures given above. Applications of spray compositions were made 19 days after planting ABUTH and 22 days after planting ECHCF. No record was found for the planting date for SIDSP. Evaluation of herbicidal inhibition was done 20 days after application.

In addition to compositions 5-01 to 5-19, spray compositions were prepared by tank mixing Formulations B and C with Fluorad FC-135 at various concentrations. Formulations B and C alone were applied as comparative treatments. Results, averaged for all replicates of each treatment, are shown in Table 5b.

TABLE 5b

| Spray composition | Glyphosate rate g a.e./ha | % Inhibition ABUTH | % Inhibition ECHCF | % Inhibition SIDSP |
|---|---|---|---|---|
| Formulation B | 150 | 16 | 23 | 30 |
|  | 250 | 17 | 33 | 57 |
|  | 350 | 24 | 43 | 65 |
| Formulation C | 150 | 18 | 58 | 53 |
|  | 250 | 30 | 71 | 79 |
|  | 350 | 49 | 83 | 94 |
| Formulation B + Fluorad FC-135 0.25% w/v | 150 | 27 | 59 | 56 |
|  | 250 | 45 | 84 | 81 |
|  | 350 | 55 | 82 | 91 |
| Formulation B + Fluorad FC-135 0.1% w/v | 150 | 17 | 43 | 56 |
|  | 250 | 21 | 56 | 75 |
|  | 350 | 64 | 80 | 90 |
| Formulation B + Fluorad FC-135 0.02% w/v | 150 | 22 | 27 | 38 |
|  | 250 | 37 | 49 | 69 |
|  | 350 | 48 | 68 | 94 |
| Formulation C + Fluorad FC-135 0.25% w/v | 150 | 41 | 41 | 59 |
|  | 250 | 57 | 53 | 85 |
|  | 350 | 67 | 67 | 94 |
| Formulation C + Fluorad FC-135 0.05% w/v | 150 | 26 | 39 | 67 |
|  | 250 | 46 | 66 | 88 |
|  | 350 | 75 | 73 | 93 |
| Formulation C + Fluorad FC-135 0.02% w/v | 150 | 30 | 52 | 66 |
|  | 250 | 67 | 50 | 89 |
|  | 350 | 61 | 88 | 92 |
| 5-01 | 150 | 35 | 62 | 64 |
|  | 250 | 63 | 77 | 90 |
|  | 350 | 71 | 83 | 85 |
| 5-02 | 150 | 35 | 44 | 67 |
|  | 250 | 53 | 79 | 86 |
|  | 350 | 58 | 92 | 90 |
| 5-03 | 150 | 37 | 50 | 71 |
|  | 250 | 53 | 76 | 90 |
|  | 350 | 73 | 63 | 97 |
| 5-04 | 150 | 29 | 46 | 61 |
|  | 250 | 43 | 77 | 85 |
|  | 350 | 70 | 85 | 96 |
| 5-05 | 150 | 12 | 36 | 59 |
|  | 250 | 43 | 55 | 83 |
|  | 350 | 53 | 77 | 87 |
| 5-06 | 150 | 19 | 69 | 67 |
|  | 250 | 62 | 47 | 84 |
|  | 350 | 58 | 60 | 95 |
| 5-07 | 150 | 14 | 59 | 59 |
|  | 250 | 39 | 63 | 75 |
|  | 350 | 46 | 77 | 91 |
| 5-08 | 150 | 36 | 37 | 64 |
|  | 250 | 38 | 68 | 82 |
|  | 350 | 47 | 80 | 79 |
| 5-09 | 150 | 8 | 35 | 27 |
|  | 250 | 9 | 51 | 56 |
|  | 350 | 36 | 58 | 67 |
| 5-10 | 150 | 5 | 33 | 24 |
|  | 250 | 15 | 73 | 47 |
|  | 350 | 30 | 66 | 67 |
| 5-11 | 150 | 38 | 49 | 73 |
|  | 250 | 62 | 75 | 89 |
|  | 350 | 71 | 75 | 98 |
| 5-12 | 150 | 7 | 41 | 21 |
|  | 250 | 18 | 67 | 38 |
|  | 350 | 30 | 64 | 61 |
| 5-13 | 150 | 39 | 72 | 65 |
|  | 250 | 65 | 55 | 76 |
|  | 350 | 70 | 68 | 90 |
| 5-14 | 150 | 51 | 53 | 66 |
|  | 250 | 60 | 82 | 85 |
|  | 350 | 65 | 83 | 95 |
| 5-15 | 150 | 15 | 59 | 61 |
|  | 250 | 31 | 54 | 83 |
|  | 350 | 57 | 67 | 84 |
| 5-16 | 150 | 36 | 79 | 66 |
|  | 250 | 50 | 60 | 95 |
|  | 350 | 71 | 95 | 95 |
| 5-17 | 150 | 30 | 52 | 75 |
|  | 250 | 54 | 60 | 84 |
|  | 350 | 48 | 84 | 93 |
| 5-18 | 150 | 43 | 75 | 69 |
|  | 250 | 47 | 78 | 88 |
|  | 350 | missing | missing | 90 |
| 5-19 | 150 | 13 | 42 | 61 |
|  | 250 | 29 | 51 | 79 |
|  | 350 | 42 | 69 | 90 |

The inclusion of methyl caprate in a composition containing lecithin and Fluorad FC-135 improved efficacy on ECHCF and SIDSP (compare compositions 5-16 and 5-13).

Example 6

Aqueous concentrate compositions were prepared containing glyphosate IPA salt and excipient ingredients as shown in Table 6a. All concentrate compositions are water-in-oil-in-water multiple emulsions and were prepared by process (vi), using Span 80 or Brij 92 (oleth-2) as emulsifier #1 and a Span 80/Tween 80 blend as emulsifier #2.

TABLE 6a

| Conc. comp. | % w/w Glyphosate a.e. | Orchex 796 | Butyl stearate | Span 80 or Brij 92 | Span 80/ Tween 80 (45/55) | % in inner aq. phase water | glyphosate |
|---|---|---|---|---|---|---|---|
| 6-01 | 0.4 | 20.7 | | 0.3 (Span) | 10.0 | 11.5 | 100 |
| 6-02 | 0.4 | | 20.7 | 0.3 (Span) | 10.0 | 11.5 | 100 |
| 6-03 | 0.4 | 20.7 | | 0.3 (Brij) | 10.0 | 11.5 | 100 |
| 6-04 | 0.4 | 20.3 | | 9.8 (Span) | 10.0 | 11.5 | 100 |
| 6-05 | 0.4 | | 20.3 | 0.8 (Span) | 10.0 | 11.5 | 100 |
| 6-06 | 0.4 | 20.3 | | 0.8 (Brij) | 10.0 | 11.5 | 100 |
| 6-07 | 0.4 | 19.5 | | 1.5 (Span) | 10.0 | 11.5 | 100 |
| 6-08 | 0.4 | | 19.5 | 1.5 (Span) | 10.0 | 11.5 | 100 |
| 6-09 | 0.4 | 19.5 | | 1.5 (Brij) | 10.0 | 11.5 | 100 |
| 6-10 | 0.4 | 20.0 | | 5.0 (Span) | 2.3 | 35.7 | 100 |
| 6-11 | 0.4 | 18.0 | | 3.0 (Span) | 5.0 | 11.5 | 100 |

TABLE 6a-continued

| | | | % w/w | | | | |
|---|---|---|---|---|---|---|---|
| Conc. comp. | Glyphosate a.e. | Orchex 796 | Butyl stearate | Span 80 or Brij 92 | Span 80/ Tween 80 (45/55) | % in inner aq. phase water | glyphosate |
| 6-12 | 0.8 | 18.0 | | 3.0 (Span) | 5.0 | 11.5 | 100 |
| 6-13 | 1.6 | 18.0 | | 3.0 (Span) | 5.0 | 11.5 | 100 |
| 6-14 | 3.2 | 18.0 | | 3.0 (Span) | 5.0 | 11.5 | 100 |
| 6-15 | 2.7 | 18.0 | | 3.0 (Span) | 5.0 | 11.5 | 30 |
| 6-16 | 5.3 | 18.0 | | 3.0 (Span) | 5.0 | 11.5 | 30 |
| 6-17 | 10.7 | 18.0 | | 3.0 (Span) | 5.0 | 11.5 | 30 |
| 6-18 | 0.4 | 18.0 | | 3.0 (Span) | 2.3 | 11.5 | 100 |

Velvetleaf (*Abutilon theophrasti*, ABUTH) and Japanese millet (*Echinochloa crus-galli*, ECHCF) plants were grown and treated by the standard procedures given above. Applications of spray compositions were made 14 days after planting ABUTH and 17 days after planting ECHCF, and evaluation of herbicidal inhibition was done 19 days after application.

Formulations C and J were applied as comparative treatments. Results, averaged for all replicates of each treatment, are shown in Table 6b.

TABLE 6b

| Concentrate composition | Glyphosate rate g a.e./ha | % Inhibition ABUTH | % Inhibition ECHCF |
|---|---|---|---|
| Formulation C | 56 | 5 | 45 |
| | 112 | 20 | 60 |
| | 224 | 79 | 84 |
| | 448 | 97 | 95 |
| Formulation J | 56 | 29 | 58 |
| | 112 | 43 | 63 |
| | 224 | 79 | 96 |
| | 448 | 97 | 99 |
| 6-01 | 112 | 48 | 48 |
| | 224 | 79 | 79 |
| | 448 | 95 | 95 |
| 6-02 | 112 | 65 | 65 |
| | 224 | 93 | 93 |
| | 448 | 96 | 96 |
| 6-03 | 112 | 3 | 3 |
| | 224 | 30 | 30 |
| | 448 | 71 | 71 |
| 6-04 | 112 | 35 | 35 |
| | 224 | 79 | 79 |
| | 448 | 90 | 90 |
| 6-05 | 112 | 55 | 65 |
| | 224 | 85 | 91 |
| | 448 | 98 | 95 |
| 6-06 | 112 | 38 | 63 |
| | 224 | 68 | 88 |
| | 448 | 85 | 98 |
| 6-07 | 112 | 30 | 63 |
| | 224 | 60 | 76 |
| | 448 | 74 | 86 |
| 6-08 | 112 | 45 | 75 |
| | 224 | 95 | 96 |
| | 448 | 99 | 98 |
| 6-09 | 112 | 36 | 70 |
| | 224 | 69 | 71 |
| | 448 | 97 | 99 |
| 6-10 | 112 | 15 | 55 |
| | 224 | 55 | 78 |
| | 448 | 79 | 90 |
| 6-11 | 112 | 11 | 23 |
| | 224 | 55 | 78 |
| | 448 | 80 | 95 |

TABLE 6b-continued

| Concentrate composition | Glyphosate rate g a.e./ha | % Inhibition ABUTH | % Inhibition ECHCF |
|---|---|---|---|
| 6-12 | 112 | 0 | 23 |
| | 224 | 40 | 20 |
| | 448 | 55 | 78 |
| 6-13 | 112 | 1 | 35 |
| | 224 | 15 | 25 |
| | 448 | 55 | 38 |
| 6-14 | 112 | 0 | 23 |
| | 224 | 0 | 23 |
| | 448 | 25 | 50 |
| 6-15 | 112 | 30 | 40 |
| | 224 | 58 | 75 |
| | 448 | 73 | 92 |
| 6-16 | 112 | 8 | 43 |
| | 224 | 64 | 55 |
| | 448 | 87 | 84 |
| 6-17 | 112 | 83 | 97 |
| | 224 | 99 | 100 |
| | 448 | 100 | 100 |
| 6-18 | 112 | 35 | 43 |
| | 224 | 60 | 60 |
| | 448 | 93 | 88 |

Significantly greater herbicidal effectiveness was obtained with compositions using butyl stearate as the oil (6-02, 6-05, 6-08) than with counterparts using Orchex 796 (6-01, 6-04, 6-07).

Example 7

Aqueous concentrate compositions were prepared containing glyphosate IPA salt and excipient ingredients as shown in Table 7a. All concentrate compositions are water-in-oil-in-water multiple emulsions and were prepared by process (vi), using Span 80 as emulsifier #1 and a Span 80/Tween 80 blend as emulsifier #2.

TABLE 7a

| | % w/w | | | | | | % in inner aq. phase | |
|---|---|---|---|---|---|---|---|---|
| Conc. comp. | Gly- phosate a.e. | Orchex 796 | Butyl stearate | Span 80 | Span 80/ Tween 80 (45/55) | water | gly- phosate |
| 7-01 | 10.7 | 18.0 | | 3.0 | 5.0 | 12.2 | 30 |
| 7-02 | 10.7 | 18.0 | | 3.0 | 5.0 | 12.2 | 20 |
| 7-03 | 10.7 | 18.0 | | 3.0 | 5.0 | 12.2 | 0 |
| 7-04 | 10.7 | 18.0 | | 3.0 | 5.0 | 12.2 | 38 |
| 7-05 | 13.7 | 18.0 | | 3.0 | 5.0 | 12.2 | 30 |

TABLE 7a-continued

| | | | | % w/w | | | % in inner aq. phase |
|---|---|---|---|---|---|---|---|
| Conc. comp. | Gly- phosate a.e. | Orchex 796 | Butyl stearate | Span 80 | Span 80/ Tween 80 (45/55) | water | gly- phosate |
| 7-06 | 13.7 | 18.0 | | 3.0 | 5.0 | 12.2 | 20 |
| 7-07 | 13.7 | 18.0 | | 3.0 | 5.0 | 12.2 | 0 |
| 7-08 | 20.5 | 18.0 | | 3.0 | 5.0 | 12.2 | 20 |
| 7-09 | 20.5 | 18.0 | | 3.0 | 5.0 | 12.2 | 0 |
| 7-10 | 10.7 | | 18.0 | 3.0 | 5.0 | 12.2 | 30 |
| 7-11 | 10.7 | | 18.0 | 3.0 | 5.0 | 12.2 | 20 |
| 7-12 | 10.7 | | 18.0 | 3.0 | 5.0 | 12.2 | 0 |
| 7-13 | 10.7 | | 18.0 | 3.0 | 5.0 | 12.2 | 38 |
| 7-14 | 13.7 | | 18.0 | 3.0 | 5.0 | 12.2 | 30 |
| 7-15 | 13.7 | | 18.0 | 3.0 | 5.0 | 12.2 | 20 |
| 7-16 | 13.7 | | 18.0 | 3.0 | 5.0 | 12.2 | 0 |
| 7-17 | 20.5 | | 18.0 | 3.0 | 5.0 | 12.2 | 20 |
| 7-18 | 20.5 | | 18.0 | 3.0 | 5.0 | 12.2 | 0 |

Velvetleaf (*Abutilon theophrasti*, ABUTH) and Japanese millet (*Echinochloa crus-galli*, ECHCF) plants were grown and treated by the standard procedures given above. Applications of spray compositions were made 13 days after planting ABUTH and 16 days after planting ECHCF, and evaluation of herbicidal inhibition was done 19 days after application.

Formulations C and J were applied as comparative treatments. Results, averaged for all replicates of each treatment, are shown in Table 7b.

TABLE 7b

| Concentrate composition | Glyphosate rate g a.e./ha | % Inhibition ABUTH | % Inhibition ECHCF |
|---|---|---|---|
| Formulation C | 50 | 1 | 11 |
| | 100 | 35 | 45 |
| | 200 | 46 | 63 |
| | 400 | 97 | 100 |
| Formulation J | 50 | 5 | 14 |
| | 100 | 33 | 40 |
| | 200 | 70 | 83 |
| | 400 | 93 | 95 |
| 7-01 | 100 | missing | missing |
| | 200 | missing | missing |
| | 400 | missing | missing |
| 7-02 | 100 | missing | missing |
| | 200 | missing | missing |
| | 400 | missing | missing |
| 7-03 | 100 | 5 | 0 |
| | 200 | 58 | 45 |
| | 400 | 75 | 78 |
| 7-04 | 100 | missing | missing |
| | 200 | missing | missing |
| | 400 | missing | missing |
| 7-05 | 100 | missing | missing |
| | 200 | missing | missing |
| | 400 | missing | missing |
| 7-06 | 100 | 6 | 5 |
| | 200 | 30 | 35 |
| | 400 | 75 | 73 |
| 7-07 | 100 | 1 | 5 |
| | 200 | 53 | 38 |
| | 400 | 75 | 78 |
| 7-08 | 100 | 8 | 5 |
| | 200 | 38 | 20 |
| | 400 | 75 | 53 |
| 7-09 | 100 | 11 | 10 |
| | 200 | 59 | 40 |
| | 400 | 78 | 65 |

TABLE 7b-continued

| Concentrate composition | Glyphosate rate g a.e./ha | % Inhibition ABUTH | % Inhibition ECHCF |
|---|---|---|---|
| 7-10 | 100 | 14 | 28 |
| | 200 | 36 | 30 |
| | 400 | 74 | 75 |
| 7-11 | 100 | 5 | 5 |
| | 200 | 30 | 40 |
| | 400 | 70 | 55 |
| 7-12 | 100 | 4 | 5 |
| | 200 | 9 | 25 |
| | 400 | 74 | 46 |
| 7-13 | 100 | 5 | 4 |
| | 200 | 39 | 23 |
| | 400 | 76 | 60 |
| 7-14 | 100 | 10 | 5 |
| | 200 | 38 | 49 |
| | 400 | 76 | 83 |
| 7-15 | 100 | 11 | 20 |
| | 200 | 51 | 43 |
| | 400 | 80 | 78 |
| 7-16 | 100 | 14 | 20 |
| | 200 | 50 | 43 |
| | 400 | 86 | 84 |
| 7-17 | 100 | 23 | 25 |
| | 200 | 65 | 53 |
| | 400 | 78 | 79 |
| 7-18 | 100 | 23 | 10 |
| | 200 | 48 | 40 |
| | 400 | 78 | 81 |

Many compositions having butyl stearate as the oil showed greater herbicidal effectiveness than their counterparts having Orchex 796 as the oil.

Example 8

Aqueous concentrate compositions were prepared containing glyphosate IPA salt and excipient ingredients as shown in Table 8a. Process (iv) was followed for all compositions, using soybean lecithin (20% phospholipid, Avanti).

TABLE 8a

| | Gly- | % w/w | | | | |
|---|---|---|---|---|---|---|
| Concentrate composition | phosate g a.e./l | Lecithin | Aerosol OT | MON 0818 | FC- 754 | Methyl caprate | PVA |
| 8-01 | 200 | 2.0 | 0.25 | | | | |
| 8-02 | 300 | 3.0 | 0.50 | | | | |
| 8-03 | 300 | 3.0 | 0.50 | | | | 2.0 |
| 8-04 | 200 | 2.0 | 0.25 | | | | 1.5 |
| 8-05 | 200 | 2.0 | 0.25 | | | 1.0 | 1.0 |
| 8-06 | 200 | 2.0 | 0.25 | | | 1.0 | 1.0 |
| 8-07 | 200 | 2.0 | 0.25 | | 2.0 | | |
| 8-08 | 200 | | 2.0 | 0.25 | | | |
| 8-09 | 300 | | 3.0 | 0.50 | | | |
| 8-10 | 300 | | 3.0 | 0.50 | | | 2.0 |
| 8-11 | 200 | | 2.0 | 0.25 | | | 1.5 |
| 8-12 | 200 | | 2.0 | 0.25 | | 1.0 | |
| 8-13 | 200 | | 2.0 | 0.25 | | 1.0 | |
| 8-14 | 200 | | 2.0 | 0.25 | | 1.0 | 1.5 |
| 8-15 | 200 | | 2.0 | 0.25 | 2.0 | | |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and 13 days after planting ECHCF, and evaluation of herbicidal inhibition was done 20 days after application.

Compositions containing PVA were too viscous to spray and were not tested for herbicidal effectiveness. Formulations B, C and J were applied as comparative treatments. Results, averaged for all replicates of each treatment, are shown in Table 8b.

TABLE 8b

| Concentrate composition | Glyphosate rate g a.e./ha | % Inhibition ABUTH | % Inhibition ECHCF |
|---|---|---|---|
| Formulation B | 112 | 5 | 4 |
| | 224 | 48 | 8 |
| | 336 | 73 | 20 |
| | 448 | 94 | 50 |
| Formulation C | 112 | 30 | 45 |
| | 224 | 91 | 81 |
| | 336 | 98 | 81 |
| | 448 | 100 | 99 |
| Formulation J | 112 | 50 | 35 |
| | 224 | 80 | 65 |
| | 336 | 97 | 88 |
| | 448 | 100 | 90 |
| 8-01 | 112 | 11 | 8 |
| | 224 | 50 | 40 |
| | 336 | 71 | 61 |
| | 448 | 93 | 78 |
| 8-02 | 112 | 5 | 6 |
| | 224 | 64 | 58 |
| | 336 | 78 | 60 |
| | 448 | 84 | 65 |
| 8-07 | 112 | 5 | 3 |
| | 224 | 46 | 38 |
| | 336 | 73 | 83 |
| | 448 | 93 | 66 |
| 8-08 | 112 | 8 | 13 |
| | 224 | 43 | 46 |
| | 336 | 73 | 65 |

TABLE 8b-continued

| Concentrate composition | Glyphosate rate g a.e./ha | % Inhibition ABUTH | % Inhibition ECHCF |
|---|---|---|---|
| | 448 | 83 | 70 |
| 8-09 | 112 | 1 | 5 |
| | 224 | 23 | 25 |
| | 336 | 65 | 33 |
| | 448 | 91 | 58 |
| 8-12 | 112 | 0 | 5 |
| | 224 | 58 | 48 |
| | 336 | 73 | 63 |
| | 448 | 91 | 63 |
| 8-13 | 112 | 0 | 10 |
| | 224 | 53 | 38 |
| | 336 | 73 | 45 |
| | 448 | 88 | 50 |
| 8-15 | 112 | 28 | 10 |
| | 224 | 50 | 53 |
| | 336 | 80 | 63 |
| | 448 | 88 | 91 |

Concentrate compositions containing lecithin and methyl caprate did not exhibit herbicidal effectiveness equal to that of the commercial standards in this test.

Example 9

Aqueous concentrate compositions were prepared containing glyphosate IPA salt and excipient ingredients as shown in Table 9a. All concentrate compositions were water-in-oil-in-water multiple emulsions and were prepared by process (vi), using Span 80 as emulsifier #1 and a Span 80/Tween 80 blend as emulsifier #2.

TABLE 9a

| | % w/w | | | | | | |
|---|---|---|---|---|---|---|---|
| Concentrate composition | Glyphosate a.e. | Butyl stearate | Methyl oleate | Span 80 | Span 80/Tween 80 (45/55) | % in inner aq. phase water | % in inner aq. phase glyphosate |
| 9-01 | 6.9 | 12.0 | | 3.0 | 5.0 | 18.8 | 50 |
| 9-02 | 6.9 | 12.0 | | 3.0 | 5.0 | 18.8 | 20 |
| 9-03 | 6.9 | 12.0 | | 3.0 | 5.0 | 18.8 | 0 |
| 9-04 | 13.8 | 12.0 | | 3.0 | 5.0 | 18.8 | 20 |
| 9-05 | 13.8 | 12.0 | | 3.0 | 5.0 | 18.8 | 0 |
| 9-06 | 30.0 | 12.0 | | 3.0 | 5.0 | 18.8 | 0 |
| 9-07 | 20.5 | 18.0 | | 3.0 | 5.0 | 12.2 | 20 |
| 9-08 | 20.5 | 18.0 | | 3.0 | 5.0 | 12.2 | 0 |
| 9-09 | 13.8 | 18.0 | | 3.0 | 5.0 | 12.2 | 20 |
| 9-10 | 13.8 | 18.0 | | 3.0 | 5.0 | 12.2 | 0 |
| 9-11 | 6.9 | 18.0 | | 3.0 | 5.0 | 12.2 | 0 |
| 9-12 | 30.0 | 18.0 | | 3.0 | 5.0 | 12.2 | 0 |
| 9-13 | 6.9 | 18.0 | | 3.0 | 5.0 | 12.2 | 50 |
| 9-14 | 6.9 | 18.0 | | 3.0 | 5.0 | 12.2 | 20 |
| 9-15 | 20.5 | | 18.0 | 3.0 | 5.0 | 12.2 | 20 |
| 9-16 | 13.8 | | 18.0 | 3.0 | 5.0 | 12.2 | 20 |

Velvetleaf (*Abutilon theophrasti*, ABUTH) and Japanese millet (*Echinochloa crus-galli*, ECHCF) plants were grown and treated by the standard procedures given above. Applications of spray compositions were made 15 days after planting ABUTH and 17 days after planting ECHCF, and evaluation of herbicidal inhibition was done 19 days after application.

Formulations B, C and J were applied as comparative treatments. Results, averaged for all replicates of each treatment, are shown in Table 9b.

TABLE 9b

| Concentrate composition | Glyphosate rate g a.e./ha | % Inhibition ABUTH | % Inhibition ECHCF |
|---|---|---|---|
| Formulation B | 224 | 20 | 30 |
|  | 336 | 49 | 40 |
|  | 448 | 66 | 48 |
| Formulation C | 224 | 73 | 80 |
|  | 336 | 88 | 98 |
|  | 448 | 93 | 99 |
| Formulation J | 224 | 56 | 69 |
|  | 336 | 83 | 85 |
|  | 448 | 88 | 90 |
| 9-01 | 224 | 55 | 35 |
|  | 336 | 73 | 66 |
|  | 448 | 80 | 78 |
| 9-02 | 224 | 55 | 45 |
|  | 336 | 70 | 60 |
|  | 448 | 83 | 79 |
| 9-03 | 224 | 45 | 40 |
|  | 336 | 75 | 76 |
|  | 448 | 78 | 83 |
| 9-04 | 224 | 40 | 58 |
|  | 336 | 65 | 68 |
|  | 448 | 84 | 98 |
| 9-05 | 224 | 53 | 55 |
|  | 336 | 75 | 85 |
|  | 448 | 79 | 88 |
| 9-06 | 224 | 49 | 69 |
|  | 336 | 69 | 76 |
|  | 448 | 83 | 98 |
| 9-07 | 224 | 38 | 45 |
|  | 336 | 58 | 63 |
|  | 448 | 73 | 75 |
| 9-08 | 224 | 40 | 48 |
|  | 336 | 40 | 40 |
|  | 448 | 55 | 55 |
| 9-09 | 224 | 63 | 53 |
|  | 336 | 74 | 78 |
|  | 448 | 79 | 83 |
| 9-10 | 224 | 68 | 48 |
|  | 336 | 73 | 73 |
|  | 448 | 88 | 83 |
| 9-11 | 224 | 68 | 46 |
|  | 336 | 80 | 80 |
|  | 448 | 85 | 97 |
| 9-12 | 224 | 50 | 54 |
|  | 336 | 71 | 58 |
|  | 448 | 76 | 79 |
| 9-13 | 224 | 71 | 65 |
|  | 336 | 81 | 87 |
|  | 448 | 85 | 89 |
| 9-14 | 224 | 66 | 58 |
|  | 336 | 75 | 75 |
|  | 448 | 78 | 86 |
| 9-15 | 224 | 54 | 49 |
|  | 336 | 50 | 65 |
|  | 448 | 75 | 75 |
| 9-16 | 224 | 10 | 30 |
|  | 336 | 44 | 43 |
|  | 448 | 54 | 45 |

Butyl stearate provided herbicidal effectiveness equal or superior to methyl oleate when used as the oil in compositions of this Example.

Example 10

Aqueous concentrate compositions were prepared containing glyphosate IPA salt and excipient ingredients as shown in Table 10a. All concentrate compositions are water-in-oil-in-water multiple emulsions and were prepared by process (vi), using Span 80 as emulsifier #1 and either Tween 20 or a Span 80/Tween 80 blend as emulsifier #2.

TABLE 10a

| | % w/w | | | | | | % in inner aq. phase | |
|---|---|---|---|---|---|---|---|---|
| Conc. comp. | Glyphosate a.e. | Butyl stearate | Lecithin | Span 80 | Tween 20 | Span 80/ Tween 80 (45/55) | water | glyphosate |
| 10-01 | 10.7 | 18.0 |  | 3.0 | 5.0 |  | 12.2 | 20 |
| 10-02 | 10.7 | 18.0 | 0.6 | 2.4 | 5.0 |  | 12.2 | 20 |
| 10-03 | 10.7 | 18.0 | 1.5 | 1.5 | 5.0 |  | 12.2 | 20 |
| 10-04 | 10.7 | 18.0 | 2.4 | 0.6 | 5.0 |  | 12.2 | 20 |
| 10-05 | 10.7 | 18.0 |  | 3.0 | 3.0 |  | 12.2 | 20 |
| 10-06 | 10.7 | 18.0 | 0.6 | 2.4 | 3.0 |  | 12.2 | 20 |
| 10-07 | 10.7 | 18.0 | 1.5 | 1.5 | 3.0 |  | 12.2 | 20 |
| 10-08 | 10.7 | 18.0 | 2.4 | 0.6 | 3.0 |  | 12.2 | 20 |
| 10-09 | 10.7 | 7.5 |  | 3.0 | 5.0 |  | 5.3 | 20 |
| 10-10 | 10.7 | 7.5 | 0.6 | 2.4 | 5.0 |  | 5.3 | 20 |
| 10-11 | 10.7 | 7.5 | 1.5 | 1.5 | 5.0 |  | 5.3 | 20 |
| 10-12 | 10.7 | 7.5 | 2.4 | 0.6 | 5.0 |  | 5.3 | 20 |
| 10-13 | 10.7 | 7.5 |  | 3.0 | 3.0 |  | 5.3 | 20 |
| 10-14 | 10.7 | 7.5 | 0.6 | 2.4 | 3.0 |  | 5.3 | 20 |
| 10-15 | 10.7 | 7.5 | 1.5 | 1.5 | 3.0 |  | 5.3 | 20 |
| 10-16 | 10.7 | 7.5 | 2.4 | 0.6 | 3.0 |  | 5.3 | 20 |
| 10-17 | 10.7 | 18.0 |  | 3.0 |  | 5.0 | 12.2 | 20 |
| 10-18 | 10.7 | 18.0 |  | 3.0 |  | 5.0 | 12.2 | 20 |

Velvetleaf (*Abutilon theophrasti*, ABUTH) and Japanese millet (*Echinochloa crus-galli*, ECHCF) plants were grown and treated by the standard procedures given above. Applications of spray compositions were made 19 days after planting ABUTH and 16 days after planting ECHCF, and evaluation of herbicidal inhibition was done 20 days after application.

Formulations B, C and J were applied as comparative treatments. Results, averaged for all replicates of each treatment, are shown in Table 10b.

TABLE 10b

| Concentrate composition | Glyphosate rate g a.e./ha | % Inhibition ABUTH | % Inhibition ECHCF |
|---|---|---|---|
| Formulation B | 100 | 3 | 10 |
|  | 200 | 27 | 20 |
|  | 300 | 48 | 40 |
|  | 400 | 68 | 43 |
| Formulation C | 100 | 20 | 50 |
|  | 200 | 50 | 67 |
|  | 300 | 73 | 83 |
|  | 400 | 82 | 99 |
| Formulation J | 100 | 22 | 30 |
|  | 200 | 50 | 57 |
|  | 300 | 65 | 72 |
|  | 400 | 88 | 98 |
| 10-01 | 100 | 17 | 40 |
|  | 200 | 55 | 72 |
|  | 300 | 67 | 75 |
|  | 400 | 80 | 63 |
| 10-02 | 100 | 12 | 33 |
|  | 200 | 53 | 47 |
|  | 300 | 72 | 67 |
|  | 400 | 77 | 70 |
| 10-03 | 100 | 0 | 15 |
|  | 200 | 0 | 33 |
|  | 300 | 15 | 43 |
|  | 400 | 40 | 47 |
| 10-04 | 100 | 2 | 12 |
|  | 200 | 13 | 27 |
|  | 300 | 23 | 33 |
|  | 400 | 27 | 52 |
| 10-05 | 100 | 8 | 43 |
|  | 200 | 43 | 40 |
|  | 300 | 73 | 53 |
|  | 400 | 73 | 90 |
| 10-06 | 100 | 10 | 37 |
|  | 200 | 33 | 75 |
|  | 300 | 63 | 63 |
|  | 400 | 83 | 87 |
| 10-07 | 100 | 5 | 33 |
|  | 200 | 33 | 60 |
|  | 300 | 57 | 80 |
|  | 400 | 75 | 75 |
| 10-08 | 100 | 27 | 37 |
|  | 200 | 33 | 75 |
|  | 300 | 50 | 95 |
|  | 400 | 73 | 99 |
| 10-09 | 112 | 5 | 33 |

TABLE 10b-continued

| Concentrate composition | Glyphosate rate g a.e./ha | % Inhibition ABUTH | % Inhibition ECHCF |
|---|---|---|---|
|  | 224 | 47 | 43 |
|  | 336 | 53 | 80 |
|  | 448 | 73 | 96 |
| 10-10 | 100 | 0 | 20 |
|  | 200 | 10 | 30 |
|  | 300 | 47 | 47 |
|  | 400 | 47 | 68 |
| 10-11 | 100 | 0 | 40 |
|  | 200 | #7 | 88 |
|  | 300 | 47 | 83 |
|  | 400 | 73 | 99 |
| 10-12 | 100 | 2 | 50 |
|  | 200 | 20 | 63 |
|  | 300 | 37 | 98 |
|  | 400 | 67 | 98 |
| 10-13 | 100 | 13 | 43 |
|  | 200 | 20 | 90 |
|  | 300 | 45 | 89 |
|  | 400 | 65 | 99 |
| 10-14 | 100 | 2 | 40 |
|  | 200 | 33 | 77 |
|  | 300 | 47 | 99 |
|  | 400 | 60 | 98 |
| 10-15 | 100 | 2 | 57 |
|  | 200 | 23 | 77 |
|  | 300 | 60 | 90 |
|  | 400 | 60 | 99 |
| 10-16 | 100 | 13 | 68 |
|  | 200 | 23 | 91 |
|  | 300 | 40 | 77 |
|  | 400 | 73 | 97 |
| 10-17 | 100 | 0 | 37 |
|  | 200 | 17 | 78 |
|  | 300 | 40 | 86 |
|  | 400 | 50 | 85 |
| 10-18 | 100 | 0 | 30 |
|  | 200 | 15 | 50 |
|  | 300 | 37 | 83 |
|  | 400 | 50 | 84 |

Several compositions containing lecithin and butyl stearate outperformed commercial standard Formulations C and J on ECHCF, but not on ABUTH, in this test.

Example 11

Aqueous concentrate compositions were prepared containing glyphosate IPA salt and excipient ingredients as shown in Table 11a. These compositions are water-in-oil-in-water multiple emulsions and were prepared by process (vi) described above, except that method of agitation was varied as indicated below.

TABLE 11a

| Conc. comp. | Glyphosate a.e. | Butyl stearate | Emuls. #1 | Emuls. #2 | Emulsifier #1 | Emulsifier #2 | Method of agitation (*) |
|---|---|---|---|---|---|---|---|
| 11-01 | 10.7 | 18.0 | 3.0 | 5.0 | Span 80/lecithin (1:4) | Tween 20 | |
| 11-02 | 10.7 | 18.0 | 3.0 | 5.0 | Span 80 | Tween 20 | |
| 11-03 | 10.7 | 18.0 | 3.0 | 5.0 | Span 80 | Tween 20 | |
| 11-04 | 10.7 | 18.0 | 3.0 | 5.0 | Span 80/lecithin (1:4) | Tween 20 | |
| 11-05 | 10.7 | 18.0 | 3.0 | 5.0 | Span 80/lecithin (1:4) | Tween 20 | |

TABLE 11a-continued

| | % w/w | | | | | | Method of agitation (*) |
|---|---|---|---|---|---|---|---|
| Conc. comp. | Glypho- sate a.e. | Butyl stearate | Emuls. #1 | Emuls. #2 | Emulsifier #1 | Emulsifier #2 | |
| 11-06 | 10.0 | 19.5 | 1.5 | 2.5 | Pluronic L-81 | Pluronic L-84 | |
| 11-07 | 10.0 | 19.9 | 1.3 | 3.8 | Pluronic L-81 | Pluronic L-84 | |
| 11-08 | 10.0 | 19.9 | 1.3 | 3.8 | Pluronic L-81 | Pluronic L-43 | |
| 11-09 | 10.0 | 19.9 | 1.3 | 3.8 | Pluronic L-81 | Pluronic L-84 | |
| 11-10 | 10.7 | 18.0 | 3.0 | 5.0 | Span 80 | Tween 20 | A |
| 11-11 | 10.7 | 18.0 | 3.0 | 5.0 | Span 80 | Tween 20 | B |
| 11-12 | 10.7 | 18.0 | 3.0 | 5.0 | Span 80 | Tween 20 | C |
| 11-13 | 10.7 | 18.0 | 3.0 | 5.0 | Span 80 | Tween 20 | D |
| 11-14 | 20.5 | 21.0 | 3.0 | 5.0 | Span 80 | Span 80/Tween 80 (45/55) | B |
| 11-15 | 13.8 | 18.0 | 3.0 | 5.0 | Span 80 | Span 80/Tween 80 (45/55) | A |
| 11-16 | 20.5 | 18.0 | 3.0 | 5.0 | Span 80 | Span 80/Tween 80 (45/55) | A |

(*) Method of agitation:
A Ultrasonic probe
B Silverson coarse
C Silverson fine
D Ultrasonic probe, hand shaking Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and ECHCF, and evaluation of herbicidal inhibition was done 21 days after application.

Formulations B, C and J were applied as comparative treatments. The test was run twice. Results of the two tests, averaged within tests for all replicates of each treatment, are shown in Tables 11b and 11c.

TABLE 11b

| | Glyphosate rate | % Inhibition | |
|---|---|---|---|
| Concentrate composition | g a.e./ha | ABUTH | ECHCF |
| Formulation B | 100 | 1 | 9 |
| | 200 | 9 | 25 |
| | 300 | 27 | 42 |
| | 400 | 44 | 53 |
| Formulation C | 100 | 10 | 64 |
| | 200 | 59 | 89 |
| | 300 | 87 | 96 |
| | 400 | 90 | 100 |
| Formulation J | 100 | 5 | 28 |
| | 200 | 51 | 72 |
| | 300 | 77 | 92 |
| | 400 | 90 | 99 |
| 11-01 | 100 | 27 | 37 |
| | 200 | 33 | 75 |
| | 300 | 50 | 95 |
| | 400 | 73 | 99 |
| 11-02 | 100 | 5 | 33 |
| | 200 | 47 | 43 |
| | 300 | 53 | 80 |
| | 400 | 73 | 96 |
| 11-03 | 100 | 13 | 43 |
| | 200 | 20 | 90 |
| | 300 | 45 | 89 |
| | 400 | 65 | 99 |
| 11-04 | 100 | 2 | 40 |
| | 200 | 33 | 77 |
| | 300 | 47 | 99 |
| | 400 | 60 | 98 |
| 11-05 | 100 | 2 | 57 |
| | 200 | 23 | 77 |
| | 300 | 60 | 90 |
| | 400 | 60 | 99 |
| 11-06 | 100 | 20 | 10 |
| | 200 | 53 | 37 |

TABLE 11b-continued

| | Glyphosate rate | % Inhibition | |
|---|---|---|---|
| Concentrate composition | g a.e./ha | ABUTH | ECHCF |
| | 300 | 68 | 60 |
| | 400 | 87 | 77 |
| 11-07 | 100 | 12 | 20 |
| | 200 | 63 | 30 |
| | 300 | 75 | 63 |
| | 400 | 89 | 77 |
| 11-08 | 100 | 12 | 20 |
| | 200 | 63 | 30 |
| | 300 | 75 | 63 |
| | 400 | 89 | 77 |
| 11-09 | 112 | 20 | 12 |
| | 224 | 47 | 40 |
| | 336 | 72 | 90 |
| | 448 | 78 | 78 |
| 11-10 | 100 | 0 | 5 |
| | 200 | 73 | 79 |
| | 300 | 85 | 99 |
| | 400 | 100 | 100 |
| 11-11 | 100 | 10 | 40 |
| | 200 | 60 | 77 |
| | 300 | 93 | 98 |
| | 400 | 98 | 98 |
| 11-12 | 100 | 67 | 23 |
| | 200 | 76 | 90 |
| | 300 | 98 | 97 |
| | 400 | 97 | 100 |
| 11-13 | 100 | 7 | 30 |
| | 200 | 75 | 57 |
| | 300 | 92 | 78 |
| | 400 | 98 | 100 |
| 11-14 | 100 | 25 | 25 |
| | 200 | 78 | 60 |
| | 300 | 90 | 83 |
| | 400 | 98 | 96 |
| 11-15 | 100 | 48 | 58 |
| | 200 | 83 | 96 |
| | 300 | 99 | 100 |
| | 400 | 100 | 100 |
| 11-16 | 100 | 69 | 35 |
| | 200 | 78 | 76 |
| | 300 | 91 | 97 |
| | 400 | 100 | 99 |

TABLE 11c

| Concentrate composition | Glyphosate rate g a.e./ha | % Inhibition ABUTH | % Inhibition ECHCF |
|---|---|---|---|
| Formulation B | 100 | 0 | 30 |
| | 200 | 8 | 50 |
| | 300 | 55 | 94 |
| | 400 | 71 | 97 |
| Formulation C | 100 | 24 | 97 |
| | 200 | 63 | 100 |
| | 300 | 80 | 100 |
| | 400 | 96 | 100 |
| Formulation J | 100 | 29 | 100 |
| | 200 | 55 | 99 |
| | 300 | 83 | 100 |
| | 400 | 97 | 100 |
| 11-01 | 100 | 4 | 82 |
| | 200 | 35 | 100 |
| | 300 | 60 | 99 |
| | 400 | 74 | 100 |
| 11-02 | 100 | 1 | 85 |
| | 200 | 35 | 100 |
| | 300 | 58 | 100 |
| | 400 | 78 | 100 |
| 11-03 | 100 | 0 | 63 |
| | 200 | 25 | 100 |
| | 300 | 58 | 100 |
| | 400 | 81 | 100 |
| 11-04 | 100 | 1 | 71 |
| | 200 | 15 | 98 |
| | 300 | 61 | 100 |
| | 400 | 75 | 100 |
| 11-05 | 100 | 30 | 81 |
| | 200 | 35 | 100 |
| | 300 | 50 | 100 |
| | 400 | 76 | 100 |
| 11-06 | 100 | 0 | 85 |
| | 200 | 55 | 99 |
| | 300 | 78 | 100 |
| | 400 | 85 | 100 |
| 11-07 | 100 | 9 | 90 |
| | 200 | 54 | 99 |
| | 300 | 74 | 100 |
| | 400 | 89 | 100 |
| 11-08 | 100 | 0 | 83 |
| | 200 | 30 | 100 |
| | 300 | 53 | 100 |
| | 400 | 79 | 100 |
| 11-09 | 112 | 8 | 94 |
| | 224 | 38 | 97 |
| | 336 | 75 | 100 |
| | 448 | 91 | 100 |
| 11-10 | 100 | 10 | 85 |
| | 200 | 50 | 96 |
| | 300 | 70 | 100 |
| | 400 | 89 | 100 |
| 11-11 | 100 | 19 | 93 |
| | 200 | 65 | 100 |
| | 300 | 75 | 100 |
| | 400 | 81 | 100 |
| 11-12 | 100 | 5 | 91 |
| | 200 | 58 | 99 |
| | 300 | 81 | 100 |
| | 400 | 79 | 100 |
| 11-13 | 100 | 8 | 89 |
| | 200 | 65 | 99 |
| | 300 | 76 | 100 |
| | 400 | 94 | 100 |
| 11-14 | 100 | 13 | 86 |
| | 200 | 33 | 98 |
| | 300 | 70 | 100 |
| | 400 | 83 | 100 |
| 11-15 | 100 | 20 | 95 |
| | 200 | 66 | 100 |
| | 300 | 73 | 100 |
| | 400 | 89 | 100 |
| 11-16 | 100 | 11 | 93 |
| | 200 | 60 | 100 |
| | 300 | 80 | 100 |
| | 400 | 78 | 100 |

Multiple emulsion compositions of this Example did not outperform the commercial standards.

Example 12

Aqueous concentrate compositions were prepared containing glyphosate IPA salt and excipient ingredients as shown in Table 12a. All concentrate compositions are water-in-oil-in-water multiple emulsions and were prepared by process (vi), using Span 80 as emulsifier #1 and Tween 20 as emulsifier #2. Compositions 12-04, 12-07, 12-09 and 12-11 were made using butyl stearate from four different suppliers.

TABLE 12a

| Conc. comp. | % w/w Glyphosate a.e. | Oil | Span 80 | Tween 20 | % in inner aq. phase Water | % in inner aq. phase Glyphosate | Type of oil |
|---|---|---|---|---|---|---|---|
| 12-01 | 10 | 18.0 | 3.0 | 5.0 | 12.1 | 20 | butyl stearate |
| 12-02 | 10 | 7.5 | 3.0 | 5.0 | 5.3 | 20 | butyl stearate |
| 12-03 | 10 | 7.5 | 3.0 | 10.0 | 5.7 | 20 | butyl stearate |
| 12-04 | 10 | 7.5 | 3.0 | 10.0 | 5.7 | 0 | butyl stearate |
| 12-05 | 10 | 7.5 | 3.0 | 10.0 | 5.7 | 0 | Exxate 700 |
| 12-06 | 10 | 7.5 | 3.0 | 10.0 | 5.7 | 0 | Exxate 1000 |
| 12-07 | 10 | 7.5 | 3.0 | 10.0 | 5.7 | 0 | butyl stearate |
| 12-08 | 10 | 7.5 | 3.0 | 10.0 | 5.7 | 0 | butyl oleate |
| 12-09 | 10 | 7.5 | 3.0 | 10.0 | 5.7 | 0 | butyl stearate |
| 12-10 | 10 | 7.5 | 3.0 | 10.0 | 5.7 | 0 | isopropyl myristate |
| 12-11 | 10 | 7.5 | 3.0 | 10.0 | 5.7 | 0 | butyl stearate |
| 12-12 | 10 | 7.5 | 3.0 | 10.0 | 5.7 | 0 | isopropyl palmitate |
| 12-13 | 10 | 7.5 | 3.0 | 10.0 | 5.7 | 0 | butyl laurate |
| 12-14 | 10 | 7.5 | 3.0 | 10.0 | 5.7 | 0 | methyl laurate |
| 12-15 | 10 | 7.5 | 3.0 | 10.0 | 5.7 | 0 | Exxol D-130 |

TABLE 12a-continued

| Conc. comp. | % w/w | | | | % in inner aq. phase | | Type of oil |
|---|---|---|---|---|---|---|---|
| | Glyphosate a.e. | Oil | Span 80 | Tween 20 | Water | Glyphosate | |
| 12-16 | 10 | 7.5 | 3.0 | 10.0 | 5.7 | 0 | Orchex 796 |
| 12-17 | 10 | 7.5 | 3.0 | 10.0 | 5.7 | 0 | methyl oleate |
| 12-18 | 10 | 7.5 | 3.0 | 10.0 | 5.7 | 0 | Isopar V |
| 12-19 | 10 | 7.5 | 3.0 | 10.0 | 5.7 | 0 | soybean oil |

Velvetleaf (*Abutilon theophrasti*, ABUTH) and Japanese millet (*Echinochloa crus-galli*, ECHCF) plants were grown and treated by the standard procedures given above. Applications of spray compositions were made 15 days after planting ABUTH and 15 days after planting ECHCF, and evaluation of herbicidal inhibition was done 21 days after application.

Formulations B and J were applied as comparative treatments. Results, averaged for all replicates of each treatment, are shown in Table 12b.

TABLE 12b

| Concentrate composition | Glyphosate rate g a.e./ha | % Inhibition | |
|---|---|---|---|
| | | ABUTH | ECHCF |
| Formulation B | 100 | 3 | 38 |
| | 200 | 35 | 89 |
| | 300 | 75 | 99 |
| | 400 | 85 | 98 |
| Formulation J | 100 | 10 | 35 |
| | 200 | 65 | 84 |
| | 300 | 87 | 100 |
| | 400 | 94 | 100 |
| 12-01 | 100 | 5 | 35 |
| | 200 | 55 | 75 |
| | 300 | 78 | 85 |
| | 400 | 88 | 98 |
| 12-02 | 100 | 0 | 35 |
| | 200 | 43 | 89 |
| | 300 | 82 | 98 |
| | 400 | 95 | 99 |
| 12-03 | 100 | 15 | 50 |
| | 200 | 63 | 95 |
| | 300 | 79 | 98 |
| | 400 | 97 | 100 |
| 12-04 | 100 | 4 | 45 |
| | 200 | 68 | 79 |
| | 300 | 90 | 93 |
| | 400 | 99 | 97 |
| 12-05 | 100 | 1 | 30 |
| | 200 | 40 | 70 |
| | 300 | 70 | 97 |
| | 400 | 89 | 100 |
| 12-06 | 100 | 3 | 35 |
| | 200 | 38 | 75 |
| | 300 | 70 | 92 |
| | 400 | 84 | 100 |
| 12-07 | 100 | 20 | 53 |
| | 200 | 76 | 96 |
| | 300 | 84 | 99 |
| | 400 | 95 | 99 |
| 12-08 | 100 | 5 | 25 |
| | 200 | 45 | 81 |
| | 300 | 79 | 94 |
| | 400 | 89 | 99 |
| 12-09 | 100 | 0 | 35 |
| | 200 | 58 | 96 |
| | 300 | 81 | 100 |
| | 400 | 89 | 100 |
| 12-10 | 100 | 15 | 8 |
| | 200 | 40 | 65 |
| | 300 | 68 | 84 |
| | 400 | 81 | 99 |
| 12-11 | 100 | 15 | 68 |
| | 200 | 53 | 83 |
| | 300 | 85 | 99 |
| | 400 | 94 | 100 |
| 12-12 | 100 | 18 | 28 |
| | 200 | 55 | 86 |
| | 300 | 78 | 85 |
| | 400 | 99 | 98 |
| 12-13 | 100 | 6 | 35 |
| | 200 | 48 | 83 |
| | 300 | 69 | 88 |
| | 400 | 81 | 97 |
| 12-14 | 100 | 13 | 30 |
| | 200 | 50 | 91 |
| | 300 | 78 | 99 |
| | 400 | 84 | 100 |
| 12-15 | 100 | 6 | 23 |
| | 200 | 35 | 87 |
| | 300 | 73 | 96 |
| | 400 | 86 | 96 |
| 12-16 | 100 | 8 | 38 |
| | 200 | 36 | 45 |
| | 300 | 70 | 99 |
| | 400 | 87 | 99 |
| 12-17 | 100 | 8 | 75 |
| | 200 | 40 | 96 |
| | 300 | 69 | 98 |
| | 400 | 84 | 98 |
| 12-18 | 100 | 3 | 38 |
| | 200 | 25 | 87 |
| | 300 | 48 | 94 |
| | 400 | 70 | 91 |
| 12-19 | 100 | 0 | 40 |
| | 200 | 20 | 97 |
| | 300 | 64 | 100 |
| | 400 | 78 | 100 |

Compositions of this Example where the oil was not a fatty acid ester (12-05, 12-06, 12-15, 12-16, 12-18, 12-19) were less herbicidally effective than those containing a fatty acid ester.

Example 13

Aqueous concentrate compositions were prepared containing glyphosate IPA salt and excipient ingredients as shown in Table 13a. All concentrate compositions are water-in-oil-in-water multiple emulsions and were prepared by process (vi), using Span 80 as emulsifier #1.

TABLE 13a

| Conc. comp. | Glyphosate a.e. | Butyl stearate | Span 80 | Emulsifier #2 | % in inner aq. phase Water | % in inner aq. phase Glyphosate | Emulsifier #2 |
|---|---|---|---|---|---|---|---|
| 13-01 | 10 | 18.0 | 3.0 | 5.0 | 12.1 | 20 | Tween 20 |
| 13-02 | 10 | 7.5 | 3.0 | 5.0 | 5.3 | 20 | Tween 20 |
| 13-03 | 10 | 7.5 | 3.0 | 10.0 | 5.7 | 0 | Tween 20 |
| 13-04 | 10 | 7.5 | 3.0 | 10.0 | 5.7 | 0 | Tween 40 |
| 13-05 | 10 | 7.5 | 3.0 | 10.0 | 5.7 | 0 | Neodol 25-9 |
| 13-06 | 10 | 7.5 | 3.0 | 10.0 | 5.7 | 0 | Neodol 25-12 |
| 13-07 | 10 | 7.5 | 3.0 | 10.0 | 5.7 | 0 | Tergitol 15-S-20 |
| 13-08 | 10 | 7.5 | 3.0 | 10.0 | 5.7 | 0 | Myrj 52 |
| 13-09 | 10 | 7.5 | 3.0 | 10.0 | 5.7 | 0 | Myrj 59 |
| 13-10 | 10 | 7.5 | 3.0 | 10.0 | 5.7 | 0 | Toximul 8240 |
| 13-11 | 15 | 7.5 | 3.0 | 10.0 | 5.7 | 0 | Tween 20 |
| 13-12 | 15 | 7.5 | 3.0 | 10.0 | 5.7 | 0 | Tween 40 |
| 13-13 | 15 | 7.5 | 3.0 | 10.0 | 5.7 | 0 | Neodol 25-9 |
| 13-14 | 15 | 7.5 | 3.0 | 10.0 | 5.7 | 0 | Neodol 25-12 |
| 13-15 | 15 | 7.5 | 3.0 | 10.0 | 5.7 | 0 | Tergitol 15-S-20 |
| 13-16 | 10 | 7.5 | 3.0 | 10.0 | 5.7 | 0 | Tween 80 |
| 13-17 | 10 | 7.5 | 3.0 | 10.0 | 5.7 | 0 | Tergitol 15-S-15 |
| 13-18 | 10 | 7.5 | 3.0 | 10.0 | 5.7 | 0 | Neodol 25-20 |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and 15 days after planting ECHCF, and evaluation of herbicidal inhibition was done 21 days after application.

Formulations B, C and J were applied as comparative treatments. Results, averaged for all replicates of each treatment, are shown in Table 13b.

TABLE 13b

| Concentrate composition | Glyphosate rate g a.e./ha | % Inhibition ABUTH | % Inhibition ECHCF |
|---|---|---|---|
| Formulation B | 100 | 3 | 28 |
| | 200 | 40 | 50 |
| | 300 | 75 | 83 |
| | 400 | 88 | 93 |
| Formulation C | 100 | 5 | 40 |
| | 200 | 51 | 94 |
| | 300 | 80 | 100 |
| | 400 | 95 | 100 |
| Formulation J | 100 | 25 | 79 |
| | 200 | 40 | 83 |
| | 300 | 79 | 98 |
| | 400 | 86 | 100 |
| 13-01 | 100 | 20 | 35 |
| | 200 | 53 | 45 |
| | 300 | 95 | 89 |
| | 400 | 99 | 81 |
| 13-02 | 100 | 9 | 30 |
| | 200 | 35 | 58 |
| | 300 | 79 | 75 |
| | 400 | 86 | 85 |
| 13-03 | 100 | 16 | 30 |
| | 200 | 56 | 66 |
| | 300 | 83 | 85 |
| | 400 | 88 | 95 |
| 13-04 | 100 | 33 | 40 |
| | 200 | 64 | 64 |
| | 300 | 81 | 91 |
| | 400 | 88 | 95 |
| 13-05 | 100 | 18 | 33 |
| | 200 | 40 | 79 |
| | 300 | 53 | 90 |
| | 400 | 79 | 96 |
| 13-06 | 100 | 25 | 40 |
| | 200 | 53 | 76 |
| | 300 | 83 | 93 |
| | 400 | 86 | 100 |
| 13-07 | 100 | 11 | 35 |
| | 200 | 44 | 84 |
| | 300 | 78 | 99 |
| | 400 | 92 | 100 |
| 13-08 | 100 | 23 | 60 |
| | 200 | 65 | 94 |
| | 300 | 83 | 99 |
| | 400 | 89 | 99 |
| 13-09 | 100 | 25 | 40 |
| | 200 | 30 | 69 |
| | 300 | 53 | 91 |
| | 400 | 66 | 99 |
| 13-10 | 100 | 5 | 35 |
| | 200 | 43 | 75 |
| | 300 | 65 | 94 |
| | 400 | 76 | 99 |
| 13-11 | 100 | 10 | 38 |
| | 200 | 48 | 84 |
| | 300 | 78 | 99 |
| | 400 | 81 | 100 |
| 13-12 | 100 | 10 | 45 |
| | 200 | 33 | 89 |
| | 300 | 70 | 98 |
| | 400 | 83 | 100 |
| 13-13 | 100 | 0 | 35 |
| | 200 | 25 | 68 |
| | 300 | 45 | 93 |
| | 400 | 63 | 96 |
| 13-14 | 100 | 15 | 45 |
| | 200 | 35 | 92 |
| | 300 | 65 | 100 |
| | 400 | 76 | 99 |
| 13-15 | 100 | 8 | 35 |
| | 200 | 60 | 86 |
| | 300 | 70 | 100 |
| | 400 | 78 | 100 |
| 13-16 | 100 | 16 | 55 |
| | 200 | 56 | 88 |
| | 300 | 82 | 100 |

TABLE 13b-continued

| Concentrate composition | Glyphosate rate g a.e./ha | % Inhibition ABUTH | ECHCF |
|---|---|---|---|
|  | 400 | 98 | 100 |
| 13-17 | 100 | 30 | 55 |
|  | 200 | 58 | 86 |
|  | 300 | 83 | 96 |
|  | 400 | 94 | 100 |
| 13-18 | 100 | 33 | 60 |
|  | 200 | 71 | 95 |
|  | 300 | 86 | 100 |
|  | 400 | 100 | 100 |

Among the most effective compositions in this test were 13-08, 13-16, 13-17 and 13-18. The choice of emulsifier #2 had a significant effect on performance.

Example 14

Aqueous concentrate compositions were prepared containing glyphosate IPA salt and excipient ingredients as shown in Table 14a. Concentrate compositions 14-01 to 14-17 are water-in-oil-in-water multiple emulsions and were prepared by process (vi), using Tween 20 as emulsifier #2. Concentrate composition 14-18 is an oil-in-water emulsion and was prepared by process (vii).

TABLE 14a

| Conc. comp. | Glyphosate a.e. | Butyl stearate | Emulsifier #1 | Tween 20 | % in inner aq. phase Water | Glyphosate | Emulsifier #1 |
|---|---|---|---|---|---|---|---|
| 14-01 | 10 | 18.0 | 3.0 | 5.0 | 12.0 | 20 | Span 80 |
| 14-02 | 10 | 7.5 | 3.0 | 5.0 | 5.3 | 20 | Span 80 |
| 14-03 | 10 | 7.5 | 3.0 | 10.0 | 5.7 | 20 | Span 80 |
| 14-04 | 10 | 7.5 | 3.0 | 10.0 | 5.7 | 0 | Span 80 |
| 14-05 | 10 | 7.5 | 3.0 | 10.0 | 5.7 | 0 | Emid 6545 |
| 14-06 | 10 | 7.5 | 3.0 | 10.0 | 5.7 | 0 | Emerest 2421 |
| 14-07 | 10 | 7.5 | 3.0 | 10.0 | 5.7 | 0 | oleth-2 |
| 14-08 | 10 | 7.5 | 3.0 | 10.0 | 5.7 | 0 | Span 65 |
| 14-09 | 10 | 7.5 | 3.0 | 10.0 | 5.7 | 0 | Span 85 |
| 14-10 | 10 | 7.5 | 3.0 | 10.0 | 5.7 | 0 | Span 60 |
| 14-11 | 10 | 7.5 | 3.0 | 10.0 | 5.7 | 0 | Agrimer AL-30 |
| 14-12 | 10 | 7.5 | 3.0 | 10.0 | 5.7 | 0 | Agrimer AL-25 |
| 14-13 | 10 | 7.5 | 3.0 | 10.0 | 5.7 | 0 | Surfynol 104 |
| 14-14 | 10 | 7.5 | 3.0 | 10.0 | 5.7 | 0 | Neodol 25-3 |
| 14-15 | 10 | 7.5 | 3.0 | 10.0 | 5.7 | 0 | Neodol 91-2.5 |
| 14-16 | 10 | 7.5 | 3.0 | 10.0 | 5.7 | 0 | Ethomeen C/12 |
| 14-17 | 10 | 7.5 | 3.0 | 10.0 | 5.7 | 0 | Ethomeen T/12 |
| 14-18 | 10 | 7.5 |  | 10.0 |  |  | none |

Velvetleaf (Abutilon theophrasti, ABUTH) and Japanese millet (Echinochloa crus-galli, ECHCF) plants were grown and treated by the standard procedures given above. Applications of spray compositions were made 19 days after planting ABUTH and 22 days after planting ECHCF, and evaluation of herbicidal inhibition was done 21 days after application.

Formulations B, C and J were applied as comparative treatments. Results, averaged for all replicates of each treatment, are shown in Table 14b.

TABLE 14b

| Concentrate composition | Glyphosate rate g a.e./ha | % Inhibition ABUTH | ECHCF |
|---|---|---|---|
| Formulation B | 100 | 18 | 50 |
|  | 200 | 18 | 63 |
|  | 300 | 53 | 75 |
|  | 400 | 43 | 84 |
| Formulation C | 100 | 25 | 85 |
|  | 200 | 48 | 96 |
|  | 300 | 78 | 100 |
|  | 400 | 86 | 100 |
| Formulation J | 100 | 35 | 92 |
|  | 200 | 49 | 99 |
|  | 300 | 78 | 99 |
|  | 400 | 83 | 99 |
| 14-01 | 100 | 43 | 63 |
|  | 200 | 65 | 88 |
|  | 300 | 85 | 93 |
|  | 400 | 85 | 100 |
| 14-02 | 100 | 35 | 70 |
|  | 200 | 45 | 76 |
|  | 300 | 83 | 99 |
|  | 400 | 94 | 100 |
| 14-03 | 100 | 50 | 74 |
|  | 200 | 71 | 97 |
|  | 300 | 88 | 98 |
|  | 400 | 89 | 99 |
| 14-04 | 100 | 64 | 75 |
|  | 200 | 75 | 86 |

TABLE 14b-continued

| Concentrate composition | Glyphosate rate g a.e./ha | % Inhibition ABUTH | ECHCF |
|---|---|---|---|
|  | 300 | 93 | 99 |
|  | 400 | 93 | 99 |
| 14-05 | 100 | 65 | 89 |
|  | 200 | 79 | 94 |
|  | 300 | 93 | 100 |
|  | 400 | 94 | 100 |
| 14-06 | 100 | 45 | 75 |
|  | 200 | 75 | 89 |

TABLE 14b-continued

| Concentrate composition | Glyphosate rate g a.e./ha | % Inhibition ABUTH | % Inhibition ECHCF |
|---|---|---|---|
|  | 300 | 85 | 97 |
|  | 400 | 83 | 99 |
| 14-07 | 100 | 16 | 45 |
|  | 200 | 59 | 83 |
|  | 300 | 80 | 90 |
|  | 400 | 90 | 99 |
| 14-08 | 100 | 43 | 84 |
|  | 200 | 70 | 97 |
|  | 300 | 84 | 93 |
|  | 400 | 84 | 100 |
| 14-09 | 100 | 58 | 60 |
|  | 200 | 70 | 89 |
|  | 300 | 80 | 97 |
|  | 400 | 89 | 99 |
| 14-10 | 100 | 50 | 66 |
|  | 200 | 74 | 94 |
|  | 300 | 92 | 100 |
|  | 400 | 97 | 100 |
| 14-11 | 100 | 45 | 73 |
|  | 200 | 70 | 90 |
|  | 300 | 83 | 100 |
|  | 400 | 83 | 100 |
| 14-12 | 100 | missing | missing |
|  | 200 | missing | missing |
|  | 300 | missing | missing |
|  | 400 | missing | missing |
| 14-13 | 100 | 80 | 96 |
|  | 200 | 89 | 99 |
|  | 300 | 96 | 100 |
|  | 400 | 99 | 100 |
| 14-14 | 100 | 35 | 65 |
|  | 200 | 75 | 98 |
|  | 300 | 95 | 99 |
|  | 400 | 88 | 99 |
| 14-15 | 100 | 51 | 85 |
|  | 200 | 55 | 83 |
|  | 300 | 83 | 96 |
|  | 400 | 81 | 98 |
| 14-16 | 100 | 55 | 94 |
|  | 200 | 65 | 99 |
|  | 300 | 83 | 99 |
|  | 400 | 84 | 100 |
| 14-17 | 100 | 75 | 99 |
|  | 200 | 35 | 97 |
|  | 300 | 92 | 100 |
|  | 400 | 81 | 99 |
| 14-18 | 100 | 45 | 90 |
|  | 200 | 69 | 75 |
|  | 300 | 84 | 100 |
|  | 400 | 94 | 100 |

Most compositions of this Example outperformed commercial standard Formulations C and J on ABUTH. Composition 14-13, using Surfynol 104 as emulsifier #1, was especially efficacious.

Example 15

Aqueous concentrate compositions were prepared containing glyphosate IPA salt and excipient ingredients as shown in Table 15a. All concentrate compositions are water-in-oil-in-water multiple emulsions and were prepared by process (vi).

TABLE 15a

| Conc. comp. | Glyphosate a.e. | Butyl stearate | Emulsifier #1 (w/w) | Emulsifier #2 (w/w) | % in inner aq. phase Water | % in inner aq. phase Glyphosate | Emulsifier #1 | Emulsifier #2 |
|---|---|---|---|---|---|---|---|---|
| 15-01 | 10 | 18.0 | 3.0 | 5.0 | 12.1 | 20 | Span 80 | Tween 20 |
| 15-02 | 10 | 7.5 | 3.0 | 5.0 | 5.3 | 20 | Span 80 | Tween 20 |
| 15-03 | 10 | 7.5 | 3.0 | 10.0 | 5.7 | 20 | Span 80 | Tween 20 |
| 15-04 | 10 | 7.5 | 3.0 | 10.0 | 5.7 | 0 | Span 80 | Tween 20 |
| 15-05 | 10 | 7.5 | 3.0 | 10.0 | 5.7 | 0 | oleth-2 | Neodol 25-12 |
| 15-06 | 10 | 7.5 | 3.0 | 10.0 | 5.7 | 0 | oleth-2 | Neodol 25-20 |
| 15-07 | 10 | 7.5 | 3.0 | 10.0 | 5.7 | 0 | oleth-2 | Tween 20 |
| 15-08 | 10 | 7.5 | 3.0 | 10.0 | 5.7 | 0 | oleth-2 | Tween 40 |
| 15-09 | 10 | 7.5 | 3.0 | 10.0 | 5.7 | 0 | oleth-2 | Tween 80 |
| 15-10 | 10 | 7.5 | 3.0 | 10.0 | 5.7 | 0 | oleth-2 | Tergitol 15-S-15 |
| 15-11 | 10 | 7.5 | 3.0 | 10.0 | 5.7 | 0 | oleth-2 | Tergitol 15-S-20 |
| 15-12 | 10 | 7.5 | 3.0 | 10.0 | 5.7 | 0 | Span 60 | Neodol 25-12 |
| 15-13 | 10 | 7.5 | 3.0 | 10.0 | 5.7 | 0 | Span 60 | Neodol 25-20 |
| 15-14 | 10 | 7.5 | 3.0 | 10.0 | 5.7 | 0 | Span 60 | Tween 20 |
| 15-15 | 10 | 7.5 | 3.0 | 10.0 | 5.7 | 0 | Span 60 | Tween 40 |
| 15-16 | 10 | 7.5 | 3.0 | 10.0 | 5.7 | 0 | Span 60 | Tween 80 |
| 15-17 | 10 | 7.5 | 3.0 | 10.0 | 5.7 | 0 | Span 60 | Tergitol 15-S-15 |
| 15-18 | 10 | 7.5 | 3.0 | 10.0 | 5.7 | 0 | Span 60 | Tergitol 15-S-20 |

Velvetleaf (*Abutilon theophrasti*, ABUTH) and Japanese millet (*Echinochloa crus-galli*, ECHCF) plants were grown and treated by the standard procedures given above. Applications of spray compositions were made 19 days after planting ABUTH and 22 days after planting ECHCF, and evaluation of herbicidal inhibition was done 20 days after application.

Formulations B, C and J were applied as comparative treatments. Results, averaged for all replicates of each treatment, are shown in Table 15b.

TABLE 15b

| Concentrate composition | Glyphosate rate g a.e./ha | % Inhibition ABUTH | % Inhibition ECHCF |
|---|---|---|---|
| Formulation B | 100 | 1 | 18 |
| | 200 | 20 | 45 |
| | 300 | 55 | 89 |
| | 400 | 55 | 89 |
| Formulation C | 100 | 8 | 85 |
| | 200 | 35 | 89 |
| | 300 | 76 | 95 |
| | 400 | 85 | 98 |
| Formulation J | 100 | 6 | 80 |
| | 200 | 30 | 80 |
| | 300 | 71 | 97 |
| | 400 | 75 | 97 |
| 15-01 | 100 | 35 | 65 |
| | 200 | 65 | 88 |
| | 300 | 78 | 75 |
| | 400 | 89 | 89 |
| 15-02 | 100 | 14 | 35 |
| | 200 | 40 | 64 |
| | 300 | 83 | 65 |
| | 400 | 58 | 79 |
| 15-03 | 100 | 28 | 38 |
| | 200 | 73 | 65 |
| | 300 | 73 | 80 |
| | 400 | 91 | 85 |
| 15-04 | 100 | 20 | 55 |
| | 200 | 65 | 60 |
| | 300 | 78 | 87 |
| | 400 | 88 | 95 |
| 15-05 | 100 | 38 | 45 |
| | 200 | 55 | 65 |
| | 300 | 81 | 84 |
| | 400 | 91 | 83 |
| 15-06 | 100 | 56 | 43 |
| | 200 | 68 | 73 |
| | 300 | 84 | 80 |
| | 400 | 94 | 80 |
| 15-07 | 100 | 44 | 70 |
| | 200 | 50 | 91 |
| | 300 | 78 | 95 |
| | 400 | 84 | 99 |
| 15-08 | 100 | 40 | 48 |
| | 200 | 70 | 85 |
| | 300 | 75 | 85 |
| | 400 | 84 | 97 |

TABLE 15b-continued

| Concentrate composition | Glyphosate rate g a.e./ha | % Inhibition ABUTH | % Inhibition ECHCF |
|---|---|---|---|
| 15-09 | 100 | 53 | 65 |
| | 200 | 73 | 66 |
| | 300 | 83 | 75 |
| | 400 | 84 | 91 |
| 15-10 | 100 | 20 | 35 |
| | 200 | 60 | 55 |
| | 300 | 76 | 86 |
| | 400 | 84 | 83 |
| 15-11 | 100 | 35 | 54 |
| | 200 | 70 | 55 |
| | 300 | 83 | 79 |
| | 400 | 95 | 86 |
| 15-12 | 100 | 35 | 55 |
| | 200 | 66 | 74 |
| | 300 | 79 | 84 |
| | 400 | 95 | 96 |
| 15-13 | 100 | 38 | 60 |
| | 200 | 74 | 66 |
| | 300 | 78 | 91 |
| | 400 | 93 | 90 |
| 15-14 | 100 | 34 | 43 |
| | 200 | 88 | 69 |
| | 300 | 78 | 92 |
| | 400 | 95 | 92 |
| 15-15 | 100 | 11 | 25 |
| | 200 | 45 | 58 |
| | 300 | 53 | 81 |
| | 400 | 83 | 87 |
| 15-16 | 100 | 30 | 53 |
| | 200 | 85 | 92 |
| | 300 | 79 | 89 |
| | 400 | 97 | 100 |
| 15-17 | 100 | 28 | 48 |
| | 200 | 66 | 78 |
| | 300 | 74 | 78 |
| | 400 | 88 | 86 |
| 15-18 | 100 | 18 | 40 |
| | 200 | 63 | 83 |
| | 300 | 76 | 79 |
| | 400 | 81 | 95 |

Several compositions of this Example outperformed commercial standard Formulations C and J on ABUTH.

Example 16

Aqueous concentrate compositions were prepared containing glyphosate IPA salt and excipient ingredients as shown in Table 16a. All concentrate compositions are water-in-oil-in-water multiple emulsions and were prepared by process (vi).

TABLE 16a

| | | % w/w | | | | | | |
|---|---|---|---|---|---|---|---|---|
| Conc. comp. | Glypho-sate a.e. | Butyl stearate | Emulsifier #1 | Emulsifier #2 | % in inner aq. phase Water | % in inner aq. phase Glyphosate | Emulsifier #1 | Emulsifier #2 |
| 16-01 | 10 | 18.0 | 3.0 | 5.0 | 13.8 | 20 | Span 80 | Tween 20 |
| 16-02 | 10 | 7.5 | 3.0 | 5.0 | 5.6 | 20 | Span 80 | Tween 20 |
| 16-03 | 10 | 6.0 | 3.0 | 10.0 | 8.0 | 0 | Emerest 2421 | Neodol 25-12 |
| 16-04 | 10 | 7.5 | 3.0 | 10.0 | 6.0 | 0 | Emerest 2421 | Neodol 25-12 |
| 16-05 | 10 | 9.0 | 3.0 | 10.0 | 4.0 | 0 | Emerest 2421 | Neodol 25-12 |
| 16-06 | 10 | 6.0 | 3.0 | 10.0 | 8.0 | 0 | Emerest 2421 | Neodol 25-20 |

TABLE 16a-continued

| | % w/w | | | | | | | |
|---|---|---|---|---|---|---|---|---|
| Conc. comp. | Glypho-sate a.e. | Butyl stearate | Emulsifier #1 | Emulsifier #2 | % in inner aq. phase Water | % in inner aq. phase Glyphosate | Emulsifier #1 | Emulsifier #2 |
| 16-07 | 10 | 7.5 | 3.0 | 10.0 | 6.0 | 0 | Emerest 2421 | Neodol 25-20 |
| 16-08 | 10 | 9.0 | 3.0 | 10.0 | 4.0 | 0 | Emerest 2421 | Neodol 25-20 |
| 16-09 | 10 | 6.0 | 3.0 | 10.0 | 8.0 | 0 | Emerest 2421 | Tergitol 15-S-15 |
| 16-10 | 10 | 7.5 | 3.0 | 10.0 | 6.0 | 0 | Emerest 2421 | Tergitol 15-S-15 |
| 16-11 | 10 | 9.0 | 3.0 | 10.0 | 4.0 | 0 | Emerest 2421 | Tergitol 15-S-15 |
| 16-12 | 10 | 6.0 | 3.0 | 10.0 | 8.0 | 0 | Neodol 25-3 | Neodol 25-12 |
| 16-13 | 10 | 7.5 | 3.0 | 10.0 | 6.0 | 0 | Neodol 25-3 | Neodol 25-12 |
| 16-14 | 10 | 9.0 | 3.0 | 10.0 | 4.0 | 0 | Neodol 25-3 | Neodol 25-12 |
| 16-15 | 10 | 6.0 | 3.0 | 10.0 | 8.0 | 0 | Neodol 25-3 | Neodol 25-20 |
| 16-16 | 10 | 7.5 | 3.0 | 10.0 | 6.0 | 0 | Neodol 25-3 | Neodol 25-20 |
| 16-17 | 10 | 9.0 | 3.0 | 10.0 | 4.0 | 0 | Neodol 25-3 | Neodol 25-20 |
| 16-18 | 10 | 6.0 | 3.0 | 10.0 | 8.0 | 0 | Neodol 25-3 | Tergitol 15-S-15 |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and 18 days after planting ECHCF, and evaluation of herbicidal inhibition was done 19 days after application.

Formulations B, C and J were applied as comparative treatments. Results, averaged for all replicates of each treatment, are shown in Table 16b.

TABLE 16b

| Concentrate composition | Glyphosate rate g a.e./ha | % Inhibition ABUTH | % Inhibition ECHCF |
|---|---|---|---|
| Formulation B | 100 | 30 | 53 |
| | 200 | 76 | 73 |
| | 300 | 78 | 84 |
| | 400 | 80 | 89 |
| Formulation C | 100 | 5 | 60 |
| | 200 | 69 | 85 |
| | 300 | 78 | 94 |
| | 400 | 96 | 99 |
| Formulation J | 100 | 38 | 55 |
| | 200 | 73 | 91 |
| | 300 | 79 | 98 |
| | 400 | 93 | 100 |
| 16-01 | 100 | 5 | 40 |
| | 200 | 43 | 53 |
| | 300 | 86 | 69 |
| | 400 | 93 | 79 |
| 16-02 | 100 | 10 | 40 |
| | 200 | 48 | 53 |
| | 300 | 71 | 71 |
| | 400 | 89 | 68 |
| 16-03 | 100 | 14 | 45 |
| | 200 | 60 | 63 |
| | 300 | 75 | 76 |
| | 400 | 78 | 80 |
| 16-04 | 100 | 50 | 35 |
| | 200 | 69 | 53 |
| | 300 | 79 | 79 |
| | 400 | 90 | 78 |
| 16-05 | 100 | 35 | 45 |
| | 200 | 76 | 78 |
| | 300 | 80 | 95 |
| | 400 | 95 | 99 |
| 16-06 | 100 | 23 | 55 |
| | 200 | 70 | 76 |
| | 300 | 80 | 95 |
| | 400 | 94 | 98 |
| 16-07 | 100 | 35 | 66 |
| | 200 | 74 | 93 |
| | 300 | 83 | 95 |
| | 400 | 96 | 99 |
| 16-08 | 100 | 35 | 40 |
| | 200 | 71 | 83 |
| | 300 | 81 | 97 |
| | 400 | 93 | 99 |
| 16-09 | 100 | 45 | 33 |
| | 200 | 63 | 74 |
| | 300 | 78 | 85 |
| | 400 | 95 | 85 |
| 16-10 | 100 | 20 | 35 |
| | 200 | 71 | 55 |
| | 300 | 78 | 83 |
| | 400 | 85 | 88 |
| 16-11 | 100 | 23 | 40 |
| | 200 | 66 | 63 |
| | 300 | 75 | 79 |
| | 400 | 86 | 87 |
| 16-12 | 100 | 20 | 40 |
| | 200 | 66 | 58 |
| | 300 | 78 | 70 |
| | 400 | 93 | 93 |
| 16-13 | 100 | 20 | 71 |
| | 200 | 69 | 75 |
| | 300 | 78 | 97 |
| | 400 | 86 | 97 |
| 16-14 | 100 | 18 | 45 |
| | 200 | 73 | 80 |
| | 300 | 83 | 92 |
| | 400 | 90 | 97 |
| 16-15 | 100 | 23 | 45 |
| | 200 | 71 | 78 |
| | 300 | 80 | 98 |
| | 400 | 91 | 100 |
| 16-16 | 100 | 25 | 73 |
| | 200 | 74 | 81 |
| | 300 | 99 | 91 |
| | 400 | 97 | 100 |
| 16-17 | 100 | 38 | 50 |
| | 200 | 76 | 83 |
| | 300 | 90 | 85 |
| | 400 | 98 | 89 |
| 16-18 | 100 | 23 | 40 |
| | 200 | 61 | 79 |
| | 300 | 83 | 93 |
| | 400 | 88 | 90 |

None of the multiple emulsion compositions of this Example outperformed both commercial standards in this study.

Example 17

Aqueous concentrate compositions were prepared containing glyphosate IPA salt and excipient ingredients as shown in Table 17a. All are water-in-oil-in-water multiple emulsions and were prepared by process (vi), using Span 80 as emulsifier #1. Different mixing devices were used in making the water-in-oil emulsion and the finished multiple emulsion as indicated in the column headed "Process".

TABLE 17a

| Conc. comp. | Glyphosate a.e. | Butyl stearate | Span 80 | Emulsifier #2 | Emulsifier #2 | % in inner aq. phase Water | % in inner aq. phase Glyphosate | Process (*) |
|---|---|---|---|---|---|---|---|---|
| 17-01 | 10.7 | 18.0 | 3.0 | 5.0 | Tween 20 | 13.8 | 30 | A |
| 17-02 | 10.7 | 18.0 | 3.0 | 5.0 | Tween 20 | 13.8 | 30 | B |
| 17-03 | 10.7 | 18.0 | 3.0 | 5.0 | Tween 20 | 13.8 | 30 | C |
| 17-04 | 10.7 | 18.0 | 3.0 | 5.0 | Tween 20 | 13.8 | 30 | D |
| 17-05 | 10.7 | 18.0 | 3.0 | 5.0 | Tween 20 | 13.8 | 30 | E |
| 17-06 | 6.9 | 18.0 | 3.0 | 5.0 | Span 80/Tween 80 (45/55) | 13.8 | 0 | A |
| 17-07 | 13.8 | 18.0 | 3.0 | 5.0 | Span 80/Tween 80 (45/55) | 13.8 | 0 | A |
| 17-08 | 20.5 | 18.0 | 3.0 | 5.0 | Span 80/Tween 80 (45/55) | 13.8 | 0 | A |
| 17-09 | 20.5 | 24.0 | 3.0 | 5.0 | Span 80/Tween 80 (45/55) | 4.6 | 0 | C |
| 17-10 | 10.7 | 18.0 | 3.0 | 5.0 | Tween 20 | 13.8 | 20 | A |
| 17-11 | 10.0 | 18.0 | 3.0 | 12.0 | Tween 20 | 15.5 | 20 | A |

| (*) Process: | W/O preparation | W/O/W preparation |
|---|---|---|
| A | Ultrasonic probe | Ultrasonic probe |
| B | Turrax medium speed | Turrax low speed |
| C | Silverson coarse | Silverson coarse |
| D | Silverson fine | Silverson fine |
| E | Silverson fine | Silverson coarse |

Velvetleaf (*Abutilon theophrasti*, ABUTH) and Japanese millet (*Echinochloa crus-galli*, ECHCF) plants were grown and treated by the standard procedures given above. Applications of spray compositions were made 20 days after planting ABUTH and 22 days after planting ECHCF, and evaluation of herbicidal inhibition was done 20 days after application. Results, averaged for all replicates of each treatment, are shown in Table 17b.

TABLE 17b

| Concentrate composition | Glyphosate rate g a.e./ha | % Inhibition ABUTH | % Inhibition ECHCF |
|---|---|---|---|
| Formulation B | 100 | 23 | 83 |
| | 200 | 60 | 93 |
| | 300 | 48 | 99 |
| | 400 | 75 | 97 |
| Formulation C | 100 | 45 | 94 |
| | 200 | 71 | 93 |
| | 300 | 88 | 99 |
| | 400 | 100 | 100 |
| Formulation J | 100 | 10 | 89 |
| | 200 | 73 | 93 |
| | 300 | 78 | 100 |
| | 400 | 96 | 98 |
| 17-01 | 100 | 25 | 68 |
| | 200 | 65 | 86 |
| | 300 | 80 | 98 |
| | 400 | 97 | 99 |
| 17-02 | 100 | 45 | 84 |
| | 200 | 70 | 90 |
| | 300 | 78 | 100 |
| | 400 | 98 | 100 |
| 17-03 | 100 | 63 | 79 |
| | 200 | 78 | 95 |
| | 300 | 83 | 100 |
| | 400 | 97 | 100 |
| 17-04 | 100 | 65 | 86 |
| | 200 | 70 | 88 |
| | 300 | 84 | 96 |
| | 400 | 97 | 100 |
| 17-05 | 100 | 43 | 84 |
| | 200 | 76 | 85 |
| | 300 | 94 | 98 |
| | 400 | 92 | 100 |
| 17-06 | 100 | 73 | 83 |
| | 200 | 85 | 98 |
| | 300 | 96 | 99 |
| | 400 | 99 | 98 |
| 17-07 | 100 | 48 | 81 |
| | 200 | 78 | 95 |
| | 300 | 93 | 98 |
| | 400 | 100 | 100 |
| 17-08 | 100 | 60 | 75 |
| | 200 | 74 | 97 |
| | 300 | 88 | 93 |
| | 400 | 97 | 98 |
| 17-09 | 100 | 51 | 63 |
| | 200 | 68 | 89 |
| | 300 | 79 | 89 |
| | 400 | 91 | 98 |
| 17-10 | 100 | 24 | 53 |

TABLE 17b-continued

| Concentrate composition | Glyphosate rate g a.e./ha | % Inhibition ABUTH | % Inhibition ECHCF |
|---|---|---|---|
|  | 200 | 68 | 89 |
|  | 300 | 73 | 83 |
|  | 400 | 95 | 91 |
| 17-11 | 100 | 33 | 58 |
|  | 200 | 70 | 94 |
|  | 300 | 84 | 82 |
|  | 400 | 93 | 93 |

The choice of mixing device in preparation of multiple emulsion compositions 17-01 to 17-05 appeared to have some effect on herbicidal effectiveness in this study.

Example 18

Aqueous concentrate compositions were prepared containing glyphosate IPA salt and excipient ingredients as shown in Table 18a. Concentrate compositions 18-01 to 18-15 are water-in-oil-in-water multiple emulsions and were prepared by process (vi). Concentrate compositions 18-16 and 18-17 are oil-in-water emulsions and were prepared by process (vii).

TABLE 18a

| Conc. comp. | Glyphosate a.e. | Butyl stearate | Emulsifier #1 | Emulsifier #2 | % in inner aq. phase Water | % in inner aq. phase Glyphosate | Emulsifier #1 | Emulsifier #2 |
|---|---|---|---|---|---|---|---|---|
| 18-01 | 10 | 18.0 | 3.0 | 5.0 | 12.0 | 20 | Span 80 | Tween 20 |
| 18-02 | 10 | 7.5 | 3.0 | 5.0 | 5.3 | 20 | Span 80 | Tween 20 |
| 18-03 | 10 | 7.5 | 3.0 | 10.0 | 5.7 | 0 | Span 80 | Tween 20 |
| 18-04 | 10 | 7.5 | 3.0 | 10.0 | 5.7 | 0 | Emerest 2421 | Neodol 25-12 |
| 18-05 | 10 | 7.5 | 3.0 | 10.0 | 5.7 | 0 | Emerest 2421 | Neodol 25-20 |
| 18-06 | 10 | 7.5 | 3.0 | 10.0 | 5.7 | 0 | Emerest 2421 | Tergitol 15-S-15 |
| 18-07 | 10 | 7.5 | 3.0 | 10.0 | 5.7 | 0 | Emid 6545 | Neodol 25-12 |
| 18-08 | 10 | 7.5 | 3.0 | 10.0 | 5.7 | 0 | Emid 6545 | Neodol 25-20 |
| 18-09 | 10 | 7.5 | 3.0 | 10.0 | 5.7 | 0 | Emid 6545 | Tergitol 15-S-15 |
| 18-10 | 10 | 7.5 | 3.0 | 10.0 | 5.7 | 0 | Neodol 25-3 | Neodol 25-12 |
| 18-11 | 10 | 7.5 | 3.0 | 10.0 | 5.7 | 0 | Neodol 25-3 | Neodol 25-20 |
| 18-12 | 10 | 7.5 | 3.0 | 10.0 | 5.7 | 0 | Neodol 25-3 | Tergitol 15-S-15 |
| 18-13 | 10 | 7.5 | 3.0 | 10.0 | 5.7 | 0 | Span 80 | Neodol 25-12 |
| 18-14 | 10 | 7.5 | 3.0 | 10.0 | 5.7 | 0 | Span 80 | Neodol 25-20 |
| 18-15 | 10 | 7.5 | 3.0 | 10.0 | 5.7 | 0 | Span 80 | Tergitol 15-S-15 |
| 18-16 | 10 | 7.5 |  |  | 10.0 |  | none | Neodol 25-12 |
| 18-17 | 10 | 7.5 |  |  | 10.0 |  | none | Neodol 25-20 |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and 18 days after planting ECHCF, and evaluation of herbicidal inhibition was done 17 days after application.

Formulations B, C and J were applied as comparative treatments. Results, averaged for all replicates of each treatment, are shown in Table 18b.

TABLE 18b

| Concentrate composition | Glyphosate rate g a.e./ha | % Inhibition ABUTH | % Inhibition ECHCF |
|---|---|---|---|
| Formulation B | 150 | 0 | 28 |
|  | 250 | 20 | 41 |
|  | 350 | 41 | 72 |
|  | 450 | 70 | 85 |
| Formulation C | 150 | 55 | 83 |
|  | 250 | 88 | 100 |
|  | 350 | 99 | 100 |
|  | 450 | 100 | 100 |
| Formulation J | 150 | 43 | 63 |
|  | 250 | 88 | 100 |
|  | 350 | 94 | 100 |
|  | 450 | 99 | 100 |
| 18-01 | 150 | 82 | 81 |
|  | 250 | 76 | 90 |
|  | 350 | 98 | 95 |
|  | 450 | 100 | 100 |
| 18-02 | 150 | 23 | 59 |
|  | 250 | 67 | 92 |
|  | 350 | 91 | 100 |
|  | 450 | 97 | 98 |
| 18-03 | 150 | 40 | 59 |
|  | 250 | 85 | 99 |
|  | 350 | 94 | 99 |
|  | 450 | 100 | 100 |
| 18-04 | 150 | 41 | 55 |

TABLE 18b-continued

| Concentrate composition | Glyphosate rate g a.e./ha | % Inhibition ABUTH | % Inhibition ECHCF |
|---|---|---|---|
|  | 250 | 83 | 97 |
|  | 350 | 90 | 99 |
|  | 450 | 94 | 99 |
| 18-05 | 150 | 49 | 80 |
|  | 250 | 84 | 85 |
|  | 350 | 94 | 99 |
|  | 450 | 99 | 100 |
| 18-06 | 150 | 38 | 57 |
|  | 250 | 78 | 93 |
|  | 350 | 94 | 99 |
|  | 450 | 98 | 97 |

TABLE 18b-continued

| Concentrate composition | Glyphosate rate g a.e./ha | % Inhibition ABUTH | % Inhibition ECHCF |
|---|---|---|---|
| 18-07 | 150 | 57 | 69 |
|  | 250 | 83 | 95 |
|  | 350 | 95 | 99 |
|  | 450 | 100 | 96 |
| 18-08 | 150 | 52 | 67 |
|  | 250 | 83 | 96 |
|  | 350 | 93 | 100 |
|  | 450 | 99 | 100 |
| 18-09 | 150 | 45 | 71 |
|  | 250 | 80 | 89 |
|  | 350 | 89 | 97 |
|  | 450 | 97 | 100 |
| 18-10 | 150 | 59 | 65 |
|  | 250 | 87 | 89 |
|  | 350 | 95 | 98 |
|  | 450 | 97 | 94 |
| 18-11 | 150 | 73 | 74 |
|  | 250 | 91 | 91 |
|  | 350 | 98 | 99 |
|  | 450 | 100 | 100 |
| 18-12 | 150 | 57 | 71 |
|  | 250 | 85 | 89 |
|  | 350 | 95 | 99 |
|  | 450 | 100 | 99 |
| 18-13 | 150 | 45 | 72 |
|  | 250 | 87 | 87 |
|  | 350 | 90 | 95 |
|  | 450 | 96 | 100 |
| 18-14 | 150 | 45 | 85 |
|  | 250 | 89 | 99 |
|  | 350 | 96 | 99 |
|  | 450 | 98 | 100 |
| 18-15 | 150 | 40 | 83 |
|  | 250 | 83 | 98 |
|  | 350 | 93 | 99 |
|  | 450 | 96 | 100 |
| 18-16 | 150 | 65 | 79 |
|  | 250 | 87 | 99 |
|  | 350 | 96 | 99 |
|  | 450 | 100 | 100 |
| 18-17 | 150 | 59 | 80 |
|  | 250 | 95 | 86 |
|  | 350 | 100 | 99 |
|  | 450 | 100 | 100 |

Simple emulsion compositions of this example containing butyl stearate (18-16 and 18-17) exhibited herbicidal effectiveness at least equal to multiple emulsion compositions having the same emulsifier #2.

Example 19

Aqueous concentrate compositions were prepared containing glyphosate IPA salt and excipient ingredients as shown in Table 19a. These compositions are water-in-oil-in-water multiple emulsions and were prepared by process (vi) described above.

TABLE 19a

| Conc. comp. | Glyphosate a.e. | Butyl stearate | Emulsifier #1 | Emulsifier #2 | % in inner aq. phase Water | % in inner aq. phase Glyphosate | Emulsifier #1 | Emulsifier #2 |
|---|---|---|---|---|---|---|---|---|
| 19-01 | 10 | 18.0 | 3.0 | 5.0 | 9.0 | 20 | Span 80 | Tween 20 |
| 19-02 | 10 | 7.5 | 3.0 | 5.0 | 4.5 | 20 | Span 80 | Tween 20 |
| 19-03 | 10 | 7.5 | 3.0 | 10.0 | 4.5 | 0 | Surfynol 104 | Neodol 25-12 |
| 19-04 | 10 | 7.5 | 3.0 | 10.0 | 4.5 | 0 | Surfynol 104 | Neodol 25-20 |
| 19-05 | 10 | 7.5 | 3.0 | 10.0 | 4.5 | 0 | Surfynol 104 | Tergitol 15-S-15 |
| 19-06 | 10 | 7.5 | 3.0 | 10.0 | 4.5 | 0 | Surfynol 104 | Tergitol 15-S-20 |
| 19-07 | 10 | 7.5 | 3.0 | 10.0 | 4.5 | 0 | Surfynol 104 | Tween 20 |
| 19-08 | 10 | 7.5 | 3.0 | 10.0 | 4.5 | 0 | Surfynol 104 | ceteareth-55 |
| 19-09 | 10 | 7.5 | 3.0 | 10.0 | 4.5 | 0 | Surfynol 104 | Tergitol 15-S-30 |
| 19-10 | 10 | 7.5 | 3.0 | 10.0 | 4.5 | 0 | Neodol 25-3 | ceteareth-55 |
| 19-11 | 10 | 7.5 | 3.0 | 10.0 | 4.5 | 0 | Neodol 25-3 | Tergitol 15-S-30 |
| 19-12 | 10 | 7.5 | 3.0 | 10.0 | 4.5 | 0 | Span 60 | ceteareth-55 |
| 19-13 | 10 | 7.5 | 3.0 | 10.0 | 4.5 | 0 | Span 60 | Tergitol 15-S-30 |
| 19-14 | 10 | 7.5 | 3.0 | 10.0 | 4.5 | 0 | oleth-2 | ceteareth-55 |
| 19-15 | 10 | 7.5 | 3.0 | 10.0 | 4.5 | 0 | oleth-2 | Tergitol 15-S-30 |
| 19-16 | 10 | 7.5 | 3.0 | 10.0 | 4.5 | 0 | Emid 6545 | ceteareth-55 |
| 19-17 | 10 | 7.5 | 3.0 | 10.0 | 4.5 | 0 | Emid 6545 | Tergitol 15-S-30 |

Velvetleaf (*Abutilon theophrasti*, ABUTH) and Japanese millet (*Echinochloa crus-galli*, ECHCF) plants were grown and treated by the standard procedures given above. Applications of spray compositions were made 35 days after planting ABUTH and 33 days after planting ECHCF, and evaluation of herbicidal inhibition was done 17 days after application.

Formulations B, C and J were applied as comparative treatments. Results, averaged for all replicates of each treatment, are shown in Table 19b.

TABLE 19b

| Concentrate composition | Glyphosate rate g a.e./ha | % Inhibition ABUTH | % Inhibition ECHCF |
|---|---|---|---|
| Formulation B | 150 | 0 | 0 |
|  | 250 | 35 | 40 |
|  | 350 | 50 | 63 |
|  | 450 | 60 | 43 |
| Formulation C | 150 | 63 | 63 |
|  | 250 | 80 | 96 |
|  | 350 | 92 | 98 |
|  | 450 | 98 | 87 |
| Formulation J | 150 | 43 | 30 |
|  | 250 | 75 | 85 |
|  | 350 | 82 | 98 |
|  | 450 | 96 | 95 |
| 19-01 | 150 | 65 | 53 |
|  | 250 | 85 | 70 |
|  | 350 | 90 | 87 |
|  | 450 | 98 | 73 |
| 19-02 | 150 | 63 | 5 |
|  | 250 | 78 | 53 |
|  | 350 | 88 | 80 |
|  | 450 | 97 | 87 |
| 19-03 | 150 | 75 | 0 |
|  | 250 | 87 | 22 |
|  | 350 | 88 | 72 |
|  | 450 | 97 | 17 |
| 19-04 | 150 | 84 | 0 |
|  | 250 | 90 | 10 |
|  | 350 | 95 | 70 |
|  | 450 | 98 | 60 |
| 19-05 | 150 | 77 | 0 |
|  | 250 | 83 | 3 |
|  | 350 | 93 | 30 |
|  | 450 | 95 | 10 |
| 19-06 | 150 | 72 | 0 |
|  | 250 | 83 | 47 |
|  | 350 | 94 | 60 |
|  | 450 | 98 | 20 |
| 19-07 | 150 | 75 | 0 |
|  | 250 | 77 | 40 |
|  | 350 | 96 | 47 |
|  | 450 | 96 | 50 |
| 19-08 | 150 | 87 | 40 |
|  | 250 | 97 | 82 |
|  | 350 | 99 | 83 |
|  | 450 | 100 | 77 |
| 19-09 | 150 | 82 | 10 |
|  | 250 | 82 | 40 |
|  | 350 | 96 | 67 |
|  | 450 | 97 | 67 |
| 19-10 | 150 | 82 | 13 |
|  | 250 | 94 | 83 |

TABLE 19b-continued

| Concentrate composition | Glyphosate rate g a.e./ha | % Inhibition ABUTH | % Inhibition ECHCF |
|---|---|---|---|
|  | 350 | 99 | 85 |
|  | 450 | 99 | 83 |
| 19-11 | 150 | 73 | 17 |
|  | 250 | 83 | 60 |
|  | 350 | 88 | 73 |
|  | 450 | 96 | 63 |
| 19-12 | 150 | 80 | 20 |
|  | 250 | 93 | 85 |
|  | 350 | 96 | 82 |
|  | 450 | 96 | 82 |
| 19-13 | 150 | 78 | 20 |
|  | 250 | 83 | 50 |
|  | 350 | 92 | 90 |
|  | 450 | 92 | 85 |
| 19-14 | 150 | 80 | 30 |
|  | 250 | 97 | 85 |
|  | 350 | 99 | 99 |
|  | 450 | 97 | 96 |
| 19-15 | 150 | 82 | 30 |
|  | 250 | 87 | 75 |
|  | 350 | 99 | 92 |
|  | 450 | 99 | 93 |
| 19-16 | 150 | 82 | 53 |
|  | 250 | 96 | 82 |
|  | 350 | 96 | 97 |
|  | 450 | 87 | 82 |
| 19-17 | 150 | 72 | 20 |
|  | 250 | 80 | 63 |
|  | 350 | 92 | 75 |
|  | 450 | 95 | 87 |

Considerable variation was seen in herbicidal effectiveness of water-in-oil-in-water multiple emulsions of this Example, especially on ECHCF. Among the most efficacious were 19-08, 19-10, 19-12, 19-14 and 19-16. All of these contained a $C_{16-18}$ alkylether surfactant, ceteareth-55. When Tergitol 1 5-S-30, a $C_{12-15}$ secondary alkylether surfactant, replaced ceteareth-55, as in 19-09, 19-11, 19-13, 19-15 and 19-17, herbicidal effectiveness, at least on ECHCF, was in most cases markedly reduced.

Example 20

Aqueous concentrate compositions were prepared containing glyphosate IPA salt and excipient ingredients as shown in Table 20a. Concentrate compositions 20-01 and 20-02 are water-in-oil-in-water multiple emulsions and were prepared by process (vi), using Span 80 as emulsifier #1. Concentrate compositions 20-03 to 20-12 and 20-14 to 20-17 are oil-in-water emulsions and were prepared by process (vii). Concentrate composition 20-13 is an aqueous solution concentrate and was prepared by process (viii), the component indicated below as "emulsifier #2" being the surfactant component.

TABLE 20a

| Conc. comp. | Glyphosate a.e. | Butyl stearate | Span 80 | Emulsifier #2 | % in inner aq. Phase Water | % in inner aq. Phase Glyphosate | Emulsifier #2 |
|---|---|---|---|---|---|---|---|
| 20-01 | 10 | 18.0 | 3.0 | 5.0 | 12.2 | 20 | Tween 20 |
| 20-02 | 10 | 7.5 | 3.0 | 5.0 | 5.3 | 20 | Tween 20 |
| 20-03 | 10 | 1.0 | | 10.0 | | | Neodol 25-20 |
| 20-04 | 10 | 3.0 | | 10.0 | | | Neodol 25-20 |
| 20-05 | 10 | 1.0 | | 5.0 | | | Neodol 25-20 |
| 20-06 | 10 | 3.0 | | 5.0 | | | Neodol 25-20 |
| 20-07 | 15 | 1.0 | | 10.0 | | | Neodol 25-20 |
| 20-08 | 15 | 3.0 | | 10.0 | | | Neodol 25-20 |
| 20-09 | 15 | 1.0 | | 5.0 | | | Neodol 25-20 |
| 20-10 | 15 | 3.0 | | 5.0 | | | Neodol 25-20 |
| 20-11 | 20 | 1.0 | | 5.0 | | | Neodol 25-20 |
| 20-12 | 20 | 1.0 | | 10.0 | | | Neodol 25-20 |
| 20-13 | 10 | | | 10.0 | | | Neodol 25-20 |
| 20-14 | 10 | 7.5 | | 10.0 | | | Neodol 25-20 |
| 20-15 | 10 | 7.5 | | 10.0 | | | Neodol 25-12 |
| 20-16 | 10 | 7.5 | | 10.0 | | | steareth-20 |
| 20-17 | 10 | 7.5 | | 10.0 | | | oleth-20 |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and 19 days after planting ECHCF, and evaluation of herbicidal inhibition was done 18 days after application.

Formulations B, C and J were applied as comparative treatments. Results, averaged for all replicates of each treatment, are shown in Table 20b.

TABLE 20b

| Concentrate composition | Glyphosate rate g a.e./ha | % Inhibition ABUTH | % Inhibition ECHCF |
|---|---|---|---|
| Formulation B | 150 | 0 | 30 |
| | 250 | 10 | 40 |
| | 350 | 37 | 73 |
| | 450 | 58 | 68 |
| Formulation C | 150 | 42 | 79 |
| | 250 | 77 | 98 |
| | 350 | 99 | 97 |
| | 450 | 97 | 93 |
| Formulation J | 150 | 43 | 67 |
| | 250 | 73 | 90 |
| | 350 | 94 | 98 |
| | 450 | 77 | 78 |
| 20-01 | 150 | 58 | 76 |
| | 250 | 75 | 77 |
| | 350 | 88 | 93 |
| | 450 | 95 | 83 |
| 20-02 | 150 | 27 | 63 |
| | 250 | 60 | 87 |
| | 350 | 82 | 98 |
| | 450 | 77 | 92 |
| 20-03 | 150 | 47 | 76 |
| | 250 | 65 | 92 |
| | 350 | 94 | 99 |
| | 450 | 95 | 91 |
| 20-04 | 150 | 70 | 86 |
| | 250 | 86 | 95 |
| | 350 | 97 | 98 |
| | 450 | 99 | 90 |
| 20-05 | 150 | 42 | 80 |
| | 250 | 72 | 90 |
| | 350 | 90 | 93 |
| | 450 | 99 | 96 |
| 20-06 | 150 | 48 | 57 |
| | 250 | 78 | 92 |
| | 350 | 94 | 99 |
| | 450 | 96 | 92 |
| 20-07 | 150 | 78 | 95 |
| | 250 | 96 | 96 |
| | 350 | 98 | 98 |
| | 450 | 100 | 97 |
| 20-08 | 150 | 88 | 96 |
| | 250 | 98 | 98 |
| | 350 | 100 | 99 |
| | 450 | 100 | 99 |
| 20-09 | 150 | 82 | 93 |
| | 250 | 94 | 96 |
| | 350 | 99 | 97 |
| | 450 | 99 | 93 |
| 20-10 | 150 | 72 | 83 |
| | 250 | 97 | 93 |
| | 350 | 99 | 100 |
| | 450 | 100 | 98 |
| 20-11 | 150 | 87 | 83 |
| | 250 | 98 | 97 |
| | 350 | 100 | 99 |
| | 450 | 100 | 99 |
| 20-12 | 150 | 93 | 99 |
| | 250 | 99 | 99 |
| | 350 | 99 | 97 |
| | 450 | 100 | 99 |
| 20-13 | 150 | 70 | 90 |
| | 250 | 91 | 88 |
| | 350 | 97 | 94 |
| | 450 | 99 | 86 |
| 20-14 | 150 | 67 | 76 |
| | 250 | 93 | 80 |
| | 350 | 98 | 95 |
| | 450 | 95 | 78 |
| 20-15 | 150 | 68 | 65 |
| | 250 | 90 | 87 |
| | 350 | 97 | 80 |
| | 450 | 98 | 93 |
| 20-16 | 150 | 83 | 73 |
| | 250 | 90 | 93 |
| | 350 | 99 | 100 |
| | 450 | 100 | 100 |
| 20-17 | 150 | 80 | 66 |

TABLE 20b-continued

| Concentrate composition | Glyphosate rate g a.e./ha | % Inhibition ABUTH | ECHCF |
|---|---|---|---|
| | 250 | 98 | 77 |
| | 350 | 99 | 83 |
| | 450 | 100 | 85 |

Very high herbicidal activity was evident in compositions 20-13 to 20-17, which have a very high ratio of surfactant to glyphosate a.e. of 1:1. Activity was too high to clearly distinguish among these compositions, but 20-16 and 20-17, containing steareth-20 and oleth-20 respectively, exbited greater effectiveness on ABUTH at the lowest glyphosate rate than 20-14 and 20-15, containing Neodol 25-20 and Neodol 25-12 respectively.

Example 21

Aqueous concentrate compositions were prepared containing glyphosate IPA salt and excipient ingredients as shown in Table 21a. Concentrate compositions 21-01 and 21-02 are water-in-oil-in-water multiple emulsions and were prepared by process (vi), using Span 80 as emulsifier #1. Concentrate compositions 21-03 to 21-12 and 21-14 to 21-17 are oil-in-water emulsions and were prepared by process (vii). Concentrate composition 21-13 is an aqueous solution concentrate and was prepared by process (viii), the component indicated below as "emulsifier #2" being the surfactant component.

TABLE 21a

| | % w/w | | | | % in inner aq. phase | | |
|---|---|---|---|---|---|---|---|
| Conc. comp. | Glypho-sate a.e. | Butyl stearate | Span 80 | Emulsifier #2 | Water | Glyphosate | Emulsifier #2 |
| 21-01 | 10 | 18.0 | 3.0 | 5.0 | 12.2 | 20 | Tween 20 |
| 21-02 | 10 | 7.5 | 3.0 | 5.0 | 5.3 | 20 | Tween 20 |
| 21-03 | 10 | 1.0 | | 10.0 | | | Tween 80 |
| 21-04 | 10 | 3.0 | | 10.0 | | | Tween 80 |
| 21-05 | 10 | 1.0 | | 5.0 | | | Tween 80 |
| 21-06 | 10 | 3.0 | | 5.0 | | | Tween 80 |
| 21-07 | 15 | 1.0 | | 10.0 | | | Tween 80 |
| 21-08 | 15 | 3.0 | | 10.0 | | | Tween 80 |
| 21-09 | 15 | 1.0 | | 5.0 | | | Tween 80 |
| 21-10 | 15 | 3.0 | | 5.0 | | | Tween 80 |
| 21-11 | 20 | 1.0 | | 5.0 | | | Tween 80 |
| 21-12 | 20 | 1.0 | | 10.0 | | | Tween 80 |
| 21-13 | 10 | | | 10.0 | | | Tween 80 |
| 21-14 | 10 | 7.5 | | 10.0 | | | Tween 80 |
| 21-15 | 10 | 7.5 | | 10.0 | | | Neodol 25-20 |
| 21-16 | 10 | 7.5 | | 10.0 | | | steareth-20 |
| 21-17 | 10 | 7.5 | | 10.0 | | | oleth-20 |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and 19 days after planting ECHCF, and evaluation of herbicidal inhibition was done 18 days after application.

Formulations B, C and J were applied as comparative treatments. Results, averaged for all replicates of each treatment, are shown in Table 21b.

TABLE 21b

| Concentrate composition | Glyphosate rate g a.e./ha | % Inhibition ABUTH | ECHCF |
|---|---|---|---|
| Formulation B | 150 | 0 | 0 |
| | 250 | 3 | 10 |
| | 350 | 17 | 20 |
| | 450 | 20 | 30 |
| Formulation C | 150 | 70 | 33 |
| | 250 | 80 | 70 |
| | 350 | 85 | 80 |
| | 450 | 97 | 77 |
| Formulation J | 150 | 7 | 20 |
| | 250 | 70 | 80 |
| | 350 | 78 | 80 |
| | 450 | 83 | 80 |
| 21-01 | 150 | 40 | 7 |
| | 250 | 48 | 20 |
| | 350 | 73 | 23 |
| | 450 | 75 | 30 |
| 21-02 | 150 | 3 | 0 |
| | 250 | 10 | 17 |
| | 350 | 47 | 23 |
| | 450 | 50 | 30 |
| 21-03 | 150 | 0 | 2 |
| | 250 | 33 | 13 |
| | 350 | 63 | 40 |
| | 450 | 68 | 43 |
| 21-04 | 150 | 17 | 7 |
| | 250 | 43 | 20 |
| | 350 | 78 | 63 |
| | 450 | 78 | 63 |
| 21-05 | 150 | 10 | 3 |
| | 250 | 20 | 13 |
| | 350 | 58 | 40 |

TABLE 21b-continued

| Concentrate composition | Glyphosate rate g a.e./ha | % Inhibition ABUTH | ECHCF |
|---|---|---|---|
| | 450 | 75 | 40 |
| 21-06 | 150 | 3 | 0 |
| | 250 | 27 | 20 |

TABLE 21b-continued

| Concentrate composition | Glyphosate rate g a.e./ha | % Inhibition ABUTH | % Inhibition ECHCF |
|---|---|---|---|
| | 350 | 60 | 23 |
| | 450 | 72 | 23 |
| 21-07 | 150 | 32 | 10 |
| | 250 | 68 | 20 |
| | 350 | 75 | 50 |
| | 450 | 86 | 60 |
| 21-08 | 150 | 27 | 20 |
| | 250 | 68 | 30 |
| | 350 | 82 | 40 |
| | 450 | 90 | 73 |
| 21-09 | 150 | 43 | 10 |
| | 250 | 60 | 33 |
| | 350 | 72 | 63 |
| | 450 | 75 | 73 |
| 21-10 | 150 | 33 | 10 |
| | 250 | 62 | 30 |
| | 350 | 77 | 60 |
| | 450 | 83 | 70 |
| 21-11 | 150 | 48 | 13 |
| | 250 | 72 | 63 |
| | 350 | 83 | 80 |
| | 450 | 87 | 80 |
| 21-12 | 150 | 23 | 13 |
| | 250 | 60 | 50 |
| | 350 | 75 | 80 |
| | 450 | 86 | 78 |
| 21-13 | 150 | 32 | 13 |
| | 250 | 47 | 40 |
| | 350 | 75 | 50 |
| | 450 | 78 | 70 |
| 21-14 | 150 | 27 | 20 |
| | 250 | 75 | 53 |
| | 350 | 82 | 70 |
| | 450 | 92 | 67 |
| 21-15 | 150 | 70 | 20 |
| | 250 | 78 | 30 |
| | 350 | 92 | 80 |
| | 450 | 93 | 80 |
| 21-16 | 150 | 68 | 40 |
| | 250 | 73 | 30 |
| | 350 | 93 | 80 |
| | 450 | 93 | 77 |
| 21-17 | 150 | 73 | 20 |
| | 250 | 85 | 30 |
| | 350 | 93 | 60 |
| | 450 | 95 | 63 |

Compositions 21-16 and 21-17, containing steareth-20 and oleth-20 respectively, exhibited very high herbicidal activity on ABUTH. At the very high surfactant to glyphosate a.e. ratio (1:1) of these compositions, no difference was evident between these compositions and an otherwise similar composition (21-15) containing Neodol 25-20 in place of steareth-20 or oleth-20.

Example 22

Aqueous concentrate compositions were prepared containing glyphosate IPA salt and excipient ingredients as shown in Table 22a. Concentrate compositions 22-01 and 22-02 are water-in-oil-in-water multiple emulsions and were prepared by process (vi), using Span 80 as emulsifier #1. Concentrate compositions 22-03 to 22-16 are oil-in-water emulsions and were prepared by process (vii).

TABLE 22a

| Concentrate composition | Glyphosate a.e. | Butyl stearate | Span 80 | Emulsifier #2 | Aerosil 90 | % in inner aq. phase Water | % in inner aq. phase Glyphosate | Emulsifier #2 |
|---|---|---|---|---|---|---|---|---|
| 22-01 | 10 | 18.0 | 3.0 | 5.0 | | 12.2 | 20 | Tween 20 |
| 22-02 | 10 | 7.5 | 3.0 | 5.0 | | 5.3 | 20 | Tween 20 |
| 22-03 | 10 | 7.5 | | 10.0 | | | | Tween 80 |
| 22-04 | 15 | 7.5 | | 10.0 | | | | Tween 80 |
| 22-05 | 15 | 7.5 | | 1.0 | 0.40 | | | Tween 80 |
| 22-06 | 15 | 7.5 | | | 0.40 | | | |
| 22-07 | 15 | 7.5 | | 5.0 | 0.40 | | | Tween 80 |
| 22-08 | 15 | 7.5 | | 10.0 | 0.25 | | | Tween 80 |
| 22-09 | 30 | 15.0 | | 10.0 | 0.80 | | | Tween 80 |
| 22-10 | 15 | 3.0 | | 10.0 | | | | Tween 80 |
| 22-11 | 15 | 1.0 | | 10.0 | | | | Tween 80 |
| 22-12 | 30 | 7.5 | | 10.0 | | | | Tween 80 |
| 22-13 | 30 | 3.0 | | 10.0 | | | | Tween 80 |
| 22-14 | 30 | 1.0 | | 10.0 | | | | Tween 80 |
| 22-15 | 30 | 7.5 | | 10.0 | 0.80 | | | Tween 80 |
| 22-16 | 30 | 3.0 | | 10.0 | 0.80 | | | Tween 80 |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and 19 days after planting ECHCF, and evaluation of herbicidal inhibition was done 17 days after application.

Formulations B, C and J were applied as comparative treatments. Results, averaged for all replicates of each treatment, are shown in Table 22b.

TABLE 22b

| Concentrate composition | Glyphosate rate g a.e./ha | % Inhibition ABUTH | % Inhibition ECHCF |
|---|---|---|---|
| Formulation B | 150 | 0 | 7 |
|  | 250 | 3 | 10 |
|  | 350 | 35 | 25 |
|  | 450 | 60 | 27 |
| Formulation C | 150 | 37 | 25 |
|  | 250 | 65 | 60 |
|  | 350 | 80 | 78 |
|  | 450 | 86 | 88 |
| Formulation J | 150 | 23 | 25 |
|  | 250 | 70 | 63 |
|  | 350 | 83 | 60 |
|  | 450 | 92 | 73 |
| 22-01 | 150 | 55 | 22 |
|  | 250 | 65 | 25 |
|  | 350 | 72 | 30 |
|  | 450 | 78 | 53 |
| 22-02 | 150 | 45 | 15 |
|  | 250 | 62 | 20 |
|  | 350 | 77 | 27 |
|  | 450 | 78 | 30 |
| 22-03 | 150 | 48 | 23 |
|  | 250 | 65 | 25 |
|  | 350 | 77 | 30 |
|  | 450 | 83 | 62 |
| 22-04 | 150 | 50 | 25 |
|  | 250 | 65 | 28 |
|  | 350 | 73 | 47 |
|  | 450 | 80 | 83 |
| 22-05 | 150 | 18 | 10 |
|  | 250 | 57 | 25 |
|  | 350 | 63 | 25 |
|  | 450 | 68 | 55 |
| 22-06 | 150 | 0 | 10 |
|  | 250 | 48 | 25 |
|  | 350 | 60 | 25 |
|  | 450 | 63 | 27 |
| 22-07 | 150 | 50 | 25 |
|  | 250 | 62 | 27 |
|  | 350 | 78 | 33 |
|  | 450 | 84 | 33 |
| 22-08 | 150 | 47 | 25 |
|  | 250 | 60 | 28 |
|  | 350 | 75 | 55 |
|  | 450 | 85 | 30 |
| 22-09 | 150 | 43 | 18 |
|  | 250 | 67 | 20 |
|  | 350 | 78 | 25 |
|  | 450 | 80 | 28 |
| 22-10 | 150 | 48 | 30 |
|  | 250 | 60 | 33 |
|  | 350 | 78 | 30 |
|  | 450 | 82 | 33 |
| 22-11 | 150 | 43 | 22 |
|  | 250 | 60 | 38 |
|  | 350 | 65 | 33 |
|  | 450 | 80 | 32 |
| 22-12 | 150 | 43 | 25 |
|  | 250 | 60 | 25 |
|  | 350 | 73 | 30 |
|  | 450 | 78 | 30 |
| 22-13 | 150 | 53 | 30 |
|  | 250 | 63 | 40 |
|  | 350 | 67 | 30 |
|  | 450 | 82 | 30 |
| 22-14 | 150 | 10 | 20 |
|  | 250 | 57 | 25 |
|  | 350 | 73 | 27 |
|  | 450 | 78 | 30 |
| 22-15 | 150 | 30 | 20 |
|  | 250 | 60 | 25 |
|  | 350 | 65 | 25 |
|  | 450 | 73 | 28 |
| 22-16 | 150 | 17 | 10 |
|  | 250 | 55 | 25 |
|  | 350 | 73 | 40 |
|  | 450 | 78 | 30 |

None of the emulsion compositions of this Example gave herbicidal effectiveness greater than obtained with the commercial standards.

Example 23

Aqueous concentrate compositions were prepared containing glyphosate IPA salt and excipient ingredients as shown in Table 23a. Concentrate compositions 23-01 and 23-02 are water-in-oil-in-water multiple emulsions and were prepared by process (vi), using Span 80 as emulsifier #1. Concentrate compositions 23-03 to 23-17 are oil-in-water emulsions and were prepared by process (vii).

TABLE 23a

| Concentrate composition | % w/w | | | | | % in inner aq. phase | | |
|---|---|---|---|---|---|---|---|---|
| | Glyphosate a.e. | Butyl stearate | Span 80 | Emulsifier #2 | Aerosil 90 | Water | Glyphosate | Emulsifier #2 |
| 23-01 | 10 | 18.0 | 3.0 | 5.0 | | 12.2 | 20 | Tween 20 |
| 23-02 | 10 | 7.5 | 3.0 | 5.0 | | 5.3 | 20 | Tween 20 |
| 23-03 | 10 | 7.5 | | 10.0 | | | | Neodol 25-20 |
| 23-04 | 15 | 7.5 | | 10.0 | | | | Neodol 25-20 |
| 23-05 | 15 | 7.5 | | 1.0 | 0.40 | | | Neodol 25-20 |
| 23-06 | 15 | 7.5 | | | 0.40 | | | Neodol 25-20 |
| 23-07 | 15 | 7.5 | | 5.0 | 0.40 | | | Neodol 25-20 |
| 23-08 | 15 | 7.5 | | 10.0 | 0.25 | | | Neodol 25-20 |
| 23-09 | 30 | 15.0 | | 10.0 | 0.80 | | | Neodol 25-20 |
| 23-10 | 15 | 3.0 | | 10.0 | | | | Neodol 25-20 |

TABLE 23a-continued

| Concentrate composition | % w/w | | | | | % in inner aq. phase | |
|---|---|---|---|---|---|---|---|
| | Glyphosate a.e. | Butyl stearate | Span 80 | Emulsifier #2 | Aerosil 90 | Water | Glyphosate | Emulsifier #2 |

| Concentrate composition | Glyphosate a.e. | Butyl stearate | Span 80 | Emulsifier #2 | Aerosil 90 | Water | Glyphosate | Emulsifier #2 |
|---|---|---|---|---|---|---|---|---|
| 23-11 | 15 | 1.0 | | 10.0 | | | | Neodol 25-20 |
| 23-12 | 15 | 7.5 | | 5.0 | | | | Neodol 25-12 |
| 23-13 | 15 | 3.0 | | 5.0 | | | | Neodol 25-12 |
| 23-14 | 10 | 3.0 | | 5.0 | | | | Neodol 25-12 |
| 23-15 | 10 | 3.0 | | 10.0 | | | | Neodol 25-12 |
| 23-16 | 10 | 7.5 | | 10.0 | | | | Neodol 25-12 |
| 23-17 | 10 | 7.5 | | 5.0 | | | | Neodol 25-12 |

Velvetleaf (*Abutilon theophrasti*, ABUTH) and Japanese millet (*Echinochloa crus-galli*, ECHCF) plants were grown and treated by the standard procedures given above Applications of spray compositions were made 20 days after planting ABUTH and 22 days after planting ECHCF, and evaluation of herbicidal inhibition was done 15 days after application.

Formulations B, C and J were applied as comparative treatments. Results, averaged for all replicates of each treatment, are shown in Table 23b.

TABLE 23b

| Concentrate composition | Glyphosate rate g a.e./ha | % Inhibition | |
|---|---|---|---|
| | | ABUTH | ECHCF |
| Formulation B | 150 | 13 | 5 |
| | 250 | 48 | 33 |
| | 350 | 57 | 40 |
| | 450 | 77 | 47 |
| Formulation C | 150 | 65 | 63 |
| | 250 | 83 | 80 |
| | 350 | 96 | 95 |
| | 450 | 96 | 96 |
| Formulation J | 150 | 50 | 57 |
| | 250 | 83 | 86 |
| | 350 | 88 | 90 |
| | 450 | 95 | 93 |
| 23-01 | 150 | 43 | 63 |
| | 250 | 73 | 99 |
| | 350 | 78 | 72 |
| | 450 | 90 | 88 |
| 23-02 | 150 | 33 | 30 |
| | 250 | 70 | 73 |
| | 350 | 82 | 53 |
| | 450 | 83 | 94 |
| 23-03 | 150 | 60 | 60 |
| | 250 | 78 | 98 |
| | 350 | 94 | 97 |
| | 450 | 92 | 98 |
| 23-04 | 150 | 53 | 57 |
| | 250 | 83 | 69 |
| | 350 | 93 | 90 |
| | 450 | 90 | 63 |
| 23-05 | 150 | 25 | 43 |
| | 250 | 65 | 53 |
| | 350 | 73 | 70 |
| | 450 | 82 | 98 |
| 23-06 | 150 | 15 | 33 |
| | 250 | 47 | 70 |
| | 350 | 70 | 60 |
| | 450 | 77 | 67 |
| 23-07 | 150 | 47 | 47 |
| | 250 | 75 | 70 |
| | 350 | 80 | 78 |
| | 450 | 88 | 90 |
| 23-08 | 150 | 53 | 43 |
| | 250 | 75 | 57 |
| | 350 | 92 | 79 |

TABLE 23b-continued

| Concentrate composition | Glyphosate rate g a.e./ha | % Inhibition | |
|---|---|---|---|
| | | ABUTH | ECHCF |
| | 450 | 93 | 93 |
| 23-09 | 150 | 32 | 40 |
| | 250 | 68 | 57 |
| | 350 | 82 | 88 |
| | 450 | 85 | 98 |
| 23-10 | 150 | 47 | 67 |
| | 250 | 78 | 78 |
| | 350 | 92 | 88 |
| | 450 | 98 | 96 |
| 23-11 | 150 | 43 | 40 |
| | 250 | 72 | 82 |
| | 350 | 83 | 97 |
| | 450 | 87 | 97 |
| 23-12 | 150 | 70 | 77 |
| | 250 | 88 | 85 |
| | 350 | 95 | 95 |
| | 450 | 98 | 96 |
| 23-13 | 150 | 63 | 67 |
| | 250 | 83 | 97 |
| | 350 | 96 | 98 |
| | 450 | 97 | 97 |
| 23-14 | 150 | 57 | 70 |
| | 250 | 83 | 85 |
| | 350 | 88 | 98 |
| | 450 | 97 | 92 |
| 23-15 | 150 | 63 | 70 |
| | 250 | 75 | 88 |
| | 350 | 93 | 95 |
| | 450 | 97 | 99 |
| 23-16 | 150 | 70 | 50 |
| | 250 | 83 | 70 |
| | 350 | 87 | 91 |
| | 450 | 96 | 96 |
| 23-17 | 150 | 43 | 37 |
| | 250 | 77 | 70 |
| | 350 | 90 | 85 |
| | 450 | 93 | 89 |

The overall level of herbicidal effectiveness in this study was extremely high, making it difficult to determine if any of the emulsion compositions showed enhancement over the commercial standards.

Example 24

Aqueous concentrate compositions were prepared containing glyphosate IPA salt and excipient ingredients as shown in Table 24a. All concentrate compositions are oil-in-water emulsions and were prepared by process (vii).

TABLE 24a

| Concentrate composition | Glyphosate g a.e./l | Butyl stearate | Surfactant | Type of surfactant |
|---|---|---|---|---|
| | | % w/w | | |
| 24-01 | 163 | 1.00 | 10.0 | Tween 80 |
| 24-02 | 163 | 1.00 | 10.0 | Neodol 25-12 |
| 24-03 | 163 | 1.00 | 10.0 | Neodol 25-20 |
| 24-04 | 163 | 1.00 | 10.0 | steareth-20 |
| 24-05 | 163 | 1.00 | 10.0 | oleth-20 |
| 24-06 | 163 | 1.00 | 10.0 | Tergitol 15-S-40 |
| 24-07 | 163 | 1.00 | 10.0 | Tergitol 15-S-15 |
| 24-08 | 163 | 1.00 | 10.0 | Tergitol 15-S-20 |
| 24-09 | 163 | 0.50 | 10.0 | Tergitol 15-S-40 |
| 24-10 | 163 | 0.50 | 10.0 | Tergitol 15-S-15 |
| 24-11 | 163 | 0.50 | 10.0 | Tergitol 15-S-20 |
| 24-12 | 163 | 0.50 | 5.0 | Tergitol 15-S-40 |
| 24-13 | 163 | 0.50 | 5.0 | Tergitol 15-S-15 |
| 24-14 | 163 | 0.50 | 5.0 | Tergitol 15-S-20 |
| 24-15 | 163 | 0.25 | 10.0 | Tergitol 15-S-40 |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and ECHCF, and evaluation of herbicidal inhibition was done 19 days after application.

Formulations B, C and J were applied as comparative treatments. Results, averaged for all replicates of each treatment, are shown in Table 24b.

TABLE 24b

| Concentrate composition | Glyphosate rate g a.e./ha | % Inhibition ABUTH | ECHCF |
|---|---|---|---|
| Formulation B | 150 | 2 | 20 |
| | 250 | 2 | 30 |
| | 350 | 5 | 53 |
| | 450 | 45 | 75 |
| Formulation C | 150 | 45 | 63 |
| | 250 | 77 | 93 |
| | 350 | 83 | 99 |
| | 450 | 93 | 100 |
| Formulation J | 150 | 15 | 40 |
| | 250 | 70 | 73 |
| | 350 | 78 | 98 |
| | 450 | 92 | 99 |
| 24-01 | 150 | 42 | 50 |
| | 250 | 72 | 89 |
| | 350 | 80 | 96 |
| | 450 | 93 | 98 |
| 24-02 | 150 | 45 | 80 |
| | 250 | 72 | 83 |
| | 350 | 85 | 91 |
| | 450 | 97 | 98 |
| 24-03 | 150 | 60 | 80 |
| | 250 | 75 | 87 |
| | 350 | 82 | 96 |
| | 450 | 86 | 99 |
| 24-04 | 150 | 65 | 60 |
| | 250 | 82 | 70 |
| | 350 | 93 | 80 |
| | 450 | 98 | 87 |
| 24-05 | 150 | 72 | 60 |
| | 250 | 83 | 87 |
| | 350 | 95 | 93 |
| | 450 | 98 | 97 |
| 24-06 | 150 | 50 | 45 |
| | 250 | 68 | 70 |
| | 350 | 77 | 85 |
| | 450 | 83 | 90 |
| 24-07 | 150 | 25 | 40 |
| | 250 | 65 | 50 |
| | 350 | 80 | 77 |
| | 450 | 83 | 80 |
| 24-08 | 150 | 37 | 33 |
| | 250 | 72 | 80 |
| | 350 | 77 | 87 |
| | 450 | 80 | 90 |
| 24-09 | 150 | 32 | 47 |
| | 250 | 65 | 73 |
| | 350 | 77 | 75 |
| | 450 | 80 | 94 |
| 24-10 | 150 | 17 | 30 |
| | 250 | 65 | 70 |
| | 350 | 75 | 70 |
| | 450 | 78 | 89 |
| 24-11 | 150 | 35 | 33 |
| | 250 | 68 | 68 |
| | 350 | 77 | 77 |
| | 450 | 92 | 75 |
| 24-12 | 150 | 13 | 35 |
| | 250 | 57 | 40 |
| | 350 | 75 | 57 |
| | 450 | 77 | 83 |
| 24-13 | 150 | 35 | 40 |
| | 250 | 63 | 43 |
| | 350 | 77 | 77 |
| | 450 | 83 | 75 |
| 24-14 | 150 | 30 | 25 |
| | 250 | 67 | 53 |
| | 350 | 78 | 85 |
| | 450 | 83 | 77 |
| 24-15 | 150 | 13 | 37 |
| | 250 | 65 | 50 |
| | 350 | 77 | 57 |
| | 450 | 87 | 82 |

At a surfactant to glyphosate a.e. weight/weight ratio of about 1:1.5, compositions containing steareth-20 or oleth-20 (24-04 and 24-05 respectively) exhibited herbicidal effectiveness on ABUTH similar to one containing Neodol 25-20 (24-03).

Example 25

Glyphosate-containing spray compositions were prepared by tank-mixing Formulations B and C with butyl stearate as shown in Table 25.

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and ECHCF, and evaluation of herbicidal inhibition was done 17 days after application.

Results, averaged for all replicates of each treatment, are shown in Table 25.

TABLE 25

| Glyphosate composition | Glyphosate rate g a.e./ha | Additive | Additive rate % v/v | % Inhibition ABUTH | ECHCF |
|---|---|---|---|---|---|
| Formulation B | 200 | none | | 10 | 30 |
| | 300 | | | 30 | 40 |
| | 400 | | | 63 | 57 |
| Formulation B | 200 | MON 0818 | 0.09 | 68 | 70 |
| | 300 | | | 80 | 85 |
| | 400 | | | 97 | 93 |

TABLE 25-continued

| Glyphosate composition | Glyphosate rate g a.e./ha | Additive | Additive rate % v/v | % Inhibition ABUTH | ECHCF |
|---|---|---|---|---|---|
| Formulation B | 200 | butyl stearate | 0.005 | 75 | 86 |
|  | 300 |  |  | 80 | 96 |
|  | 400 |  |  | 83 | 97 |
| Formulation B | 200 | butyl stearate | 0.01 | 73 | 82 |
|  | 300 |  |  | 77 | 88 |
|  | 400 |  |  | 88 | 86 |
| Formulation B | 200 | butyl stearate | 0.05 | 65 | 82 |
|  | 300 |  |  | 78 | 82 |
|  | 400 |  |  | 94 | 96 |
| Formulation B | 200 | butyl stearate | 0.1 | 75 | 68 |
|  | 300 |  |  | 80 | 82 |
|  | 400 |  |  | 94 | 94 |
| Formulation B | 200 | butyl stearate | 0.2 | 75 | 70 |
|  | 300 |  |  | 83 | 73 |
|  | 400 |  |  | 95 | 96 |
| Formulation B | 200 | butyl stearate | 0.5 | 80 | 73 |
|  | 300 |  |  | 96 | 82 |
|  | 400 |  |  | 96 | 83 |
| Formulation B | 200 | butyl stearate | 1.0 | 90 | 82 |
|  | 300 |  |  | 93 | 85 |
|  | 400 |  |  | 97 | 87 |

Surprisingly the addition of extremely low concentrations of butyl stearate to Formulation B greatly enhanced herbicidal effectiveness in this study.

Example 26

Aqueous concentrate compositions were prepared containing glyphosate IPA salt and excipient ingredients as shown in Table 26a. Process (v) was followed for all compositions using soybean lecithin (45% phospholipid, Avanti).

TABLE 26a

| Concentrate composition | % w/w | | | | | | |
|---|---|---|---|---|---|---|---|
|  | Glyphosate a.e. | Lecithin | Butyl stearate | Fluorad FC-754 | MON 0818 | Ethomeen T/25 | Ethanol |
| 26-01 | 20 | 2.0 | 0.5 |  |  | 1.25 | 1.0 |
| 26-02 | 20 | 2.0 | 0.5 |  | 1.00 | 1.00 | 1.0 |
| 26-03 | 20 | 2.0 | 0.5 |  | 1.25 |  | 1.0 |
| 26-04 | 20 | 6.0 | 1.5 |  |  | 3.00 | 3.0 |
| 26-05 | 20 | 6.0 | 1.5 |  | 2.00 | 2.00 | 2.0 |
| 26-06 | 20 | 6.0 | 1.5 |  | 3.00 |  | 3.0 |
| 26-07 | 20 | 2.0 | 0.5 |  |  | 0.50 |  |
| 26-08 | 20 | 2.0 | 0.5 |  |  | 2.50 |  |
| 26-09 | 20 | 2.0 | 0.5 |  | 1.25 | 1.25 |  |
| 26-10 | 20 | 6.0 | 1.5 |  |  | 0.50 |  |
| 26-11 | 20 | 6.0 | 1.5 |  |  | 3.00 |  |
| 26-12 | 20 | 6.0 | 1.5 |  |  | 6.00 |  |
| 26-13 | 20 | 6.0 | 1.5 |  | 3.00 | 3.00 |  |
| 26-14 | 20 | 2.0 |  | 2.0 | 0.50 |  |  |
| 26-15 | 20 | 6.0 |  | 3.0 | 6.00 |  |  |
| 26-16 | 20 | 6.0 |  | 6.0 | 6.00 |  |  |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and ECHCF, and evaluation of herbicidal inhibition was done 15 days after application.

Formulation J was applied as a comparative treatment. Results, averaged for all replicates of each treatment, are shown in Table 26b.

TABLE 26b

| Concentrate composition | Glyphosate rate g a.e./ha | % Inhibition ABUTH | ECHCF |
|---|---|---|---|
| Formulation J | 150 | 38 | 45 |
|  | 250 | 80 | 63 |
|  | 350 | 78 | 82 |
|  | 450 | 75 | 55 |
| 26-01 | 150 | 23 | 27 |
|  | 250 | 57 | 53 |
|  | 350 | 70 | 85 |
|  | 450 | 70 | 83 |
| 26-02 | 150 | 7 | 25 |
|  | 250 | 52 | 45 |
|  | 350 | 82 | 88 |
|  | 450 | 82 | 90 |
| 26-03 | 150 | 38 | 35 |
|  | 250 | 50 | 40 |
|  | 350 | 82 | 92 |
|  | 450 | 83 | 93 |
| 26-04 | 150 | 40 | 48 |
|  | 250 | 73 | 75 |
|  | 350 | 78 | 92 |
|  | 450 | 88 | 92 |
| 26-05 | 150 | 50 | 53 |
|  | 250 | 68 | 80 |
|  | 350 | 85 | 98 |
|  | 450 | 89 | 96 |
| 26-06 | 150 | 50 | 43 |
|  | 250 | 55 | 80 |
|  | 350 | 78 | 97 |
|  | 450 | 85 | 91 |
| 26-07 | 150 | 3 | 28 |
|  | 250 | 22 | 43 |
|  | 350 | 67 | 72 |
|  | 450 | 73 | 75 |
| 26-08 | 150 | 43 | 33 |
|  | 250 | 77 | 63 |
|  | 350 | 89 | 78 |
|  | 450 | 97 | 85 |
| 26-09 | 150 | 57 | 27 |
|  | 250 | 95 | 63 |
|  | 350 | 89 | 86 |
|  | 450 | 98 | 88 |
| 26-10 | 150 | 32 | 23 |
|  | 250 | 33 | 55 |
|  | 350 | 73 | 82 |
|  | 450 | 67 | 60 |
| 26-11 | 150 | 45 | 32 |
|  | 250 | 78 | 72 |
|  | 350 | 95 | 92 |
|  | 450 | 98 | 96 |
| 26-12 | 150 | 67 | 42 |
|  | 250 | 80 | 75 |
|  | 350 | 96 | 88 |
|  | 450 | 97 | 90 |
| 26-13 | 150 | 73 | 42 |
|  | 250 | 83 | 77 |
|  | 350 | 96 | 91 |
|  | 450 | 98 | 88 |
| 26-14 | 150 | 57 | 30 |
|  | 250 | 77 | 72 |
|  | 350 | 84 | 80 |
|  | 450 | 96 | 75 |
| 26-15 | 150 | 72 | 38 |
|  | 250 | 88 | 82 |
|  | 350 | 98 | 92 |
|  | 450 | 98 | 87 |
| 26-16 | 150 | 85 | 49 |
|  | 250 | 97 | 47 |
|  | 350 | 97 | 83 |
|  | 450 | 98 | 85 |

Performing very well in this test, particularly on ECHCF, were a number of concentrate compositions containing lecithin and butyl stearate.

Example 27

Aqueous concentrate compositions were prepared containing glyphosate IPA salt and excipient ingredients as shown in Table 27a. All are oil-in-water emulsions and were prepared by process (vii).

TABLE 27a

| Concentrate composition | Glyphosate g a.e./l | Butyl stearate | Surfactant | Type of surfactant |
|---|---|---|---|---|
| | | % w/w | | |
| 27-01 | 163 | 1.0 | 10.0 | Tween 80 |
| 27-02 | 163 | 1.0 | 10.0 | Neodol 25-12 |
| 27-03 | 163 | 1.0 | 10.0 | Neodol 25-20 |
| 27-04 | 163 | 1.0 | 10.0 | steareth-20 |
| 27-05 | 163 | 1.0 | 10.0 | oleth-20 |
| 27-06 | 163 | 1.0 | 10.0 | Tergitol 15-S-40 |
| 27-07 | 163 | 1.0 | 10.0 | Tergitol 15-S-15 |
| 27-08 | 163 | 1.0 | 10.0 | Tergitol 15-S-20 |
| 27-09 | 163 | 0.5 | 10.0 | Tergitol 15-S-40 |
| 27-10 | 163 | 0.3 | 10.0 | Tergitol 15-S-15 |
| 27-11 | 163 | 0.3 | 10.0 | Tergitol 15-S-20 |
| 27-12 | 163 | 0.3 | 10.0 | Tergitol 15-S-40 |
| 27-13 | 163 | 0.3 | 5.0 | Tergitol 15-S-15 |
| 27-14 | 163 | 0.3 | 5.0 | Tergitol 15-S-20 |
| 27-15 | 163 | 0.3 | 5.0 | Tergitol 15-S-40 |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and ECHCF, and evaluation of herbicidal inhibition was done 21 days after application.

Formulations B, C and J were applied as comparative treatments. Results, averaged for all replicates of each treatment, are shown in Table 27b.

TABLE 27b

| Concentrate composition | Glyphosate rate g a.e./ha | % Inhibition ABUTH | % Inhibition ECHCF |
|---|---|---|---|
| Formulation B | 150 | 0 | 23 |
| | 250 | 0 | 40 |
| | 350 | 5 | 53 |
| | 450 | 13 | 57 |
| Formulation C | 150 | 0 | 47 |
| | 250 | 28 | 87 |
| | 350 | 72 | 98 |
| | 450 | 97 | 97 |
| Formulation J | 150 | 5 | 40 |
| | 250 | 20 | 63 |
| | 350 | 67 | 93 |
| | 450 | 82 | 92 |
| 27-01 | 150 | 2 | 40 |
| | 250 | 30 | 50 |
| | 350 | 50 | 70 |
| | 450 | 57 | 85 |
| 27-02 | 150 | 10 | 50 |
| | 250 | 33 | 50 |
| | 350 | 75 | 72 |
| | 450 | 75 | 88 |
| 27-03 | 150 | 17 | 53 |
| | 250 | 60 | 60 |
| | 350 | 70 | 92 |
| | 450 | 78 | 94 |
| 27-04 | 150 | 57 | 45 |
| | 250 | 70 | 70 |
| | 350 | 82 | 93 |
| | 450 | 83 | 95 |
| 27-05 | 150 | 47 | 45 |
| | 250 | 70 | 80 |
| | 350 | 80 | 88 |
| | 450 | 88 | 92 |
| 27-06 | 150 | 2 | 42 |
| | 250 | 20 | 60 |
| | 350 | 35 | 75 |
| | 450 | 58 | 89 |
| 27-07 | 150 | 0 | 42 |
| | 250 | 30 | 68 |
| | 350 | 40 | 75 |
| | 450 | 77 | 82 |
| 27-08 | 150 | 2 | 40 |
| | 250 | 25 | 60 |
| | 350 | 50 | 83 |
| | 450 | 75 | 86 |
| 27-09 | 150 | 2 | 43 |
| | 250 | 27 | 83 |
| | 350 | 40 | 73 |
| | 450 | 70 | 78 |
| 27-10 | 150 | 2 | 42 |
| | 250 | 32 | 47 |
| | 350 | 43 | 63 |
| | 450 | 70 | 82 |
| 27-11 | 150 | 0 | 30 |
| | 250 | 25 | 53 |
| | 350 | 35 | 75 |
| | 450 | 70 | 75 |
| 27-12 | 150 | 2 | 40 |
| | 250 | 13 | 57 |
| | 350 | 25 | 75 |
| | 450 | 40 | 83 |
| 27-13 | 150 | 5 | 42 |
| | 250 | 23 | 62 |
| | 350 | 38 | 63 |
| | 450 | 67 | 60 |
| 27-14 | 150 | 2 | 33 |
| | 250 | 13 | 48 |
| | 350 | 30 | 53 |
| | 450 | 70 | 88 |
| 27-15 | 150 | 2 | 33 |
| | 250 | 18 | 48 |
| | 350 | 30 | 75 |
| | 450 | 43 | 65 |

In this test, at a surfactant to glyphosate a.e. weight/weight ratio of about 1: 1.5, compositions containing steareth-20 or oleth-20 (27-04 and 27-05 respectively) exhibited greater herbicidal effectiveness on both ABUTH and ECHCF than one containing Neodol 25-20 (27-03).

Example 28

Aqueous concentrate compositions were prepared containing glyphosate ammonium or IPA salt and excipient ingredients as shown in Table 28a. Concentrate composition 28-01 is a water-in-oil-in-water multiple emulsion and was prepared by process (vi), using Span 80 as emulsifier #1. Concentrate compositions 28-02 to 28-11 and 28-17 are oil-in-water emulsions and were prepared by process (vii). Concentrate compositions 28-12 to 28-16 are aqueous solution concentrates and were prepared by process (viii), the component indicated below as "emulsifier #2" being the surfactant component.

TABLE 28a

| Conc. comp. | Glyphosate a.e. | Butyl stearate | Span 80 | Emulsifier #2 | % in inner aq. phase Water | % in inner aq. phase Glyphosate | Emulsifier #2 | Glyphosate salt |
|---|---|---|---|---|---|---|---|---|
| 28-01 | 10 | 18.0 | 3.0 | 5.0 | 9.0 | 20 | Tween 20 | IPA |
| 28-02 | 15 | 1.0 | | | 10.0 | | Tween 80 | IPA |
| 28-03 | 15 | 1.0 | | | 10.0 | | Neodol 25-12 | IPA |
| 28-04 | 15 | 1.0 | | | 10.0 | | Neodol 25-20 | IPA |
| 28-05 | 15 | 1.0 | | | 10.0 | | steareth-20 | IPA |
| 28-06 | 15 | 1.0 | | | 10.0 | | oleth-20 | IPA |
| 28-07 | 15 | 1.0 | | | 10.0 | | Tween 80 | ammonium |
| 28-08 | 15 | 1.0 | | | 10.0 | | Neodol 25-12 | ammonium |
| 28-09 | 15 | 1.0 | | | 10.0 | | Neodol 25-20 | ammonium |
| 28-10 | 15 | 1.0 | | | 10.0 | | steareth-20 | ammonium |
| 28-11 | 15 | 1.0 | | | 10.0 | | oleth-20 | ammonium |
| 28-12 | 15 | | | | 10.0 | | Tween 80 | IPA |
| 28-13 | 15 | | | | 10.0 | | Neodol 25-12 | IPA |
| 28-14 | 15 | | | | 10.0 | | Neodol 25-20 | IPA |
| 28-15 | 15 | | | | 10.0 | | steareth-20 | IPA |
| 28-16 | 15 | | | | 10.0 | | oleth-20 | IPA |
| 28-17 | 15 | 1.0 | | | 10.0 | | Emerest 2661 | IPA |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and ECHCF, and evaluation of herbicidal inhibition was done 20 days after application.

Formulations B, C and J were applied as comparative treatments. Results, averaged for all replicates of each treatment, are shown in Table 28b.

TABLE 28b

| Concentrate composition | Glyphosate rate g a.e./ha | % Inhibition ABUTH | % Inhibition ECHCF |
|---|---|---|---|
| Formulation B | 150 | 2 | 5 |
| | 250 | 3 | 25 |
| | 350 | 28 | 30 |
| | 450 | 53 | 50 |
| Formulation C | 150 | 5 | 25 |
| | 250 | 60 | 50 |
| | 350 | 85 | 83 |
| | 450 | 88 | 88 |
| Formulation J | 150 | 2 | 10 |
| | 250 | 70 | 40 |
| | 350 | 82 | 53 |
| | 450 | 87 | 83 |
| 28-01 | 150 | 23 | 20 |
| | 250 | 72 | 30 |
| | 350 | 80 | 80 |
| | 450 | 85 | 69 |
| 28-02 | 150 | 5 | 18 |
| | 250 | 72 | 38 |
| | 350 | 82 | 63 |
| | 450 | 85 | 83 |
| 28-03 | 150 | 25 | 20 |
| | 250 | 70 | 57 |
| | 350 | 85 | 68 |
| | 450 | 90 | 83 |
| 28-04 | 150 | 25 | 27 |
| | 250 | 77 | 67 |
| | 350 | 85 | 62 |
| | 450 | 88 | 70 |
| 28-05 | 150 | 60 | 25 |
| | 250 | 82 | 62 |
| | 350 | 87 | 73 |
| | 450 | 85 | 80 |
| 28-06 | 150 | 50 | 32 |
| | 250 | 78 | 78 |

TABLE 28b-continued

| Concentrate composition | Glyphosate rate g a.e./ha | % Inhibition ABUTH | % Inhibition ECHCF |
|---|---|---|---|
| | 350 | 91 | 91 |
| | 450 | 98 | 98 |
| 28-07 | 150 | 5 | 25 |
| | 250 | 55 | 77 |
| | 350 | 77 | 86 |
| | 450 | 83 | 99 |
| 28-08 | 150 | 0 | 13 |
| | 250 | 58 | 78 |
| | 350 | 80 | 85 |
| | 450 | 85 | 87 |
| 28-09 | 150 | 7 | 25 |
| | 250 | 57 | 72 |
| | 350 | 77 | 83 |
| | 450 | 91 | 92 |
| 28-10 | 150 | 50 | 25 |
| | 250 | 80 | 55 |
| | 350 | 86 | 87 |
| | 450 | 92 | 82 |
| 28-11 | 150 | 53 | 30 |
| | 250 | 78 | 80 |
| | 350 | 87 | 89 |
| | 450 | 95 | 98 |
| 28-12 | 150 | 0 | 25 |
| | 250 | 50 | 77 |
| | 350 | 77 | 90 |
| | 450 | 83 | 94 |
| 28-13 | 150 | 2 | 30 |
| | 250 | 55 | 75 |
| | 350 | 72 | 92 |
| | 450 | 85 | 80 |
| 28-14 | 150 | 12 | 30 |
| | 250 | 75 | 78 |
| | 350 | 84 | 90 |
| | 450 | 96 | 94 |
| 28-15 | 150 | 55 | 35 |
| | 250 | 78 | 80 |
| | 350 | 80 | 94 |
| | 450 | 86 | 98 |
| 28-16 | 150 | 50 | 35 |
| | 250 | 73 | 63 |
| | 350 | 84 | 83 |
| | 450 | 89 | 95 |
| 28-17 | 150 | 0 | 10 |
| | 250 | 10 | 53 |

TABLE 28b-continued

| Concentrate composition | Glyphosate rate g a.e./ha | % Inhibition ABUTH | % Inhibition ECHCF |
|---|---|---|---|
| | 350 | 53 | 83 |
| | 450 | 62 | 87 |

Compositions containing steareth-20 or oleth-20 (28-05, 28-06, 28-10, 28-11, 28-15, 28-16) generally exhibited superior herbicidal effectiveness to counterparts containing Neodol 25-20 (28-04, 28-09, 28-14), at least on ABUTH. The presence of a small amount of butyl stearate tended to enhance effectiveness on ABUTH (compare 28-05 and 28-06 with 28-15 and 28-16).

Example 29

Aqueous concentrate compositions were prepared containing glyphosate IPA salt and excipient ingredients as shown in Table 29a. Concentrate composition 29-01 is a water-in-oil-in-water multiple emulsion and was prepared by process (vi), using Span 80 as emulsifier #1. Concentrate compositions 29-03 to 29-08 and 29-14, 29-16, & 29-17 are oil-in-water emulsions and were prepared by process (vii). Concentrate compositions 29-09 to 29-13, and 29-15 are aqueous solution concentrates and were prepared by process (viii).

TABLE 29a

| Concentrate composition | Glyphosate a.e. | Butyl stearate | Span 80 | Emulsifier #2 | % in inner aq. phase Water | % in inner aq. phase Glyphosate | Emulsifier #2 |
|---|---|---|---|---|---|---|---|
| | | | % w/w | | | | |
| 29-01 | 10 | 18.0 | 3.0 | 2.5 | 9.0 | 20 | Tween 20 |
| 29-02 | 15 | 1.0 | | 10.0 | | | Emerest 2661 |
| 29-03 | 15 | 1.0 | | 10.0 | | | Tween 80 |
| 29-04 | 15 | 1.0 | | 10.0 | | | oleth-20 |
| 29-05 | 15 | 1.0 | | 10.0 | | | Neodol 25-20 |
| 29-06 | 15 | 1.0 | | 10.0 | | | ceteareth-27 |
| 29-07 | 15 | 1.0 | | 10.0 | | | ceteareth-55 |
| 29-08 | 15 | 1.0 | | 10.0 | | | Genapol UD-110 |
| 29-09 | 15 | | | 10.0 | | | ceteareth-27 |
| 29-10 | 15 | | | 10.0 | | | ceteareth-55 |
| 29-11 | 15 | | | 10.0 | | | Genapol UD-110 |
| 29-12 | 15 | | | 10.0 | | | oleth-20 |
| 29-13 | 10 | | | 10.0 | | | oleth-20 |
| 29-14 | 10 | 1.0 | | 10.0 | | | oleth-20 |
| 29-15 | 20 | | | 10.0 | | | oleth-20 |
| 29-16 | 15 | 0.5 | | 5.0 | | | oleth-20 |
| 29-17 | 15 | 0.5 | | 10.0 | | | oleth-20 |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and ECHCF, and evaluation of herbicidal inhibition was done 18 days after application.

Formulations B, C and J were applied as comparative treatments. Results, averaged for all replicates of each treatment, are shown in Table 29b.

TABLE 29b

| Concentrate composition | Glyphosate rate g a.e./ha | % Inhibition ABUTH | % Inhibition ECHCF |
|---|---|---|---|
| Formulation B | 150 | 0 | 0 |
| | 250 | 8 | 20 |
| | 350 | 27 | 40 |
| | 450 | 62 | 50 |
| Formulation C | 150 | 27 | 50 |
| | 250 | 75 | 70 |
| | 350 | 92 | 80 |
| | 450 | 97 | 92 |
| Formulation J | 150 | 23 | 30 |
| | 250 | 72 | 50 |
| | 350 | 94 | 63 |
| | 450 | 95 | 80 |
| 29-01 | 150 | 22 | 30 |
| | 250 | 60 | 40 |
| | 350 | 83 | 57 |
| | 450 | 90 | 67 |
| 29-02 | 150 | 12 | 33 |
| | 250 | 45 | 50 |
| | 350 | 73 | 63 |
| | 450 | 83 | 83 |
| 29-03 | 150 | 27 | 43 |
| | 250 | 68 | 50 |
| | 350 | 80 | 63 |
| | 450 | 87 | 87 |
| 29-04 | 150 | 68 | 47 |
| | 250 | 95 | 73 |
| | 350 | 99 | 78 |
| | 450 | 95 | 90 |
| 29-05 | 150 | 50 | 50 |

TABLE 29b-continued

| Concentrate composition | Glyphosate rate g a.e./ha | % Inhibition ABUTH | % Inhibition ECHCF |
|---|---|---|---|
| | 250 | 77 | 77 |
| | 350 | 90 | 83 |
| | 450 | 98 | 83 |
| 29-06 | 150 | 78 | 67 |
| | 250 | 93 | 82 |
| | 350 | 97 | 87 |
| | 450 | 99 | 97 |

TABLE 29b-continued

| Concentrate composition | Glyphosate rate g a.e./ha | % Inhibition ABUTH | ECHCF |
|---|---|---|---|
| 29-07 | 150 | 87 | 57 |
|  | 250 | 96 | 73 |
|  | 350 | 99 | 85 |
|  | 450 | 99 | 97 |
| 29-08 | 150 | 42 | 30 |
|  | 250 | 73 | 53 |
|  | 350 | 82 | 85 |
|  | 450 | 95 | 89 |
| 29-09 | 150 | 67 | 40 |
|  | 250 | 95 | 73 |
|  | 350 | 99 | 95 |
|  | 450 | 99 | 98 |
| 29-10 | 150 | 85 | 60 |
|  | 250 | 96 | 68 |
|  | 350 | 96 | 91 |
|  | 450 | 100 | 88 |
| 29-11 | 150 | 13 | 10 |
|  | 250 | 67 | 50 |
|  | 350 | 78 | 60 |
|  | 450 | 88 | 73 |
| 29-12 | 150 | 72 | 43 |
|  | 250 | 97 | 68 |
|  | 350 | 98 | 83 |
|  | 450 | 99 | 93 |
| 29-13 | 150 | 73 | 57 |
|  | 250 | 88 | 70 |
|  | 350 | 98 | 87 |
|  | 450 | 99 | 96 |
| 29-14 | 150 | 80 | 50 |
|  | 250 | 96 | 70 |
|  | 350 | 99 | 85 |
|  | 450 | 98 | 88 |
| 29-15 | 150 | 70 | 43 |
|  | 250 | 96 | 53 |
|  | 350 | 97 | 82 |
|  | 450 | 99 | 89 |
| 29-16 | 150 | 62 | 53 |
|  | 250 | 88 | 72 |
|  | 350 | 99 | 81 |
|  | 450 | 99 | 91 |
| 29-17 | 150 | 72 | 58 |
|  | 250 | 95 | 68 |
|  | 350 | 100 | 89 |
|  | 450 | 100 | 93 |

The greatest herbicidal effectiveness in this test was exhibited by compositions containing a $C_{16-18}$ alkylether surfactant (oleth-20, ceteareth-27 or ceteareth-55).

Example 30

Aqueous concentrate compositions were prepared containing glyphosate IPA salt and excipient ingredients as shown in Table 30a. All are oil-in-water emulsions and were prepared by process (vii).

TABLE 30a

| Concentrate composition | Glyphosate g a.e./l | % w/w Butyl stearate | Surfactant | Type of surfactant |
|---|---|---|---|---|
| 30-01 | 163 | 1.00 | 10.0 | Tween 80 |
| 30-02 | 163 | 1.00 | 10.0 | Emerest 2661 |
| 30-03 | 326 | 1.00 | 10.0 | Genapol UD-110 |
| 30-04 | 326 | 0.50 | 10.0 | Genapol UD-110 |
| 30-05 | 326 | 0.25 | 10.0 | Genapol UD-110 |
| 30-06 | 163 | 0.25 | 10.0 | Genapol UD-110 |
| 30-07 | 163 | 1.00 | 10.0 | Genapol UD-110 |
| 30-08 | 163 | 1.00 | 10.0 | Neodol 1-9 |
| 30-09 | 163 | 1.00 | 10.0 | Neodol 1-12 |
| 30-10 | 163 | 1.00 | 10.0 | Neodol 25-20 |
| 30-11 | 163 | 1.00 | 10.0 | Neodol 25-12 |
| 30-12 | 163 | 1.00 | 10.0 | Neodox 25-11 |
| 30-13 | 163 | 1.00 | 10.0 | laureth-23 |
| 30-14 | 163 | 1.00 | 10.0 | ceteth-20 |
| 30-15 | 163 | 1.00 | 10.0 | steareth-20 |
| 30-16 | 163 | 1.00 | 10.0 | oleth-20 |

Velvetleaf (*Abutilon theophrasti*, ABUTH) and Japanese millet (*Echinochloa crus-galli*, ECHCF) plants were grown and treated by the standard procedures given above. Applications of spray compositions were made 15 days after planting ABUTH and ECHCF, and evaluation of herbicidal inhibition was done 23 days after application.

Formulations B, C and J were applied as comparative treatments. Results, averaged for all replicates of each treatment, are shown in Table 30b.

TABLE 30b

| Concentrate composition | Glyphosate rate g a.e./ha | % Inhibition ABUTH | ECHCF |
|---|---|---|---|
| Formulation B | 150 | 0 | 0 |
|  | 250 | 25 | 22 |
|  | 350 | 60 | 40 |
|  | 450 | 65 | 52 |
| Formulation C | 150 | 43 | 52 |
|  | 250 | 72 | 83 |
|  | 350 | 87 | 98 |
|  | 450 | 97 | 95 |
| Formulation J | 150 | 50 | 43 |
|  | 250 | 75 | 91 |
|  | 350 | 86 | 96 |
|  | 450 | 95 | 97 |
| 30-01 | 150 | 50 | 30 |
|  | 250 | 75 | 75 |
|  | 350 | 85 | 87 |
|  | 450 | 90 | 92 |
| 30-02 | 150 | 35 | 47 |
|  | 250 | 58 | 77 |
|  | 350 | 75 | 85 |
|  | 450 | 80 | 96 |
| 30-03 | 150 | 33 | 32 |
|  | 250 | 57 | 53 |
|  | 350 | 75 | 78 |
|  | 450 | 84 | 94 |
| 30-04 | 150 | 20 | 25 |
|  | 250 | 55 | 68 |
|  | 350 | 78 | 91 |
|  | 450 | 82 | 97 |
| 30-05 | 150 | 37 | 12 |
|  | 250 | 58 | 42 |
|  | 350 | 81 | 70 |
|  | 450 | 86 | 73 |
| 30-06 | 150 | 50 | 8 |
|  | 250 | 65 | 40 |
|  | 350 | 81 | 65 |
|  | 450 | 92 | 85 |
| 30-07 | 150 | 50 | 30 |
|  | 250 | 63 | 48 |
|  | 350 | 84 | 68 |
|  | 450 | 98 | 84 |
| 30-08 | 150 | 43 | 35 |
|  | 250 | 52 | 65 |
|  | 350 | 73 | 85 |
|  | 450 | 84 | 85 |
| 30-09 | 150 | 55 | 40 |

TABLE 30b-continued

| Concentrate composition | Glyphosate rate g a.e./ha | % Inhibition ABUTH | ECHCF |
|---|---|---|---|
| | 250 | 68 | 58 |
| | 350 | 79 | 65 |
| | 450 | 97 | 73 |
| 30-10 | 150 | 69 | 40 |
| | 250 | 81 | 68 |
| | 350 | 94 | 92 |
| | 450 | 99 | 96 |
| 30-11 | 150 | 58 | 50 |
| | 250 | 84 | 60 |
| | 350 | 90 | 83 |
| | 450 | 94 | 93 |
| 30-12 | 150 | 50 | 40 |
| | 250 | 57 | 67 |
| | 350 | 65 | 84 |
| | 450 | 75 | 98 |
| 30-13 | 150 | 57 | 53 |
| | 250 | 78 | 73 |
| | 350 | 89 | 97 |
| | 450 | 98 | 97 |
| 30-14 | 150 | 68 | 67 |
| | 250 | 85 | 73 |
| | 350 | 97 | 98 |
| | 450 | 100 | 97 |
| 30-15 | 150 | 72 | 50 |
| | 250 | 88 | 89 |
| | 350 | 89 | 98 |
| | 450 | 99 | 97 |
| 30-16 | 150 | 65 | 53 |
| | 250 | 87 | 72 |
| | 350 | 97 | 85 |
| | 450 | 100 | 95 |

Activity overall in this test was very high, and differences among compositions in herbicidal effectivess are difficult to discern clearly.

Example 31

Aqueous concentrate compositions were prepared containing glyphosate IPA salt and excipient ingredients as shown in Table 31a. All are oil-in-water emulsions and were prepared by process (vii).

TABLE 31a

| | | % w/w | | |
|---|---|---|---|---|
| Concentrate composition | Glyphosate g a.e./l | Butyl Stearate | Surfactant | Type of surfactant |
| 31-01 | 163 | 1.00 | 10.0 | Tween 80 |
| 31-02 | 163 | 1.00 | 10.0 | Emerest 2661 |
| 31-03 | 163 | 1.00 | 10.0 | Neodol 25-20 |
| 31-04 | 163 | 1.00 | 10.0 | oleth-20 |
| 31-05 | 163 | 0.50 | 5.0 | oleth-20 |
| 31-06 | 163 | 0.25 | 2.5 | oleth-20 |
| 31-07 | 163 | 0.50 | 2.5 | oleth-20 |
| 31-08 | 163 | 0.50 | 1.0 | oleth-20 |
| 31-09 | 163 | 0.25 | 5.0 | oleth-20 |
| 31-10 | 326 | 1.00 | 10.0 | Neodol 1-12 |
| 31-11 | 326 | 0.50 | 10.0 | Neodol 1-12 |
| 31-12 | 326 | 0.25 | 10.0 | Neodol 1-12 |
| 31-13 | 326 | 1.00 | 5.0 | Neodol 1-12 |
| 31-14 | 326 | 0.50 | 5.0 | Neodol 1-12 |
| 31-15 | 326 | 0.25 | 5.0 | Neodol 1-12 |
| 31-16 | 326 | 0.10 | 5.0 | Neodol 1-12 |

Velvetleaf (*Abutilon theophrasti*, ABUTH) and Japanese millet (*Echinochloa crus-galli*, ECHCF) plants were grown and treated by the standard procedures given above. Applications of spray compositions were made 15 days after planting ABUTH and ECHCF, and evaluation of herbicidal inhibition was done 20 days after application.

Formulations B, C and J were applied as comparative treatments. Results, averaged for all replicates of each treatment, are shown in Table 31b.

TABLE 31b

| Concentrate composition | Glyphosate rate g a.e./ha | % Inhibition ABUTH | ECHCF |
|---|---|---|---|
| Formulation B | 150 | 7 | 50 |
| | 250 | 45 | 60 |
| | 350 | 73 | 73 |
| | 450 | 80 | 78 |
| Formulation C | 150 | 75 | 77 |
| | 250 | 87 | 100 |
| | 350 | 96 | 99 |
| | 450 | 99 | 97 |
| Formulation J | 150 | 72 | 77 |
| | 250 | 83 | 89 |
| | 350 | 97 | 99 |
| | 450 | 97 | 98 |
| 31-01 | 150 | 60 | 75 |
| | 250 | 80 | 85 |
| | 350 | 93 | 97 |
| | 450 | 98 | 98 |
| 31-02 | 150 | 57 | 75 |
| | 250 | 70 | 83 |
| | 350 | 87 | 83 |
| | 450 | 90 | 94 |
| 31-03 | 150 | 77 | 80 |
| | 250 | 87 | 92 |
| | 350 | 97 | 87 |
| | 450 | 99 | 98 |
| 31-04 | 150 | 80 | 89 |
| | 250 | 93 | 92 |
| | 350 | 99 | 99 |
| | 450 | 100 | 99 |
| 31-05 | 150 | 83 | 83 |
| | 250 | 92 | 93 |
| | 350 | 97 | 90 |
| | 450 | 100 | 93 |
| 31-06 | 150 | 77 | 77 |
| | 250 | 80 | 91 |
| | 350 | 90 | 99 |
| | 450 | 98 | 99 |
| 31-07 | 150 | 77 | 83 |
| | 250 | 82 | 89 |
| | 350 | 90 | 91 |
| | 450 | 97 | 98 |
| 31-08 | 150 | 47 | 82 |
| | 250 | 73 | 82 |
| | 350 | 80 | 97 |
| | 450 | 92 | 91 |
| 31-09 | 150 | 73 | 78 |
| | 250 | 87 | 88 |
| | 350 | 97 | 94 |
| | 450 | 99 | 99 |
| 31-10 | 150 | 52 | 67 |
| | 250 | 70 | 80 |
| | 350 | 93 | 88 |
| | 450 | 93 | 94 |
| 31-11 | 150 | 40 | 68 |
| | 250 | 72 | 85 |
| | 350 | 87 | 96 |
| | 450 | 93 | 96 |
| 31-12 | 150 | 37 | 60 |
| | 250 | 68 | 83 |
| | 350 | 85 | 85 |
| | 450 | 93 | 75 |
| 31-13 | 150 | 28 | 63 |
| | 250 | 53 | 80 |
| | 350 | 85 | 97 |
| | 450 | 88 | 97 |
| 31-14 | 150 | 37 | 63 |
| | 250 | 58 | 73 |
| | 350 | 83 | 96 |
| | 450 | 90 | 91 |

TABLE 31b-continued

| Concentrate composition | Glyphosate rate g a.e./ha | % Inhibition ABUTH | ECHCF |
|---|---|---|---|
| 31-15 | 150 | 30 | 70 |
|  | 250 | 47 | 83 |
|  | 350 | 82 | 89 |
|  | 450 | 87 | 89 |
| 31-16 | 150 | 40 | 53 |
|  | 250 | 53 | 82 |
|  | 350 | 80 | 80 |
|  | 450 | 88 | 77 |

Composition 31-04, containing 1% butyl stearate and 10% oleth-20 (surfactant to glyphosate a.e. weight/weight ratio about 1:1.5), exhibited marginally greater herbicidal effectiveness than composition 31-03, containing 1% butyl stearate and 10% Neodol 25-20. At this very high surfactant to glyphosate ratio, however, both performed extremely well. Surprisingly, when the butyl stearate and oleth-20 concentrations were significantly lowered, this high level of performance was maintained to a remarkable degree. Even when butyl stearate was reduced to 0.25% and oleth-20 to 2.5% (surfactant to glyphosate a.e. ratio about 1:6), as in composition 31-06, herbicidal effectiveness was still similar to that obtained with commercial standard Formulations C and J.

Example 32

Aqueous concentrate compositions were prepared containing glyphosate IPA salt and excipient ingredients as shown in Table 32a. Concentrate compositions 32-01 to 32-08 and 32-11 to 32-16 are oil-in-water emulsions and were prepared by process (vii). Concentrate compositions 32-09 and 32-10 are aqueous solution concentrates and were prepared by process (viii).

TABLE 32a

| Concentrate composition | Glyphosate a.e. | % w/w Butyl Stearate | Surfactant | Type of surfactant |
|---|---|---|---|---|
| 32-01 | 15.0 | 0.25 | 5.0 | Emerest 2661 |
| 32-02 | 15.0 | 0.25 | 5.0 | Tween 80 |
| 32-03 | 15.0 | 0.25 | 5.0 | Neodol 25-20 |
| 32-04 | 15.0 | 0.25 | 5.0 | laureth-23 |
| 32-05 | 15.0 | 0.25 | 5.0 | ceteth-20 |
| 32-06 | 15.0 | 0.25 | 2.5 | Tween 80 |
| 32-07 | 15.0 | 0.10 | 1.0 | Tween 80 |
| 32-08 | 15.0 | 1.00 | 10.0 | Tween 80 |
| 32-09 | 15.0 |  | 5.0 | laureth-23 |
| 32-10 | 15.0 |  | 5.0 | ceteth-20 |
| 32-11 | 15.0 | 1.00 | 10.0 | Neodol 25-20 |
| 32-12 | 15.0 | 1.00 | 10.0 | oleth-20 |
| 32-13 | 15.0 | 0.50 | 5.0 | oleth-20 |
| 32-14 | 15.0 | 0.25 | 5.0 | oleth-20 |
| 32-15 | 15.0 | 0.25 | 2.5 | oleth-20 |
| 32-16 | 15.0 | 0.25 | 5.0 | Genapol UD-110 |

Velvetleaf (*Abutilon theophrasti*, ABUTH) and Japanese millet (*Echinochloa crus-galli*, ECHCF) plants were grown and treated by the standard procedures given above. Applications of spray compositions were made 12 days after planting ABUTH and ECHCF, and evaluation of herbicidal inhibition was done 16 days after application.

Formulations B, C and J were applied as comparative treatments. Results, averaged for all replicates of each treatment, are shown in Table 32b.

TABLE 32b

| Concentrate composition | Glyphosate rate g a.e./ha | % Inhibition ABUTH | ECHCF |
|---|---|---|---|
| Formulation B | 150 | 2 | 10 |
|  | 250 | 5 | 20 |
|  | 350 | 43 | 30 |
|  | 450 | 58 | 43 |
| Formulation C | 150 | 68 | 50 |
|  | 250 | 92 | 79 |
|  | 350 | 96 | 90 |
|  | 450 | 98 | 85 |
| Formulation J | 150 | 57 | 43 |
|  | 250 | 90 | 63 |
|  | 350 | 95 | 80 |
|  | 450 | 95 | 95 |
| 32-01 | 150 | 7 | 33 |
|  | 250 | 50 | 43 |
|  | 350 | 77 | 53 |
|  | 450 | 80 | 93 |
| 32-02 | 150 | 17 | 50 |
|  | 250 | 72 | 70 |
|  | 350 | 80 | 80 |
|  | 450 | 80 | 93 |
| 32-03 | 150 | 43 | 40 |
|  | 250 | 75 | 68 |
|  | 350 | 87 | 75 |
|  | 450 | 96 | 95 |
| 32-04 | 150 | 33 | 47 |
|  | 250 | 73 | 63 |
|  | 350 | 80 | 77 |
|  | 450 | 90 | 93 |
| 32-05 | 150 | 73 | 37 |
|  | 250 | 92 | 57 |
|  | 350 | 95 | 88 |
|  | 450 | 95 | 73 |
| 32-06 | 150 | 25 | 35 |
|  | 250 | 68 | 47 |
|  | 350 | 80 | 92 |
|  | 450 | 88 | 85 |
| 32-07 | 150 | 3 | 30 |
|  | 250 | 57 | 40 |
|  | 350 | 77 | 53 |
|  | 450 | 80 | 67 |
| 32-08 | 150 | 53 | 43 |
|  | 250 | 77 | 62 |
|  | 350 | 80 | 88 |
|  | 450 | 93 | 80 |
| 32-09 | 150 | 32 | 60 |
|  | 250 | 77 | 53 |
|  | 350 | 93 | 73 |
|  | 450 | 97 | 93 |
| 32-10 | 150 | 75 | 35 |
|  | 250 | 92 | 77 |
|  | 350 | 96 | 77 |
|  | 450 | 97 | 93 |
| 32-11 | 150 | 75 | 53 |
|  | 250 | 90 | 78 |
|  | 350 | 95 | 89 |
|  | 450 | 98 | 97 |
| 32-12 | 150 | 80 | 43 |
|  | 250 | 95 | 73 |
|  | 350 | 96 | 92 |
|  | 450 | 98 | 89 |
| 32-13 | 150 | 75 | 53 |
|  | 250 | 92 | 97 |
|  | 350 | 97 | 99 |
|  | 450 | 96 | 93 |
| 32-14 | 150 | 78 | 70 |
|  | 250 | 90 | 92 |
|  | 350 | 93 | 97 |
|  | 450 | 95 | 93 |
| 32-15 | 150 | 70 | 60 |
|  | 250 | 83 | 98 |
|  | 350 | 95 | 99 |
|  | 450 | 97 | 99 |
| 32-16 | 150 | 27 | 52 |
|  | 250 | 75 | 73 |

TABLE 32b-continued

| Concentrate composition | Glyphosate rate g a.e./ha | % Inhibition ABUTH | ECHCF |
|---|---|---|---|
| | 350 | 80 | 98 |
| | 450 | 83 | 99 |

Extremely high herbicidal effectiveness was again observed with a composition (32-15) containing 15% glyphosate a.e. and just 2.5% oleth-20 together with 0.25% butyl stearate. A comparison of 15% glyphosate a.e. compositions containing 5% alkylether surfactant and 0.25% butyl stearate provided the following ranking of alkylethers in descending order of effectiveness: oleth-20 (32-14) >ceteth-20 (32-05)>Neodol 25-20 (32-03)=laureth-23 (67-04).

Example 33

Aqueous concentrate compositions were prepared containing glyphosate IPA salt and excipient ingredients as shown in Table 33a. All are oil-in-water emulsions and were prepared by process (vii).

TABLE 33a

| Concentrate composition | Glyphosate g a.e./l | Butyl stearate | Surfactant | Type of surfactant |
|---|---|---|---|---|
| | | % w/w | | |
| 33-01 | 163 | 0.50 | 5.0 | oleth-20 |
| 33-02 | 163 | 0.25 | 5.0 | oleth-20 |
| 33-03 | 163 | 0.25 | 2.5 | oleth-20 |
| 33-04 | 163 | 1.00 | 10.0 | oleth-20 |
| 33-05 | 163 | 0.50 | 5.0 | steareth-20 |
| 33-06 | 163 | 0.25 | 5.0 | steareth-20 |
| 33-07 | 163 | 0.25 | 2.5 | steareth-20 |
| 33-08 | 163 | 1.00 | 10.0 | steareth-20 |

Velvetleaf (*Abutilon theophrasti*, ABUTH) and Japanese millet (*Echinochloa crus-galli*, ECHCF) plants were grown and treated by the standard procedures given above. Applications of spray compositions were made 14 days after planting ABUTH and ECHCF, and evaluation of herbicidal inhibition was done 16 days after application.

Formulations B, C and J were applied as comparative treatments. Results, averaged for all replicates of each treatment, are shown in Table 33b.

TABLE 33b

| Concentrate composition | Glyphosate rate g a.e./ha | % Inhibition ABUTH | ECHCF |
|---|---|---|---|
| Formulation B | 150 | 0 | 30 |
| | 250 | 20 | 43 |
| | 350 | 43 | 53 |
| | 450 | 68 | 57 |
| Formulation C | 150 | 60 | 47 |
| | 250 | 75 | 53 |
| | 350 | 87 | 80 |
| | 450 | 87 | 78 |
| Formulation J | 150 | 42 | 43 |
| | 250 | 83 | 60 |
| | 350 | 87 | 73 |
| | 450 | 93 | 87 |
| 33-01 | 150 | 60 | 60 |
| | 250 | 78 | 63 |

TABLE 33b-continued

| Concentrate composition | Glyphosate rate g a.e./ha | % Inhibition ABUTH | ECHCF |
|---|---|---|---|
| | 350 | 87 | 89 |
| | 450 | 92 | 78 |
| 33-02 | 150 | 70 | 43 |
| | 250 | 80 | 91 |
| | 350 | 87 | 86 |
| | 450 | 96 | 87 |
| 33-03 | 150 | 52 | 43 |
| | 250 | 75 | 72 |
| | 350 | 83 | 93 |
| | 450 | 87 | 94 |
| 33-04 | 150 | 72 | 50 |
| | 250 | 93 | 73 |
| | 350 | 97 | 95 |
| | 450 | 97 | 91 |
| 33-05 | 150 | 72 | 43 |
| | 250 | 80 | 78 |
| | 350 | 87 | 91 |
| | 450 | 93 | 85 |
| 33-06 | 150 | 68 | 40 |
| | 250 | 80 | 50 |
| | 350 | 93 | 75 |
| | 450 | 95 | 85 |
| 33-07 | 150 | 63 | 37 |
| | 250 | 78 | 55 |
| | 350 | 87 | 84 |
| | 450 | 83 | 82 |
| 33-08 | 150 | 70 | 50 |
| | 250 | 80 | 70 |
| | 350 | 92 | 84 |
| | 450 | 94 | 98 |

All compositions containing butyl stearate and either oleth-20 or steareth-20 showed a very high level of performance by comparison with commercial standard Formulations C and J.

Example 34

Aqueous concentrate compositions were prepared containing glyphosate IPA salt and excipient ingredients as shown in Table 34a. All are oil-in-water emulsions and were prepared by process (vii).

TABLE 34a

| Concentrate composition | Glyphosate g a.e./l | Butyl stearate | Surfactant | Type of surfactant |
|---|---|---|---|---|
| | | % w/w | | |
| 34-01 | 163 | 0.50 | 5.0 | oleth-20 |
| 34-02 | 163 | 0.25 | 5.0 | oleth-20 |
| 34-03 | 163 | 0.25 | 2.5 | oleth-20 |
| 34-04 | 163 | 1.00 | 10.0 | oleth-20 |
| 34-05 | 163 | 0.50 | 5.0 | steareth-20 |
| 34-06 | 163 | 0.25 | 5.0 | steareth-20 |
| 34-07 | 163 | 0.25 | 2.5 | steareth-20 |
| 34-08 | 163 | 1.00 | 10.0 | steareth-20 |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and ECHCF, and evaluation of herbicidal inhibition was done 18 days after application.

Formulations B, C and J were applied as comparative treatments. Results, averaged for all replicates of each treatment, are shown in Table 34b.

TABLE 34b

| Concentrate composition | Glyphosate rate g a.e./ha | % Inhibition ABUTH | ECHCF |
|---|---|---|---|
| Formulation B | 150 | 3 | 10 |
| | 250 | 28 | 23 |
| | 350 | 72 | 37 |
| | 450 | 73 | 50 |
| Formulation C | 150 | 57 | 43 |
| | 250 | 87 | 62 |
| | 350 | 93 | 83 |
| | 450 | 99 | 95 |
| Formulation J | 150 | 27 | 47 |
| | 250 | 70 | 53 |
| | 350 | 92 | 75 |
| | 450 | 94 | 92 |
| 34-01 | 150 | 68 | 50 |
| | 250 | 85 | 47 |
| | 350 | 97 | 70 |
| | 450 | 99 | 83 |
| 34-02 | 150 | 67 | 40 |
| | 250 | 78 | 50 |
| | 350 | 96 | 63 |
| | 450 | 99 | 68 |
| 34-03 | 150 | 52 | 40 |
| | 250 | 72 | 50 |
| | 350 | 95 | 63 |
| | 450 | 97 | 85 |
| 34-04 | 150 | 72 | 40 |
| | 250 | 97 | 53 |
| | 350 | 97 | 77 |
| | 450 | 99 | 90 |
| 34-05 | 150 | 75 | 40 |
| | 250 | 0 | 53 |
| | 350 | 88 | 53 |
| | 450 | 96 | 78 |
| 34-06 | 150 | 98 | 40 |
| | 250 | 93 | 50 |
| | 350 | 97 | 68 |
| | 450 | 97 | 82 |
| 34-07 | 150 | 73 | 40 |
| | 250 | 92 | 50 |
| | 350 | 98 | 63 |
| | 450 | 98 | 80 |
| 34-08 | 150 | 77 | 43 |
| | 250 | 93 | 57 |
| | 350 | 97 | 77 |
| | 450 | 98 | 88 |

All compositions containing butyl stearate and either oleth-20 or steareth-20 showed a very high level of performance by comparison with commercial standard Formulations C and J.

Example 35

Aqueous concentrate compositions were prepared containing glyphosate IPA salt and excipient ingredients as shown in Table 35a. Concentrate composition 35-03 is an aqueous solution concentrate and was prepared by process (viii). Concentrate compositions 35-01, 35-02 and 35-04 to 35-09 are aqueous solution concentrates containing colloidal particulate and were prepared by process (ix).

TABLE 35a

| Concentrate composition | Glyphosate g a.e./l | Butyl stearate | % w/w Ethomeen T/25 | Neodol 1-7 | PG-2069 | Aluminum oxide C |
|---|---|---|---|---|---|---|
| 35-01 | 484 | | | | | 0.4 |
| 35-02 | 484 | | 5.0 | | | 0.4 |
| 35-03 | 484 | | 5.0 | | | |
| 35-04 | 484 | | 6.0 | 1.0 | | 0.4 |
| 35-05 | 484 | | 7.0 | 2.0 | | 0.4 |
| 35-06 | 484 | 0.3 | 6.0 | 1.0 | | 0.4 |
| 35-07 | 484 | | 4.0 | | 1.0 | 0.4 |
| 35-08 | 484 | | 5.0 | | 2.0 | 0.4 |
| 35-09 | 484 | 0.3 | 4.0 | | 1.0 | 0.4 |

Velvetleaf (*Abutilon theophrasti*, ABUTH) and Japanese millet (*Echinochloa crus-galli*, ECHCF) plants were grown and treated by the standard procedures given above. Applications of spray compositions were made 14 days after planting ABUTH and ECHCF, and evaluation of herbicidal inhibition was done 17 days after application.

Formulations B and J were applied as comparative treatments. Results, averaged for all replicates of each treatment, are shown in Table 35b.

TABLE 35b

| Concentrate composition | Glyphosate rate g a.e./ha | % Inhibition ABUTH | ECHCF |
|---|---|---|---|
| Formulation B | 150 | 0 | 23 |
| | 250 | 38 | 30 |
| | 350 | 65 | 40 |
| | 450 | 75 | 40 |
| Formulation J | 150 | 65 | 50 |
| | 250 | 77 | 80 |
| | 350 | 93 | 93 |
| | 450 | 98 | 94 |
| 35-01 | 150 | 58 | 33 |
| | 250 | 65 | 40 |
| | 350 | 78 | 43 |
| | 450 | 78 | 47 |
| 35-02 | 150 | 32 | 20 |
| | 250 | 63 | 33 |
| | 350 | 72 | 40 |
| | 450 | 83 | 47 |
| 35-03 | 150 | 67 | 43 |
| | 250 | 93 | 75 |
| | 350 | 93 | 84 |
| | 450 | 100 | 87 |
| 35-04 | 150 | 72 | 43 |
| | 250 | 94 | 82 |
| | 350 | 98 | 89 |
| | 450 | 100 | 95 |
| 35-05 | 150 | 63 | 40 |
| | 250 | 77 | 60 |
| | 350 | 97 | 83 |
| | 450 | 99 | 82 |
| 35-06 | 150 | 70 | 40 |
| | 250 | 78 | 72 |
| | 350 | 98 | 83 |
| | 450 | 99 | 93 |
| 35-07 | 150 | 65 | 78 |
| | 250 | 87 | missing |
| | 350 | 88 | 89 |
| | 450 | 99 | 95 |
| 35-08 | 150 | 73 | 63 |
| | 250 | 78 | 88 |
| | 350 | 82 | 94 |
| | 450 | 82 | 77 |
| 35-09 | 150 | 58 | 55 |
| | 250 | 78 | 83 |
| | 350 | 88 | 86 |
| | 450 | 99 | 91 |

The addition of butyl stearate did not enhance herbicidal effectiveness of the compositions of this Example (compare 35-06 with 35-04 and 35-09 with 35-07).

Example 36

Aqueous spray compositions were prepared containing glyphosate IPA salt and excipient ingredients as shown in Table 36a. Process (iii) was followed for spray compositions 36-01 to 36-22 and 36-26 to 36-72, using soybean lecithin (45% phospholipid, Avanti). Process (i) was followed for spray compositions 36-23 to 36-25.

TABLE 36a

| Spray composition | % w/w | | |
|---|---|---|---|
| | Lecithin | Butyl stearate | MON 0818 |
| 36-01 | 0.10 | 0.10 | |
| 36-02 | 0.10 | 0.08 | |
| 36-03 | 0.10 | 0.05 | |
| 36-04 | 0.10 | 0.03 | |
| 36-05 | 0.10 | 0.01 | |
| 36-06 | 0.08 | 0.10 | |
| 36-07 | 0.05 | 0.10 | |
| 36-08 | 0.03 | 0.10 | |
| 36-09 | 0.01 | 0.10 | |
| 36-10 | 0.08 | 0.01 | |
| 36-11 | 0.05 | 0.01 | |
| 36-12 | 0.03 | 0.01 | |
| 36-13 | 0.01 | 0.01 | |
| 36-14 | 0.01 | 0.03 | |
| 36-15 | 0.01 | 0.05 | |
| 36-16 | 0.01 | 0.08 | |
| 36-17 | 0.03 | 0.03 | |
| 36-18 | 0.05 | 0.05 | |
| 36-19 | 0.08 | 0.08 | |
| 36-20 | 0.08 | 0.03 | |
| 36-21 | 0.03 | 0.08 | |
| 36-22 | 0.05 | | |
| 36-23 | | 0.05 | |
| 36-24 | | | 0.09 |
| 36-25 | | | 0.03 |
| 36-26 | 0.09 | 0.02 | 0.09 |
| 36-27 | 0.09 | 0.02 | 0.05 |
| 36-28 | 0.01 | 0.01 | 0.01 |
| 36-29 | 0.01 | 0.01 | 0.03 |
| 36-30 | 0.01 | 0.01 | 0.05 |
| 36-31 | 0.01 | 0.01 | 0.08 |
| 36-32 | 0.01 | 0.01 | 0.10 |
| 36-33 | 0.01 | 0.05 | 0.01 |
| 36-34 | 0.01 | 0.05 | 0.03 |
| 36-35 | 0.01 | 0.05 | 0.05 |
| 36-36 | 0.01 | 0.05 | 0.08 |
| 36-37 | 0.01 | 0.05 | 0.10 |
| 36-38 | 0.01 | 0.10 | 0.01 |
| 36-39 | 0.01 | 0.10 | 0.03 |
| 36-40 | 0.01 | 0.10 | 0.05 |
| 36-41 | 0.01 | 0.10 | 0.08 |
| 36-42 | 0.01 | 0.10 | 0.10 |
| 36-43 | 0.05 | 0.01 | 0.01 |
| 36-44 | 0.05 | 0.01 | 0.03 |
| 36-45 | 0.05 | 0.01 | 0.05 |
| 36-46 | 0.05 | 0.01 | 0.08 |
| 36-47 | 0.05 | 0.01 | 0.10 |
| 36-48 | 0.05 | 0.05 | 0.01 |
| 36-49 | 0.05 | 0.05 | 0.03 |
| 36-50 | 0.05 | 0.05 | 0.05 |
| 36-51 | 0.05 | 0.05 | 0.08 |
| 36-52 | 0.05 | 0.05 | 0.10 |
| 36-53 | 0.05 | 0.10 | 0.01 |
| 36-54 | 0.05 | 0.10 | 0.03 |
| 36-55 | 0.05 | 0.10 | 0.05 |
| 36-56 | 0.05 | 0.10 | 0.08 |
| 36-57 | 0.05 | 0.10 | 0.10 |
| 36-58 | 0.10 | 0.01 | 0.01 |
| 36-59 | 0.10 | 0.01 | 0.03 |
| 36-60 | 0.10 | 0.01 | 0.05 |
| 36-61 | 0.10 | 0.01 | 0.08 |
| 36-62 | 0.10 | 0.01 | 0.10 |
| 36-63 | 0.10 | 0.05 | 0.01 |
| 36-64 | 0.10 | 0.05 | 0.03 |
| 36-65 | 0.10 | 0.05 | 0.05 |
| 36-66 | 0.10 | 0.05 | 0.08 |
| 36-67 | 0.10 | 0.05 | 0.10 |
| 36-68 | 0.10 | 0.10 | 0.01 |
| 36-69 | 0.10 | 0.10 | 0.03 |
| 36-70 | 0.10 | 0.10 | 0.05 |
| 36-71 | 0.10 | 0.10 | 0.08 |
| 36-72 | 0.10 | 0.10 | 0.10 |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and ECHCF, and evaluation of herbicidal inhibition was done 15 days after application.

Formulations C and J were applied as comparative treatments. Results, averaged for all replicates of each treatment, are shown in Table 36b.

TABLE 36b

| Spray composition | Glyphosate rate g a.e./ha | % Inhibition | |
|---|---|---|---|
| | | ABUTH | ECHCF |
| Formulation C | 280 | 71 | 73 |
| Formulation J | 280 | 65 | 77 |
| 36-01 | 280 | 60 | 49 |
| 36-02 | 280 | 46 | 47 |
| 36-03 | 280 | 34 | 48 |
| 36-04 | 280 | 33 | 35 |
| 36-05 | 280 | 50 | 33 |
| 36-06 | 280 | 49 | 52 |
| 36-07 | 280 | 39 | 42 |
| 36-08 | 280 | 48 | 38 |
| 36-09 | 280 | 51 | 42 |
| 36-10 | 280 | 37 | 30 |
| 36-11 | 280 | 48 | 30 |
| 36-12 | 280 | 56 | 34 |
| 36-13 | 280 | 41 | 45 |
| 36-14 | 280 | 52 | 56 |
| 36-15 | 280 | 38 | 40 |
| 36-16 | 280 | 53 | 33 |
| 36-17 | 280 | 45 | 40 |
| 36-18 | 280 | 52 | 38 |
| 36-19 | 280 | 37 | 34 |
| 36-20 | 280 | 36 | 28 |
| 36-21 | 280 | 40 | 38 |
| 36-22 | 280 | 44 | 47 |
| 36-23 | 280 | 60 | 42 |
| 36-24 | 280 | 92 | 76 |
| 36-25 | 280 | 87 | 69 |
| 36-26 | 280 | 89 | 88 |
| 36-27 | 280 | 79 | 80 |
| 36-28 | 280 | 74 | 73 |
| 36-29 | 280 | 91 | 76 |
| 36-30 | 280 | 94 | 92 |
| 36-31 | 280 | 87 | 81 |
| 36-32 | 280 | 93 | 77 |
| 36-33 | 280 | 88 | 73 |
| 36-34 | 280 | 92 | 85 |
| 36-35 | 280 | 90 | 82 |
| 36-36 | 280 | 92 | 77 |
| 36-37 | 280 | 87 | 77 |
| 36-38 | 280 | 88 | 77 |
| 36-39 | 280 | 84 | 74 |
| 36-40 | 280 | 87 | 68 |
| 36-41 | 280 | 93 | 76 |
| 36-42 | 280 | 94 | 78 |
| 36-43 | 280 | 80 | 59 |
| 36-44 | 280 | 69 | 54 |
| 36-45 | 280 | 88 | 74 |

TABLE 36b-continued

| Spray composition | Glyphosate rate g a.e./ha | % Inhibition ABUTH | ECHCF |
|---|---|---|---|
| 36-46 | 280 | 94 | 79 |
| 36-47 | 280 | 95 | 79 |
| 36-48 | 280 | 71 | 63 |
| 36-49 | 280 | 81 | 72 |
| 36-50 | 280 | 81 | 79 |
| 36-51 | 280 | 79 | 85 |
| 36-52 | 280 | 98 | 69 |
| 36-53 | 280 | 69 | 70 |
| 36-54 | 280 | 74 | 69 |
| 36-55 | 280 | 84 | 78 |
| 36-56 | 280 | 86 | 68 |
| 36-57 | 280 | 98 | 82 |
| 36-58 | 280 | 71 | 69 |
| 36-59 | 280 | 95 | 79 |
| 36-60 | 280 | 92 | 70 |
| 36-61 | 280 | 93 | 70 |
| 36-62 | 280 | 98 | 80 |
| 36-63 | 280 | 81 | 74 |
| 36-64 | 280 | 84 | 73 |
| 36-65 | 280 | 89 | 70 |
| 36-66 | 280 | 91 | 65 |
| 36-67 | 280 | 94 | 81 |
| 36-68 | 280 | 87 | 81 |
| 36-69 | 280 | 72 | 79 |
| 36-70 | 280 | 87 | 76 |
| 36-71 | 280 | 94 | 71 |
| 36-72 | 280 | 97 | 73 |

Compositions outperforming commercial standard Formulations C and J on both ABUTH and ECHCF in this test included 36-26, 36-27, 36-30, 36-34, 36-35, 36-51 and 36-57, all containing lecithin, butyl stearate and MON 0818.

Example 37

Aqueous concentrate compositions were prepared containing glyphosate IPA salt and excipient ingredients as shown in Table 37a. All contain colloidal particulates and were prepared by process (ix).

All compositions of this example showed acceptable storage stability. The compositions containing oleth-20 were not acceptably storage-stable in the absence of the colloidal particulate.

TABLE 37a

| Concentrate composition | Glyphosate g a.e./l | % w/w Butyl stearate | Oleth-20 | Aerosil | Type of Aerosil |
|---|---|---|---|---|---|
| 37-01 | 488 | | 3.0 | 0.4 | OX-50 |
| 37-02 | 488 | | 3.0 | 0.8 | OX-50 |
| 37-03 | 488 | | 3.0 | 1.5 | OX-50 |
| 37-04 | 488 | | | 0.4 | OX-50 |
| 37-05 | 488 | | | 0.8 | OX-50 |
| 37-06 | 488 | | | 1.5 | OX-50 |
| 37-07 | 488 | | 3.0 | 0.4 | MOX-80 |
| 37-08 | 488 | | 3.0 | 0.8 | MOX-80 |
| 37-09 | 488 | | 3.0 | 1.5 | MOX-80 |
| 37-10 | 488 | | | 0.4 | MOX-80 |
| 37-11 | 488 | | | 0.8 | MOX-80 |
| 37-12 | 488 | | | 1.5 | MOX-80 |
| 37-13 | 488 | | 3.0 | 0.4 | MOX-170 |
| 37-14 | 488 | | 3.0 | 0.8 | MOX-170 |
| 37-15 | 488 | | 3.0 | 1.5 | MOX-170 |
| 37-16 | 488 | | | 0.4 | MOX-170 |
| 37-17 | 488 | | | 0.8 | MOX-170 |
| 37-18 | 488 | | | 1.5 | MOX-170 |
| 37-19 | 488 | 3.0 | 3.0 | 1.5 | MOX-80 |

Velvetleaf (*Abutilon theophrasti*, ABUTH) and Japanese millet (*Echinochloa crus-galli*, ECHCF) plants were grown and treated by the standard procedures given above. Applications of spray compositions were made 14 days after planting ABUTH and ECHCF, and evaluation of herbicidal inhibition was done 20 days after application.

Formulations B and J were applied as comparative treatments. Results, averaged for all replicates of each treatment, are shown in Table 37b.

TABLE 37b

| Concentrate composition | Glyphosate rate g a.e./ha | % Inhibition ABUTH | ECHCF |
|---|---|---|---|
| Formulation B | 150 | 0 | 27 |
| | 250 | 17 | 37 |
| | 350 | 47 | 57 |
| | 450 | 60 | 60 |
| Formulation J | 150 | 57 | 50 |
| | 250 | 82 | 87 |
| | 350 | 95 | 99 |
| | 450 | 98 | 99 |
| 37-01 | 150 | 37 | 60 |
| | 250 | 73 | 70 |
| | 350 | 96 | 97 |
| | 450 | 96 | 99 |
| 37-02 | 150 | 43 | 50 |
| | 250 | 73 | 63 |
| | 350 | 93 | 96 |
| | 450 | 98 | 99 |
| 37-03 | 150 | 53 | 60 |
| | 250 | 83 | 87 |
| | 350 | 87 | 97 |
| | 450 | 98 | 98 |
| 37-04 | 150 | 45 | 40 |
| | 250 | 57 | 60 |
| | 350 | 78 | 95 |
| | 450 | 94 | 100 |
| 37-05 | 150 | 47 | 50 |
| | 250 | 60 | 82 |
| | 350 | 92 | 96 |
| | 450 | 95 | 99 |
| 37-06 | 150 | 38 | 53 |
| | 250 | 68 | 96 |
| | 350 | 82 | 99 |
| | 450 | 83 | 95 |
| 37-07 | 150 | 50 | 57 |
| | 250 | 87 | 88 |
| | 350 | 91 | 99 |
| | 450 | 98 | 98 |
| 37-08 | 150 | 53 | 50 |
| | 250 | 88 | 85 |
| | 350 | 96 | 97 |
| | 450 | 97 | 100 |
| 37-09 | 150 | 40 | 30 |
| | 250 | 37 | 47 |
| | 350 | 57 | 80 |
| | 450 | 77 | 94 |
| 37-10 | 150 | 47 | 50 |
| | 250 | 70 | 95 |
| | 350 | 75 | 99 |
| | 450 | 77 | 98 |
| 37-11 | 150 | 27 | 60 |
| | 250 | 72 | 85 |
| | 350 | 82 | 98 |

TABLE 37b-continued

| Concentrate composition | Glyphosate rate g a.e./ha | % Inhibition ABUTH | % Inhibition ECHCF |
|---|---|---|---|
| 37-12 | 450 | 75 | 99 |
|  | 150 | 37 | 57 |
|  | 250 | 73 | 86 |
|  | 350 | 80 | 99 |
|  | 450 | 85 | 100 |
| 37-13 | 150 | 45 | 53 |
|  | 250 | 85 | 94 |
|  | 350 | 95 | 100 |
|  | 450 | 98 | 99 |
| 37-14 | 150 | 50 | 50 |
|  | 250 | 78 | 83 |
|  | 350 | 94 | 98 |
|  | 450 | 98 | 99 |
| 37-15 | 150 | 53 | 67 |
|  | 250 | 75 | 88 |
|  | 350 | 93 | 97 |
|  | 450 | 96 | 99 |
| 37-16 | 150 | 42 | 50 |
|  | 250 | 47 | 96 |
|  | 350 | 70 | 98 |
|  | 450 | 90 | 99 |
| 37-17 | 150 | 27 | 83 |
|  | 250 | 57 | 98 |
|  | 350 | 87 | 99 |
|  | 450 | 87 | 100 |
| 37-18 | 150 | 33 | 60 |
|  | 250 | 47 | 94 |
|  | 350 | 83 | 99 |
|  | 450 | 93 | 99 |
| 37-19 | 150 | 45 | 47 |
|  | 250 | 80 | 73 |
|  | 350 | 96 | 94 |
|  | 450 | 99 | 98 |

Remarkably high levels of herbicidal effectiveness were obtained in this test with compositions containing oleth-20 at a weight/weight ratio to glyphosate a.e. of about 1:14, and stabilized with colloidal particulates. In some cases the colloidal particulate alone contributed a major part of the efficacy enhancement. Composition 37-19, containing butyl stearate, was among the most efficacious compositions in the test. Results with composition 37-09 are out of line with other data and an application problem is suspected.

Example 38

Aqueous concentrate compositions were prepared containing glyphosate IPA salt and excipient ingredients as shown in Table 38a. All were prepared by process (x), using soybean lecithin (45% phospholipid, Avanti).

TABLE 38a

| Concentrate composition | Glyphosate g a.e./l | % w/w Lecithin | % w/w Butyl stearate | % w/w Ethomeen T/25 |
|---|---|---|---|---|
| 38-01 | 200 | 6.0 | 2 | 6.0 |
| 38-02 | 200 |  | 3 | 6.0 |
| 38-03 | 200 |  | 1.5 | 9.0 |
| 38-04 | 200 |  | 3 | 9.0 |
| 38-05 | 200 | 6.0 | 1.5 | 9.0 |
| 38-06 | 200 | 6.0 | 1.5 | 3.0 |
| 38-07 | 200 |  |  | 9.0 |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and ECHCF, and evaluation of herbicidal inhibition was done 15 days after application.

Formulations B and J were applied as comparative treatments. Results, averaged for all replicates of each treatment, are shown in Table 38b.

TABLE 38b

| Concentrate composition | Glyphosate rate g a.e./ha | % Inhibition ABUTH | % Inhibition ECHCF |
|---|---|---|---|
| Formulation B | 150 | 29 | 22 |
|  | 250 | 41 | 29 |
|  | 350 | 53 | 32 |
|  | 450 | 68 | 35 |
| Formulation J | 150 | 43 | 32 |
|  | 250 | 76 | 43 |
|  | 350 | 86 | 47 |
|  | 450 | 94 | 66 |
| 38-01 | 150 | 67 | 33 |
|  | 250 | 85 | 40 |
|  | 350 | 96 | 71 |
|  | 450 | 97 | 59 |
| 38-02 | 150 | 65 | 36 |
|  | 250 | 81 | 52 |
|  | 350 | 97 | 68 |
|  | 450 | 98 | 62 |
| 38-03 | 150 | 67 | 40 |
|  | 250 | 85 | 77 |
|  | 350 | 94 | 77 |
|  | 450 | 97 | 63 |
| 38-04 | 150 | 69 | 38 |
|  | 250 | 86 | 58 |
|  | 350 | 93 | 84 |
|  | 450 | 98 | 62 |
| 38-05 | 150 | 73 | 40 |
|  | 250 | 83 | 53 |
|  | 350 | 93 | 75 |
|  | 450 | 96 | 61 |
| 38-06 | 150 | 45 | 30 |
|  | 250 | 71 | 38 |
|  | 350 | 91 | 45 |
|  | 450 | 89 | 39 |
| 38-07 | 150 | 59 | 39 |
|  | 250 | 83 | 44 |
|  | 350 | 95 | 63 |
|  | 450 | 95 | 70 |

Data for the 450 g a.e./ha glyphosate rate in this study are unreliable. Application error is suspected. The high levels of Ethomeen T/25 included in compositions of this Example tends to obscure the effects of lecithin and butyl stearate, but composition 38-05, for example, showed outstanding effectiveness.

Example 39

Aqueous concentrate compositions were prepared containing glyphosate IPA salt and excipient ingredients as shown in Table 39a. Concentrate compositions 39-01 to 39-04, 39-06, 39-08, 39-09, 39-11, 39-12, 39-14 and 39-16 are oil-in-water emulsions and were prepared by process (vii). Concentrate compositions 39-05, 39-07, 39-10, 39-13, 39-15 and 39-17 are aqueous solution concentrates and were prepared by process (viii).

TABLE 39a

| Concentrate composition | Glyphosate g a.e./l | % w/w Butyl stearate | % w/w Surfactant | Type of surfactant |
|---|---|---|---|---|
| 39-01 | 163 | 0.25 | 2.5 | Neodol 1-12 |
| 39-02 | 163 | 0.25 | 2.5 | laureth-23 |
| 39-03 | 163 | 0.25 | 2.5 | steareth-10 |
| 39-04 | 163 | 0.25 | 2.5 | steareth-20 |
| 39-05 | 163 |  | 2.5 | steareth-20 |

TABLE 39a-continued

| Concentrate composition | Glyphosate g a.e./l | % w/w Butyl stearate | Surfactant | Type of surfactant |
|---|---|---|---|---|
| 39-06 | 163 | 0.25 | 2.5 | steareth-100 |
| 39-07 | 163 |  | 2.5 | steareth-100 |
| 39-08 | 163 | 0.25 | 2.5 | oleth-10 |
| 39-09 | 163 | 0.25 | 2.5 | oleth-20 |
| 39-10 | 163 |  | 2.5 | oleth-20 |
| 39-11 | 163 | 0.25 | 2.5 | ceteth-10 |
| 39-12 | 163 | 0.25 | 2.5 | ceteth-20 |
| 39-13 | 163 |  | 2.5 | ceteth-20 |
| 39-14 | 326 | 0.50 | 5.0 | ceteareth-27 |
| 39-15 | 326 |  | 5.0 | ceteareth-27 |
| 39-16 | 163 | 0.25 | 2.5 | ceteareth-55 |
| 39-17 | 163 |  | 2.5 | ceteareth-55 |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and ECHCF, and evaluation of herbicidal inhibition was done 15 days after application.

Formulations B, C and J were applied as comparative treatments. Results, averaged for all replicates of each treatment, are shown in Table 39b.

TABLE 39b

| Concentrate composition | Glyphosate rate g a.e./ha | % Inhibition ABUTH | ECHCF |
|---|---|---|---|
| Formulation B | 150 | 0 | 33 |
|  | 250 | 20 | 43 |
|  | 350 | 63 | 63 |
|  | 450 | 75 | 70 |
| Formulation C | 150 | 53 | 55 |
|  | 250 | 80 | 87 |
|  | 350 | 94 | 97 |
|  | 450 | 98 | 99 |
| Formulation J | 150 | 40 | 57 |
|  | 250 | 80 | 90 |
|  | 350 | 96 | 99 |
|  | 450 | 98 | 99 |
| 39-01 | 150 | 52 | 40 |
|  | 250 | 65 | 73 |
|  | 350 | 77 | 70 |
|  | 450 | 77 | 70 |
| 39-02 | 150 | 37 | 70 |
|  | 250 | 75 | 80 |
|  | 350 | 83 | 97 |
|  | 450 | 95 | 99 |
| 39-03 | 150 | 47 | 53 |
|  | 250 | 77 | 86 |
|  | 350 | 83 | 97 |
|  | 450 | 93 | 100 |
| 39-04 | 150 | 80 | 60 |
|  | 250 | 93 | 83 |
|  | 350 | 96 | 85 |
|  | 450 | 99 | 99 |
| 39-05 | 150 | 80 | 43 |
|  | 250 | 93 | 79 |
|  | 350 | 96 | 94 |
|  | 450 | 98 | 96 |
| 39-06 | 150 | 77 | 53 |
|  | 250 | 85 | 83 |
|  | 350 | 94 | 99 |
|  | 450 | 97 | 99 |
| 39-07 | 150 | 63 | 50 |
|  | 250 | 80 | 88 |
|  | 350 | 85 | 96 |
|  | 450 | 96 | 99 |
| 39-08 | 150 | 27 | 45 |
|  | 250 | 75 | 83 |
|  | 350 | 77 | 99 |
|  | 450 | 96 | 98 |
| 39-09 | 150 | 75 | 57 |
|  | 250 | 80 | 82 |
|  | 350 | 97 | 95 |
|  | 450 | 99 | 98 |
| 39-10 | 150 | 70 | 40 |
|  | 250 | 85 | 83 |
|  | 350 | 97 | 98 |
|  | 450 | 99 | 99 |
| 39-11 | 150 | 53 | 37 |
|  | 250 | 75 | 63 |
|  | 350 | 88 | 93 |
|  | 450 | 92 | 98 |
| 39-12 | 150 | 70 | 40 |
|  | 250 | 78 | 75 |
|  | 350 | 90 | 91 |
|  | 450 | 98 | 98 |
| 39-13 | 150 | 72 | 40 |
|  | 250 | 92 | 80 |
|  | 350 | 97 | 90 |
|  | 450 | 99 | 97 |
| 39-14 | 150 | 78 | 53 |
|  | 250 | 89 | 88 |
|  | 350 | 97 | 95 |
|  | 450 | 99 | 100 |
| 39-15 | 150 | 80 | 60 |
|  | 250 | 95 | 97 |
|  | 350 | 98 | 100 |
|  | 450 | 99 | 99 |
| 39-16 | 150 | 60 | 63 |
|  | 250 | 87 | 78 |
|  | 350 | 96 | 94 |
|  | 450 | 98 | 99 |
| 39-17 | 150 | 73 | 60 |
|  | 250 | 85 | 57 |
|  | 350 | 93 | 80 |
|  | 450 | 99 | 85 |

In combination with butyl stearate, steareth-20 (composition 39-04) gave greater herbicidal effectiveness than steareth-10 (39-03) on ABUTH. Similarly, oleth-20 (39-09) was more efficacious than oleth-10 (39-08) and ceteth-20 (39-12) than ceteth-10 (39-11). In the absence of butyl stearate, ceteareth-55 (39-17) was noticeably weaker on ECHCF than ceteareth-27 (39-15) but inclusion of butyl stearate (39-16) tended to correct this weakness. Note that while compositions 39-14 and 39-15 contained twice as high a concentration of excipients as the other compositions of the test, the concentration of glyphosate was also twice as high, thus the concentrations as sprayed were the same.

Example 40

Aqueous concentrate compositions were prepared containing glyphosate IPA salt and excipient ingredients as shown in Table 40a. Concentrate compositions 40-01 to 40-05, 40-07, 40-08, 40-10 and 40-12 to 40-16 are oil-in-water emulsions and were prepared by process (vii). Concentrate compositions 40-06, 40-09 and 40-11 are aqueous solution concentrates and were prepared by process (viii).

TABLE 40a

| Concentrate composition | Glyphosate g a.e./l | Butyl stearate | % w/w Surfactant | Type of surfactant |
|---|---|---|---|---|
| 40-01 | 163 | 0.25 | 2.5 | Neodol 1-12 |
| 40-02 | 163 | 0.25 | 2.5 | laureth-23 |
| 40-03 | 163 | 0.25 | 2.5 | steareth-10 |
| 40-04 | 163 | 0.25 | 2.5 | steareth-20 |
| 40-05 | 163 | 0.25 | 2.5 | Pluronic F-68 |
| 40-06 | 163 |  | 2.5 | Pluronic F-68 |
| 40-07 | 326 | 1.00 | 5.0 | Pluronic F-108 |
| 40-08 | 326 | 0.50 | 5.0 | Pluronic F-108 |
| 40-09 | 326 |  | 5.0 | Pluronic F-108 |
| 40-10 | 163 | 0.25 | 2.5 | Pluronic F-127 |
| 40-11 | 163 |  | 2.5 | Pluronic F-127 |
| 40-12 | 326 | 0.50 | 5.0 | ceteareth-27 |
| 40-13 | 163 | 0.25 | 2.5 | ceteareth-55 |
| 40-14 | 163 | 0.25 | 2.5 | oleth-20 |
| 40-15 | 163 | 0.25 | 2.5 | ceteth-20 |
| 40-16 | 163 | 0.25 | 2.5 | steareth-100 |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and ECHCF, and evaluation of herbicidal inhibition was done 15 days after application.

Formulations B, C and J were applied as comparative treatments. Results, averaged for all replicates of each treatment, are shown in Table 40b.

TABLE 40b

| Concentrate composition | Glyphosate rate g a.e./ha | % Inhibition ABUTH | ECHCF |
|---|---|---|---|
| Formulation B | 150 | 5 | 0 |
|  | 250 | 47 | 5 |
|  | 350 | 70 | 23 |
|  | 450 | 75 | 43 |
| Formulation C | 150 | 73 | 47 |
|  | 250 | 99 | 50 |
|  | 350 | 98 | 67 |
|  | 450 | 99 | 75 |
| Formulation J | 150 | 73 | 43 |
|  | 250 | 89 | 50 |
|  | 350 | 97 | 83 |
|  | 450 | 98 | 77 |
| 40-01 | 150 | 37 | 30 |
|  | 250 | 70 | 33 |
|  | 350 | 77 | 40 |
|  | 450 | 90 | 47 |
| 40-02 | 150 | 52 | 37 |
|  | 250 | 77 | 67 |
|  | 350 | 90 | 77 |
|  | 450 | 92 | 75 |
| 40-03 | 150 | 40 | 30 |
|  | 250 | 77 | 70 |
|  | 350 | 80 | 82 |
|  | 450 | 90 | 83 |
| 40-04 | 150 | 75 | 37 |
|  | 250 | 95 | 53 |
|  | 350 | 99 | 91 |
|  | 450 | 99 | 82 |
| 40-05 | 150 | 58 | 37 |
|  | 250 | 65 | 53 |
|  | 350 | 80 | 80 |
|  | 450 | 75 | 68 |
| 40-06 | 150 | 40 | 30 |
|  | 250 | 75 | 33 |
|  | 350 | 78 | 43 |
|  | 450 | 80 | 43 |
| 40-07 | 150 | 50 | 30 |
|  | 250 | 75 | 33 |
|  | 350 | 78 | 53 |
|  | 450 | 86 | 53 |
| 40-08 | 150 | 47 | 30 |
|  | 250 | 75 | 33 |
|  | 350 | 77 | 40 |
|  | 450 | 80 | 50 |
| 40-09 | 150 | 43 | 33 |
|  | 250 | 77 | 40 |
|  | 350 | 78 | 63 |
|  | 450 | 83 | 50 |
| 40-10 | 150 | 27 | 40 |
|  | 250 | 77 | 43 |
|  | 350 | 80 | 50 |
|  | 450 | 92 | 40 |
| 40-11 | 150 | 37 | 30 |
|  | 250 | 72 | 33 |
|  | 350 | 80 | 60 |
|  | 450 | 95 | 40 |
| 40-12 | 150 | 78 | 37 |
|  | 250 | 98 | 40 |
|  | 350 | 99 | 53 |
|  | 450 | 100 | 50 |
| 40-13 | 150 | 75 | 30 |
|  | 250 | 88 | 40 |
|  | 350 | 98 | 47 |
|  | 450 | 100 | 65 |
| 40-14 | 150 | 73 | 30 |
|  | 250 | 87 | 40 |
|  | 350 | 98 | 50 |
|  | 450 | 99 | 53 |
| 40-15 | 150 | 72 | 30 |
|  | 250 | 93 | 40 |
|  | 350 | 96 | 43 |
|  | 450 | 99 | 50 |
| 40-16 | 150 | 73 | 40 |
|  | 250 | 83 | 40 |
|  | 350 | 98 | 40 |
|  | 450 | 100 | 47 |

Composition 40-04 containing steareth-20 outperformed its counterpart 40-03 containing steareth-10, though both gave greater herbicidal effectiveness, especially on ECHCF, than 40-02 containing Neodol 1–12.

Example 41

Aqueous concentrate compositions were prepared containing glyphosate IPA salt and excipient ingredients as shown in Table 41a. Concentrate compositions 41-01 to 41-07 and 41-09 to 41-15 are oil-in-water emulsions and were prepared by process (vii). Concentrate compositions 41-08 and 41-16 are aqueous solution concentrates and were prepared by process (viii).

TABLE 41a

| Concentrate composition | Glyphosate g a.e./l | % w/w Oil | Surfactant | Type of Oil | Type of surfactant |
|---|---|---|---|---|---|
| 41-01 | 163 | 0.5 | 5.0 | methyl stearate | oleth-20 |
| 41-02 | 163 | 0.5 | 5.0 | butyl stearate | oleth-20 |
| 41-03 | 163 | 0.5 | 5.0 | methyl oleate | oleth-20 |
| 41-04 | 163 | 0.5 | 5.0 | butyl oleate | oleth-20 |
| 41-05 | 163 | 0.5 | 5.0 | methyl laurate | oleth-20 |
| 41-06 | 163 | 0.5 | 5.0 | butyl laurate | oleth-20 |
| 41-07 | 163 | 0.5 | 5.0 | Orchex 796 | oleth-20 |
| 41-08 | 163 |  | 5.0 | none | oleth-20 |

TABLE 41a-continued

| Concentrate composition | Glyphosate g a.e./l | % w/w Oil | % w/w Surfactant | Type of Oil | Type of surfactant |
|---|---|---|---|---|---|
| 41-09 | 163 | 0.5 | 5.0 | methyl stearate | Neodol 1-9 |
| 41-10 | 163 | 0.5 | 5.0 | butyl stearate | Neodol 1-9 |
| 41-11 | 163 | 0.5 | 5.0 | methyl oleate | Neodol 1-9 |
| 41-12 | 163 | 0.5 | 5.0 | butyl oleate | Neodol 1-9 |
| 41-13 | 163 | 0.5 | 5.0 | methyl laurate | Neodol 1-9 |
| 41-14 | 163 | 0.5 | 5.0 | butyl laurate | Neodol 1-9 |
| 41-15 | 163 | 0.5 | 5.0 | Orchex 796 | Neodol 1-9 |
| 41-16 | 163 |  | 5.0 | none | Neodol 1-9 |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and ECHCF, and evaluation of herbicidal inhibition was done 19 days after application.

Formulations B, C and J were applied as comparative treatments. Results, averaged for all replicates of each treatment, are shown in Table 41b.

TABLE 41b

| Concentrate composition | Glyphosate rate g a.e./ha | % Inhibition ABUTH | % Inhibition ECHCF |
|---|---|---|---|
| Formulation B | 150 | 3 | 10 |
|  | 250 | 58 | 57 |
|  | 350 | 78 | 53 |
|  | 450 | 77 | 53 |
| Formulation C | 150 | 60 | 98 |
|  | 250 | 87 | 99 |
|  | 350 | 95 | 98 |
|  | 450 | 99 | 100 |
| Formulation J | 150 | 60 | 75 |
|  | 250 | 89 | 87 |
|  | 350 | 93 | 90 |
|  | 450 | 98 | 99 |
| 41-01 | 150 | 75 | 96 |
|  | 250 | 99 | 97 |
|  | 350 | 97 | 99 |
|  | 450 | 99 | 100 |
| 41-02 | 150 | 60 | 60 |
|  | 250 | 97 | 67 |
|  | 350 | 99 | 98 |
|  | 450 | 100 | 95 |
| 41-03 | 150 | 63 | 40 |
|  | 250 | 83 | 82 |
|  | 350 | 97 | 86 |
|  | 450 | 97 | 88 |
| 41-04 | 150 | 73 | 40 |
|  | 250 | 94 | 82 |
|  | 350 | 97 | 100 |
|  | 450 | 99 | 100 |
| 41-05 | 150 | 67 | 47 |
|  | 250 | 86 | 67 |
|  | 350 | 97 | 88 |
|  | 450 | 99 | 100 |
| 41-06 | 150 | 60 | 43 |
|  | 250 | 78 | 91 |
|  | 350 | 97 | 83 |
|  | 450 | 94 | 86 |
| 41-07 | 150 | 70 | 53 |
|  | 250 | 80 | 53 |
|  | 350 | 97 | 82 |
|  | 450 | 97 | 92 |
| 41-08 | 150 | 70 | 62 |
|  | 250 | 83 | 83 |
|  | 350 | 91 | 87 |
|  | 450 | 98 | 98 |
| 41-09 | 150 | 45 | 42 |
|  | 250 | 72 | 72 |
|  | 350 | 77 | 73 |
|  | 450 | 78 | 89 |
| 41-10 | 150 | 40 | 30 |
|  | 250 | 82 | 80 |
|  | 350 | 78 | 98 |
|  | 450 | 89 | 93 |
| 41-11 | 150 | 40 | 30 |
|  | 250 | 65 | 60 |
|  | 350 | 77 | 90 |
|  | 450 | 96 | 92 |
| 41-12 | 150 | 20 | 30 |
|  | 250 | 63 | 73 |
|  | 350 | 80 | 75 |
|  | 450 | 93 | 86 |
| 41-13 | 150 | 20 | 27 |
|  | 250 | 67 | 60 |
|  | 350 | 82 | 91 |
|  | 450 | 88 | 92 |
| 41-14 | 150 | 7 | 30 |
|  | 250 | 72 | 81 |
|  | 350 | 87 | 78 |
|  | 450 | 80 | 85 |
| 41-15 | 150 | 20 | 23 |
|  | 250 | 65 | 60 |
|  | 350 | 77 | 81 |
|  | 450 | 87 | 88 |
| 41-16 | 150 | 12 | 30 |
|  | 250 | 57 | 53 |
|  | 350 | 68 | 85 |
|  | 450 | 85 | 85 |

Composition 41-08, containing as sole excipient substance oleth-20 at a 1:3 weight/weight ratio to glyphosate a.e., exhibited high herbicidal effectiveness, at least equal to commercial standard Formulations C and J on ABUTH but a little weaker on ECHCF. By comparison, composition 41-16, wherein the sole excipient substance was Neodol 1–9 at the same ratio to glyphosate, had much weaker activity. Addition of a small amount of fatty acid ester in most cases enhanced effectiveness, especially on ECHCF. In this study the most efficacious composition was 41-01, containing oleth-20 and methyl stearate. When added to Neodol 1–9, butyl stearate was more efficacious than methyl stearate, methyl oleate or butyl oleate. The mineral oil Orchex 796 did not substitute effectively for butyl stearate, either with oleth-20 or with Neodol 1–9.

Example 42

Aqueous concentrate compositions were prepared containing glyphosate IPA salt and excipient ingredients as shown in Table 42a. Concentrate compositions 42-01, 42-03, 42-05 to 42-08, 42-10 and 42-14 to 42-17 are oil-in-water emulsions and were prepared by process (vii). Concentrate compositions 42-02, 42-04, 42-09 and 42-11 to 42-13 are aqueous solution concentrates and were prepared by process (viii). Some compositions contained a coupling agent as indicated in Table 42a; the coupling agent was added with the surfactant.

TABLE 42a

| Conc. comp. | Glyphosate g a.e./l | Butyl stearate | Surfactant (% w/w) | Coupling agent | Type of coupling agent | Type of surfactant |
|---|---|---|---|---|---|---|
| 42-01 | 326 | 1.0 | 5.0 | 2.5 | Arcosolve DPM | oleth-20 |
| 42-02 | 326 |  | 5.0 | 2.5 | Arcosolve DPM | oleth-20 |
| 42-03 | 163 | 0.5 | 2.5 |  | none | oleth-20 |
| 42-04 | 163 |  | 2.5 |  | none | oleth-20 |
| 42-05 | 326 | 1.0 | 5.0 |  | none | ceteareth-27 |
| 42-06 | 326 | 1.0 | 5.0 | 2.5 | PEG-400 | ceteareth-27 |
| 42-07 | 326 | 1.0 | 5.0 | 2.5 | Dowanol TPNB | ceteareth-27 |
| 42-08 | 326 | 1.0 | 5.0 | 2.5 | Dowanol PNB | ceteareth-27 |
| 42-09 | 163 |  | 2.5 |  | none | ceteareth-27 |
| 42-10 | 326 | 0.5 | 5.0 |  | none | ceteareth-27 |
| 42-11 | 326 |  | 5.0 | 2.5 | PEG-400 | ceteareth-27 |
| 42-12 | 326 |  | 5.0 | 2.5 | Dowanol TPNB | ceteareth-27 |
| 42-13 | 326 |  | 5.0 | 2.5 | Dowanol PNB | ceteareth-27 |
| 42-14 | 163 | 0.5 | 2.5 |  | none | Neodol 1-9 |
| 42-15 | 163 | 0.5 | 2.5 |  | none | laureth-23 |
| 42-16 | 163 | 0.5 | 2.5 |  | none | steareth-20 |
| 42-17 | 163 | 0.5 | 2.5 |  | none | ceteareth-27 |

Velvetleaf (*Abutilon theophrasti*, ABUTH) and Japanese millet (*Echinochloa crus-galli*, ECHCF) plants were grown and treated by the standard procedures given above. Applications of spray compositions were made 16 days after planting ABUTH and ECHCF, and evaluation of herbicidal inhibition was done 18 days after application.

Formulations B, C and J were applied as comparative treatments. Results, averaged for all replicates of each treatment, are shown in Table 42b.

TABLE 42b

| Concentrate composition | Glyphosate rate g a.e./ha | % Inhibition ABUTH | ECHCF |
|---|---|---|---|
| Formulation B | 150 | 0 | 5 |
|  | 250 | 38 | 20 |
|  | 350 | 63 | 30 |
|  | 450 | 70 | 70 |
| Formulation C | 150 | 70 | 75 |
|  | 250 | 92 | 94 |
|  | 350 | 99 | 99 |
|  | 450 | 99 | 98 |
| Formulation J | 150 | 65 | 50 |
|  | 250 | 88 | 92 |
|  | 350 | 97 | 99 |
|  | 450 | 98 | 97 |
| 42-01 | 150 | 58 | 83 |
|  | 250 | 77 | 88 |
|  | 350 | 93 | 96 |
|  | 450 | 93 | 99 |
| 42-02 | 150 | 40 | 76 |
|  | 250 | 75 | 100 |
|  | 350 | 92 | 100 |
|  | 450 | 92 | 100 |
| 42-03 | 150 | 48 | 75 |
|  | 250 | 83 | 96 |
|  | 350 | 92 | 100 |
|  | 450 | 99 | 100 |
| 42-04 | 150 | 40 | 82 |
|  | 250 | 78 | 99 |
|  | 350 | 87 | 99 |
|  | 450 | 98 | 100 |
| 42-05 | 150 | 68 | 92 |
|  | 250 | 87 | 99 |
|  | 350 | 95 | 99 |
|  | 450 | 99 | 99 |
| 42-06 | 150 | 55 | 60 |
|  | 250 | 83 | 99 |
|  | 350 | 97 | 99 |
|  | 450 | 98 | 98 |
| 42-07 | 150 | 63 | 57 |
|  | 250 | 80 | 96 |
|  | 350 | 95 | 97 |
|  | 450 | 99 | 98 |
| 42-08 | 150 | 73 | 75 |
|  | 250 | 90 | 90 |
|  | 350 | 95 | 97 |
|  | 450 | 100 | 97 |
| 42-09 | 150 | 73 | 68 |
|  | 250 | 87 | 73 |
|  | 350 | 92 | 90 |
|  | 450 | 97 | 95 |
| 42-10 | 150 | 70 | 63 |
|  | 250 | 87 | 80 |
|  | 350 | 98 | 94 |
|  | 450 | 99 | 96 |
| 42-11 | 150 | 73 | 60 |
|  | 250 | 90 | 77 |
|  | 350 | 99 | 93 |
|  | 450 | 100 | 95 |
| 42-12 | 150 | 72 | 67 |
|  | 250 | 83 | 75 |
|  | 350 | 90 | 82 |
|  | 450 | 99 | 94 |
| 42-13 | 150 | 73 | 70 |
|  | 250 | 80 | 83 |
|  | 350 | 99 | 94 |
|  | 450 | 100 | 92 |
| 42-14 | 150 | 5 | 20 |
|  | 250 | 55 | 63 |
|  | 350 | 77 | 93 |
|  | 450 | 78 | 99 |
| 42-15 | 150 | 43 | 57 |
|  | 250 | 78 | 88 |
|  | 350 | 88 | 98 |
|  | 450 | 90 | 98 |
| 42-16 | 150 | 65 | 57 |
|  | 250 | 83 | 82 |
|  | 350 | 88 | 98 |
|  | 450 | 95 | 97 |
| 42-17 | 150 | 72 | 50 |
|  | 250 | 80 | 93 |
|  | 350 | 88 | 90 |
|  | 450 | 95 | 97 |

The superiority of herbicidal effectiveness provided by $C_{16-18}$ alkylethers (oleth-20, ceteareth-27, steareth-20) over that provided by shorter chain alkylethers (Neodol 1–9, laureth-23) was very pronounced in this test.

Example 43

Aqueous concentrate compositions were prepared containing glyphosate IPA salt and excipient ingredients as shown in Table 43a. Concentrate compositions 43-01 to 43-07 and 43-09 to 43-15 are oil-in-water emulsions and were prepared by process (vii). Concentrate compositions 43-08 and 43-16 are aqueous solution concentrates and were prepared by process (viii).

TABLE 43a

| Concentrate composition | Glyphosate g a.e./l | % w/w Oil | % w/w Surfactant | Type of oil | Type of surfactant |
|---|---|---|---|---|---|
| 43-01 | 163 | 0.5 | 5.0 | methyl stearate | steareth-20 |
| 43-02 | 163 | 0.5 | 5.0 | butyl stearate | steareth-20 |
| 43-03 | 163 | 0.5 | 5.0 | methyl oleate | steareth-20 |
| 43-04 | 163 | 0.5 | 5.0 | butyl oleate | steareth-20 |
| 43-05 | 163 | 0.5 | 5.0 | methyl laurate | steareth-20 |
| 43-06 | 163 | 0.5 | 5.0 | butyl laurate | steareth-20 |
| 43-07 | 163 | 0.5 | 5.0 | Orchex 796 | steareth-20 |
| 43-08 | 163 |  | 5.0 | none | steareth-20 |
| 43-09 | 163 | 0.5 | 5.0 | methyl stearate | ceteareth-27 |
| 43-10 | 163 | 0.5 | 5.0 | butyl stearate | ceteareth-27 |
| 43-11 | 163 | 0.5 | 5.0 | methyl oleate | ceteareth-27 |
| 43-12 | 163 | 0.5 | 5.0 | butyl oleate | ceteareth-27 |
| 43-13 | 163 | 0.5 | 5.0 | methyl laurate | ceteareth-27 |
| 43-14 | 163 | 0.5 | 5.0 | butyl laurate | ceteareth-27 |
| 43-15 | 163 | 0.5 | 5.0 | Orchex 796 | ceteareth-27 |
| 43-16 | 163 |  | 5.0 | none | ceteareth-27 |

Velvetleaf (*Abutilon theophrasti*, ABUTH) and Japanese millet (*Echinochloa crus-galli*, ECHCF) plants were grown and treated by the standard procedures given above. Applications of spray compositions were made 19 days after planting ABUTH and ECHCF, and evaluation of herbicidal inhibition was done 18 days after application.

Formulations B, C and J were applied as comparative treatments. Results, averaged for all replicates of each treatment, are shown in Table 43b.

TABLE 43b

| Concentrate composition | Glyphosate rate g a.e./ha | % Inhibition ABUTH | % Inhibition ECHCF |
|---|---|---|---|
| Formulation B | 150 | 15 | 5 |
|  | 250 | 57 | 20 |
|  | 350 | 83 | 50 |
|  | 450 | 78 | 73 |
| Formulation C | 150 | 65 | 63 |
|  | 250 | 87 | 93 |
|  | 350 | 92 | 94 |
|  | 450 | 98 | 100 |
| Formulation J | 150 | 50 | 73 |
|  | 250 | 90 | 90 |
|  | 350 | 94 | 98 |
|  | 450 | 98 | 99 |
| 43-01 | 150 | 72 | 70 |
|  | 250 | 88 | 85 |
|  | 350 | 96 | 83 |
|  | 450 | 99 | 86 |
| 43-02 | 150 | 73 | 53 |
|  | 250 | 83 | 87 |
|  | 350 | 97 | 99 |
|  | 450 | 97 | 98 |
| 43-03 | 150 | 68 | 33 |
|  | 250 | 87 | 92 |
|  | 350 | 93 | 97 |
|  | 450 | 98 | 93 |
| 43-04 | 150 | 72 | 50 |
|  | 250 | 87 | 88 |
|  | 350 | 94 | 86 |
|  | 450 | 98 | 97 |
| 43-05 | 150 | 72 | 67 |
|  | 250 | 83 | 82 |
|  | 350 | 99 | 97 |
|  | 450 | 98 | 98 |
| 43-06 | 150 | 73 | 33 |
|  | 250 | 95 | 83 |
|  | 350 | 99 | 95 |
|  | 450 | 99 | 88 |
| 43-07 | 150 | 73 | 55 |
|  | 250 | 93 | 73 |
|  | 350 | 95 | 83 |
|  | 450 | 98 | 91 |
| 43-08 | 150 | 75 | 40 |
|  | 250 | 94 | 60 |
|  | 350 | 98 | 86 |
|  | 450 | 99 | 92 |
| 43-09 | 150 | 77 | 50 |
|  | 250 | 90 | 50 |
|  | 350 | 98 | 92 |
|  | 450 | 99 | 98 |
| 43-10 | 150 | 72 | 53 |
|  | 250 | 92 | 77 |
|  | 350 | 96 | 86 |
|  | 450 | 99 | 99 |
| 43-11 | 150 | 72 | 60 |
|  | 250 | 87 | 87 |
|  | 350 | 97 | 97 |
|  | 450 | 97 | 99 |
| 43-12 | 150 | 70 | 57 |
|  | 250 | 90 | 90 |
|  | 350 | 96 | 96 |
|  | 450 | 98 | 99 |
| 43-13 | 150 | 68 | 40 |
|  | 250 | 90 | 77 |
|  | 350 | 99 | 95 |
|  | 450 | 99 | 98 |
| 43-14 | 150 | 77 | 33 |
|  | 250 | 94 | 70 |
|  | 350 | 96 | 82 |
|  | 450 | 99 | 93 |
| 43-15 | 150 | 75 | 30 |
|  | 250 | 96 | 75 |
|  | 350 | 97 | 88 |
|  | 450 | 99 | 92 |
| 43-16 | 150 | 77 | 40 |
|  | 250 | 99 | 47 |
|  | 350 | 98 | 67 |
|  | 450 | 98 | 78 |

Steareth-20 and ceteareth-27, as sole excipient substances (compositions 43-08 and 43-16 respectively) provided excellent herbicidal effectiveness, but further enhancements, especially on ECHCF, were obtained by inclusion of a small amount of fatty acid ester in the composition.

Example 44

Aqueous concentrate compositions were prepared containing glyphosate IPA salt and excipient ingredients as shown in Table 44a. Process (vii) was followed for concentrate composition 44-08 and process (x) for concentrate compositions 44-01 to 44-07 and 44-09, using soybean lecithin (45% phospholipid, Avanti).

TABLE 44a

| Concentrate composition | Glyphosate g a.e./l | % w/w | | |
|---|---|---|---|---|
| | | Lecithin | Butyl stearate | MON 0818 |
| 44-01 | 220 | 4.0 | | 6.0 |
| 44-02 | 220 | 4.0 | 0.5 | 6.0 |
| 44-03 | 220 | 4.0 | 1.0 | 6.0 |
| 44-04 | 220 | 4.0 | 2.0 | 6.0 |
| 44-05 | 220 | 2.0 | 0.5 | 2.0 |
| 44-06 | 220 | 2.0 | 0.5 | 4.0 |
| 44-07 | 220 | 2.0 | 0.5 | 6.0 |
| 44-08 | 220 | | 0.5 | 6.0 |
| 44-09 | 220 | 6.0 | 1.5 | 6.0 |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and ECHCF, and evaluation of herbicidal inhibition was done 18 days after application.

Formulations B and C were applied as comparative treatments. Results, averaged for all replicates of each treatment, are shown in Table 44b.

TABLE 44b

| Concentrate composition | Glyphosate rate g a.e./ha | % Inhibition | |
|---|---|---|---|
| | | ABUTH | ECHCF |
| Formulation B | 150 | 40 | 59 |
| | 250 | 68 | 61 |
| | 350 | 90 | 91 |
| | 450 | 93 | 94 |
| Formulation C | 150 | 74 | 78 |
| | 250 | 93 | 90 |
| | 350 | 97 | 96 |
| | 450 | 100 | 94 |
| 44-01 | 150 | 79 | 85 |
| | 250 | 93 | 98 |
| | 350 | 96 | 97 |
| | 450 | 97 | 95 |
| 44-02 | 150 | 71 | 87 |
| | 250 | 93 | 96 |
| | 350 | 96 | 94 |
| | 450 | 98 | 94 |
| 44-03 | 150 | 87 | 99 |
| | 250 | 94 | 100 |
| | 350 | 99 | 97 |
| | 450 | 97 | 94 |
| 44-04 | 150 | 89 | 100 |
| | 250 | 94 | 99 |
| | 350 | 97 | 98 |
| | 450 | 98 | 95 |
| 44-05 | 150 | 73 | 100 |
| | 250 | 90 | 100 |
| | 350 | 95 | 98 |
| | 450 | 96 | 94 |
| 44-06 | 150 | 80 | 99 |
| | 250 | 94 | 96 |
| | 350 | 95 | 100 |
| | 450 | 99 | 98 |
| 44-07 | 150 | 88 | 83 |
| | 250 | 94 | 92 |
| | 350 | 96 | 92 |
| | 450 | 100 | 90 |
| 44-08 | 150 | 81 | 91 |
| | 250 | 92 | 96 |
| | 350 | 97 | 89 |
| | 450 | 99 | 92 |
| 44-09 | 150 | 90 | 96 |
| | 250 | 93 | 93 |

TABLE 44b-continued

| Concentrate composition | Glyphosate rate g a.e./ha | % Inhibition | |
|---|---|---|---|
| | | ABUTH | ECHCF |
| | 350 | 95 | 95 |
| | 450 | 94 | 98 |

Herbicidal effectiveness overall was very high under the conditions of this study but a tendency can be discerned in compositions 44-01 to 44-04 for performance to improve as butyl stearate concentration was increased from zero to 2%.

Example 45

Aqueous concentrate compositions were prepared containing glyphosate IPA salt and excipient ingredients as shown in Table 45a. Concentrate composition 45-08 to 45-14 are oil-in-water emulsions and were prepared by process (vii). Concentrate compositions 45-15 to 45-17 are aqueous solution concentrates and were prepared by process (viii). Concentrate compositions 45-01 to 45-07 contain colloidal particulates and were prepared by process (ix).

Compositions 45-08 to 45-17 (all containing 163 g a.e./l glyphosate) showed acceptable storage stability. However, at a glyphosate loading of 400 g a.e./l (as in compositions 45-01 to 45-07) storage-stable compositions containing 0.5–1% butyl stearate and 5–10% alkylether surfactant could not be made except with the addition of colloidal particulate as shown below.

TABLE 45a

| Concentrate composition | Glyphosate g a.e./l | % w/w | | | Type of surfactant |
|---|---|---|---|---|---|
| | | Butyl stearate | Surfactant | Aerosil 90 | |
| 45-01 | 400 | 1.0 | 10.0 | 1.0 | ceteareth-27 |
| 45-02 | 400 | 1.0 | 10.0 | 1.0 | steareth-20 |
| 45-03 | 400 | 0.5 | 5.0 | 1.0 | ceteareth-27 |
| 45-04 | 400 | 0.5 | 5.0 | 1.0 | steareth-20 |
| 45-05 | 400 | 1.0 | 5.0 | 1.0 | ceteareth-27 |
| 45-06 | 400 | 1.0 | 5.0 | 1.0 | steareth-20 |
| 45-07 | 400 | 1.0 | 5.0 | 1.0 | steareth-30 |
| 45-08 | 163 | 0.5 | 5.0 | | oleth-20 |
| 45-09 | 163 | 0.5 | 5.0 | | steareth-20 |
| 45-10 | 163 | 0.5 | 5.0 | | ceteth-20 |
| 45-11 | 163 | 0.5 | 5.0 | | laureth-23 |
| 45-12 | 163 | 0.5 | 5.0 | | ceteareth-27 |
| 45-13 | 163 | 0.5 | 5.0 | | Neodol 25-12 |
| 45-14 | 163 | 0.5 | 5.0 | | Neodol 25-20 |
| 45-15 | 163 | | 5.0 | | steareth-20 |
| 45-16 | 163 | | 5.0 | | ceteth-20 |
| 45-17 | 163 | | 5.0 | | laureth-23 |

Velvetleaf (*Abutilon theophrasti*, ABUTH) and Japanese millet (*Echinochloa crus-galli*, ECHCF) plants were grown and treated by the standard procedures given above. Applications of spray compositions were made 18 days after planting ABUTH and ECHCF, and evaluation of herbicidal inhibition was done 19 days after application.

Formulations B, C and J were applied as comparative treatments. Results, averaged for all replicates of each treatment, are shown in Table 45b.

TABLE 45b

| Concentrate composition | Glyphosate rate g a.e./ha | % Inhibition ABUTH | ECHCF |
|---|---|---|---|
| Formulation B | 150 | 0 | 40 |
|  | 250 | 20 | 60 |
|  | 350 | 68 | 82 |
|  | 450 | 83 | 96 |
| Formulation C | 150 | 68 | 93 |
|  | 250 | 93 | 99 |
|  | 350 | 100 | 100 |
|  | 450 | 100 | 100 |
| Formulation J | 150 | 43 | 89 |
|  | 250 | 93 | 100 |
|  | 350 | 100 | 100 |
|  | 450 | 100 | 100 |
| 45-01 | 150 | 78 | 97 |
|  | 250 | 96 | 100 |
|  | 350 | 98 | 100 |
|  | 450 | 100 | 100 |
| 45-02 | 150 | 91 | 98 |
|  | 250 | 100 | 100 |
|  | 350 | 100 | 100 |
|  | 450 | 100 | 100 |
| 45-03 | 150 | 90 | 97 |
|  | 250 | 99 | 99 |
|  | 350 | 100 | 100 |
|  | 450 | 100 | 100 |
| 45-04 | 150 | 77 | 98 |
|  | 250 | 100 | 100 |
|  | 350 | 100 | 100 |
|  | 450 | 100 | 100 |
| 45-05 | 150 | 82 | 93 |
|  | 250 | 100 | 99 |
|  | 350 | 100 | 100 |
|  | 450 | 100 | 100 |
| 45-06 | 150 | 83 | 85 |
|  | 250 | 100 | 99 |
|  | 350 | 100 | 100 |
|  | 450 | 100 | 100 |
| 45-07 | 150 | 83 | 87 |
|  | 250 | 100 | 100 |
|  | 350 | 100 | 100 |
|  | 450 | 100 | 100 |
| 45-08 | 150 | 90 | 92 |
|  | 250 | 100 | 100 |
|  | 350 | 100 | 100 |
|  | 450 | 100 | 100 |
| 45-09 | 150 | 90 | 85 |
|  | 250 | 100 | 98 |
|  | 350 | 100 | 100 |
|  | 450 | 100 | 100 |
| 45-10 | 150 | 80 | 85 |
|  | 250 | 100 | 92 |
|  | 350 | 100 | 100 |
|  | 450 | 100 | 100 |
| 45-11 | 150 | 83 | 88 |
|  | 250 | 96 | 99 |
|  | 350 | 100 | 98 |
|  | 450 | 100 | 100 |
| 45-12 | 150 | 93 | 85 |
|  | 250 | 100 | 99 |
|  | 350 | 100 | 100 |
|  | 450 | 100 | 100 |
| 45-13 | 150 | 72 | 73 |
|  | 250 | 92 | 97 |
|  | 350 | 100 | 99 |
|  | 450 | 100 | 100 |
| 45-14 | 150 | 72 | 80 |
|  | 250 | 99 | 99 |
|  | 350 | 100 | 100 |
|  | 450 | 100 | 100 |
| 45-15 | 150 | 100 | 93 |
|  | 250 | 100 | 99 |
|  | 350 | 100 | 100 |
|  | 450 | 100 | 100 |
| 45-16 | 150 | 100 | 98 |
|  | 250 | 100 | 100 |
|  | 350 | 100 | 100 |
|  | 450 | 100 | 100 |
| 45-17 | 150 | 83 | 83 |
|  | 250 | 100 | 99 |
|  | 350 | 100 | 99 |
|  | 450 | 100 | 99 |

Outstanding herbicidal effectiveness was provided by compositions containing $C_{16-18}$ alkylether surfactants (ceteareth-27, steareth-20, steareth-30, oleth-20, ceteth-20). High-loaded (400 g a.e./l) glyphosate compositions containing a $C_{16-18}$ alkylether surfactant, butyl stearate and a colloidal particulate (Aerosil 90) to stabilize the compositions performed especially impressively in this test.

Example 46

Aqueous concentrate compositions were prepared containing glyphosate IPA salt and excipient ingredients as shown in Table 46a. Process (v) was followed for compositions 46-01 to 46-12, 46-15 and 46-16, and process (x) for compositions 46-13 and 46-14, using soybean lecithin (45% phospholipid, Avanti). Order of addition of ingredients was varied for certain compositions as indicated below.

TABLE 46a

| Concentrate composition | Glyphosate g/l a.e. | % w/w Lecithin | Fluorad FC-754/135 | Benzalkonium Cl | Butyl stearate | MON 0818 | Order of addition (*) |
|---|---|---|---|---|---|---|---|
| 46-01 | 345 | 4.0 |  | 0.66 |  |  |  |
| 46-02 | 345 | 4.0 |  | 1.00 |  |  |  |
| 46-03 | 347 | 3.0 |  | 3.00 |  |  |  |
| 46-04 | 347 | 4.0 |  | 4.00 |  |  |  |
| 46-05 | 347 | 4.0 |  | 5.00 |  |  |  |
| 46-06 | 345 | 4.6 |  | 4.60 |  |  |  |
| 46-07 | 348 | 4.0 | 2.0 (754) | 1.10 |  |  |  |
| 46-08 | 351 | 4.0 | 4.0 (754) | 1.00 |  |  | A |
| 46-09 | 346 | 3.9 | 4.2 (754) | 1.00 |  |  | B |
| 46-10 | 350 | 4.0 | 2.0 (135) | 1.10 |  |  |  |
| 46-11 | 352 | 4.0 | 4.0 (135) | 1.00 |  |  | A |
| 46-12 | 349 | 4.0 | 4.0 (135) | 1.00 |  |  | B |

TABLE 46a-continued

| | | | | | | |
|---|---|---|---|---|---|---|
| 46-13 | 348 | 4.0 | 4.0 (754) | 0.50 | 0.57 | |
| 46-14 | 347 | 4.0 | | 0.50 | 0.52 | |
| 46-15 | 348 | 3.7 | | 0.48 | | 3.7 |
| 46-16 | 348 | 4.0 | | 0.58 | | 4.0 |

| | (*) Order of addition | | | | |
|---|---|---|---|---|---|
| | 1st | 2nd | 3rd | 4th | 5th |
| A | lecithin | water | Benzalkonium Cl | FC-135/754 | glyphosate |
| B | glyphosate | FC-135/754 | Benzalkonium Cl | water | glyphosate |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and ECHCF, and evaluation of herbicidal inhibition was done 21 days after application.

Formulations B and J were applied as comparative treatments. Results, averaged for all replicates of each treatment, are shown in Table 46b.

TABLE 46b

| Concentrate composition | Glyphosate rate g a.e./ha | % Inhibition ABUTH | % Inhibition ECHCF |
|---|---|---|---|
| Formulation B | 100 | 5 | 5 |
| | 200 | 15 | 20 |
| | 300 | 47 | 30 |
| | 400 | 65 | 37 |
| Formulation J | 100 | 0 | 8 |
| | 200 | 70 | 37 |
| | 300 | 78 | 70 |
| | 400 | 83 | 73 |
| 46-01 | 100 | 3 | 10 |
| | 200 | 17 | 27 |
| | 300 | 45 | 37 |
| | 400 | 75 | 40 |
| 46-02 | 100 | 2 | 5 |
| | 200 | 13 | 30 |
| | 300 | 43 | 40 |
| | 400 | 75 | 47 |
| 46-03 | 100 | 0 | 8 |
| | 200 | 17 | 43 |
| | 300 | 65 | 78 |
| | 400 | 78 | 83 |
| 46-04 | 100 | 2 | 10 |
| | 200 | 30 | 37 |
| | 300 | 68 | 72 |
| | 400 | 75 | 88 |
| 46-05 | 100 | 2 | 20 |
| | 200 | 25 | 65 |
| | 300 | 63 | 88 |
| | 400 | 82 | 83 |
| 46-06 | 100 | 10 | 17 |
| | 200 | 25 | 33 |
| | 300 | 47 | 77 |
| | 400 | 83 | 75 |
| 46-07 | 100 | 0 | 10 |
| | 200 | 48 | 30 |
| | 300 | 73 | 37 |
| | 400 | 83 | 43 |
| 46-08 | 100 | 3 | 10 |
| | 200 | 33 | 30 |
| | 300 | 68 | 37 |
| | 400 | 78 | 40 |
| 46-09 | 100 | 5 | 10 |
| | 200 | 40 | 27 |
| | 300 | 65 | 50 |
| | 400 | 70 | 57 |
| 46-10 | 100 | 0 | 10 |
| | 200 | 30 | 27 |
| | 300 | 67 | 40 |
| | 400 | 73 | 40 |
| 46-11 | 100 | 0 | 10 |
| | 200 | 33 | 27 |
| | 300 | 52 | 37 |
| | 400 | 82 | 40 |
| 46-12 | 100 | 0 | 10 |
| | 200 | 40 | 20 |
| | 300 | 65 | 40 |
| | 400 | 72 | 40 |
| 46-13 | 100 | 0 | 10 |
| | 200 | 40 | 20 |
| | 300 | 60 | 33 |
| | 400 | 78 | 33 |
| 46-14 | 100 | 0 | 10 |
| | 200 | 7 | 47 |
| | 300 | 28 | 33 |
| | 400 | 43 | 43 |
| 46-15 | 100 | 0 | 13 |
| | 200 | 27 | 33 |
| | 300 | 73 | 53 |
| | 400 | 77 | 67 |
| 46-16 | 100 | 0 | 13 |
| | 200 | 30 | 37 |
| | 300 | 75 | 47 |
| | 400 | 77 | 68 |

Most concentrate compositions of this Example showed enhanced glyphosate effectiveness by comparison with Formulation B but did not equal the efficacy of commercial standard Formulation J in this test.

Example 47

Aqueous concentrate compositions were prepared containing glyphosate IPA salt and excipient ingredients as shown in Table 47a. Concentrate composition 47-01 to 47-09, 47-11 to 47-14, 47-16 and 47-17 are oil-in-water emulsions and were prepared by process (vii). Concentrate compositions 47-10 and 47-15 are aqueous solution concentrates and were prepared by process (viii).

TABLE 47a

| Conc. comp. | Glyphosate g a.e./l | Oil | Oleth-20 | Other surfactant | Type of oil | Other surfactant |
|---|---|---|---|---|---|---|
| 47-01 | 163 | 0.25 | 2.5 | | methyl laurate | |
| 47-02 | 163 | 0.25 | 2.5 | | methyl myristate | |
| 47-03 | 163 | 0.25 | 2.5 | | methyl palmitoleate | |
| 47-04 | 163 | 0.25 | 2.5 | | methyl palmitate | |
| 47-05 | 163 | 0.25 | 2.5 | | methyl linoleate | |
| 47-06 | 163 | 0.25 | 2.5 | | methyl oleate | |
| 47-07 | 163 | 0.25 | 2.5 | | methyl stearate | |
| 47-08 | 163 | 0.25 | 2.5 | | ethyl stearate | |
| 47-09 | 163 | 0.25 | 2.5 | | butyl stearate | |
| 47-10 | 163 | | 2.5 | | none | |
| 47-11 | 163 | 0.25 | | 2.5 | methyl palmitoleate | MON 0818 |
| 47-12 | 163 | 0.25 | | 2.5 | methyl palmitate | MON 0818 |
| 47-13 | 163 | 0.25 | | 2.5 | methyl oleate | MON 0818 |
| 47-14 | 163 | 0.25 | | 2.5 | methyl stearate | MON 0818 |
| 47-15 | 163 | | | 2.5 | none | MON 0818 |
| 47-16 | 163 | 0.25 | | 2.5 | butyl stearate | laureth-23 |
| 47-17 | 163 | 0.25 | | 2.5 | butyl stearate | Neodol 1-9 |

Velvetleaf (*Abutilon theophrasti*, ABUTH) and Japanese millet (*Echinochloa crus-galli*, ECHCF) plants were grown and treated by the standard procedures given above. Applications of spray compositions were made 20 days after planting ABUTH and ECHCF, and evaluation of herbicidal inhibition was done 16 days after application.

Formulations B, C and J were applied as comparative treatments. Results, averaged for all replicates of each treatment, are shown in Table 47b.

TABLE 47b

| Concentrate composition | Glyphosate rate g a.e./ha | % Inhibition ABUTH | % Inhibition ECHCF |
|---|---|---|---|
| Formulation B | 100 | 2 | 35 |
| | 200 | 52 | 67 |
| | 300 | 77 | 83 |
| | 400 | 78 | 87 |
| Formulation C | 100 | 25 | 77 |
| | 200 | 72 | 99 |
| | 300 | 87 | 100 |
| | 400 | 99 | 100 |
| Formulation J | 100 | 13 | 73 |
| | 200 | 70 | 97 |
| | 300 | 90 | 100 |
| | 400 | 97 | 100 |
| 47-01 | 100 | 22 | 55 |
| | 200 | 65 | 86 |
| | 300 | 78 | 98 |
| | 400 | 89 | 98 |
| 47-02 | 100 | 20 | 63 |
| | 200 | 67 | 91 |
| | 300 | 83 | 99 |
| | 400 | 97 | 100 |
| 47-03 | 100 | 30 | 75 |
| | 200 | 63 | 98 |
| | 300 | 83 | 99 |
| | 400 | 94 | 100 |
| 47-04 | 100 | 23 | 63 |
| | 200 | 60 | 98 |
| | 300 | 90 | 99 |
| | 400 | 95 | 100 |
| 47-05 | 100 | 27 | 57 |
| | 200 | 62 | 91 |
| | 300 | 83 | 96 |
| | 400 | 93 | 98 |
| 47-06 | 100 | 23 | 50 |
| | 200 | 63 | 89 |
| | 300 | 83 | 99 |
| 47-07 | 400 | 96 | 99 |
| | 100 | 25 | 53 |
| | 200 | 65 | 94 |
| | 300 | 83 | 99 |
| | 400 | 92 | 99 |
| 47-08 | 100 | 13 | 47 |
| | 200 | 53 | 88 |
| | 300 | 89 | 97 |
| | 400 | 95 | 99 |
| 47-09 | 100 | 27 | 53 |
| | 200 | 60 | 85 |
| | 300 | 83 | 97 |
| | 400 | 97 | 98 |
| 47-10 | 100 | 13 | 53 |
| | 200 | 62 | 94 |
| | 300 | 83 | 97 |
| | 400 | 88 | 99 |
| 47-11 | 100 | 23 | 60 |
| | 200 | 50 | 90 |
| | 300 | 85 | 98 |
| | 400 | 95 | 99 |
| 47-12 | 100 | 17 | 55 |
| | 200 | 35 | 94 |
| | 300 | 78 | 98 |
| | 400 | 94 | 99 |
| 47-13 | 100 | 8 | 50 |
| | 200 | 43 | 90 |
| | 300 | 73 | 98 |
| | 400 | 90 | 99 |
| 47-14 | 100 | 30 | 63 |
| | 200 | 45 | 92 |
| | 300 | 80 | 98 |
| | 400 | 94 | 98 |
| 47-15 | 100 | 20 | 63 |
| | 200 | 70 | 96 |
| | 300 | 82 | 99 |
| | 400 | 94 | 98 |
| 47-16 | 100 | 18 | 62 |
| | 200 | 62 | 83 |
| | 300 | 80 | 97 |
| | 400 | 97 | 97 |
| 47-17 | 100 | 17 | 52 |
| | 200 | 58 | 85 |
| | 300 | 75 | 90 |
| | 400 | 95 | 98 |

No great or consistent enhancement of herbicidal effectiveness of glyphosate compositions containing oleth-20 was obtained by adding a small amount of any of a variety of fatty acid esters in this study (compare 47-10 with 47-01 to 47-09).

Example 48

Aqueous concentrate compositions were prepared containing glyphosate IPA salt and excipient ingredients as shown in Table 48a. Concentrate composition 48-01 to 48-09, 48-11 to 48-14, 48-16 and 48-17 are oil-in-water emulsions and were prepared by process (vii). Concentrate compositions 48-10 and 48-15 are aqueous solution concentrates and were prepared by process (viii).

TABLE 48a

| Concentrate composition | Glyphosate g a.e./l | % w/w Oil | Oleth-20 | Other surfactant | Type of oil | Other surfactant |
|---|---|---|---|---|---|---|
| 48-01 | 163 | 0.25 | 2.5 | | isopropyl myristate | |
| 48-02 | 163 | 0.25 | 2.5 | | ethyl myristate | |
| 48-03 | 163 | 0.25 | 2.5 | | methyl palmitate | |
| 48-04 | 163 | 0.25 | 2.5 | | ethyl palmitate | |
| 48-05 | 163 | 0.25 | 2.5 | | ethyl linoleate | |
| 48-06 | 163 | 0.25 | 2.5 | | ethyl oleate | |
| 48-07 | 163 | 0.25 | 2.5 | | methyl stearate | |
| 48-08 | 163 | 0.25 | 2.5 | | ethyl stearate | |
| 48-09 | 163 | 0.25 | 2.5 | | butyl stearate | |
| 48-10 | 163 | | 2.5 | | none | |
| 48-11 | 163 | 0.25 | | 2.5 | methyl palmitate | MON 0818 |
| 48-12 | 163 | 0.25 | | 2.5 | methyl stearate | MON 0818 |
| 48-13 | 163 | 0.25 | | 2.5 | ethyl stearate | MON 0818 |
| 48-14 | 163 | 0.25 | | 2.5 | ethyl oleate | MON 0818 |
| 48-15 | 163 | | | 2.5 | none | MON 0818 |
| 48-16 | 163 | 0.25 | | 2.5 | butyl stearate | laureth-23 |
| 48-17 | 163 | 0.25 | | 2.5 | butyl stearate | Neodol 1-9 |

Velvetleaf (*Abutilon theophrasti*, ABUTH) and Japanese millet (*Echinochloa crus-galli*, ECHCF) plants were grown and treated by the standard procedures given above. Applications of spray compositions were made 19 days after planting ABUTH and ECHCF, and evaluation of herbicidal inhibition was done 18 days after application.

Formulations B, C and J were applied as comparative treatments. Results, averaged for all replicates of each treatment, are shown in Table 48b.

TABLE 48b

| Concentrate composition | Glyphosate rate g a.e./ha | % Inhibition ABUTH | % Inhibition ECHCF |
|---|---|---|---|
| Formulation B | 100 | 12 | 33 |
| | 200 | 45 | 43 |
| | 300 | 73 | 63 |
| | 400 | 80 | 63 |
| Formulation C | 100 | 43 | 57 |
| | 200 | 75 | 88 |
| | 300 | 95 | 99 |
| | 400 | 100 | 99 |
| Formulation J | 100 | 53 | 60 |
| | 200 | 77 | 75 |
| | 300 | 96 | 95 |
| | 400 | 99 | 98 |
| 48-01 | 100 | 35 | 40 |
| | 200 | 73 | 72 |
| | 300 | 83 | 91 |
| | 400 | 99 | 97 |
| 48-02 | 100 | 38 | 30 |
| | 200 | 70 | 43 |
| | 300 | 87 | 82 |
| | 400 | 96 | 80 |
| 48-03 | 100 | 25 | 27 |
| | 200 | 68 | 50 |
| | 300 | 90 | 73 |
| | 400 | 96 | 82 |
| 48-04 | 100 | 27 | 27 |
| | 200 | 75 | 50 |
| | 300 | 80 | 73 |
| | 400 | 96 | 80 |
| 48-05 | 100 | 33 | 27 |
| | 200 | 68 | 43 |
| | 300 | 83 | 70 |
| | 400 | 97 | 91 |
| 48-06 | 100 | 33 | 28 |
| | 200 | 72 | 53 |
| | 300 | 83 | 60 |
| | 400 | 99 | 70 |
| 48-07 | 100 | 37 | 25 |
| | 200 | 72 | 40 |
| | 300 | 83 | 50 |
| | 400 | 97 | 65 |
| 48-08 | 100 | 32 | 25 |
| | 200 | 73 | 43 |
| | 300 | 87 | 60 |
| | 400 | 98 | 67 |
| 48-09 | 100 | 35 | 25 |
| | 200 | 75 | 43 |
| | 300 | 95 | 57 |
| | 400 | 98 | 63 |
| 48-10 | 100 | 35 | 27 |
| | 200 | 73 | 40 |
| | 300 | 83 | 76 |
| | 400 | 97 | 73 |

TABLE 48b-continued

| Concentrate composition | Glyphosate rate g a.e./ha | % Inhibition ABUTH | ECHCF |
|---|---|---|---|
| 48-11 | 100 | 35 | 33 |
|  | 200 | 67 | 67 |
|  | 300 | 80 | 86 |
|  | 400 | 92 | 70 |
| 48-12 | 100 | 25 | 30 |
|  | 200 | 67 | 70 |
|  | 300 | 83 | 76 |
|  | 400 | 88 | 80 |
| 48-13 | 100 | 27 | 33 |
|  | 200 | 70 | 66 |
|  | 300 | 78 | 63 |
|  | 400 | 93 | 60 |
| 48-14 | 100 | 33 | 30 |
|  | 200 | 67 | 47 |
|  | 300 | 80 | 70 |
|  | 400 | 92 | 77 |
| 48-15 | 100 | 20 | 30 |
|  | 200 | 68 | 40 |
|  | 300 | 83 | 75 |
|  | 400 | 90 | 72 |
| 48-16 | 100 | 30 | 25 |
|  | 200 | 62 | 43 |
|  | 300 | 73 | 73 |
|  | 400 | 77 | 70 |
| 48-17 | 100 | 30 | 23 |
|  | 200 | 58 | 40 |
|  | 300 | 75 | 60 |
|  | 400 | 80 | 73 |

In this study, isopropyl myristate (composition 48-01) was the most effective of the fatty acid esters tested as additives to oleth-20 (48-10) in glyphosate compositions.

Example 49

Aqueous concentrate compositions were prepared containing glyphosate IPA salt and excipient ingredients as shown in Table 49a. Concentrate composition 49-01 to 49-09 are oil-in-water emulsions and were prepared by process (vii). Concentrate compositions 49-14 to 49-17 are aqueous solution concentrates and were prepared by process (viii).

TABLE 49a

| Concentrate composition | Glyphosate g a.e./l | % w/w Oil | % w/w Surfactant | Type of oil | Type of surfactant |
|---|---|---|---|---|---|
| 49-01 | 163 | 0.25 | 2.5 | butyl stearate | laureth-23 |
| 49-02 | 163 | 0.25 | 2.5 | butyl stearate | steareth-20 |
| 49-03 | 163 | 0.25 | 2.5 | butyl stearate | ceteareth-20 |
| 49-04 | 163 | 0.25 | 2.5 | butyl stearate | ceteareth-15 |
| 49-05 | 163 | 0.25 | 2.5 | butyl stearate | Neodol 44-13 |
| 49-06 | 163 | 0.25 | 2.5 | methyl stearate | steareth-20 |
| 49-07 | 163 | 0.25 | 2.5 | methyl stearate | ceteareth-20 |
| 49-08 | 163 | 0.25 | 2.5 | methyl stearate | ceteareth-15 |
| 49-09 | 163 | 0.25 | 2.5 | methyl stearate | Neodol 44-13 |
| 49-10 | 163 | 0.25 | 2.5 | methyl palmitate | steareth-20 |
| 49-11 | 163 | 0.25 | 2.5 | methyl palmitate | ceteareth-20 |
| 49-12 | 163 | 0.25 | 2.5 | methyl palmitate | ceteareth-15 |
| 49-13 | 163 | 0.25 | 2.5 | methyl palmitate | Neodol 44-13 |
| 49-14 | 163 |  | 2.5 | none | steareth-20 |
| 49-15 | 163 |  | 2.5 | none | ceteareth-20 |
| 49-16 | 163 |  | 2.5 | none | ceteareth-15 |
| 49-17 | 163 |  | 2.5 | none | Neodol 44-13 |

Velvetleaf (*Abutilon theophrasti*, ABUTH) and Japanese millet (*Echinochloa crus-galli*, ECHCF) plants were grown and treated by the standard procedures given above. Applications of spray compositions were made 24 days after planting ABUTH and ECHCF, and evaluation of herbicidal inhibition was done 16 days after application.

Formulations B, C and J were applied as comparative treatments. Results, averaged for all replicates of each treatment, are shown in Table 49b.

TABLE 49b

| Concentrate composition | Glyphosate rate g a.e./ha | % Inhibition ABUTH | ECHCF |
|---|---|---|---|
| Formulation B | 100 | 10 | 37 |
|  | 200 | 30 | 40 |
|  | 300 | 43 | 57 |
|  | 400 | 23 | 33 |
| Formulation C | 100 | 50 | 67 |
|  | 200 | 75 | 96 |
|  | 300 | 85 | 99 |
|  | 400 | 94 | 100 |
| Formulation J | 100 | 40 | 75 |
|  | 200 | 73 | 94 |
|  | 300 | 93 | 98 |
|  | 400 | 95 | 99 |
| 49-01 | 100 | 63 | 77 |
|  | 200 | 67 | 94 |
|  | 300 | 77 | 99 |
|  | 400 | 88 | 96 |
| 49-02 | 100 | 63 | 75 |
|  | 200 | 83 | 88 |
|  | 300 | 93 | 98 |
|  | 400 | 95 | 99 |
| 49-03 | 100 | 67 | 75 |
|  | 200 | 82 | 95 |
|  | 300 | 95 | 99 |
|  | 400 | 98 | 99 |
| 49-04 | 100 | 60 | 75 |
|  | 200 | 82 | 97 |
|  | 300 | 96 | 99 |
|  | 400 | 98 | 100 |
| 49-05 | 100 | 63 | 73 |
|  | 200 | 75 | 89 |
|  | 300 | 80 | 98 |
|  | 400 | 87 | 97 |
| 49-06 | 100 | 58 | 63 |
|  | 200 | 78 | 93 |
|  | 300 | 93 | 99 |
|  | 400 | 98 | 100 |
| 49-07 | 100 | 60 | 67 |
|  | 200 | 78 | 93 |
|  | 300 | 93 | 99 |
|  | 400 | 100 | 99 |
| 49-08 | 100 | missing | missing |
|  | 200 | missing | missing |
|  | 300 | 78 | 95 |
|  | 400 | 98 | 99 |
| 49-09 | 100 | 23 | 30 |
|  | 200 | 65 | 83 |
|  | 300 | 80 | 98 |
|  | 400 | 93 | 99 |
| 49-10 | 100 | 65 | 67 |
|  | 200 | 83 | 95 |
|  | 300 | 97 | 99 |
|  | 400 | 99 | 99 |
| 49-11 | 100 | 72 | 73 |
|  | 200 | 90 | 98 |
|  | 300 | 96 | 97 |
|  | 400 | 99 | 99 |
| 49-12 | 100 | 68 | 63 |
|  | 200 | 90 | 92 |
|  | 300 | 98 | 99 |
|  | 400 | 97 | 99 |
| 49-13 | 100 | 43 | 73 |
|  | 200 | 72 | 87 |
|  | 300 | 83 | 98 |
|  | 400 | 93 | 96 |
| 49-14 | 100 | 62 | 77 |
|  | 200 | 78 | 99 |

TABLE 49b-continued

| Concentrate composition | Glyphosate rate g a.e./ha | % Inhibition ABUTH | ECHCF |
|---|---|---|---|
|  | 300 | 95 | 99 |
|  | 400 | 98 | 100 |
| 49-15 | 100 | 52 | 60 |
|  | 200 | 78 | 93 |
|  | 300 | 94 | 98 |
|  | 400 | 97 | 99 |
| 49-16 | 100 | 38 | 68 |
|  | 200 | 68 | 99 |
|  | 300 | 87 | 97 |
|  | 400 | 94 | 99 |
| 49-17 | 100 | 55 | 75 |
|  | 200 | 68 | 91 |
|  | 300 | 83 | 96 |
|  | 400 | 87 | 98 |

Herbicidal effectiveness exceeding that of commercial standard composition J, at least on ABUTH, was recorded with several compositions, including 49-02 (steareth-20 plus butyl stearate), 49-03 (ceteareth-20 plus butyl stearate), 49-04 (ceteareth-15 plus butyl stearate), 49-10 (steareth-20 plus methyl palmitate), 49-11 (ceteareth-20 plus methyl palmitate) and 49-12 (ceteareth-15 plus methyl palmitate). Compositions lacking fatty acid ester performed slightly less well overall than those containing butyl stearate or methyl palmitate.

Example 50

Spray compositions were prepared containing glyphosate IPA salt and excipient ingredients as shown in Table 50a. Compositions were prepared by simple mixing of ingredients. Soybean lecithin (45% phospholipid, Avanti), where included, was first prepared with sonication in water to make a homogeneous composition. Four different concentrations of glyphosate (not shown in Table 50a) were prepared, calculated to provide, when applied in a spray volume of 93 l/ha, the glyphosate rates shown in Table 50b.

Velvetleaf (*Abutilon theophrasti*, ABUTH), Japanese millet (*Echinochloa crus-galli*, ECHCF) and Prickly sida (*Sida spinosa*, SIDSP) plants were grown and treated by the standard procedures given above. Applications of spray compositions were made 14 days after planting ABUTH and ECHCF and 21 days after planting SIDSP. Evaluation of herbicidal inhibition was done 14 days after application.

Formulations B and C were applied as comparative treatments, representing technical glyphosate IPA salt and a commercial formulation of glyphosate IPA salt respectively. Results, averaged for all replicates of each treatment, are shown in Table 50b.

TABLE 50b

| Spray composition | Glyphosate rate g a.e./ha | % Inhibition ABUTH | ECHCF | SIDSP |
|---|---|---|---|---|
| Formulation B (technical) | 50 | 0 | 0 | 0 |
|  | 100 | 38 | 35 | 35 |
|  | 200 | 87 | 50 | 90 |
|  | 300 | 95 | 88 | 94 |
| Formulation C (commercial) | 50 | 0 | 2 | 0 |
|  | 100 | 32 | 55 | 25 |
|  | 200 | 85 | 97 | 93 |
|  | 300 | 96 | 99 | 96 |
| 50-01 | 50 | 78 | 53 | 88 |
|  | 100 | 90 | 60 | 95 |
|  | 200 | 99 | 96 | 99 |
|  | 300 | 99 | 97 | 98 |
| 50-02 | 50 | 25 | 15 | 43 |
|  | 100 | 72 | 30 | 82 |
|  | 200 | 94 | 62 | 93 |
|  | 300 | 95 | 77 | 94 |
| 50-03 | 50 | 20 | 8 | 32 |
|  | 100 | 52 | 22 | 78 |
|  | 200 | 87 | 55 | 91 |
|  | 300 | 95 | 65 | 93 |
| 50-04 | 50 | 62 | 37 | 85 |
|  | 100 | 82 | 68 | 92 |
|  | 200 | 97 | 96 | 95 |
|  | 300 | 98 | 95 | 97 |
| 50-05 | 50 | 15 | 10 | 25 |
|  | 100 | 47 | 27 | 23 |
|  | 200 | 85 | 62 | 87 |
|  | 300 | 90 | 63 | 92 |
| 50-06 | 50 | 0 | 2 | 0 |
|  | 100 | 20 | 15 | 20 |
|  | 200 | 85 | 60 | 82 |
|  | 300 | 90 | 65 | 90 |
| 50-07 | 50 | 67 | 27 | 82 |
|  | 100 | 87 | 55 | 93 |

TABLE 50a

| Spray comp. | Lecithin | Fluorad FC-754 | Butyl stearate | Methyl oleate | Oleth-20 | Lecithin supplied as | Methyl oleate supplied as |
|---|---|---|---|---|---|---|---|
| 50-01 | 0.05 | 0.050 |  |  |  | soybean lecithin |  |
| 50-02 | 0.05 |  | 0.050 |  |  | soybean lecithin |  |
| 50-03 | 0.05 |  |  |  |  | soybean lecithin |  |
| 50-04 |  | 0.050 |  |  |  |  |  |
| 50-05 |  |  | 0.050 |  |  |  |  |
| 50-06 | 0.05 |  |  |  |  | LI-700 |  |
| 50-07 |  |  | 0.005 |  | 0.05 |  |  |
| 50-08 |  |  |  | 0.01 | 0.05 |  |  |
| 50-09 |  |  |  |  | 0.05 |  |  |
| 50-10 |  |  | 0.005 |  |  |  |  |
| 50-11 |  |  |  | 0.01 |  |  | pure |
| 50-12 |  |  |  | 0.01 |  |  | methylated seed oil |

TABLE 50b-continued

| Spray composition | Glyphosate rate g a.e./ha | % Inhibition ABUTH | ECHCF | SIDSP |
|---|---|---|---|---|
|  | 200 | 94 | 92 | 96 |
|  | 300 | 97 | 99 | 97 |
| 50-08 | 50 | 62 | 30 | 75 |
|  | 100 | 78 | 63 | 91 |
|  | 200 | 93 | 96 | 96 |
|  | 300 | 94 | 98 | 98 |
| 50-09 | 50 | 65 | 45 | 77 |
|  | 100 | 80 | 73 | 95 |
|  | 200 | 93 | 98 | 97 |
|  | 300 | 95 | 99 | 99 |
| 50-10 | 50 | 10 | 25 | 5 |
|  | 100 | 23 | 35 | 37 |
|  | 200 | 90 | 50 | 93 |
|  | 300 | 92 | 73 | 94 |
| 50-11 | 50 | 10 | 25 | 0 |
|  | 100 | 52 | 33 | 43 |
|  | 200 | 88 | 72 | 93 |
|  | 300 | 94 | 78 | 94 |
| 50-12 | 50 | 0 | 15 | 0 |
|  | 100 | 43 | 35 | 33 |
|  | 200 | 91 | 70 | 90 |
|  | 300 | 94 | 82 | 93 |

Results of this test using glyphosate as the exogenous chemical are summarized as follows:

Butyl stearate alone at 0.05% (50-05) did not greatly enhance effectiveness.

The combination of lecithin and butyl stearate (50-02) gave surprisingly strong enhancement of effectiveness, suggesting a synergistic interaction between these two excipient substances.

Oleth-20 at the low concentration of 0.05% (50-09) gave extremely high effectiveness, superior to that obtained with the commercial standard. Addition of 0.005% butyl stearate (50-07) or 0.01% methyl oleate (50-08) did not provide further enhancement.

Example 51

Spray compositions were prepared containing paraquat dichloride and excipient ingredients. Compositions 51-01 to 51-12 were exactly like compositions 50-01 to 50-12 except that a different active ingredient was used and a range of active ingredient concentrations was selected appropriate to the active ingredient being applied.

Velvetleaf (Abutilon theophrasti, ABUTH), Japanese millet (Echinochloa crus-galli, ECHCF) and prickly sida (Sida spinosa, SIDSP) plants were grown and treated by the standard procedures given above. Applications of spray compositions were made 14 days after planting ABUTH, 8 days after planting ECHCF and 21 days after planting SIDSP. Evaluation of herbicidal inhibition was done 12 days after application.

Standards included technical paraquat dichloride and Gramoxone, a commercial formulation of paraquat from Zeneca. Results, averaged for all replicates of each treatment, are shown in Table 51.

TABLE 51

| Spray composition | Paraquat rate g a.i./ha | % Inhibition ABUTH | ECHCF | SIDSP |
|---|---|---|---|---|
| Paraquat dichloride | 25 | 50 | 83 | 55 |
| (technical) | 50 | 57 | 78 | 60 |
|  | 100 | 73 | 84 | 69 |
|  | 200 | 85 | 95 | 99 |
| Gramoxone | 25 | 40 | 72 | 40 |
| (commercial) | 50 | 60 | 70 | 52 |
|  | 100 | 72 | 58 | 55 |
|  | 200 | 72 | 89 | 63 |
| 51-01 | 25 | 75 | 93 | 67 |
|  | 50 | 82 | 97 | 91 |
|  | 100 | 95 | 98 | 97 |
|  | 200 | 100 | 99 | 99 |
| 51-02 | 25 | 67 | 80 | 48 |
|  | 50 | 68 | 87 | 65 |
|  | 100 | 88 | 97 | 93 |
|  | 200 | 96 | 99 | 98 |
| 51-03 | 25 | 55 | 65 | 42 |
|  | 50 | 62 | 87 | 65 |
|  | 100 | 83 | 96 | 93 |
|  | 200 | 95 | 99 | 97 |
| 51-04 | 25 | 53 | 82 | 45 |
|  | 50 | 63 | 94 | 53 |
|  | 100 | 88 | 99 | 86 |
|  | 200 | 92 | 99 | 98 |
| 51-05 | 25 | 58 | 67 | 50 |
|  | 50 | 60 | 62 | 45 |
|  | 100 | 70 | 73 | 62 |
|  | 200 | 85 | 90 | 88 |
| 51-06 | 25 | 53 | 77 | 43 |
|  | 50 | 60 | 92 | 40 |
|  | 100 | 80 | 93 | 55 |
|  | 200 | 96 | 99 | 78 |
| 51-07 | 25 | 65 | 80 | 45 |
|  | 50 | 82 | 92 | 70 |
|  | 100 | 96 | 96 | 89 |
|  | 200 | 100 | 98 | 99 |
| 51-08 | 25 | 67 | 80 | 37 |
|  | 50 | 82 | 90 | 71 |
|  | 100 | 97 | 98 | 65 |
|  | 200 | 99 | 99 | 93 |
| 51-09 | 25 | 72 | 90 | 50 |
|  | 50 | 80 | 97 | 57 |
|  | 100 | 91 | 99 | 94 |
|  | 200 | 97 | 100 | 97 |
| 51-10 | 25 | 67 | 87 | 45 |
|  | 50 | 68 | 75 | 57 |
|  | 100 | 78 | 93 | 63 |
|  | 200 | 82 | 97 | 82 |
| 51-11 | 25 | 65 | 80 | 45 |
|  | 50 | 73 | 77 | 62 |
|  | 100 | 90 | 95 | 62 |
|  | 200 | 94 | 98 | 78 |
| 51-12 | 25 | 67 | 78 | 37 |
|  | 50 | 75 | 90 | 55 |
|  | 100 | 77 | 97 | 90 |
|  | 200 | 85 | 99 | 92 |

Results of this test using paraquat as the exogenous chemical are summarized as follows:

Butyl stearate alone at 0.05% (51-05) did not enhance effectiveness.

The combination of lecithin and butyl stearate (51-02) gave surprisingly strong enhancement of effectiveness, suggesting a synergistic interaction between these two excipient substances.

Oleth-20 at the low concentration of 0.05% (51-09) gave extremely high effectiveness, superior to that obtained with the commercial standard. Addition of 0.005% butyl stearate (51-07) or 0.01% methyl oleate (51-08) did not provide further enhancement.

Example 52

Spray compositions were prepared containing acifluorfen sodium salt and excipient ingredients. Compositions 52-01 to 52-12 were exactly like compositions 50-01 to 50-12 respectively except that a different active ingredient was used and a range of active ingredient concentrations was selected appropriate to the active ingredient being applied.

Velvetleaf (*Abutilon theophrasti*, ABUTH), Japanese millet (*Echinochloa crus-galli*, ECHCF) and prickly sida (*Sida spinosa*, SIDSP) plants were grown and treated by the standard procedures given above. Applications of spray compositions were made 15 days after planting ABUTH, 9 days after planting ECHCF and 22 days after planting SIDSP. Evaluation of herbicidal inhibition was done 10 days after application.

Standards included technical acifluorfen sodium and Blazer, a commercial formulation of acifluorfen from Rohm & Haas. Results, averaged for all replicates of each treatment, are shown in Table 52.

TABLE 52

| Spray composition | Acifluorfen rate g a.i./ha | % Inhibition ABUTH | ECHCF | SIDSP |
|---|---|---|---|---|
| Acifluorfen | 25 | 20 | 2 | 15 |
| (technical) | 50 | 32 | 7 | 17 |
|  | 100 | 52 | 18 | 35 |
|  | 200 | 62 | 35 | 40 |
| Blazer | 25 | 30 | 30 | 5 |
| (commercial) | 50 | 53 | 53 | 12 |
|  | 100 | 55 | 55 | 7 |
|  | 200 | 65 | 65 | 32 |
| 52-01 | 25 | 60 | 7 | 20 |
|  | 50 | 63 | 20 | 20 |
|  | 100 | 65 | 43 | 33 |
|  | 200 | 80 | 70 | 48 |
| 52-02 | 25 | 25 | 7 | 5 |
|  | 50 | 42 | 12 | 25 |
|  | 100 | 60 | 30 | 22 |
|  | 200 | 68 | 68 | 50 |
| 52-03 | 25 | 22 | 5 | 10 |
|  | 50 | 55 | 7 | 33 |
|  | 100 | 62 | 25 | 27 |
|  | 200 | 65 | 55 | 48 |
| 52-04 | 25 | 57 | 7 | 13 |
|  | 50 | 67 | 10 | 32 |
|  | 100 | 67 | 35 | 32 |
|  | 200 | 70 | 70 | 45 |
| 52-05 | 25 | 30 | 3 | 15 |
|  | 50 | 47 | 27 | 27 |
|  | 100 | 55 | 42 | 37 |
|  | 200 | 65 | 60 | 38 |
| 52-06 | 25 | 28 | 0 | 3 |
|  | 50 | 50 | 0 | 10 |
|  | 100 | 55 | 30 | 25 |
|  | 200 | 67 | 58 | 47 |
| 52-07 | 25 | 35 | 20 | 17 |
|  | 50 | 55 | 35 | 27 |
|  | 100 | 58 | 63 | 32 |
|  | 200 | 67 | 67 | 55 |
| 52-08 | 25 | 40 | 20 | 8 |
|  | 50 | 57 | 30 | 28 |
|  | 100 | 60 | 60 | 30 |
|  | 200 | 70 | 77 | 48 |
| 52-09 | 25 | 47 | 20 | 22 |
|  | 50 | 55 | 35 | 35 |
|  | 100 | 62 | 65 | 38 |
|  | 200 | 68 | 82 | 50 |
| 52-10 | 25 | 28 | 0 | 5 |
|  | 50 | 48 | 0 | 10 |
|  | 100 | 53 | 5 | 25 |
|  | 200 | 62 | 35 | 40 |
| 52-11 | 25 | 35 | 0 | 5 |
|  | 50 | 43 | 0 | 30 |

TABLE 52-continued

| Spray composition | Acifluorfen rate g a.i./ha | % Inhibition ABUTH | ECHCF | SIDSP |
|---|---|---|---|---|
|  | 100 | 50 | 0 | 35 |
|  | 200 | 65 | 43 | 47 |
| 52-12 | 25 | 40 | 5 | 5 |
|  | 50 | 55 | 18 | 35 |
|  | 100 | 60 | 47 | 38 |
|  | 200 | 70 | 62 | 48 |

Results of this test using acifluorfen as the exogenous chemical are summarized as follows:

Butyl stearate at 0.05% alone (52-05) and in combination with lecithin (52-02) enhanced effectiveness, particularly on ECHCF.

Oleth-20 at the low concentration of 0.05% (52-09) gave effectiveness superior to that obtained with the commercial standard. Addition of 0.005% butyl stearate (52-07) or 0.01% methyl oleate (52-08) did not provide further enhancement.

Example 53

Spray compositions were prepared containing asulam and excipient ingredients. Compositions 53-01 to 53-12 were exactly like compositions 50-01 to 50-12 respectively except that a different active ingredient was used and a range of active ingredient concentrations was selected appropriate to the active ingredient being applied.

Velvetleaf (*Abutilon theophrasti*, ABUTH), Japanese millet (*Echinochloa crus-galli,* ECHCF) and prickly sida (*Sida spinosa,* SIDSP) plants were grown and treated by the standard procedures given above. Applications of spray compositions were made 14 days after planting ABUTH, 11 days after planting ECHCF and 21 days after planting SIDSP. Evaluation of herbicidal inhibition was done 14 days after application.

Standards included technical asulam and Asulox, a commercial formulation of asulam from Rhône-Poulenc. Results, averaged for all replicates of each treatment, are shown in Table 53.

TABLE 53

| Spray composition | Asulam rate g a.i./ha | % Inhibition ABUTH | ECHCF | SIDSP |
|---|---|---|---|---|
| Asulam | 200 | 0 | 12 | 0 |
| (technical) | 400 | 17 | 27 | 5 |
|  | 800 | 48 | 32 | 20 |
|  | 1400 | 42 | 50 | 37 |
| Asulox | 200 | 3 | 5 | 0 |
| (commercial) | 400 | 27 | 30 | 20 |
|  | 800 | 52 | 45 | 25 |
|  | 1400 | 50 | 60 | 40 |
| 53-01 | 200 | 5 | 8 | 13 |
|  | 400 | 23 | 45 | 22 |
|  | 800 | 50 | 50 | 30 |
|  | 1400 | 60 | 65 | 48 |
| 53-02 | 200 | 0 | 20 | 17 |
|  | 400 | 33 | 40 | 20 |
|  | 800 | 47 | 48 | 33 |
|  | 1400 | 53 | 68 | 55 |
| 53-03 | 200 | 3 | 20 | 3 |
|  | 400 | 28 | 52 | 7 |
|  | 800 | 50 | 50 | 23 |
|  | 1400 | 50 | 58 | 43 |

TABLE 53-continued

| Spray composition | Asulam rate g a.i./ha | % Inhibition ABUTH | ECHCF | SIDSP |
|---|---|---|---|---|
| 53-04 | 200 | 3 | 40 | 7 |
|  | 400 | 35 | 45 | 18 |
|  | 800 | 52 | 50 | 25 |
|  | 1400 | 58 | 60 | 42 |
| 53-05 | 200 | 0 | 10 | 3 |
|  | 400 | 23 | 30 | 18 |
|  | 800 | 33 | 50 | 32 |
|  | 1400 | 45 | 57 | 38 |
| 53-06 | 200 | 2 | 30 | 10 |
|  | 400 | 8 | 47 | 17 |
|  | 800 | 50 | 55 | 28 |
|  | 1400 | 52 | 63 | 40 |
| 53-07 | 200 | 0 | 43 | 3 |
|  | 400 | 22 | 48 | 17 |
|  | 800 | 40 | 55 | 28 |
|  | 1400 | 52 | 60 | 33 |
| 53-08 | 200 | 7 | 47 | 22 |
|  | 400 | 20 | 48 | 22 |
|  | 800 | 53 | 55 | 30 |
|  | 1400 | 57 | 60 | 33 |
| 53-09 | 200 | 0 | 45 | 7 |
|  | 400 | 25 | 50 | 7 |
|  | 800 | 53 | 60 | 32 |
|  | 1400 | 55 | 63 | 37 |
| 53-10 | 200 | 22 | 37 | 10 |
|  | 400 | 27 | 45 | 10 |
|  | 800 | 50 | 43 | 23 |
|  | 1400 | 52 | 52 | 27 |
| 53-11 | 200 | 25 | 33 | 5 |
|  | 400 | 15 | 37 | 13 |
|  | 800 | 48 | 42 | 25 |
|  | 1400 | 42 | 52 | 28 |
| 53-12 | 200 | 3 | 25 | 17 |
|  | 400 | 13 | 42 | 18 |
|  | 800 | 50 | 45 | 30 |
|  | 1400 | 52 | 50 | 33 |

Results of this test using asulam as the exogenous chemical are summarized as follows:

Butyl stearate alone at 0.05% (53-05) enhanced effectiveness on ECHCF.

The combination of lecithin and butyl stearate (53-02) gave greater enhancement of effectiveness than either excipient substance alone.

Oleth-20 at the low concentration of 0.05% (53-09) gave, at low exogenous chemical rates, effectiveness on ECHCF superior to that obtained with the commercial standard. Addition of 0.005% butyl stearate (53-07) or 0.01% methyl oleate (53-08) did not provide further enhancement.

Example 54

Spray compositions were prepared containing dicamba sodium salt and excipient ingredients. Compositions 54-01 to 54-12 were exactly like compositions 50-01 to 50-12 respectively except that a different active ingredient was used and a range of active ingredient concentrations was selected appropriate to the active ingredient being applied.

Velvetleaf (*Abutilon theophrasti*, ABUTH), Japanese millet (*Echinochloa crus-galli*, ECHCF) and prickly sida (*Sida spinosa*, SIDSP) plants were grown and treated by the standard procedures given above. Applications of spray compositions were made 14 days after planting ABUTH, 8 days after planting ECHCF and 21 days after planting SIDSP. Evaluation of herbicidal inhibition was done 17 days after application.

Standards included technical dicamba sodium and Banvel, a commercial formulation of dicamba from Sandoz. Results, averaged for all replicates of each treatment, are shown in Table 54.

TABLE 54

| Spray composition | Dicamba rate g a.i./ha | % Inhibition ABUTH | ECHCF | SIDSP |
|---|---|---|---|---|
| Dicamba (technical) | 25 | 47 | 0 | 30 |
|  | 50 | 63 | 0 | 40 |
|  | 100 | 82 | 0 | 50 |
|  | 200 | 93 | 5 | 58 |
| Banvel (commercial) | 25 | 47 | 0 | 35 |
|  | 50 | 68 | 0 | 40 |
|  | 100 | 91 | 0 | 53 |
|  | 200 | 93 | 3 | 63 |
| 54-01 | 25 | 42 | 0 | 38 |
|  | 50 | 67 | 0 | 48 |
|  | 100 | 92 | 0 | 67 |
|  | 200 | 93 | 3 | 73 |
| 54-02 | 25 | 43 | 0 | 43 |
|  | 50 | 58 | 0 | 50 |
|  | 100 | 85 | 0 | 62 |
|  | 200 | 89 | 8 | 72 |
| 54-03 | 25 | 50 | 0 | 32 |
|  | 50 | 65 | 0 | 45 |
|  | 100 | 90 | 0 | 60 |
|  | 200 | 94 | 13 | 68 |
| 54-04 | 25 | 43 | 0 | 35 |
|  | 50 | 65 | 0 | 42 |
|  | 100 | 94 | 0 | 53 |
|  | 200 | 94 | 13 | 67 |
| 54-05 | 25 | 50 | 0 | 35 |
|  | 50 | 68 | 0 | 40 |
|  | 100 | 88 | 0 | 53 |
|  | 200 | 92 | 15 | 60 |
| 54-06 | 25 | 40 | 0 | 40 |
|  | 50 | 65 | 0 | 45 |
|  | 100 | 88 | 0 | 52 |
|  | 200 | 92 | 8 | 70 |
| 54-07 | 25 | 45 | 0 | 42 |
|  | 50 | 57 | 0 | 45 |
|  | 100 | 88 | 0 | 62 |
|  | 200 | 88 | 20 | 68 |
| 54-08 | 25 | 40 | 0 | 38 |
|  | 50 | 62 | 0 | 45 |
|  | 100 | 97 | 18 | 62 |
|  | 200 | 93 | 17 | 73 |
| 54-09 | 25 | 33 | 0 | 35 |
|  | 50 | 60 | 0 | 45 |
|  | 100 | 93 | 0 | 63 |
|  | 200 | 96 | 15 | 73 |
| 54-10 | 25 | 35 | 0 | 30 |
|  | 50 | 57 | 0 | 43 |
|  | 100 | 90 | 0 | 50 |
|  | 200 | 90 | 3 | 70 |
| 54-11 | 25 | 45 | 0 | 30 |
|  | 50 | 53 | 0 | 42 |
|  | 100 | 89 | 0 | 55 |
|  | 200 | 92 | 0 | 73 |
| 54-12 | 25 | 38 | 0 | 37 |
|  | 50 | 60 | 0 | 45 |
|  | 100 | 96 | 0 | 52 |
|  | 200 | 93 | 0 | 70 |

Results of this test using dicamba as the exogenous chemical are summarized as follows:

Butyl stearate alone at 0.05% (54-05) provided slight enhancement of effectiveness.

The combination of lecithin and butyl stearate (54-02) gave greater enhancement of effectiveness on SIDSP than either of these two excipient substances alone.

Oleth-20 at the low concentration of 0.05% (54-09) gave effectiveness on SIDSP superior to that obtained with the commercial standard. Addition of 0.005% butyl stearate (54-07) or 0.01% methyl oleate (54-08) did not provide significant further enhancement.

Example 55

Spray compositions were prepared containing metsulfuron-methyl and excipient ingredients. Compositions 55-01 to 55-12 were exactly like compositions 50-01 to 50-12 respectively except that a different active ingredient was used and a range of active ingredient concentrations was selected appropriate to the active ingredient being applied.

Velvetleaf (*Abutilon theophrasti*, ABUTH), Japanese millet (*Echinochloa crus-galli*, ECHCF) and prickly sida (*Sida spinosa*, SIDSP) plants were grown and treated by the standard procedures given above. Applications of spray compositions were made 14 days after planting ABUTH, 8 days after planting ECHCF and 21 days after planting SIDSP. Evaluation of herbicidal inhibition was done 14 days after application.

Standards included technical metsulfuron-methyl and Ally, a commercial formulation of metsulfuron from Du Pont. Results, averaged for all replicates of each treatment, are shown in Table 55.

TABLE 55

| Spray composition | Metsulfuron rate g a.i./ha | % Inhibition ABUTH | ECHCF | SIDSP |
|---|---|---|---|---|
| Metsulfuron | 0.5 | 72 | 0 | 5 |
| (technical) | 1 | 90 | 0 | 23 |
| | 5 | 96 | 0 | 50 |
| | 10 | 97 | 30 | 55 |
| Ally | 0.5 | 75 | 0 | 5 |
| (commercial) | 1 | 85 | 0 | 22 |
| | 5 | 95 | 0 | 42 |
| | 10 | 97 | 25 | 53 |
| 55-01 | 0.5 | 95 | 0 | 47 |
| | 1 | 96 | 20 | 53 |
| | 5 | 97 | 25 | 62 |
| | 10 | 98 | 45 | 62 |
| 55-02 | 0.5 | 87 | 0 | 40 |
| | 1 | 90 | 10 | 55 |
| | 5 | 95 | 10 | 58 |
| | 10 | 96 | 40 | 63 |
| 55-03 | 0.5 | 87 | 0 | 27 |
| | 1 | 90 | 0 | 40 |
| | 5 | 96 | 10 | 57 |
| | 10 | 97 | 33 | 63 |
| 55-04 | 0.5 | 90 | 0 | 33 |
| | 1 | 95 | 10 | 50 |
| | 5 | 98 | 17 | 62 |
| | 10 | 99 | 28 | 58 |
| 55-05 | 0.5 | 85 | 0 | 27 |
| | 1 | 90 | 0 | 33 |
| | 5 | 95 | 0 | 47 |
| | 10 | 95 | 13 | 60 |
| 55-06 | 0.5 | 77 | 0 | 30 |
| | 1 | 89 | 10 | 47 |
| | 5 | 96 | 17 | 62 |
| | 10 | 98 | 33 | 60 |
| 55-07 | 0.5 | 94 | 0 | 55 |
| | 1 | 97 | 10 | 60 |
| | 5 | 98 | 43 | 60 |
| | 10 | 97 | 55 | 65 |
| 55-08 | 0.5 | 93 | 0 | 55 |
| | 1 | 96 | 5 | 58 |
| | 5 | 97 | 42 | 60 |
| | 10 | 97 | 50 | 60 |
| 55-09 | 0.5 | 93 | 0 | 55 |
| | 1 | 97 | 10 | 62 |
| | 5 | 98 | 55 | 62 |
| | 10 | 98 | 65 | 63 |
| 55-10 | 0.5 | 85 | 0 | 28 |
| | 1 | 82 | 0 | 30 |
| | 5 | 95 | 10 | 52 |
| | 10 | 96 | 17 | 57 |
| 55-11 | 0.5 | 73 | 0 | 25 |
| | 1 | 88 | 20 | 28 |
| | 5 | 94 | 25 | 53 |
| | 10 | 96 | 32 | 57 |
| 55-12 | 0.5 | 75 | 0 | 32 |
| | 1 | 85 | 20 | 37 |
| | 5 | 94 | 23 | 55 |
| | 10 | 96 | 25 | 57 |

Results of this test using metsulfuron as the exogenous chemical are summarized as follows:

Butyl stearate alone at 0.05% (55-05) enhanced effectiveness to a level superior to that obtained with the commercial standard.

The combination of lecithin and butyl stearate (55-02) gave greater enhancement of effectiveness than was obtained with either of these two excipient substances alone.

Oleth-20 at the low concentration of 0.05% (55-09) gave high effectiveness, superior to that obtained with the commercial standard. Addition of 0.005% butyl stearate (55-07) or 0.01% methyl oleate (55-08) did not provide further enhancement.

Example 56

Spray compositions were prepared containing imazethapyr and excipient ingredients. Compositions 56-01 to 56-12 were exactly like compositions 50-01 to 50-12 respectively except that a different active ingredient was used and a range of active ingredient concentrations was selected appropriate to the active ingredient being applied.

Velvetleaf (*Abutilon theophrasti*, ABUTH), Japanese millet (*Echinochloa crus-galli,* ECHCF) and prickly sida (*Sida spinosa*, SIDSP) plants were grown and treated by the standard procedures given above. Applications of spray compositions were made 14 days after planting ABUTH, 14 days after planting ECHCF and 21 days after planting SIDSP. Evaluation of herbicidal inhibition was done 14 days after application.

Standards included technical imazethapyr and Pursuit, a commercial formulation of imazethapyr from American Cyanamid. Results, averaged for all replicates of each treatment, are shown in Table 56.

TABLE 56

| | Imazethapyr rate | % Inhibition | | |
|---|---|---|---|---|
| Spray composition | g a.i./ha | ABUTH | ECHCF | SIDSP |
| Imazethapyr | 5 | 78 | 5 | 20 |
| (technical) | 10 | 83 | 20 | 30 |
| | 25 | 93 | 35 | 40 |
| | 50 | 94 | 53 | 50 |
| Pursuit | 5 | 70 | 5 | 25 |
| (commercial) | 10 | 73 | 33 | 30 |
| | 25 | 90 | 50 | 42 |
| | 50 | 93 | 62 | 57 |
| 56-01 | 5 | 70 | 45 | 35 |
| | 10 | 75 | 62 | 52 |
| | 25 | 92 | 63 | 57 |
| | 50 | 93 | 72 | 62 |
| 56-02 | 5 | 73 | 57 | 32 |
| | 10 | 75 | 67 | 43 |
| | 25 | 90 | 70 | 52 |
| | 50 | 92 | 72 | 57 |

TABLE 56-continued

| Spray composition | Imazethapyr rate g a.i./ha | % Inhibition ABUTH | ECHCF | SIDSP |
|---|---|---|---|---|
| 56-03 | 5 | 70 | 42 | 27 |
|  | 10 | 78 | 42 | 35 |
|  | 25 | 90 | 53 | 45 |
|  | 50 | 92 | 62 | 52 |
| 56-04 | 5 | 73 | 55 | 33 |
|  | 10 | 77 | 68 | 45 |
|  | 25 | 93 | 68 | 47 |
|  | 50 | 94 | 68 | 60 |
| 56-05 | 5 | 73 | 47 | 32 |
|  | 10 | 73 | 45 | 40 |
|  | 25 | 90 | 62 | 47 |
|  | 50 | 91 | 68 | 52 |
| 56-06 | 5 | 78 | 72 | 30 |
|  | 10 | 83 | 70 | 35 |
|  | 25 | 93 | 77 | 62 |
|  | 50 | 94 | 78 | 58 |
| 56-07 | 5 | 82 | 75 | 38 |
|  | 10 | 90 | 90 | 52 |
|  | 25 | 93 | 93 | 53 |
|  | 50 | 97 | 97 | 62 |
| 56-08 | 5 | 75 | 77 | 38 |
|  | 10 | 90 | 92 | 50 |
|  | 25 | 95 | 93 | 57 |
|  | 50 | 97 | 99 | 63 |
| 56-09 | 5 | 78 | 80 | 40 |
|  | 10 | 83 | 89 | 63 |
|  | 25 | 93 | 93 | 62 |
|  | 50 | 96 | 93 | 60 |
| 56-10 | 5 | 85 | 50 | 37 |
|  | 10 | 77 | 50 | 45 |
|  | 25 | 91 | 63 | 48 |
|  | 50 | 93 | 75 | 57 |
| 56-11 | 5 | 75 | 38 | 43 |
|  | 10 | 80 | 38 | 37 |
|  | 25 | 92 | 62 | 45 |
|  | 50 | 93 | 73 | 53 |
| 56-12 | 5 | 75 | 55 | 38 |
|  | 10 | 83 | 60 | 43 |
|  | 25 | 92 | 67 | 53 |
|  | 50 | 93 | 77 | 55 |

Results of this test using imazethapyr as the exogenous chemical are summarized as follows:

Butyl stearate alone at 0.05% (56-05) significantly enhanced effectiveness on ECHCF and slightly on SIDSP.

The combination of lecithin and butyl stearate (56-02) gave enhancement of effectiveness on ECHCF greater than that obtained with either of these two excipient substances alone.

Oleth-20 at the low concentration of 0.05% (56-09) gave extremely high effectiveness, greatly superior to that obtained with the commercial standard, especially on ECHCF. Addition of 0.005% butyl stearate (56-07) further enhanced performance of low exogenous chemical rates on ABUTH more effectively than addition of 0.01% methyl oleate (56-08).

Example 57

Spray compositions were prepared containing fluazifop-p-butyl and excipient ingredients. Compositions 57-01 to 57-12 were exactly like compositions 50-01 to 50-12 respectively except that a different active ingredient was used and a range of active ingredient concentrations was selected appropriate to the active ingredient being applied.

Velvetleaf (*Abutilon theophrasti*, ABUTH), Japanese millet (*Echinochloa crus-galli*, ECHCF) and broadleaf signalgrass (*Brachiaria platyphylla*, BRAPP) plants were grown and treated by the standard procedures given above. Applications of spray compositions were made 15 days after planting ABUTH, 15 days after planting ECHCF and 16 days after planting BRAPP. Evaluation of herbicidal inhibition was done 10 days after application.

Standards included technical fluazifop-p-butyl and Fusilade 5, a commercial formulation of fluazifop-p-butyl from Zeneca. Results, averaged for all replicates of each treatment, are shown in Table 57.

TABLE 57

| Spray composition | Fluazifop-p rate g a.i./ha | % Inhibition ABUTH | ECHCF | BRAPP |
|---|---|---|---|---|
| Fluazifop-p-butyl (technical) | 2 | 0 | 0 | 20 |
|  | 5 | 0 | 3 | 35 |
|  | 15 | 5 | 45 | 65 |
|  | 30 | 5 | 57 | 78 |
| Fusilade 5 (commercial) | 2 | 0 | 0 | 27 |
|  | 5 | 0 | 27 | 33 |
|  | 15 | 5 | 52 | 78 |
|  | 30 | 7 | 75 | 85 |
| 57-01 | 2 | 0 | 0 | 20 |
|  | 5 | 2 | 27 | 30 |
|  | 15 | 5 | 58 | 78 |
|  | 30 | 10 | 87 | 83 |
| 57-02 | 2 | 0 | 7 | 25 |
|  | 5 | 0 | 35 | 30 |
|  | 15 | 2 | 58 | 75 |
|  | 30 | 8 | 78 | 75 |
| 57-03 | 2 | 0 | 0 | 18 |
|  | 5 | 0 | 8 | 27 |
|  | 15 | 0 | 45 | 75 |
|  | 30 | 0 | 55 | 75 |
| 57-04 | 2 | 0 | 20 | 32 |
|  | 5 | 2 | 42 | 25 |
|  | 15 | 2 | 55 | 72 |
|  | 30 | 5 | 80 | 78 |
| 57-05 | 2 | 0 | 13 | 32 |
|  | 5 | 2 | 42 | 32 |
|  | 15 | 2 | 55 | 72 |
|  | 30 | 7 | 58 | 73 |
| 57-06 | 2 | 2 | 17 | 23 |
|  | 5 | 0 | 20 | 25 |
|  | 15 | 0 | 50 | 75 |
|  | 30 | 0 | 73 | 77 |
| 57-07 | 2 | 0 | 50 | 40 |
|  | 5 | 0 | 52 | 60 |
|  | 15 | 0 | 67 | 80 |
|  | 30 | 0 | 92 | 85 |
| 57-08 | 2 | 0 | 43 | 35 |
|  | 5 | 0 | 55 | 37 |
|  | 15 | 7 | 88 | 82 |
|  | 30 | 3 | 96 | 85 |
| 57-09 | 2 | 0 | 47 | 18 |
|  | 5 | 0 | 50 | 35 |
|  | 15 | 0 | 80 | 80 |
|  | 30 | 3 | 93 | 85 |
| 57-10 | 2 | 0 | 23 | 10 |
|  | 5 | 0 | 37 | 42 |
|  | 15 | 5 | 55 | 75 |
|  | 30 | 10 | 58 | 80 |
| 57-11 | 2 | 0 | 7 | 10 |
|  | 5 | 0 | 30 | 28 |
|  | 15 | 0 | 50 | 62 |
|  | 30 | 12 | 53 | 68 |
| 57-12 | 2 | 0 | 5 | 20 |
|  | 5 | 0 | 7 | 35 |
|  | 15 | 5 | 48 | 68 |
|  | 30 | 12 | 60 | 77 |

Results of this test using fluazifop-p-butyl as the exogenous chemical are summarized as follows:

Butyl stearate alone at 0.05% (57-05) and in combination with lecithin (57-02) enhanced effectiveness, especially on ECHCF.

Oleth-20 at the low concentration of 0.05% (57-09) gave extremely high effectiveness on ECHCF, superior to that obtained with the commercial standard. Addition of 0.005% butyl stearate (57-07) or 0.01% methyl oleate (57-08) did not provide significant further enhancement.

Example 58

Spray compositions were prepared containing alachlor and excipient ingredients. Compositions 58-01 to 58-12 were exactly like compositions 50-01 to 50-12 respectively except that a different active ingredient was used and a range of active ingredient concentrations was selected appropriate to the active ingredient being applied.

Velvetleaf (*Abutilon theophrasti*, ABUTH), Japanese millet (*Echinochloa crus-galli*, ECHCF) and prickly sida (*Sida spinosa*, SIDSP) plants were grown and treated by the standard procedures given above. Applications of spray compositions were made 14 days after planting ABUTH, 8 days after planting ECHCF and 14 days after planting SIDSP. Evaluation of herbicidal inhibition was done 9 days after application.

Standards included technical alachlor and Lasso, a commercial formulation of alachlor from Monsanto Company. Results, averaged for all replicates of each treatment, are shown in Table 58.

TABLE 58

| Spray composition | Alachlor rate g a.i./ha | % Inhibition ABUTH | ECHCF | SIDSP |
|---|---|---|---|---|
| Alachlor | 500 | 0 | 0 | 0 |
| (technical) | 1000 | 0 | 0 | 0 |
|  | 2000 | 0 | 0 | 0 |
|  | 4000 | 0 | 0 | 0 |
| Lasso | 500 | 0 | 0 | 0 |
| (commercial) | 1000 | 0 | 5 | 13 |
|  | 2000 | 0 | 30 | 17 |
|  | 4000 | 15 | 43 | 65 |
| 58-01 | 500 | 0 | 0 | 0 |
|  | 1000 | 0 | 0 | 0 |
|  | 2000 | 0 | 0 | 0 |
|  | 4000 | 10 | 0 | 7 |
| 58-02 | 500 | 0 | 0 | 0 |
|  | 1000 | 0 | 0 | 0 |
|  | 2000 | 0 | 22 | 7 |
|  | 4000 | 12 | 47 | 12 |
| 58-03 | 500 | 0 | 0 | 0 |
|  | 1000 | 0 | 0 | 0 |
|  | 2000 | 0 | 0 | 0 |
|  | 4000 | 10 | 0 | 0 |
| 58-04 | 500 | 0 | 0 | 0 |
|  | 1000 | 0 | 0 | 0 |
|  | 2000 | 0 | 0 | 0 |
|  | 4000 | 5 | 0 | 15 |
| 58-05 | 500 | 0 | 0 | 0 |
|  | 1000 | 0 | 0 | 0 |
|  | 2000 | 0 | 0 | 0 |
|  | 4000 | 3 | 0 | 5 |
| 58-06 | 500 | 0 | 0 | 0 |
|  | 1000 | 0 | 0 | 0 |
|  | 2000 | 0 | 13 | 7 |
|  | 4000 | 0 | 37 | 12 |
| 58-07 | 500 | 0 | 0 | 0 |
|  | 1000 | 0 | 8 | 0 |
|  | 2000 | 0 | 28 | 15 |
|  | 4000 | 12 | 50 | 20 |
| 58-08 | 500 | 0 | 0 | 0 |
|  | 1000 | 0 | 8 | 0 |
|  | 2000 | 0 | 8 | 0 |
|  | 4000 | 5 | 20 | 5 |
| 58-09 | 500 | 0 | 0 | 0 |
|  | 1000 | 0 | 0 | 0 |
|  | 2000 | 0 | 3 | 0 |
|  | 4000 | 12 | 42 | 32 |
| 58-10 | 500 | 0 | 0 | 0 |

TABLE 58-continued

| Spray composition | Alachlor rate g a.i./ha | % Inhibition ABUTH | ECHCF | SIDSP |
|---|---|---|---|---|
|  | 1000 | 0 | 0 | 0 |
|  | 2000 | 0 | 0 | 0 |
|  | 4000 | 0 | 0 | 0 |
| 58-11 | 500 | 0 | 0 | 0 |
|  | 1000 | 0 | 0 | 0 |
|  | 2000 | 0 | 0 | 0 |
|  | 4000 | 0 | 0 | 0 |
| 58-12 | 500 | 0 | 0 | 0 |
|  | 1000 | 0 | 0 | 0 |
|  | 2000 | 0 | 0 | 0 |
|  | 4000 | 0 | 0 | 0 |

None of the compositions tested enhanced post-emergence foliar-applied herbicidal effectiveness of alachlor in this test. Alachlor is not known as a foliar-applied herbicide.

Example 59

Spray compositions were prepared containing glufosinate ammonium salt and excipient ingredients. Compositions 59-01 to 59-12 were exactly like compositions 50-01 to 50-12 respectively except that a different active ingredient was used and a range of active ingredient concentrations was selected appropriate to the active ingredient being applied.

Velvetleaf (*Abutilon theophrasti*, ABUTH), Japanese millet (*Echinochloa crus-galli*, ECHCF) and prickly sida (*Sida spinosa*, SIDSP) plants were grown and treated by the standard procedures given above. Applications of spray compositions were made 14 days after planting ABUTH, 10 days after planting ECHCF and 17 days after planting SIDSP. Evaluation of herbicidal inhibition was done 11 days after application.

Standards included technical glufosinate ammonium and Liberty, a commercial formulation of glufosinate from AgrEvo. Results, averaged for all replicates of each treatment, are shown in Table 59.

TABLE 59

| Spray composition | Glufosinate rate g a.i./ha | % Inhibition ABUTH | ECHCF | SIDSP |
|---|---|---|---|---|
| Glufosinate | 50 | 0 | 0 | 5 |
| (technical) | 100 | 47 | 0 | 10 |
|  | 300 | 90 | 23 | 96 |
|  | 600 | 98 | 43 | 94 |
| Liberty | 50 | 77 | 70 | 20 |
| (commercial) | 100 | 88 | 96 | 93 |
|  | 300 | 98 | 100 | 97 |
|  | 600 | 99 | 100 | 99 |
| 59-01 | 50 | 77 | 33 | 70 |
|  | 100 | 95 | 58 | 93 |
|  | 300 | 98 | 95 | 97 |
|  | 600 | 99 | 99 | 98 |
| 59-02 | 50 | 33 | 30 | 50 |
|  | 100 | 63 | 32 | 93 |
|  | 300 | 96 | 52 | 90 |
|  | 600 | 98 | 96 | 97 |
| 59-03 | 50 | 15 | 30 | 38 |
|  | 100 | 50 | 33 | 87 |
|  | 300 | 92 | 40 | 94 |
|  | 600 | 98 | 70 | 98 |
| 59-04 | 50 | 92 | 47 | 50 |
|  | 100 | 90 | 53 | 85 |
|  | 300 | 98 | 98 | 96 |

TABLE 59-continued

| Spray composition | Glufosinate rate g a.i./ha | % Inhibition ABUTH | ECHCF | SIDSP |
|---|---|---|---|---|
| | 600 | 98 | 99 | 98 |
| 59-05 | 50 | 35 | 20 | 20 |
| | 100 | 37 | 30 | 20 |
| | 300 | 97 | 45 | 78 |
| | 600 | 91 | 53 | 92 |
| 59-06 | 50 | 10 | 0 | 20 |
| | 100 | 20 | 3 | 20 |
| | 300 | 89 | 47 | 82 |
| | 600 | 91 | 94 | 89 |
| 59-07 | 50 | 50 | 35 | 70 |
| | 100 | 73 | 52 | 80 |
| | 300 | 95 | 87 | 98 |
| | 600 | 98 | 98 | 97 |
| 59-08 | 50 | 48 | 30 | 88 |
| | 100 | 83 | 50 | 93 |
| | 300 | 98 | 97 | 96 |
| | 600 | 98 | 99 | 96 |
| 59-09 | 50 | 58 | 35 | 92 |
| | 100 | 91 | 62 | 93 |
| | 300 | 98 | 96 | 97 |
| | 600 | 98 | 99 | 96 |
| 59-10 | 50 | 30 | 30 | 0 |
| | 100 | 43 | 35 | 10 |
| | 300 | 96 | 43 | 92 |
| | 600 | 95 | 70 | 91 |
| 59-11 | 50 | 33 | 35 | 0 |
| | 100 | 53 | 35 | 7 |
| | 300 | 96 | 43 | 89 |
| | 600 | 97 | 88 | 93 |
| 59-12 | 50 | 37 | 5 | 5 |
| | 100 | 37 | 20 | 10 |
| | 300 | 95 | 40 | 88 |
| | 600 | 97 | 85 | 93 |

Results of this test using glufosinate as the exogenous chemical are summarized as follows:

Butyl stearate alone at 0.05% (59-05) enhanced effectiveness on ECHCF.

The combination of lecithin and butyl stearate (59-02) gave greater enhancement of effectiveness than either of these two excipient substances alone.

Oleth-20 at the low concentration of 0.05% (59-09) gave extremely high effectiveness, superior on SIDSP to that obtained with the commercial standard. Addition of 0.005% butyl stearate (59-07) or 0.01% methyl oleate (59-08) did not provide further enhancement.

Example 60

Aqueous concentrate compositions were prepared containing glyphosate IPA salt and excipient ingredients as shown in Table 60a. Concentrate compositions 60-01 to 60-12 and 60-14 to 60-16 are oil-in-water emulsions and were prepared by process (vii). Concentrate composition 60-13 is an aqueous solution concentrate and was prepared by process (viii).

TABLE 60a

| Concentrate composition | Glyphosate g a.e./l | % w/w Oil | % w/w Surfactant | Type of oil | Type of surfactant |
|---|---|---|---|---|---|
| 60-01 | 163 | 0.5 | 5.0 | butyl stearate | steareth-30 |
| 60-02 | 163 | 0.5 | 5.0 | methyl stearate | steareth-30 |
| 60-03 | 163 | 0.5 | 5.0 | butyl stearate | Neodol 44-13 |
| 60-04 | 163 | 0.5 | 5.0 | methyl stearate | Neodol 44-13 |
| 60-05 | 163 | 0.5 | 5.0 | butyl stearate | ceteareth-15 |
| 60-06 | 163 | 0.5 | 5.0 | methyl stearate | ceteareth-15 |
| 60-07 | 163 | 0.5 | 5.0 | butyl stearate | laureth-23 |
| 60-08 | 163 | 0.5 | 5.0 | butyl stearate | oleth-20 |
| 60-09 | 163 | 0.5 | 5.0 | butyl stearate | steareth-20 |
| 60-10 | 163 | 0.5 | 5.0 | butyl stearate | ceteareth-27 |
| 60-11 | 163 | 0.3 | 5.0 | butyl stearate | ceteareth-27 |
| 60-12 | 163 | 0.3 | 2.5 | butyl stearate | ceteareth-27 |
| 60-13 | 163 | | 5.0 | none | ceteareth-27 |
| 60-14 | 163 | 0.5 | 5.0 | methyl stearate | ceteareth-27 |
| 60-15 | 163 | 0.5 | 5.0 | methyl stearate | steareth-20 |
| 60-16 | 163 | 0.5 | 5.0 | methyl stearate | oleth-20 |

Velvetleaf (*Abutilon theophrasti*, ABUTH) and Japanese millet (*Echinochloa crus-galli*, ECHCF) plants were grown and treated by the standard procedures given above. Applications of spray compositions were made 20 days after planting ABUTH and ECHCF, and evaluation of herbicidal inhibition was done 16 days after application.

Formulations B, C and J were applied as comparative treatments. Results, averaged for all replicates of each treatment, are shown in Table 60b.

TABLE 60b

| Concentrate composition | Glyphosate rate g a.e./ha | % Inhibition ABUTH | ECHCF |
|---|---|---|---|
| Formulation B | 100 | 45 | 57 |
| | 200 | 35 | 53 |
| | 300 | 50 | 57 |
| | 400 | 38 | 33 |
| Formulation C | 100 | 70 | 98 |
| | 200 | 90 | 99 |
| | 300 | 97 | 100 |
| | 400 | 100 | 100 |
| Formulation J | 100 | 72 | 88 |
| | 200 | 93 | 99 |
| | 300 | 97 | 99 |
| | 400 | 98 | 99 |
| 60-01 | 100 | 83 | 97 |
| | 200 | 97 | 100 |
| | 300 | 99 | 100 |
| | 400 | 100 | 100 |
| 60-02 | 100 | 80 | 99 |
| | 200 | 96 | 100 |
| | 300 | 99 | 100 |
| | 400 | 99 | 100 |
| 60-03 | 100 | 73 | 98 |
| | 200 | 92 | 100 |
| | 300 | 98 | 99 |
| | 400 | 99 | 100 |
| 60-04 | 100 | 73 | 98 |
| | 200 | 87 | 99 |
| | 300 | 97 | 99 |
| | 400 | 99 | 100 |
| 60-05 | 100 | 80 | 98 |
| | 200 | 87 | 100 |
| | 300 | 98 | 100 |
| | 400 | 100 | 100 |
| 60-06 | 100 | 78 | 97 |
| | 200 | 95 | 98 |
| | 300 | 98 | 100 |
| | 400 | 99 | 100 |
| 60-07 | 100 | 78 | 98 |
| | 200 | 88 | 100 |

TABLE 60b-continued

| Concentrate composition | Glyphosate rate g a.e./ha | % Inhibition ABUTH | ECHCF |
|---|---|---|---|
|  | 300 | 96 | 100 |
|  | 400 | 98 | 100 |
| 60-08 | 100 | 75 | 98 |
|  | 200 | 93 | 99 |
|  | 300 | 97 | 99 |
|  | 400 | 100 | 99 |
| 60-09 | 100 | 83 | 93 |
|  | 200 | 95 | 100 |
|  | 300 | 98 | 100 |
|  | 400 | 100 | 100 |
| 60-10 | 100 | 80 | 97 |
|  | 200 | 95 | 98 |
|  | 300 | 98 | 99 |
|  | 400 | 100 | 100 |
| 60-11 | 100 | 80 | 97 |
|  | 200 | 93 | 99 |
|  | 300 | 98 | 100 |
|  | 400 | 100 | 99 |
| 60-12 | 100 | 77 | 93 |
|  | 200 | 88 | 100 |
|  | 300 | 99 | 100 |
|  | 400 | 99 | 100 |
| 60-13 | 100 | 80 | 73 |
|  | 200 | 95 | 95 |
|  | 300 | 99 | 100 |
|  | 400 | 100 | 100 |
| 60-14 | 100 | 77 | 94 |
|  | 200 | 92 | 99 |
|  | 300 | 98 | 100 |
|  | 400 | 100 | 99 |
| 60-15 | 100 | 78 | 92 |
|  | 200 | 94 | 99 |
|  | 300 | 98 | 100 |
|  | 400 | 99 | 100 |
| 60-16 | 100 | 77 | 93 |
|  | 200 | 90 | 98 |
|  | 300 | 98 | 99 |
|  | 400 | 99 | 100 |

Extremely high herbicidal effectiveness was provided by ceteareth-27 (composition 60-13); this was further enhanced by addition of a small amount of butyl stearate (60-10, 60-11) or methyl stearate (60-14). Compositions performing better than commercial standard Formulations C and J, at least on ABUTH, included those containing steareth-30, steareth-20 or ceteareth-27; in this test oleth-20 was not quite as effective as these saturated alkylethers.

Example 61

Aqueous concentrate compositions were prepared containing glyphosate IPA salt and excipient ingredients as shown in Table 61a. Concentrate composition 61-17 is an oil-in-water emulsion and was prepared by process (vii). Concentrate compositions 61-01 to 61-16 and 61-18 were prepared by process (x) using soybean lecithin (45% phospholipid, Avanti).

TABLE 61a

| Concentrate composition | Glyphosate g a.e./l | % w/w | | | | |
|---|---|---|---|---|---|---|
|  |  | Lecithin | Butyl stearate | Ethomeen T/25 | Ceteareth-20 | Ceteareth-27 |
| 61-01 | 220 | 0.75 | 0.75 | 1.5 |  |  |
| 61-02 | 220 | 0.75 | 0.75 | 1.5 |  |  |
| 61-03 | 220 | 0.75 | 0.75 | 3.0 |  |  |
| 61-04 | 220 | 0.75 | 7.50 | 1.5 |  |  |
| 61-05 | 220 | 0.75 | 7.50 | 3.0 |  |  |
| 61-06 | 220 | 3.75 | 3.75 | 3.0 |  |  |
| 61-07 | 220 | 1.50 | 1.50 | 3.0 |  |  |
| 61-08 | 220 | 1.50 | 1.50 | 1.5 |  |  |
| 61-09 | 220 | 3.75 | 3.75 | 1.5 | 1.5 |  |
| 61-10 | 220 | 1.50 | 1.50 | 1.5 | 1.5 |  |
| 61-11 | 220 | 3.75 | 7.50 | 1.5 | 1.5 |  |
| 61-12 | 220 | 3.75 | 1.50 | 1.5 | 1.5 |  |
| 61-13 | 220 | 0.75 | 3.75 | 1.5 |  | 1.5 |
| 61-14 | 220 | 0.75 | 7.50 | 1.5 |  | 1.5 |
| 61-15 | 220 | 0.75 | 3.75 | 3.0 |  | 3.0 |
| 61-16 | 220 | 0.75 | 7.50 | 3.0 |  | 3.0 |
| 61-17 | 220 |  | 7.50 | 3.0 |  |  |
| 61-18 | 220 | 0.75 | 7.50 |  |  | 3.0 |

Velvetleaf (*Abutilon theophrasti*, ABUTH) and Japanese millet (*Echinochloa crus-galli*, ECHCF) plants were grown and treated by the standard procedures given above. Applications of spray compositions were made 23 days after planting ABUTH and ECHCF, and evaluation of herbicidal inhibition was done 18 days after application.

Formulations B and J were applied as comparative treatments. Results, averaged for all replicates of each treatment, are shown in Table 61b.

TABLE 61b

| Concentrate composition | Glyphosate rate g a.e./ha | % Inhibition ABUTH | ECHCF |
|---|---|---|---|
| Formulation B | 100 | 12 | 62 |
|  | 200 | 5 | 55 |
|  | 300 | 23 | 63 |
|  | 400 | 43 | 78 |
| Formulation J | 100 | 27 | 82 |
|  | 200 | 62 | 98 |
|  | 300 | 88 | 95 |
|  | 400 | 96 | 99 |
| 61-01 | 100 | 13 | 79 |
|  | 200 | 68 | 95 |
|  | 300 | 82 | 99 |
|  | 400 | 95 | 91 |
| 61-02 | 100 | 27 | 82 |
|  | 200 | 60 | 97 |
|  | 300 | 81 | 95 |
|  | 400 | 87 | 99 |
| 61-03 | 100 | 37 | 77 |
|  | 200 | 62 | 96 |
|  | 300 | 78 | 98 |
|  | 400 | 89 | 90 |
| 61-04 | 100 | 37 | 84 |
|  | 200 | 57 | 95 |
|  | 300 | 84 | 99 |
|  | 400 | 89 | 100 |
| 61-05 | 100 | 33 | 77 |
|  | 200 | 65 | 100 |
|  | 300 | 78 | 97 |
|  | 400 | 88 | 97 |
| 61-06 | 100 | 43 | 78 |
|  | 200 | 62 | 95 |
|  | 300 | 87 | 97 |
|  | 400 | 95 | 96 |
| 61-07 | 100 | 48 | 78 |
|  | 200 | 80 | 91 |
|  | 300 | 90 | 99 |
|  | 400 | 76 | 93 |
| 61-08 | 100 | 48 | 83 |
|  | 200 | 67 | 89 |
|  | 300 | 86 | 96 |

TABLE 61b-continued

| Concentrate composition | Glyphosate rate g a.e./ha | % Inhibition ABUTH | % Inhibition ECHCF |
|---|---|---|---|
|  | 400 | 93 | 97 |
| 61-09 | 100 | 62 | 84 |
|  | 200 | 82 | 98 |
|  | 300 | 85 | 99 |
|  | 400 | 91 | 97 |
| 61-10 | 100 | 63 | 80 |
|  | 200 | 75 | 96 |
|  | 300 | 85 | 99 |
|  | 400 | 99 | 99 |
| 61-11 | 100 | 42 | 75 |
|  | 200 | 78 | 98 |
|  | 300 | 92 | 99 |
|  | 400 | 93 | 100 |
| 61-12 | 100 | 52 | 80 |
|  | 200 | 73 | 93 |
|  | 300 | 86 | 99 |
|  | 400 | 97 | 97 |
| 61-13 | 100 | 55 | 83 |
|  | 200 | 75 | 97 |
|  | 300 | 97 | 99 |
|  | 400 | 92 | 99 |
| 61-14 | 100 | 52 | 87 |
|  | 200 | 73 | 95 |
|  | 300 | 91 | 97 |
|  | 400 | 87 | 98 |
| 61-15 | 100 | 57 | 83 |
|  | 200 | 92 | 96 |
|  | 300 | 98 | 100 |
|  | 400 | 100 | 98 |
| 61-16 | 100 | 79 | 88 |
|  | 200 | 87 | 97 |
|  | 300 | 99 | 99 |
|  | 400 | 97 | 94 |
| 61-17 | 100 | 58 | 83 |
|  | 200 | 47 | 94 |
|  | 300 | 88 | 98 |
|  | 400 | 91 | 93 |
| 61-18 | 100 | 58 | 87 |
|  | 200 | 75 | 91 |
|  | 300 | 83 | 99 |
|  | 400 | 91 | 98 |

Outstanding herbicidal effectiveness was provided by composition 61-18, containing lecithin, ceteareth-27 and butyl stearate. Addition of 3% Ethomeen T/25 (61-16) further enhanced effectiveness. Slightly reduced effectiveness at the lowest glyphosate rate was observed on ABUTH when the butyl stearate concentration was cut in half (61-15).

Example 62

Aqueous concentrate compositions were prepared containing glyphosate IPA salt and excipient ingredients as shown in Table 62a. Concentrate compositions 62-01 to 62-04, 62-06, 62-08, 62-10 and 62-18 are oil-in-water emulsions and were prepared by process (vii). Concentrate compositions 62-05, 62-07 and 62-09 are aqueous solution concentrates and were prepared by process (viii). Concentrate compositions 62-11 to 62-17 contain colloidal particulates and were prepared by process (ix).

The compositions of this example all showed acceptable storage stability. The compositions shown as containing colloidal particulate were not storage-stable unless the colloidal particulate was included as shown.

TABLE 62a

| Concentrate composition | Glyphosate g a.e./l | Butyl stearate % w/w | Surfactant % w/w | Aerosil 380 % w/w | Type of surfactant |
|---|---|---|---|---|---|
| 62-01 | 163 | 0.5 | 5.0 |  | steareth-20 |
| 62-02 | 163 | 0.5 | 5.0 |  | ceteareth-27 |
| 62-03 | 163 | 0.5 | 5.0 |  | oleth-20 |
| 62-04 | 163 | 0.5 | 5.0 |  | ceteth-20 |
| 62-05 | 163 |  | 5.0 |  | ceteth-20 |
| 62-06 | 163 | 0.5 | 5.0 |  | Neodol 44-13 |
| 62-07 | 163 |  | 5.0 |  | Neodol 44-13 |
| 62-08 | 163 | 0.5 | 5.0 |  | ceteareth-15 |
| 62-09 | 163 |  | 5.0 |  | ceteareth-15 |
| 62-10 | 163 | 0.5 | 5.0 |  | steareth-30 |
| 62-11 | 360 | 1.0 | 10.0 | 1.25 | ceteth-20 |
| 62-12 | 360 | 1.0 | 10.0 | 1.25 | Neodol 44-13 |
| 62-13 | 360 | 1.0 | 10.0 | 1.25 | ceteareth-15 |
| 62-14 | 360 | 1.0 | 10.0 | 1.25 | steareth-30 |
| 62-15 | 360 | 1.0 | 10.0 | 1.25 | steareth-20 |
| 62-16 | 360 | 1.0 | 10.0 | 1.25 | oleth-20 |
| 62-17 | 360 | 1.0 | 10.0 | 1.25 | ceteareth-27 |
| 62-18 | 163 | 0.5 | 5.0 |  | laureth-23 |

Velvetleaf (*Abutilon theophrasti*, ABUTH) and Japanese millet (*Echinochloa crus-galli*, ECHCF) plants were grown and treated by the standard procedures given above. Applications of spray compositions were made 22 days after planting ABUTH and ECHCF, and evaluation of herbicidal inhibition was done 18 days after application.

Formulations B and J were applied as comparative treatments. Results, averaged for all replicates of each treatment, are shown in Table 62b.

TABLE 62b

| Concentrate composition | Glyphosate rate g a.e./ha | % Inhibition ABUTH | % Inhibition ECHCF |
|---|---|---|---|
| Formulation B | 100 | 0 | 30 |
|  | 200 | 2 | 60 |
|  | 300 | 17 | 75 |
|  | 400 | 50 | 73 |
| Formulation J | 100 | 20 | 63 |
|  | 200 | 42 | 98 |
|  | 300 | 75 | 100 |
|  | 400 | 83 | 98 |
| 62-01 | 100 | 27 | 57 |
|  | 200 | 67 | 98 |
|  | 300 | 80 | 99 |
|  | 400 | 87 | 98 |
| 62-02 | 100 | 27 | 63 |
|  | 200 | 53 | 87 |
|  | 300 | 77 | 99 |
|  | 400 | 87 | 99 |
| 62-03 | 100 | 12 | 50 |
|  | 200 | 53 | 99 |
|  | 300 | 65 | 100 |
|  | 400 | 83 | 99 |
| 62-04 | 100 | 20 | 63 |
|  | 200 | 50 | 98 |
|  | 300 | 73 | 98 |
|  | 400 | 87 | 98 |
| 62-05 | 100 | 18 | 70 |
|  | 200 | 57 | 93 |
|  | 300 | 80 | 99 |
|  | 400 | 83 | 99 |
| 62-06 | 100 | 17 | 63 |
|  | 200 | 35 | 95 |
|  | 300 | 60 | 100 |
|  | 400 | 75 | 100 |
| 62-07 | 100 | 3 | 43 |
|  | 200 | 43 | 95 |
|  | 300 | 62 | 100 |

TABLE 62b-continued

| Concentrate composition | Glyphosate rate g a.e./ha | % Inhibition ABUTH | ECHCF |
|---|---|---|---|
| | 400 | 68 | 96 |
| 62-08 | 100 | 20 | 43 |
| | 200 | 43 | 88 |
| | 300 | 75 | 99 |
| | 400 | 80 | 97 |
| 62-09 | 100 | 37 | 57 |
| | 200 | 55 | 93 |
| | 300 | 83 | 100 |
| | 400 | 83 | 99 |
| 62-10 | 100 | 37 | 50 |
| | 200 | 60 | 96 |
| | 300 | 83 | 99 |
| | 400 | 88 | 99 |
| 62-11 | 100 | 8 | 37 |
| | 200 | 37 | 93 |
| | 300 | 68 | 99 |
| | 400 | 70 | 97 |
| 62-12 | 100 | 13 | 43 |
| | 200 | 40 | 91 |
| | 300 | 67 | 100 |
| | 400 | 77 | 96 |
| 62-13 | 100 | 25 | 40 |
| | 200 | 40 | 80 |
| | 300 | 62 | 97 |
| | 400 | 78 | 98 |
| 62-14 | 100 | 23 | 33 |
| | 200 | 37 | 86 |
| | 300 | 75 | 99 |
| | 400 | 78 | 94 |
| 62-15 | 100 | 23 | 30 |
| | 200 | 43 | 78 |
| | 300 | 53 | 93 |
| | 400 | 78 | 98 |
| 62-16 | 100 | 23 | 37 |
| | 200 | 37 | 95 |
| | 300 | 63 | 97 |
| | 400 | 78 | 95 |
| 62-17 | 100 | 18 | 50 |
| | 200 | 45 | 88 |
| | 300 | 75 | 69 |
| | 400 | 73 | 93 |
| 62-18 | 100 | missing | missing |
| | 200 | missing | missing |
| | 300 | missing | missing |
| | 400 | missing | missing |

Compositions exhibiting herbicidal effectiveness greater than that provided by commercial standard Formulation J included 62-01 (steareth-20 plus butyl stearate), 62-09 (ceteareth-15) and 62-10 (steareth-20 plus butyl stearate).

Example 63

Aqueous concentrate compositions were prepared containing glyphosate IPA salt and excipient ingredients as shown in Table 63a. All are oil-in-water emulsions and were prepared by process (vii).

TABLE 63a

| Concentrate composition | Glyphosate g a.e./l | % w/w Butyl stearate | Surfactant | Type of surfactant |
|---|---|---|---|---|
| 63-01 | 163 | 1.00 | 10.0 | laureth-23 |
| 63-02 | 163 | 0.50 | 5.0 | laureth-23 |
| 63-03 | 163 | 0.25 | 2.5 | laureth-23 |
| 63-04 | 163 | 1.00 | 10.0 | Neodol 1-9 |
| 63-05 | 163 | 0.50 | 5.0 | Neodol 1-9 |

TABLE 63a-continued

| Concentrate composition | Glyphosate g a.e./l | % w/w Butyl stearate | Surfactant | Type of surfactant |
|---|---|---|---|---|
| 63-06 | 163 | 0.25 | 2.5 | Neodol 1-9 |
| 63-07 | 163 | 1.00 | 10.0 | steareth-10 |
| 63-08 | 163 | 0.50 | 5.0 | steareth-10 |
| 63-09 | 163 | 0.25 | 2.5 | steareth-10 |
| 63-10 | 163 | 0.50 | 5.0 | steareth-20 |
| 63-11 | 163 | 0.25 | 2.5 | steareth-20 |
| 63-12 | 163 | 0.25 | 1.0 | steareth-20 |
| 63-13 | 163 | 0.50 | 5.0 | oleth-20 |
| 63-14 | 163 | 0.25 | 2.5 | oleth-20 |
| 63-15 | 163 | 0.25 | 1.0 | oleth-20 |
| 63-16 | 163 | 0.50 | 5.0 | ceteareth-27 |
| 63-17 | 163 | 0.25 | 2.5 | ceteareth-27 |
| 63-18 | 163 | 0.25 | 1.0 | ceteareth-27 |

Velvetleaf (*Abutilon theophrasti*, ABUTH) and Japanese millet (*Echinochloa crus-galli*, ECHCF) plants were grown and treated by the standard procedures given above. Applications of spray compositions were made 21 days after planting ABUTH and ECHCF, and evaluation of herbicidal inhibition was done 20 days after application.

Formulations B and J were applied as comparative treatments. Results, averaged for all replicates of each treatment, are shown in Table 63b.

TABLE 63b

| Concentrate composition | Glyphosate rate g a.e./ha | % Inhibition ABUTH | ECHCF |
|---|---|---|---|
| Formulation B | 100 | 0 | 42 |
| | 200 | 0 | 43 |
| | 300 | 23 | 50 |
| | 400 | 0 | 28 |
| Formulation J | 100 | 0 | 73 |
| | 200 | 57 | 85 |
| | 300 | 68 | 93 |
| | 400 | 87 | 94 |
| 63-01 | 100 | 18 | 75 |
| | 200 | 58 | 92 |
| | 300 | 85 | 90 |
| | 400 | 94 | 95 |
| 63-02 | 100 | 3 | 77 |
| | 200 | 47 | 90 |
| | 300 | 65 | 89 |
| | 400 | 87 | 95 |
| 63-03 | 100 | 13 | 80 |
| | 200 | 53 | 88 |
| | 300 | 72 | 98 |
| | 400 | 82 | 99 |
| 63-04 | 100 | 0 | 0 |
| | 200 | 53 | 88 |
| | 300 | 67 | 95 |
| | 400 | 83 | 95 |
| 63-05 | 100 | 2 | 60 |
| | 200 | 50 | 83 |
| | 300 | 70 | 93 |
| | 400 | 85 | 92 |
| 63-06 | 100 | 0 | 52 |
| | 200 | 55 | 83 |
| | 300 | 62 | 96 |
| | 400 | 77 | 98 |
| 63-07 | 100 | 8 | 70 |
| | 200 | 68 | 95 |
| | 300 | 91 | 99 |
| | 400 | 95 | 100 |
| 63-08 | 100 | 10 | 65 |
| | 200 | 67 | 99 |

TABLE 63b-continued

| Concentrate composition | Glyphosate rate g a.e./ha | % Inhibition ABUTH | ECHCF |
|---|---|---|---|
|  | 300 | 78 | 99 |
|  | 400 | 93 | 100 |
| 63-09 | 100 | 5 | 80 |
|  | 200 | 52 | 98 |
|  | 300 | 75 | 100 |
|  | 400 | 86 | 98 |
| 63-10 | 100 | 0 | 65 |
|  | 200 | 62 | 84 |
|  | 300 | 58 | 94 |
|  | 400 | 75 | 100 |
| 63-11 | 100 | 5 | 83 |
|  | 200 | 50 | 99 |
|  | 300 | 63 | 97 |
|  | 400 | 87 | 99 |
| 63-12 | 100 | 10 | 76 |
|  | 200 | 60 | 96 |
|  | 300 | 72 | 100 |
|  | 400 | 100 | 100 |
| 63-13 | 100 | 20 | 85 |
|  | 200 | 67 | 100 |
|  | 300 | 91 | 100 |
|  | 400 | 96 | 98 |
| 63-14 | 100 | 23 | 68 |
|  | 200 | 62 | 89 |
|  | 300 | 80 | 100 |
|  | 400 | 99 | 99 |
| 63-15 | 100 | 5 | 57 |
|  | 200 | 55 | 93 |
|  | 300 | 89 | 95 |
|  | 400 | 90 | 98 |
| 63-16 | 100 | 30 | 68 |
|  | 200 | 68 | 94 |
|  | 300 | 83 | 98 |
|  | 400 | 100 | 100 |
| 63-17 | 100 | 43 | 68 |

TABLE 63b-continued

| Concentrate composition | Glyphosate rate g a.e./ha | % Inhibition ABUTH | ECHCF |
|---|---|---|---|
|  | 200 | 62 | 99 |
|  | 300 | 78 | 100 |
|  | 400 | 100 | 99 |
| 63-18 | 100 | 25 | 52 |
|  | 200 | 53 | 84 |
|  | 300 | 85 | 94 |
|  | 400 | 98 | 95 |

Compositions having a 1:3 or lower weight/weight ratio of surfactant to glyphosate a.e., yet outperforming commercial standard Formulation J at least on ABUTH in this test, included those containing just 1 % alkylether surfactant (ratio about 1:15) together with 0.25% butyl stearate, where the alkylether surfactant was steareth-20 (63-12), oleth-20 (63-15) or ceteareth-27 (63-18).

Example 64

Dry granular concentrate compositions were prepared containing glyphosate ammonium salt and excipient ingredients as shown in Table 64a. The preparation procedure was as follows. Ammonium glyphosate powder was added to a blender. Excipient ingredients were slowly added, together with sufficient water to wet the powder and form a stiff dough. The blender was operated for sufficient time to thoroughly mix all ingredients. The dough was then transferred to extrusion apparatus and was extruded to form granules, which were finally dried in a fluid bed dryer.

TABLE 64a

| Conc. comp. | Glyphosate a.e. | Lecithin | Butyl stearate | Surfactant | Colloidal particulate | Type of surfactant | Type of colloidal particulate |
|---|---|---|---|---|---|---|---|
| 64-01 | 68.7 |  |  | 21.0 |  | steareth-20 |  |
| 64-02 | 66.0 |  | 2.2 | 22.0 |  | steareth-20 |  |
| 64-03 | 66.1 |  |  | 24.0 |  | oleth-20 |  |
| 64-04 | 66.0 |  | 2.2 | 22.0 |  | oleth-20 |  |
| 64-05 | 67.9 | 10.0 | 2.0 | 10.0 |  | MON 0818 |  |
| 64-06 | 59.2 | 10.0 |  | 20.0 + 2.0 |  | FC-754 + MON 0818 |  |
| 64-07 | 68.0 |  |  | 21.0 | 0.8 | tallowamine 20EO | Aerosil 90 |
| 64-08 | 68.0 |  |  | 21.0 | 0.8 | tallowamine 20EO | Aluminum oxide C |
| 64-09 | 66.1 |  |  | 24.0 |  | ceteth-20 |  |
| 64-10 | 66.0 |  | 2.2 | 22.0 |  | ceteth-20 |  |
| 64-11 | 71.2 |  |  | 16.1 | 2.0 | ceteth-20 | Aerosil 380 |
| 64-12 | 71.1 |  |  | 16.3 | 1.0 | ceteth-20 | Aerosil blend (*) |
| 64-13 | 71.2 |  |  | 16.1 | 2.0 | steareth-20 | Aerosil 380 |
| 64-14 | 71.2 |  |  | 16.1 | 1.0 | steareth-20 | Aerosil blend (*) |
| 64-15 | 68.0 |  |  | 20.0 | 1.9 | oleth-20 | Aerosil-380 |
| 64-16 | 70.8 |  |  | 16.6 | 1.0 | oleth-20 | Aerosil blend (*) |

(*) Aerosil MOX-80 + Aerosil MOX-170 (1:1)

Velvetleaf (*Abutilon theophrasti*, ABUTH) and Japanese millet (*Echinochloa crus-galli*, ECHCF) plants were grown and treated by the standard procedures given above. Applications of spray compositions were made 21 days after planting ABUTH and ECHCF, and evaluation of herbicidal inhibition was done 20 days after application.

Formulations J and K were applied as comparative treatments. Results, averaged for all replicates of each treatment, are shown in Table 64b.

TABLE 64b

| Concentrate composition | Glyphosate rate g a.e./ha | % Inhibition ABUTH | ECHCF |
|---|---|---|---|
| Formulation J | 100 | 52 | 80 |
|  | 200 | 90 | 96 |
|  | 300 | 96 | 100 |
|  | 400 | 97 | 99 |
| Formulation K | 100 | 33 | 70 |
|  | 200 | 67 | 93 |
|  | 300 | 83 | 99 |
|  | 400 | 93 | 100 |
| 64-01 | 100 | 47 | 60 |
|  | 200 | 87 | 98 |
|  | 300 | 97 | 98 |
|  | 400 | 100 | 98 |
| 64-02 | 100 | 47 | 63 |
|  | 200 | 80 | 94 |
|  | 300 | 90 | 99 |
|  | 400 | 98 | 100 |
| 64-03 | 100 | 62 | 62 |
|  | 200 | 83 | 93 |
|  | 300 | 97 | 96 |
|  | 400 | 97 | 100 |
| 64-04 | 100 | 47 | 57 |
|  | 200 | 78 | 94 |
|  | 300 | 87 | 100 |
|  | 400 | 98 | 100 |
| 64-05 | 100 | 25 | 53 |
|  | 200 | 60 | 88 |
|  | 300 | 80 | 97 |
|  | 400 | 83 | 98 |
| 64-06 | 100 | 35 | 37 |
|  | 200 | 65 | 62 |
|  | 300 | 83 | 83 |
|  | 400 | 90 | 95 |
| 64-07 | 100 | 63 | 55 |
|  | 200 | 72 | 97 |
|  | 300 | 83 | 100 |
|  | 400 | 94 | 100 |
| 64-08 | 100 | 30 | 65 |
|  | 200 | 72 | 94 |
|  | 300 | 87 | 100 |
|  | 400 | 92 | 99 |
| 64-09 | 100 | 37 | 63 |

TABLE 64b-continued

| Concentrate composition | Glyphosate rate g a.e./ha | % Inhibition ABUTH | ECHCF |
|---|---|---|---|
|  | 200 | 77 | 83 |
|  | 300 | 88 | 99 |
|  | 400 | 97 | 99 |
| 64-10 | 100 | 40 | 55 |
|  | 200 | 83 | 93 |
|  | 300 | 94 | 96 |
|  | 400 | 98 | 99 |
| 64-11 | 100 | 42 | 55 |
|  | 200 | 78 | 94 |
|  | 300 | 88 | 92 |
|  | 400 | 94 | 99 |
| 64-12 | 100 | 38 | 58 |
|  | 200 | 78 | 97 |
|  | 300 | 92 | 97 |
|  | 400 | 95 | 100 |
| 64-13 | 100 | 25 | 50 |
|  | 200 | 80 | 88 |
|  | 300 | 96 | 95 |
|  | 400 | 98 | 98 |
| 64-14 | 100 | 50 | 53 |
|  | 200 | 88 | 92 |
|  | 300 | 98 | 99 |
|  | 400 | 99 | 99 |
| 64-15 | 100 | 33 | 57 |
|  | 200 | 75 | 91 |
|  | 300 | 94 | 97 |
|  | 400 | 98 | 99 |
| 64-16 | 100 | 33 | 55 |
|  | 200 | 77 | 90 |
|  | 300 | 88 | 99 |
|  | 400 | 96 | 100 |

Several dry granular compositions of this Example outperformed commercial standard composition K, at least on ABUTH. They included 64-01 to 64-04 and 64-10 to 64-16, all containing an alkylether surfactant (steareth-20, oleth-20 or ceteth-20).

Example 65

Aqueous concentrate compositions were prepared containing glyphosate IPA salt and excipient ingredients as shown in Table 65a. All were prepared by process (x) using soybean lecithin (45% phospholipid, Avanti), except that compositions 65-09 and 65-10 were processed by ultrasonication instead of by use of a microfluidizer as indicated in the column of Table 65a headed "Process".

TABLE 65a

| | | % w/w | | | | | | |
|---|---|---|---|---|---|---|---|---|
| Conc. comp. | Glyphosate g a.e./l | Lecithin | Butyl stearate | Ethomeen T/25 | MON 0818 | Ceteareth-20 | Ceteareth-27 | Process (*) |
| 65-01 | 220 | 0.75 | 3.75 | 3.0 | | | 3.0 | B |
| 65-02 | 220 | 0.75 | 0.75 | 3.0 | | | 3.0 | B |
| 65-03 | 220 | 0.75 | 3.75 | 3.0 | | 3.0 | | B |
| 65-04 | 220 | 0.75 | 0.75 | 3.0 | | 3.0 | | B |
| 65-05 | 220 | 6.00 | 1.50 | 3.0 | | 3.0 | | B |
| 65-06 | 220 | 6.00 | 1.50 | 3.0 | | | 3.0 | B |
| 65-07 | 220 | 4.00 | 1.00 | 3.0 | | 3.0 | | B |
| 65-08 | 220 | 4.00 | 1.00 | 3.0 | | | 3.0 | B |
| 65-09 | 220 | 0.75 | 3.75 | 3.0 | | | 3.0 | A |
| 65-10 | 220 | 0.75 | 0.75 | 3.0 | | | 3.0 | A |
| 65-11 | 220 | 0.75 | 3.75 | 6.0 | | | | B |

TABLE 65a-continued

| | | | % w/w | | | | | |
|---|---|---|---|---|---|---|---|---|
| Conc. comp. | Glyphosate g a.e./l | Lecithin | Butyl stearate | Ethomeen T/25 | MON 0818 | Ceteareth-20 | Ceteareth-27 | Process (*) |
| 65-12 | 220 | 0.75 | 3.75 | | | 6.0 | | B |
| 65-13 | 345 | 6.00 | 1.50 | 4.5 | 4.5 | | | B |
| 65-14 | 345 | 6.00 | 1.50 | 6.0 | | | 3.0 | B |
| 65-15 | 345 | 6.00 | 1.50 | 6.0 | 6.0 | | | B |
| 65-16 | 345 | 0.50 | 7.50 | 12.0 | | | | B |
| 65-17 | 345 | 6.00 | 1.50 | 4.5 | 4.5 | | 3.0 | B |

(*) Process:
A Ultrasonicated
B Microfluidized, 3 cycles

Velvetleaf (*Abutilon theophrasti*, ABUTH) and Japanese millet (*Echinochloa crus-galli*, ECHCF) plants were grown and treated by the standard procedures given above. Applications of spray compositions were made 19 days after planting ABUTH and ECHCF, and evaluation of herbicidal inhibition was done 15 days after application.

Formulations B and J were applied as comparative treatments. Results, averaged for all replicates of each treatment, are shown in Table 65b.

TABLE 65b

| Concentrate composition | Glyphosate rate g a.e./ha | % Inhibition ABUTH | % Inhibition ECHCF |
|---|---|---|---|
| Formulation B | 150 | 45 | 82 |
| | 250 | 55 | 71 |
| | 350 | 80 | 72 |
| | 450 | 88 | 77 |
| Formulation J | 150 | 55 | 83 |
| | 250 | 89 | 88 |
| | 350 | 97 | 93 |
| | 450 | 99 | 93 |
| | 550 | 99 | 87 |
| 65-01 | 150 | 92 | 83 |
| | 250 | 96 | 96 |
| | 350 | 99 | 96 |
| | 450 | 100 | 86 |
| 65-02 | 150 | 85 | 93 |
| | 250 | 97 | 78 |
| | 350 | 97 | 90 |
| | 450 | 99 | 90 |
| 65-03 | 150 | 87 | 85 |
| | 250 | 98 | 92 |
| | 350 | 99 | 95 |
| | 450 | 100 | 95 |
| 65-04 | 150 | 87 | 89 |
| | 250 | 97 | 92 |
| | 350 | 99 | 94 |
| | 450 | 99 | 91 |
| 65-05 | 150 | 87 | 77 |
| | 250 | 98 | 89 |
| | 350 | 99 | 93 |
| | 450 | 99 | 84 |
| 65-06 | 150 | 12 | 18 |
| | 250 | 96 | 73 |
| | 350 | 99 | 85 |
| | 450 | 99 | 84 |
| 65-07 | 150 | 82 | 89 |
| | 250 | 88 | 96 |
| | 350 | 96 | 98 |
| | 450 | 97 | 97 |
| 65-08 | 150 | 88 | 94 |
| | 250 | 95 | 90 |
| | 350 | 99 | 98 |
| | 450 | 99 | 98 |
| 65-09 | 150 | 94 | 94 |
| | 250 | 95 | 100 |
| | 350 | 97 | 99 |
| | 450 | 99 | 98 |
| 65-10 | 150 | 94 | 94 |
| | 250 | 98 | 99 |
| | 350 | 99 | 97 |
| | 450 | 99 | 96 |
| 65-11 | 150 | 83 | 81 |
| | 250 | 94 | 88 |
| | 350 | 98 | 93 |
| | 450 | 99 | 99 |
| 65-12 | 150 | 68 | 79 |
| | 250 | 95 | 96 |
| | 350 | 98 | 100 |
| | 450 | 99 | 98 |
| 65-13 | 150 | 86 | 98 |
| | 250 | 95 | 98 |
| | 350 | 99 | 100 |
| | 450 | 100 | 98 |
| 65-14 | 150 | 85 | 98 |
| | 250 | 98 | 98 |
| | 350 | 99 | 98 |
| | 450 | 100 | 98 |
| 65-15 | 150 | 86 | 95 |
| | 250 | 97 | 97 |
| | 350 | 99 | 95 |
| | 450 | 100 | 96 |
| 65-16 | 150 | 93 | 94 |
| | 250 | 98 | 98 |
| | 350 | 99 | 98 |
| | 450 | 100 | 97 |
| 65-17 | 150 | 95 | 96 |
| | 250 | 98 | 100 |
| | 350 | 100 | 100 |
| | 450 | 100 | 98 |

Many compositions containing lecithin and butyl stearate outperformed commercial standard Formulation J in this test.

Example 66

Aqueous and dry granular concentrate compositions were prepared as shown in Table 66a. Dry granular concentrate compositions 66-01 to 66-11 contain glyphosate ammonium salt, and were prepared by the process described in Example 64.

Aqueous concentrate compositions 66-12 to 66-16 contain glyphosate IPA salt and were prepared by process (v) using soybean lecithin (45% phospholipid, Avanti).

TABLE 66a

| Conc. comp. | Glyphosate g a.e./l | Glyphosate a.e. | Lecithin | Butyl stearate | Surfactant | Colloidal particulate | Type of surfactant | Type of colloidal particulate |
|---|---|---|---|---|---|---|---|---|
| 66-01 | | 68.7 | | | 21.0 | | steareth-20 | |
| 66-02 | | 66.1 | | | 24.0 | | oleth-20 | |
| 66-03 | | 67.9 | 10.0 | 2.0 | 10.0 | | MON 0818 | |
| 66-04 | | 59.2 | 10.0 | | 20.0 + 2.0 | | FC-754 + MON 0818 | |
| 66-05 | | 66.1 | | | 24.0 | | ceteth-20 | |
| 66-06 | | 71.2 | | | 16.1 | 2.0 | steareth-20 | Aerosil 380 |
| 66-07 | | 71.2 | | | 16.1 | 2.0 | steareth-20 | Aerosil blend |
| 66-08 | | 68.0 | | | 20.0 | 1.9 | oleth-20 | Aerosil 380 |
| 66-09 | | 63.5 | | | 25.0 | 2.0 | steareth-20 | Aerosil blend |
| 66-10 | | 67.9 | | | 20.0 | 2.0 | steareth-20 | Aerosil blend |
| 66-11 | | 72.2 | | | 15.0 | 2.0 | steareth-20 | Aerosil blend |
| 66-12 | 370 | | | 4.7 | 4.7 | | steareth-20 | |
| 66-13 | 350 | | | 4.9 | 4.9 | | ceteareth-27 | |
| 66-14 | 348 | | | 5.0 | 5.0 | | ceteareth-15 | |
| 66-15 | 348 | | | 5.0 | 5.0 | | oleth-20 | |
| 66-16 | 351 | | | 4.4 | 5.0 | | steareth-30 | |

Aerosil blend: Aerosil MOX-80 + Aerosil MOX-170 (1:1)

Velvetleaf (*Abutilon theophrasti*, ABUTH) and Japanese millet (*Echinochloa crus-galli*, ECHCF) plants were grown and treated by the standard procedures given above. Applications of spray compositions were made 20 days after planting ABUTH and ECHCF, and evaluation of herbicidal inhibition was done 16 days after application.

Formulations J and K were applied as comparative treatments. Results, averaged for all replicates of each treatment, are shown in Table 66b.

TABLE 66b

| Concentrate composition | Glyphosate rate g a.e./ha | % Inhibition ABUTH | % Inhibition ECHCF |
|---|---|---|---|
| Formulation J | 100 | 0 | 20 |
| | 200 | 28 | 57 |
| | 300 | 58 | 96 |
| | 400 | 73 | 99 |
| Formulation K | 100 | 22 | 13 |
| | 200 | 42 | 83 |
| | 300 | 48 | 91 |
| | 400 | 58 | 95 |
| 66-01 | 100 | 28 | 30 |
| | 200 | 48 | 80 |
| | 300 | 80 | 97 |
| | 400 | 85 | 99 |
| 66-02 | 100 | 43 | 52 |
| | 200 | 68 | 80 |
| | 300 | 72 | 88 |
| | 400 | 86 | 94 |
| 66-03 | 100 | 23 | 37 |
| | 200 | 50 | 83 |
| | 300 | 75 | 88 |
| | 400 | 85 | 96 |
| 66-04 | 100 | 50 | 45 |
| | 200 | 73 | 80 |
| | 300 | 85 | 92 |
| | 400 | 95 | 94 |
| 66-05 | 100 | 18 | 45 |
| | 200 | 65 | 83 |
| | 300 | 87 | 95 |
| | 400 | 94 | 86 |
| 66-06 | 100 | 47 | 50 |
| | 200 | 62 | 68 |
| | 300 | 82 | 94 |
| | 400 | 91 | 87 |
| 66-07 | 100 | 50 | 47 |
| | 200 | 60 | 78 |
| | 300 | 87 | 87 |
| | 400 | 93 | 93 |
| 66-08 | 100 | 30 | 55 |
| | 200 | 55 | 77 |
| | 300 | 82 | 85 |
| | 400 | 88 | 97 |
| 66-09 | 100 | 45 | 50 |
| | 200 | 57 | 78 |
| | 300 | 83 | 83 |
| | 400 | 84 | 89 |
| 66-10 | 100 | 42 | 50 |
| | 200 | 57 | 80 |
| | 300 | 73 | 91 |
| | 400 | 91 | 90 |
| 66-11 | 100 | 28 | 48 |
| | 200 | 50 | 75 |
| | 300 | 70 | 87 |
| | 400 | 82 | 89 |
| 66-12 | 100 | 20 | 40 |
| | 200 | 63 | 80 |
| | 300 | 67 | 96 |
| | 400 | 80 | 88 |
| 66-13 | 100 | 27 | 35 |
| | 200 | 50 | 85 |
| | 300 | 77 | 90 |
| | 400 | 84 | 86 |
| 66-14 | 100 | 27 | 25 |
| | 200 | 40 | 70 |
| | 300 | 68 | 94 |
| | 400 | 89 | 91 |
| 66-15 | 100 | 17 | 20 |
| | 200 | 47 | 82 |
| | 300 | 58 | 89 |
| | 400 | 91 | 95 |
| 66-16 | 100 | 22 | 20 |
| | 200 | 41 | 80 |
| | 300 | 84 | 89 |
| | 400 | 99 | 98 |

All compositions of the invention in this study exhibited greater herbicidal effectiveness on both ABUTH and ECHCF, in some cases by a very substantial margin, than commercial standard Formulation K.

Example 67

Aqueous concentrate compositions were prepared containing glyphosate IPA salt and excipient ingredients as shown in Table 67a. Concentrate compositions 67-01 to 67-07, 67-17 and 67-18 were prepared by process (v). Concentrate compositions 67-08 to 67-15 were prepared by process (x). Concentrate composition 67-16 was prepared by process (viii).

TABLE 67a

| Conc. comp. | Glyphosate g a.e./l | Lecithin | Fluorad FC-754 | Butyl stearate | Ethomeen T/25 | Ceteareth-20 | Arcosolve DPM | Ceteareth-27 |
|---|---|---|---|---|---|---|---|---|
| 67-01 | 348 | 3.0 | 3.00 | | 0.75 | | | |
| 67-02 | 348 | 3.8 | 3.75 | | 5.00 | | | |
| 67-03 | 348 | 3.8 | 3.75 | | 7.50 | | | |
| 67-04 | 348 | 2.0 | 5.00 | | 0.75 | | | |
| 67-05 | 348 | 5.0 | 5.00 | | 0.75 | | | |
| 67-06 | 348 | 2.0 | 2.00 | | | | | |
| 67-07 | 348 | 1.0 | 1.00 | | | | | |
| 67-08 | 220 | 1.5 | | 1.5 | 3.00 | 3.0 | | |
| 67-09 | 220 | 1.5 | | 1.5 | 3.00 | | | 3.0 |
| 67-10 | 220 | 1.5 | | 1.5 | 6.00 | 3.0 | | |
| 67-11 | 220 | 1.5 | | 1.5 | 6.00 | | | 3.0 |
| 67-12 | 220 | 3.0 | | 1.5 | 3.00 | 3.0 | | |
| 67-13 | 220 | 3.0 | | 1.5 | 3.00 | | | 3.0 |
| 67-14 | 348 | 1.5 | | 1.5 | 6.00 | 3.0 | | |
| 67-15 | 348 | 3.0 | | 1.5 | 3.00 | 3.0 | | |
| 67-16 | 348 | | 3.00 | | | | | |
| 67-17 | 348 | 3.0 | | | | | 3.0 | |
| 67-18 | 348 | 5.0 | | | 13.00 | | 5.0 | |

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and ECHCF, and evaluation of herbicidal inhibition was done 18 days after application.

Formulations B and J were applied as comparative treatments. Results, averaged for all replicates of each treatment, are shown in Table 67b.

TABLE 67b

| Concentrate composition | Glyphosate rate g a.e./ha | % Inhibition ABUTH | ECHCF |
|---|---|---|---|
| Formulation B | 100 | 28 | 32 |
| | 200 | 41 | 37 |
| | 300 | 73 | 64 |
| | 400 | 22 | 30 |
| Formulation J | 100 | 38 | 32 |
| | 200 | 82 | 73 |
| | 300 | 89 | 91 |
| | 400 | 97 | 89 |
| 67-01 | 100 | 73 | 28 |
| | 200 | 90 | 66 |
| | 300 | 97 | 92 |
| | 400 | 100 | 96 |
| 67-02 | 100 | 77 | 32 |
| | 200 | 87 | 67 |
| | 300 | 84 | 78 |
| | 400 | 98 | 84 |
| 67-03 | 100 | 79 | 33 |
| | 200 | 82 | 66 |
| | 300 | 99 | 81 |
| | 400 | 97 | 88 |
| 67-04 | 100 | 69 | 35 |
| | 200 | 95 | 59 |
| | 300 | 96 | 84 |
| | 400 | 92 | 91 |
| 67-05 | 100 | 82 | 32 |
| | 200 | 92 | 55 |
| | 300 | 96 | 71 |
| | 400 | 94 | 87 |
| 67-06 | 100 | 83 | 33 |
| | 200 | 100 | 52 |
| | 300 | 100 | 68 |
| | 400 | 99 | 75 |
| 67-07 | 100 | 77 | 35 |
| | 200 | 90 | 58 |
| | 300 | 95 | 71 |
| | 400 | 94 | 90 |
| 67-08 | 100 | 51 | 40 |
| | 200 | 89 | 75 |
| | 300 | 96 | 92 |
| | 400 | 95 | 98 |
| 67-09 | 100 | 76 | 57 |
| | 200 | 98 | 81 |
| | 300 | 97 | 86 |
| | 400 | 96 | 98 |
| 67-10 | 100 | 69 | 60 |
| | 200 | 98 | 63 |
| | 300 | 95 | 82 |
| | 400 | 99 | 90 |
| 67-11 | 100 | 61 | 60 |
| | 200 | 94 | 84 |
| | 300 | 97 | 89 |
| | 400 | 99 | 97 |
| 67-12 | 100 | 64 | 53 |
| | 200 | 95 | 82 |
| | 300 | 96 | 90 |
| | 400 | 95 | 98 |
| 67-13 | 100 | 61 | 58 |
| | 200 | 94 | 78 |
| | 300 | 88 | 87 |
| | 400 | 100 | 94 |
| 67-14 | 100 | 56 | 61 |
| | 200 | 88 | 77 |
| | 300 | 91 | 82 |
| | 400 | 97 | 89 |
| 67-15 | 100 | 42 | 52 |

TABLE 67b-continued

| Concentrate composition | Glyphosate rate g a.e./ha | % Inhibition ABUTH | ECHCF |
|---|---|---|---|
|  | 200 | 82 | 80 |
|  | 300 | 86 | 90 |
|  | 400 | 97 | 92 |
| 67-16 | 100 | 64 | 49 |
|  | 200 | 86 | 75 |
|  | 300 | 97 | 88 |
|  | 400 | 100 | 82 |
| 67-17 | 100 | 57 | 32 |
|  | 200 | 88 | 66 |
|  | 300 | 95 | 73 |
|  | 400 | 100 | 88 |
| 67-18 | 100 | 52 | 35 |
|  | 200 | 70 | 77 |
|  | 300 | 82 | 79 |
|  | 400 | 97 | 73 |

Compositions 67-08 to 67-15, containing lecithin, butyl stearate, Ethomeen T/25 and a $C_{16-18}$ alkylether surfactant (ceteareth-20 or ceteareth-27) exhibited a very high degree of herbicidal effectiveness. Not only was performance, at least of 67-08 to 67-13, on ABUTH substantially better than that of Formulation J, these compositions performed considerably better than Formulation J on ECHCF as well.

Example 68

Aqueous concentrate compositions were prepared containing glyphosate IPA salt and excipient ingredients as shown in Table 68a. All contain colloidal particulates and were prepared by process (ix).

The compositions of this example all showed acceptable storage stability. The compositions shown as containing colloidal particulate were not storage-stable unless the colloidal particulate was included as shown.

Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and ECHCF, and evaluation of herbicidal inhibition was done 19 days after application.

Formulations B and J were applied as comparative treatments. Results, averaged for all replicates of each treatment, are shown in Table 68b.

TABLE 68b

| Concentrate composition | Glyphosate rate g a.e./ha | % Inhibition ABUTH | ECHCF |
|---|---|---|---|
| Formulation B | 100 | 0 | 60 |
|  | 200 | 15 | 73 |
|  | 300 | 33 | 88 |
|  | 400 | 57 | 91 |
| Formulation J | 100 | 5 | 70 |
|  | 200 | 37 | 92 |
|  | 300 | 80 | 99 |
|  | 400 | 77 | 96 |
| 68-01 | 100 | 13 | 88 |
|  | 200 | 32 | 85 |
|  | 300 | 48 | 98 |
|  | 400 | 90 | 93 |
| 68-02 | 100 | 10 | 70 |
|  | 200 | 45 | 98 |
|  | 300 | 72 | 99 |
|  | 400 | 80 | 98 |
| 68-03 | 100 | 3 | 77 |
|  | 200 | 25 | 94 |
|  | 300 | 47 | 98 |
|  | 400 | 75 | 99 |
| 68-04 | 100 | 7 | 67 |
|  | 200 | 23 | 94 |
|  | 300 | 40 | 99 |
|  | 400 | 7 | 47 |
| 68-05 | 100 | 7 | 76 |
|  | 200 | 25 | 88 |
|  | 300 | 45 | 96 |
|  | 400 | 75 | 97 |

TABLE 68a

| Conc. comp. | Glyphosate g a.e./l | % w/w Oil | Surfactant | Aerosil 380 | Type of oil | Type of surfactant |
|---|---|---|---|---|---|---|
| 68-01 | 360 | 1.0 | 10.0 | 1.25 | butyl stearate | oleth-20 |
| 68-02 | 360 | 1.0 | 10.0 | 1.25 | stearylamine | oleth-20 |
| 68-03 | 360 | 1.0 | 10.0 | 1.25 | stearyl alcohol | oleth-20 |
| 68-04 | 360 | 1.0 | 10.0 | 1.25 | docosane | oleth-20 |
| 68-05 | 360 |  | 10.0 | 1.25 | none | oleth-20 |
| 68-06 | 360 | 1.0 | 10.0 | 1.25 | butyl stearate | steareth-30 |
| 68-07 | 360 | 1.0 | 10.0 | 1.25 | stearylamine | steareth-30 |
| 68-08 | 360 | 1.0 | 10.0 | 1.25 | stearyl alcohol | steareth-30 |
| 68-09 | 360 | 1.0 | 10.0 | 1.25 | docosane | steareth-30 |
| 68-10 | 360 |  | 10.0 | 1.25 | none | steareth-30 |
| 68-11 | 360 |  | 5.0 + 5.0 | 1.25 | none | oleth-20 + steareth-20 |
| 68-12 | 360 |  | 5.0 + 5.0 | 1.25 | none | oleth-20 + steareth-30 |
| 68-13 | 360 |  | 5.0 + 5.0 | 1.25 | none | oleth-20 + ceteareth-27 |
| 68-14 | 360 |  | 5.0 + 5.0 | 1.25 | none | oleth-20 + ceteareth-15 |
| 68-15 | 360 |  | 5.0 + 5.0 | 1.25 | none | steareth-30 + steareth-20 |
| 68-16 | 360 |  | 5.0 + 5.0 | 1.25 | none | steareth-30 + ceteareth-27 |
| 68-17 | 360 |  | 5.0 + 5.0 | 1.25 | none | steareth-30 + ceteareth-15 |
| 68-18 | 360 |  | 10.0 | 1.25 | none | laureth-23 |

TABLE 68b-continued

| Concentrate composition | Glyphosate rate g a.e./ha | % Inhibition ABUTH | % Inhibition ECHCF |
|---|---|---|---|
| 68-06 | 100 | 12 | 96 |
|  | 200 | 30 | 97 |
|  | 300 | 45 | 98 |
|  | 400 | 15 | 60 |
| 68-07 | 100 | 8 | 83 |
|  | 200 | 12 | 97 |
|  | 300 | 35 | 94 |
|  | 400 | 50 | 98 |
| 68-08 | 100 | 15 | 72 |
|  | 200 | 30 | 88 |
|  | 300 | 40 | 99 |
|  | 400 | 0 | 33 |
| 68-09 | 100 | 5 | 73 |
|  | 200 | 15 | 94 |
|  | 300 | 47 | 99 |
|  | 400 | 5 | 53 |
| 68-10 | 100 | 7 | 79 |
|  | 200 | 15 | 95 |
|  | 300 | 45 | 98 |
|  | 400 | 62 | 99 |
| 68-11 | 100 | 5 | 84 |
|  | 200 | 13 | 98 |
|  | 300 | 30 | 98 |
|  | 400 | 55 | 100 |
| 68-12 | 100 | 3 | 95 |
|  | 200 | 17 | 99 |
|  | 300 | 28 | 99 |
|  | 400 | 67 | 100 |
| 68-13 | 100 | 5 | 90 |
|  | 200 | 17 | 99 |
|  | 300 | 30 | 100 |
|  | 400 | 60 | 98 |
| 68-14 | 100 | 3 | 98 |
|  | 200 | 25 | 97 |
|  | 300 | 38 | 100 |
|  | 400 | 57 | 100 |
| 68-15 | 100 | 5 | 97 |
|  | 200 | 25 | 97 |
|  | 300 | 40 | 100 |
|  | 400 | 40 | 99 |
| 68-16 | 100 | 10 | 97 |
|  | 200 | 15 | 98 |
|  | 300 | 52 | 100 |
|  | 400 | 0 | 47 |
| 68-17 | 100 | 7 | 97 |
|  | 200 | 25 | 94 |
|  | 300 | 40 | 98 |
|  | 400 | 33 | 97 |
| 68-18 | 100 | 7 | 96 |
|  | 200 | 25 | 99 |
|  | 300 | 55 | 100 |
|  | 400 | 73 | 100 |

Percent inhibition data for the 400 g a.e./ha glyphosate rate in this test are unreliable and should be ignored. Neither oleth-20 (composition 68-05) nor steareth-20 (68-10) provided herbicidal effectiveness equal to Formulation J in this study, and no great or consistent further enhancement was obtained by adding butyl stearate.

Example 69

Aqueous concentrate compositions were prepared containing glyphosate IPA salt and excipient ingredients as shown in Table 69a. Concentrate compositions 69-01 to 69-03 are oil-in-water emulsions and were prepared by process (vii). Compositions 69-04 to 69-18 all contain colloidal particulates and were prepared by process (ix). Different mixing methods were employed in the final stage of preparation of these compositions, as indicated in the column of Table 69a headed "Process".

The compositions of this example all showed acceptable storage stability. The compositions shown as containing colloidal particulate were not storage-stable unless the colloidal particulate was included as shown.

TABLE 69a

| Concentrate composition | Glyphosate g a.e./l | Butyl stearate % w/w | Surfactant % w/w | Aerosil 380 % w/w | Type of surfactant | Process (*) |
|---|---|---|---|---|---|---|
| 69-01 | 163 | 0.5 | 5.0 |  | oleth-20 |  |
| 69-02 | 163 | 0.5 | 5.0 |  | steareth-20 |  |
| 69-03 | 163 | 0.5 | 5.0 |  | ceteareth-27 |  |
| 69-04 | 360 | 1.0 | 10.0 | 1.25 | ceteareth-15 | A |
| 69-05 | 360 | 1.0 | 10.0 | 1.25 | ceteth-20 | A |
| 69-06 | 360 | 1.0 | 10.0 | 1.25 | steareth-20 | A |
| 69-07 | 360 | 1.0 | 10.0 | 1.25 | oleth-20 | A |
| 69-08 | 360 | 1.0 | 10.0 | 1.25 | ceteareth-27 | A |
| 69-09 | 360 | 1.0 | 10.0 | 1.25 | steareth-30 | A |
| 69-10 | 360 |  | 10.0 | 1.25 | steareth-30 | A |
| 69-11 | 360 | 1.0 | 10.0 | 1.25 | oleth-20 | A |
| 69-12 | 360 | 1.0 | 10.0 | 1.25 | oleth-20 | B |
| 69-13 | 360 | 1.0 | 10.0 | 1.25 | oleth-20 | C |
| 69-14 | 360 | 1.0 | 10.0 | 1.25 | oleth-20 | D |
| 69-15 | 360 | 1.0 | 10.0 | 1.25 | oleth-20 | E |
| 69-16 | 360 | 1.0 | 10.0 | 1.25 | oleth-20 | F |
| 69-17 | 360 | 1.0 | 10.0 | 1.25 | oleth-20 | G |
| 69-18 | 360 | 1.0 | 10.0 | 1.25 | oleth-20 | A |

(*) Process:
A Silverson mixer, medium screen, 3 minutes at 7000 rpm
B Silverson mixer, coarse screen, 3 minutes at 7000 rpm
C Fann mixer, 50% output, 5 minutes
D Turrax mixer, 3 minutes at 8000 rpm
E Overhead stirrer, low speed
F Overhead stirrer, high speed
G Hand shaking, 3 minutes Velvetleaf (*Abutilon theophrasti*, ABUTH) and Japanese millet (*Echinochloa crus-galli*, ECHCF) plants were grown and treated by the standard procedures given above. Applications of spray compositions were made 17 days after planting ABUTH and ECHCF, and evaluation of herbicidal inhibition was done 19 days after application.

Formulations B and J were applied as comparative treatments. Results, averaged for all replicates of each treatment, are shown in Table 69b.

TABLE 69b

| Concentrate composition | Glyphosate rate g a.e./ha | % Inhibition ABUTH | % Inhibition ECHCF |
|---|---|---|---|
| Formulation B | 100 | 20 | 40 |
|  | 200 | 45 | 50 |
|  | 300 | 65 | 72 |
|  | 400 | 78 | 85 |
| Formulation J | 100 | 43 | 53 |
|  | 200 | 80 | 80 |
|  | 300 | 96 | 82 |
|  | 400 | 99 | 94 |
| 69-01 | 100 | 45 | 57 |
|  | 200 | 80 | 72 |
|  | 300 | 89 | 78 |
|  | 400 | 98 | 83 |
| 69-02 | 100 | 53 | 57 |
|  | 200 | 80 | 78 |
|  | 300 | 89 | 77 |
|  | 400 | 93 | 83 |
| 69-03 | 100 | 45 | 60 |
|  | 200 | 83 | 75 |
|  | 300 | 97 | 73 |
|  | 400 | 97 | 85 |
| 69-04 | 100 | 45 | 45 |
|  | 200 | 80 | 80 |
|  | 300 | 83 | 83 |
|  | 400 | 95 | 95 |

TABLE 69b-continued

| Concentrate composition | Glyphosate rate g a.e./ha | % Inhibition ABUTH | % Inhibition ECHCF |
|---|---|---|---|
| 69-05 | 100 | 42 | 42 |
|  | 200 | 77 | 77 |
|  | 300 | 93 | 93 |
|  | 400 | 98 | 98 |
| 69-06 | 100 | 30 | 30 |
|  | 200 | 42 | 42 |
|  | 300 | 27 | 30 |
|  | 400 | 3 | 20 |
| 69-07 | 100 | 40 | 40 |
|  | 200 | 77 | 75 |
|  | 300 | 90 | 93 |
|  | 400 | 97 | 86 |
| 69-08 | 100 | 43 | 50 |
|  | 200 | 80 | 80 |
|  | 300 | 92 | 93 |
|  | 400 | 96 | 98 |
| 69-09 | 100 | 0 | 2 |
|  | 200 | 82 | 75 |
|  | 300 | 83 | 96 |
|  | 400 | 90 | 88 |
| 69-10 | 100 | 57 | 60 |
|  | 200 | 80 | 70 |
|  | 300 | 88 | 88 |
|  | 400 | 95 | 93 |
| 69-11 | 100 | 35 | 47 |
|  | 200 | 72 | 75 |
|  | 300 | 80 | 75 |
|  | 400 | 85 | 77 |
| 69-12 | 100 | 47 | 47 |
|  | 200 | 72 | 77 |
|  | 300 | 80 | 90 |
|  | 400 | 86 | 78 |
| 69-13 | 100 | 55 | 50 |
|  | 200 | 75 | 83 |
|  | 300 | 78 | 92 |
|  | 400 | 91 | 92 |
| 69-14 | 100 | 52 | 50 |
|  | 200 | 75 | 78 |
|  | 300 | 83 | 88 |
|  | 400 | 99 | 92 |
| 69-15 | 100 | 47 | 47 |
|  | 200 | 70 | 73 |
|  | 300 | 87 | 87 |
|  | 400 | 75 | 63 |
| 69-16 | 100 | 43 | 40 |
|  | 200 | 78 | 75 |
|  | 300 | 88 | 88 |
|  | 400 | 87 | 91 |
| 69-17 | 100 | 43 | 43 |
|  | 200 | 67 | 88 |
|  | 300 | 80 | 75 |
|  | 400 | 92 | 83 |
| 69-18 | 100 | 27 | 40 |
|  | 200 | 63 | 57 |
|  | 300 | 82 | 73 |
|  | 400 | 87 | 70 |

Results obtained with composition 69-06 are out of line with other data in this Example and an error in formulation or application is suspected. Some differences in herbicidal effectiveness were evident when a composition containing 360 g a.e./l glyphosate, 1% butyl stearate, 10% oleth-20 and 1.25% Aerosil 380 was processed in different ways (69-11 to 69-17). However, as compositions 69-07 and 69-11 were identically processed yet differed in effectiveness, no firm conclusions can be drawn from this test.

Example 70

Aqueous concentrate compositions were prepared containing glyphosate IPA salt and excipient ingredients as shown in Table 70a. All contain colloidal particulates and were prepared by process (ix).

The compositions of this example all showed acceptable storage stability. The compositions shown as containing colloidal particulate were not storage-stable unless the colloidal particulate was included as shown.

TABLE 70a

| Concentrate composition | Glyphosate a.e. % w/w | Oil % w/w | Surfactant % w/w | Aerosil 380 % w/w | Type of oil | Type of surfactant |
|---|---|---|---|---|---|---|
| 70-01 | 31 | 1.0 | 10.0 | 1.25 | Butyl stearate | steareth-20 |
| 70-02 | 31 | 1.0 | 10.0 | 1.25 | Butyl stearate | oleth-20 |
| 70-03 | 31 | 1.0 | 10.0 | 1.25 | Butyl stearate | steareth-30 |
| 70-04 | 31 |  | 10.0 | 1.25 | none | steareth-30 |

Velvetleaf (*Abutilon theophrasti*, ABUTH) and Japanese millet (*Echinochloa crus-galli*, ECHCF) plants were grown and treated by the standard procedures given above. Treatments were applied at four different hours of the day. Applications of spray compositions were made 16 days after planting ABUTH and ECHCF, and evaluation of herbicidal inhibition was done 22 days after application.

Formulation J was applied as comparative treatments. Results, averaged for all replicates of each treatment, are shown in Table 70b.

TABLE 70b

| Concentrate composition | Hour when applied | Glyphosate rate g a.e./ha | % Inhibition ABUTH | % Inhibition ECHCF |
|---|---|---|---|---|
| Formulation J | 1000 | 100 | 5 | 33 |
|  |  | 200 | 42 | 75 |
|  |  | 300 | 67 | 83 |
|  |  | 400 | 77 | 93 |
| 70-01 | 1000 | 100 | 7 | 33 |
|  |  | 200 | 40 | 70 |
|  |  | 300 | 50 | 82 |
|  |  | 400 | 78 | 91 |
| 70-02 | 1000 | 100 | 18 | 33 |
|  |  | 200 | 37 | 73 |
|  |  | 300 | 48 | 91 |
|  |  | 400 | 80 | 92 |
| 70-03 | 1000 | 100 | 30 | 33 |
|  |  | 200 | 40 | 75 |
|  |  | 300 | 82 | 85 |
|  |  | 400 | 83 | 80 |
| 70-04 | 1000 | 100 | 30 | 30 |
|  |  | 200 | 43 | 78 |
|  |  | 300 | 78 | 92 |
|  |  | 400 | 93 | 95 |
| Formulation J | 1200 | 100 | 5 | 38 |
|  |  | 200 | 35 | 87 |
|  |  | 300 | 53 | 96 |
|  |  | 400 | 88 | 99 |
| 70-01 | 1200 | 100 | 10 | 30 |
|  |  | 200 | 47 | 91 |
|  |  | 300 | 70 | 89 |
|  |  | 400 | 78 | 97 |
| 70-02 | 1200 | 100 | 5 | 37 |
|  |  | 200 | 40 | 75 |
|  |  | 300 | 48 | 87 |
|  |  | 400 | 70 | 94 |
| 70-03 | 1200 | 100 | 20 | 37 |
|  |  | 200 | 50 | 82 |
|  |  | 300 | 78 | 98 |
|  |  | 400 | 83 | 97 |
| 70-04 | 1200 | 100 | 33 | 33 |
|  |  | 200 | 45 | 93 |
|  |  | 300 | 75 | 98 |
|  |  | 400 | 95 | 100 |
| Formulation J | 1400 | 100 | 15 | 40 |

TABLE 70b-continued

| Concentrate composition | Hour when applied | Glyphosate rate g a.e./ha | % Inhibition ABUTH | % Inhibition ECHCF |
|---|---|---|---|---|
|  |  | 200 | 30 | 90 |
|  |  | 300 | 55 | 100 |
|  |  | 400 | 80 | 100 |
| 70-01 | 1400 | 100 | 17 | 40 |
|  |  | 200 | 45 | 70 |
|  |  | 300 | 75 | 97 |
|  |  | 400 | 80 | 98 |
| 70-02 | 1400 | 100 | 17 | 47 |
|  |  | 200 | 35 | 83 |
|  |  | 300 | 67 | 97 |
|  |  | 400 | 63 | 97 |
| 70-03 | 1400 | 100 | 30 | 40 |
|  |  | 200 | 63 | 80 |
|  |  | 300 | 77 | 97 |
|  |  | 400 | 78 | 100 |
| 70-04 | 1400 | 100 | 23 | 40 |
|  |  | 200 | 45 | 87 |
|  |  | 300 | 73 | 100 |
|  |  | 400 | 78 | 100 |
| Formulation J | 1600 | 100 | 10 | 37 |
|  |  | 200 | 32 | 83 |
|  |  | 300 | 52 | 97 |
|  |  | 400 | 75 | 98 |
| 70-01 | 1600 | 100 | 27 | 43 |
|  |  | 200 | 40 | 89 |
|  |  | 300 | 77 | 99 |
|  |  | 400 | 95 | 99 |
| 70-02 | 1600 | 100 | 20 | 53 |
|  |  | 200 | 40 | 95 |
|  |  | 300 | 53 | 98 |
|  |  | 400 | 80 | 98 |
| 70-03 | 1600 | 100 | 27 | 60 |
|  |  | 200 | 60 | 93 |
|  |  | 300 | 78 | 97 |
|  |  | 400 | 96 | 100 |
| 70-04 | 1600 | 100 | 15 | 37 |
|  |  | 200 | 43 | 83 |
|  |  | 300 | 67 | 97 |
|  |  | 400 | 78 | 96 |

Composition 70-03 illustrates the consistency of high-level performance obtainable with, in this case, steareth-30 at an approximately 1:3 weight/weight ratio to glyphosate a.e., together with a small amount of butyl stearate and Aerosil 380. An average of percent inhibition of ABUTH across all four glyphosate rates shows the following comparison of 70-03 with Formulation J, applied at four different hours of the day:

| Hour | Formulation J | Composition 70-03 |
|---|---|---|
| 1000 | 48 | 59 |
| 1200 | 45 | 58 |
| 1400 | 48 | 62 |
| 1600 | 42 | 65 |

The preceding description of specific embodiments of the present invention is not intended to be a complete list of every possible embodiment of the invention. Persons skilled in this field will recognize that modifications can be made to the specific embodiments described here that would be within the scope of the present invention.

What is claimed is:

1. A plant treatment composition comprising:
   (a) an exogenous chemical;
   (b) in a weight ratio of about 1:3 to about 1:100 to the exogenous chemical, a first excipient substance which is a compound or mixture of compounds having the formula:

$$R^{14}-CO-A-R^{15}$$

wherein $R^{14}$ is a hydrocarbyl group having about 5 to about 21 carbon atoms, $R^{15}$ is a hydrocarbyl group having 1 to about 14 carbon atoms, the total number of carbon atoms in $R^{14}$ and $R^{15}$ is about 11 to about 27, and A is O or NH; and (c) a second excipient substance which is an alkylether surfactant or mixture of such surfactants having the formula:

$$R^{12}-O-(CH_2CH_2O)_n(CH(CH_3)CH_2O)_m-R^{13}$$

wherein $R^{12}$ is an alkyl or alkenyl group having about 16 to about 22 carbon atoms, n is an average number of about 15 to about 100, m is an average number of 0 to about 5 and $R^{13}$ is hydrogen or $C_{1-4}$ alkyl.

2. The composition of claim 1 wherein the weight/weight ratio of second excipient substance to the exogenous chemical is from about 1:3 to about 1:100.

3. The composition of claim 1 wherein $R^{14}$ is saturated in from about 40 to 100 percent by weight of all compounds having the stated formula present in the composition.

4. The composition of claim 1 wherein $R^{14}$ has about 11 to about 21 carbon atoms, $R^{15}$ has 1 to about 6 carbon atoms and A is O.

5. The composition of claim 1 wherein the first excipient substance is a $C_{1-4}$ alkyl ester of a $C_{12-18}$ fatty acid.

6. The composition of claim 1 wherein the first excipient substance is a $C_{1-4}$ alkyl ester of a $C_{12-18}$ saturated fatty acid.

7. The composition of claim 1 wherein the first excipient substance is a propyl, isopropyl or butyl ester of a $C_{12-18}$ fatty acid.

8. The composition of claim 1 wherein the first excipient substance is butyl stearate.

9. The composition of claim 1, further comprising water in an amount effective to make the composition a dilute aqueous composition ready for application to foliage of a plant.

10. The composition of claim 1 wherein the exogenous chemical is a foliar-applied exogenous chemical.

11. The composition of claim 10 wherein the exogenous chemical is a pesticide, gametocide or plant growth regulator.

12. The composition of claim 11 wherein the exogenous chemical is a herbicide, nematicide or plant growth regulator.

13. The composition of claim 12 wherein the exogenous chemical is a herbicide.

14. The composition of claim 13 wherein the herbicide is selected from the group consisting of acetanilides, bipyridyls, cyclohexenones, dinitroanilines, diphenylethers, fatty acids, hydroxybenzonitriles, imidazolinones, phenoxies, phenoxypropionates, substituted ureas, sulfonylureas, thiocarbamates and triazines.

15. The composition of claim 13 wherein the herbicide is selected from the group consisting of acetochlor, alachlor, metolachlor, aminotriazole, asulam, bentazon, bialaphos, diquat, paraquat, bromacil, clethodim, sethoxydim, dicamba, diflufenican, pendimethalin, acifluorfen, $C_{9-10}$ fatty acids, fomesafen, oxyfluorfen, fosamine, flupoxam, glufosinate, glyphosate, bromoxynil, imazaquin, imazethapyr, isoxaben, norflurazon, 2,4-D, diclofop, fluazifop, quizalofop, picloram, propanil, fluometuron, isoproturon, chlorimuron, chlorsulfuron, halosulfuron, metsulfuron, primisulfuron, sulfometuron, sulfosulfuron, triallate, atrazine, metribuzin, triclopyr and herbicidal derivatives thereof.

16. The composition of claim 15 wherein the herbicide is glyphosate or a herbicidal derivative thereof.

17. The composition of claim 16 wherein the herbicide is glyphosate in its acid form.

18. The composition of claim 12 wherein the exogenous chemical is water-soluble.

19. The composition of claim 18 wherein the exogenous chemical is a salt having an anion portion and a cation portion.

20. The composition of claim 19 wherein at least one of said anion and cation portions is biologically active and has a molecular weight of less than about 300.

21. The composition of claim 20 wherein the exogenous chemical is paraquat or diquat.

22. The composition of claim 20 wherein the exogenous chemical exhibits systemic biological activity in the plant.

23. The composition of claim 22 wherein the exogenous chemical has one or more functional groups selected from the group consisting of amine, amide, carboxylate, phosphonate and phosphinate groups.

24. The composition of claim 23 wherein the exogenous chemical is a salt of 3,4,4-trifluoro-3-butenoic acid or of N-(3,4,4-trifluoro-1-oxo-3-butenyl)glycine that exhibits nematicidal activity.

25. The composition of claim 23 wherein the exogenous chemical is a herbicidal or plant growth regulating compound having at least one of each of amine, carboxylate and either phosphonate or phosphinate functional groups.

26. The composition of claim 25 wherein the herbicidal or plant growth regulating compound is a salt of glufosinate.

27. The composition of claim 26 wherein the salt of glufosinate is the ammonium salt.

28. The composition of claim 25 wherein the herbicidal or plant growth regulating compound is a salt of N-phosphonomethylglycine.

29. The composition of claim 28 wherein the salt of N-phosphonomethylglycine is selected from the group consisting of sodium, potassium, ammonium, mono-, di-, tri- and tetra-$C_{1-4}$-alkylammonium, mono-, di- and tri-$C_{1-4}$-alkanolammonium, mono-, di- and tri-$C_{1-4}$-alkylsulfonium and sulfoxonium salts.

30. The composition of claim 29 wherein the salt of N-phosphonomethylglycine is the ammonium, monoisopropylammonium or trimethylsulfonium salt.

31. The composition of claim 1, wherein m is 0 and $R^{13}$ is hydrogen.

32. The composition of claim 1, wherein n is from about 20 to about 40.

33. The composition of claim 1, wherein $R^{12}$ is a saturated straight-chain alkyl group.

34. The composition of claim 33, wherein the alkylether is a cetyl or stearyl ether or mixture thereof.

35. A herbicidal composition that comprises:
(a) N-phosphonomethylglycine or a herbicidal derivative thereof,
(b) butyl stearate, and
(c) an alkylether surfactant or mixture of such surfactants having the formula $$R^{12}-O-(CH_2CH_2O)_n(CH(CH_3)CH_2O)_m-R^{13}$$

wherein $R^{12}$ is an alkyl or alkenyl group having about 16 to about 22 carbon atoms, n is an average number of about 10 to about 100, m is an average number of 0 to about 5 and $R^{13}$ is hydrogen or $C_{1-4}$ alkyl.

36. The composition of claim 1, wherein the composition is a shelf-stable concentrate composition comprising the exogenous chemical in an amount of about 15 to about 90 percent by weight.

37. The composition of claim 36, wherein the composition is a solid composition comprising the exogenous chemical substance in an amount of about 30 to about 90 percent by weight.

38. The composition of claim 37, wherein the composition is a water-soluble or water-dispersible granular formulation.

39. The composition of claim 36, further comprising a liquid diluent, and wherein the composition comprises the exogenous chemical substance in an amount of about 15 to about 60 percent by weight.

40. The composition of claim 39 wherein the exogenous chemical substance is water-soluble and is present in an aqueous phase of the composition in an amount of about 15 to about 45 percent by weight of the composition.

41. The composition of claim 40, wherein the composition is an emulsion having an oil phase and the first excipient substance is present predominantly in the oil phase.

42. The composition of claim 41, wherein the composition is an oil-in-water emulsion.

43. The composition of claim 41, wherein the composition is a water-in-oil emulsion.

44. The composition of claim 41, wherein the composition is a water-in-oil-in-water multiple emulsion.

45. The composition of claim 41, further comprising a solid inorganic particulate colloidal material.

46. The composition of claim 45, wherein the colloidal material comprises particles having an average surface area of about 50 to about 400 $m^2/g$.

47. The composition of claim 45, wherein the colloidal material comprises particles having an average surface area of about 180 to about 400 $m^2/g$.

48. The composition of claim 45, wherein the colloidal material comprises particles of an inorganic oxide selected from the oxides of silicon, aluminum and titanium.

49. A plant treatment method, comprising contacting foliage of a plant with a biologically effective amount of a composition according to any of claims 1 to 35.

50. A plant treatment method, comprising the steps of:
(a) contacting foliage of a plant with a biologically effective amount of an exogenous chemical, and
(b) contacting the same foliage with an aqueous composition that comprises (i) a first excipient substance which is a compound or mixture of compounds having the formula:

$$R^{14}-CO-A-R^{15}$$

wherein $R^{14}$ is a hydrocarbyl group having about 5 to about 21 carbon atoms, $R^{15}$ is a hydrocarbyl group having 1 to about 14 carbon atoms, the total number of carbon atoms in $R^{14}$ and $R^{15}$ is about 11 to about 27, and A is O or NH; and (ii) a second excipient substance which is an alkylether surfactant or mixture of such surfactants having the formula:

$$R^{12}-O-(CH_2CH_2O)_n(CH(CH_3)CH_2O)_m-R^{13}$$

wherein $R^{12}$ is an alkyl or alkenyl group having about 16 to about 22 carbon atoms, n is an average number of about 15 to about 100, m is an average number of 0 to about 5 and $R^{13}$ is hydrogen or $C_{1-4}$alkyl;
wherein the first excipient substance is applied in a weight ratio to the exogenous chemical of about 1:3 to about 1:100; and wherein step (b) occurs simultaneously with or within about 96 hours before or after step (a).

* * * * *